US012643954B2

(12) United States Patent
Aznar Benitah et al.

(10) Patent No.: US 12,643,954 B2
(45) Date of Patent: Jun. 2, 2026

(54) ANTI-CD36 ANTIBODIES AND THEIR USE TO TREAT CANCER

(71) Applicant: ONA Therapeutics, S.L., Barcelona (ES)

(72) Inventors: Salvador Aznar Benitah, Barcelona (ES); Mercè De Frias Sánchez, Barcelona (ES); Salvador Guardiola Bagán, Barcelona (ES); Valerie Vanhooren, Barcelona (ES); Beatriz Morancho Armisen, Barcelona (ES)

(73) Assignee: ONA THERAPEUTICS, S.L., Barcelona (ES)

( * ) Notice: Subject to any disclaimer, the term of this patent is extended or adjusted under 35 U.S.C. 154(b) by 864 days.

(21) Appl. No.: 17/905,745

(22) PCT Filed: Mar. 5, 2021

(86) PCT No.: PCT/IB2021/051881
§ 371 (c)(1),
(2) Date: Sep. 6, 2022

(87) PCT Pub. No.: WO2021/176424
PCT Pub. Date: Sep. 10, 2021

(65) Prior Publication Data
US 2023/0235073 A1 Jul. 27, 2023

Related U.S. Application Data

(60) Provisional application No. 63/117,529, filed on Nov. 24, 2020, provisional application No. 62/986,174, filed on Mar. 6, 2020.

(30) Foreign Application Priority Data

Mar. 6, 2020 (EP) ..................................... 20382166

(51) Int. Cl.
C07K 16/28 (2006.01)
A61K 39/00 (2006.01)
A61P 35/04 (2006.01)

(52) U.S. Cl.
CPC .......... C07K 16/2896 (2013.01); A61K 39/00 (2013.01); A61P 35/04 (2018.01); *C07K 2317/565* (2013.01); *C07K 2317/92* (2013.01)

(58) Field of Classification Search
CPC .......... C07K 16/2896; C07K 2317/565; C07K 2317/92; C07K 16/2818; C07K 16/28; C07K 16/30; C07K 2317/24; A61K 39/00; A61K 39/395; A61K 38/00; A61K 2039/507; A61K 2039/505; A61P 35/04; A61P 35/00; Y02A 50/30
See application file for complete search history.

(56) References Cited

U.S. PATENT DOCUMENTS

| | | | |
|---|---|---|---|
| 4,816,397 | A | 3/1989 | Boss et al. |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,500,362 | A | 3/1996 | Robinson et al. |
| 5,516,637 | A | 5/1996 | Huang et al. |
| 5,571,698 | A | 11/1996 | Ladner et al. |
| 5,580,717 | A | 12/1996 | Dower et al. |
| 5,624,821 | A | 4/1997 | Winter et al. |
| 5,648,260 | A | 7/1997 | Winter et al. |
| 5,658,727 | A | 8/1997 | Barbas et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,821,047 | A | 10/1998 | Garrard et al. |
| 5,821,337 | A | 10/1998 | Carter et al. |
| 5,965,726 | A | 10/1999 | Pavlakis et al. |
| 5,969,108 | A | 10/1999 | McCafferty et al. |
| 6,054,297 | A | 4/2000 | Carter et al. |
| 6,174,666 | B1 | 1/2001 | Pavlakis et al. |
| 6,291,664 | B1 | 9/2001 | Pavlakis et al. |
| 6,414,132 | B1 | 7/2002 | Pavlakis et al. |
| 6,737,056 | B1 | 5/2004 | Presta |
| 6,794,498 | B2 | 9/2004 | Pavlakis et al. |
| 6,808,710 | B1 | 10/2004 | Wood et al. |
| 7,332,581 | B2 | 2/2008 | Presta |
| 7,371,826 | B2 | 5/2008 | Presta |

(Continued)

FOREIGN PATENT DOCUMENTS

| | | |
|---|---|---|
| WO | WO-9002809 A1 | 3/1990 |
| WO | WO-9110737 A1 | 7/1991 |

(Continued)

OTHER PUBLICATIONS

International Search Report and Written Opinion for International Application No. PCT/IB2021/050747, European Patent Office, Germany, mailed on Apr. 29, 2021, 10 pages.

(Continued)

*Primary Examiner* — Nelson B Moseley, II

(74) *Attorney, Agent, or Firm* — Sterne, Kessler, Goldstein & Fox P.L.L.C.

(57) ABSTRACT

The claimed invention relates to treating cancer by targeting CD36, a fatty acid receptor. The claimed invention also relates to treating cancer metastases by targeting CD36. The invention involves using anti-CD36 antibodies as blockers or inhibitors of CD36 activity.

32 Claims, 38 Drawing Sheets

Specification includes a Sequence Listing.

(56) References Cited

U.S. PATENT DOCUMENTS

| | | | |
|---|---|---|---|
| 7,488,802 | B2 | 2/2009 | Collins et al. |
| 7,635,757 | B2 | 12/2009 | Freeman et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,609,089 | B2 | 12/2013 | Langermann et al. |
| 8,779,105 | B2 | 7/2014 | Korman et al. |
| 8,900,587 | B2 | 12/2014 | Carven et al. |
| 9,580,507 | B2 | 2/2017 | Korman et al. |
| 11,535,680 | B2 | 12/2022 | Aznar Benitah et al. |
| 12,286,484 | B2 | 4/2025 | Aznar Benitah et al. |
| 2004/0009171 | A1 | 1/2004 | Gerritsen et al. |
| 2004/0014194 | A1 | 1/2004 | Beyer et al. |
| 2004/0076621 | A1* | 4/2004 | Watt .................. C12N 15/1138 |
| | | | 514/44 A |
| 2005/0014934 | A1 | 1/2005 | Hinton et al. |
| 2009/0317368 | A1 | 12/2009 | Chen |
| 2014/0341917 | A1 | 11/2014 | Nastri et al. |
| 2015/0079109 | A1 | 3/2015 | Li et al. |
| 2016/0272708 | A1 | 9/2016 | Chen |
| 2019/0106503 | A1 | 4/2019 | Aznar Benitah et al. |
| 2021/0380712 | A1 | 12/2021 | Aznar Benitah et al. |
| 2023/0086099 | A1 | 3/2023 | Aznar Benitah et al. |
| 2025/0206836 | A1 | 6/2025 | Aznar Benitah et al. |

FOREIGN PATENT DOCUMENTS

| | | | |
|---|---|---|---|
| WO | WO-9201047 | A1 | 1/1992 |
| WO | WO-9218619 | A1 | 10/1992 |
| WO | WO-9311236 | A1 | 6/1993 |
| WO | WO-9429351 | A2 | 12/1994 |
| WO | WO-9515982 | A2 | 6/1995 |
| WO | WO-9520401 | A1 | 8/1995 |
| WO | WO-9713844 | A1 | 4/1997 |
| WO | WO-03032813 | A2 | 4/2003 |
| WO | WO-03099196 | A2 | 12/2003 |
| WO | WO-2004056312 | A2 | 7/2004 |
| WO | WO-2006121168 | A1 | 11/2006 |
| WO | WO-2008156712 | A1 | 12/2008 |
| WO | WO-2009014708 | A2 | 1/2009 |
| WO | WO-2009114335 | A2 | 9/2009 |
| WO | WO-2011066389 | A1 | 6/2011 |
| WO | WO-2011161699 | A2 | 12/2011 |
| WO | WO-2012130831 | A1 | 10/2012 |
| WO | WO-2012145493 | A1 | 10/2012 |
| WO | WO-2013079174 | A1 | 6/2013 |
| WO | WO-2013173223 | A1 | 11/2013 |
| WO | WO-2013181634 | A2 | 12/2013 |
| WO | WO-2014179664 | A2 | 11/2014 |
| WO | WO-2014194302 | A2 | 12/2014 |
| WO | WO-2014206107 | A1 | 12/2014 |
| WO | WO-2015017600 | A1 | 2/2015 |
| WO | WO-2015035606 | A1 | 3/2015 |
| WO | WO-2015085847 | A1 | 6/2015 |
| WO | WO-2015112800 | A1 | 7/2015 |
| WO | WO-2015112900 | A1 | 7/2015 |
| WO | WO-2016016871 | A1 | 2/2016 |
| WO | WO-2016106159 | A1 | 6/2016 |
| WO | WO-2016149201 | A2 | 9/2016 |
| WO | WO-2016168716 | A1 | 10/2016 |
| WO | WO-2016197367 | A1 | 12/2016 |
| WO | WO-2017019846 | A1 | 2/2017 |
| WO | WO-2017020291 | A1 | 2/2017 |
| WO | WO-2017020858 | A1 | 2/2017 |
| WO | WO-2017024465 | A1 | 2/2017 |
| WO | WO-2017024515 | A1 | 2/2017 |
| WO | WO-2017025016 | A1 | 2/2017 |
| WO | WO-2017025051 | A1 | 2/2017 |
| WO | WO-2017034916 | A1 | 3/2017 |
| WO | WO-2017040790 | A1 | 3/2017 |
| WO | WO-2017055411 | A1 | 4/2017 |
| WO | WO-2017106061 | A1 | 6/2017 |
| WO | WO-2017123557 | A1 | 7/2017 |
| WO | WO-2017132827 | A1 | 8/2017 |
| WO | WO-2017133540 | A1 | 8/2017 |
| WO | WO-2019158581 | A1 | 8/2019 |
| WO | WO-2020053833 | A1 | 3/2020 |
| WO | WO-2021152548 | A1 | 8/2021 |

OTHER PUBLICATIONS

Alghazeer, R., et al., "Cytotoxicity of oxidised lipids in cultured colonal human intestinal cancer cells (caco-2 cells)," Toxicology Letters 180(3):202-211, Elsevier BV, Netherlands (2008).

Balaban, S., et al., "Obesity and Cancer Progression: Is there a Role of Fatty Acid Metabolism?" BioMed Research International 2015:274585, Hindawi Publishing Corporation, United States (2015).

Coburn, C.T., et al., "Defective uptake and utilization of long chain fatty acids in muscle and adipose tissues of CD36 knockout mice," J Biol Chem 275(42):32523-9, American Society for Biochemistry and Molecular Biology Inc., United States (2000).

Defilippis, R.A., et al., "CD36 repression activates a multicellular stromal program shared by high mammographic density and tumor tissues," Cancer Discov 2(9):826-39, American Association for Cancer Research Inc., United States (2012).

Geloen, A., et al., "CD36 Inhibitors Reduce Postprandial Hypertriglyceridemia and Protect against Diabetic Dyslipidemia and Atherosclerosis," PLoS One 7(5):e37633, Public Library of Science, United States (2012).

Hale, J.S., et al., "Cancer stem cell-specific scavenger receptor 36 drives glioblastoma progression," Stem Cells 32(7):1756-58, Wiley-Blackwell, United States (2014).

Ibrahimi, A., et al., "Muscle-specific overexpression of FAT/CD36 enhances fatty acid oxidation by contracting muscle, reduces plasma triglycerides and fatty acids, and increases plasma glucose and insulin," Journal of Biological Chemistry 274(38):26761-26766, American Society for Biochemistry and Molecular Biology Inc., United States (1999).

Lai, K.C., et al., "Blocking TNF-α inhibits angiogenesis and growth of IFIT2-depleted metastatic oral squamous cell carcinoma cells," Cancer Letters 370(2):207-215, Elsevier BV, Netherlands (2015).

Nguyen, D.X., et al., "Genetic determinants of cancer metastasis," Nat Rev Genet 8(5):341-352, Nature Publishing Group, United Kingdom (2007).

Nguyen, D.X., et al., "Metastasis: from dissemination to organ-specific colonization," Nature Rev. Cancer 9(4):274-284, Nature Publishing Group, United Kingdom (2009).

Pascual, G., et al., "Targeting metastasis-initiating cells through the fatty acid receptor CD36," Nature 541(7635):41-45, Nature Publishing Group, United Kingdom (2016).

Pepino, M.Y., et al., "Structure-function of CD36 and importance of fatty acid signal transduction in fat metabolism," Annual Review of Nutrition 34:281-303, Annual Reviews Inc., United States (2014).

Miyazaki, H., et al., "Overexpression of nm23-H2/NDP Kinase B in a Human Oral Squamous Cell Carcinoma Cell Line Results in Reduced Metastasis, Differentiated Phenotype in the Metastatic Site, and Growth Factor-independent Proliferative Activity in Culture," Clin Cancer Res 5 (12):4301-4307, American Association for Cancer Research, United States (Dec. 1999).

Omura, K., "Current status of oral cancer treatment strategies: surgical treatments for oral squamous cell carcinoma," Int J Clin Oncol 19(3):423-30, Springer Nature, Switzerland (Apr. 2014).

Sato, S., et al., "Inhibition of CD44v9 upregulates the invasion ability of oral squamous cell carcinoma cells," Oral Oncology 39:27-30, Elsevier, Netherlands (Apr. 2014).

Keir, M.E., et al., "PD-1 and its ligands in tolerance and immunity," Annu. Rev. Immunol. 26:677-704, Annual Reviews, United States (2008).

Dong, H., et al., "B7-H1, a third member of the B7 family, co-stimulates T-cell proliferation and interleukin-10 secretion," Nat. Med. 5:1365-1369, Springer, Germany (Dec. 1999).

Terme, M., et al., "IL-18 induces PD-1-dependent immunosuppression in cancer," Cancer Res. 71:5393-5399, American Association for Cancer Research, United States (Aug. 2011).

(56) References Cited

OTHER PUBLICATIONS

Pardoll, D.M., "The blockade of immune checkpoints in cancer immunotherapy," Nat. Rev. Cancer 12:252-264, Springer, Germany (Mar. 2012).

Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).

Nishimura, H., et al., "Autoimmune dilated cardiomyopathy in PD-1 receptor-deficient mice," Science 291:319-322, American Association for the Advancement of Science, United States (Jan. 2001).

Dong, H., et al., "Tumor-associated B7-H1 promotes T-cell apoptosis: a potential mechanism of immune evasion," Nat. Med. 8:793-800, Springer, Germany (Aug. 2002).

Topalian, S. L., et al., "Safety, Activity, and Immune Correlates of Anti-PD-1 Antibody in Cancer," The New England Journal of Medicine 366(26):2443-2454, Massachusetts Medical Society, United States (Jun. 2012).

Hamid, O., et al., "Safety and Tumor Responses with Lambrolizumab (Anti-PD-1) in Melanoma," The New England Journal of Medicine 369(2):134-144, Massachusetts Medical Society, United States (Jul. 2013).

Holliger, P., and Hudson, P.J., "Engineered antibody fragments and the rise of single domains," Nature Biot. 23(9):1126-1136, Springer, Germany (Sep. 2005).

Kermorvant-Duchemin, E., et al., "Trans-arachidonic acids generated during nitrative stress induce a thrombospondin-1-dependent microvascular degeneration," Nat. Med. 11(12):1339-1345, Springer, Germany (Dec. 2005).

Mwaikambo, B.R., et al., "Activation of CD36 inhibits and induces regression of inflammatory corneal neovascularization," Investigative Ophthalmology & Visual Science 47:4356-4364, Association for Research in Vision and Ophthalmology, United States (Oct. 2006).

GenBank, "Human hPD-1 (hPD-1) mRNA, complete cds," Accession No. U64863.1, accessed at https://www.ncbi.nlm.nih.gov/nuccore/U64863.1/, accessed on Jan. 25, 2023, 3 pages.

Okazaki, T., et al., "New regulatory co-receptors: inducible co-stimulator and PD-1," Curr. Opin. Immunol. 14:391779-82, Elsevier, Netherlands (Dec. 2002).

Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).

Hutloff, A., et al., "ICOS is an inducible T-cell co-stimulator structurally and functionally related to CD28," Nature 397:263-266, Springer, Germany (Jan. 1991).

Hansen, J.A., et al., "Monoclonal Antibodies Identifying a Novel T-Cell Antigen and Ia Antigens of Human Lymphocytes," Immunogenetics 10:247-260, Springer Science+Business Media, Germany (Feb. 1980).

Ishida, Y., et al., "Induced Expression of PD-1, a Novel Member of the Immunoglobulin Gene Superfamily, Upon Programmed Cell Death," The EMBO Journal (11):3887-3895, Oxford University Press, United Kingdom (Nov. 1992).

Agata, Y., et al., "Expression of the PD-1 antigen on the surface of stimulated mouse T and B lymphocytes," Int Immunol 8:765-72, Oxford University Press, United Kingdom (May 1996).

Thomas, M. L., "Of ITAMs and ITIMs: turning on and off the B cell antigen receptor," J Exp Med 181:1953-6, Rockefeller University Press, United States (Jun. 1999).

Vivier, E. and Daeron, M., "Immunoreceptor Tyrosine-based Inhibition Motifs," Immunology Today 18(6):286-291, Elsevier, United Kingdom (Jun. 1997).

Freeman, G.J., et al., "Engagement of the PD-1 immunoinhibitory receptor by a novel B7 family member leads to negative regulation of lymphocyte activation," J Exp Med 192:1027-34, Rockefeller University Press, United States (Oct. 2002).

Latchman, Y., et al., "PD-L2 is a Second Ligand for PD-1 and Inhibits T Cell Activation," Nature Immunology 2(3):261-268, Nature Publishing Group, United Kingdom (Mar. 2001).

Carter, L., et al., "PD-1:PD-L inhibitory pathway affects both CD4(+) and CD8(+) T cells and is overcome by IL-2," Eur J Immunol 32:634-43, Wiley-VCH, United States (Mar. 2002).

Dong, H., et al., "B7-H1 pathway and its role in the evasion of tumor immunity," J. Mol. Med. 81:281-7, Springer Science+ Business Media, Germany (May 2003).

Blank, C., et al., "Interaction of PD-L1 on tumor cells with PD-1 on tumor-specific T cells as a mechanism of immune evasion: implications for tumor immunotherapy," Cancer Immunol. Immunother. 54:307-314, Springer Science+Business Media, Germany (Apr. 2005).

Konishi, J., et al., "B7-H1 expression on non-small cell lung cancer cells and its relationship with tumor-infiltrating lymphocytes and their PD-1 expression," Clin. Cancer Res. 10:5094-100, American Association for Cancer Research, United States (Aug. 2004).

Iwai, Y., et al., "Involvement of PD-L1 on tumor cells in the escape from host immune system and tumor immunotherapy by PD-L1 blockade," Proc. Nat'l. Acad. Sci. USA 99:12293-7, National Academy of Sciences, United States (Sep. 2002).

Brown, J., et al., "Blockade of programmed death-1 ligands on dendritic cells enhances T cell activation and cytokine production," J. Immunol. 170:1257-66, American Association of Immunologists, United States (Feb. 2003).

Salama, A.D., et al., "Critical Role of the Programmed Death-1 (PD-1) Pathway in Regulation of Experimental Autoimmune Encephalomyelitis," The Journal of Experimental Medicine 198(1):71-78, The Rockefeller University Press, United States (Jul. 2003).

Prokunina, L., and Alarcon-Riquelme, M., "The genetic basis of systemic lupus erythematosus—knowledge of today and thoughts for tomorrow," Hum Mol Genet 13:R143-8, Oxford University Press, United Kingdom (Apr. 2003).

Nielsen, C., et al., "A putative regulatory polymorphism in PD-1 is associated with nephropathy in a population-based cohort of systemic lupus erythematosus patients," Lupus 13:510-516, BMJ Publishing Group, United Kingdom (2004).

Okazaki, T., et al., "PD-1 immunoreceptor Inhibits B Cell Receptor-mediated Signaling by Recruiting src Homology 2-domain-containing Tyrosine Phosphatase 2 to Phosphotyrosine," Proceedings of the National Academy of Sciences 98(24):13866-13871, National Academy of Sciences, United States (Nov. 2001).

GenBank, "RecName: Full=Programmed cell death 1 ligand 1; Short=PD-L1; Short=PDCD1 ligand 1; Short-Programmed death ligand 1; Short=hPD-L1; AltName: Full=B7 homolog 1; Short=B7-H1; AltName: CD_antigen=CD274; Flags: Precursor," Accession No. Q9NZQ7, accessed at https://www.ncbi.nlm.nih.gov/protein/83287884/, accessed on Jan. 25, 2023, 9 pages.

Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).

"Pembrolizumab," Definition, National Cancer Institute, accessed at http://www.cancer.gov/drugdictionary?cdrid=695789, accessed on May 25, 2017, 2 pages.

"Anti-PD-1 monoclonal antibody MEDI0680," Definition, National Cancer Institute, accessed at http://www.cancer.gov/drugdictionary?cdrid=756047, accessed on May 25, 2017, 1 page.

Liu, S., et al., "Ongoing clinical trials of PD-1 and PD-L1 inhibitors for lung cancer in China," J. Hematol. Oncol. 10:136, Springer, Germany (Jul. 2017).

Herbst, R., et al., "A study of MPDL3280A, an engineered PD-L1 antibody in patients with locally advanced or metastatic tumors.," J Clin Oncol 31(15):3000, American Society of Clinical Oncology, United States (2013).

Khleif, S., et al., "MEDI4736, An Anti-PD-L1 Antibody with Modified Fc Domain: Preclinical Evaluation and Early Clinical Results from a Phase 1 Study in Patients with Advanced Solid

(56) References Cited

OTHER PUBLICATIONS

Tumors," Proceedings from the European Cancer Congress 2013, Abstract 802, Amsterdam, The Netherlands (Sep. 27-Oct. 1, 2013).

Zhang, F., et al., "Structural basis of a novel PD-L1 nanobody for immune checkpoint blockade," Cell Discov. 7:3, Springer, Germany (Mar. 2017).

Gorelik, L., et al., "Preclinical Characterization of a Novel Fully Human IgG1 anti-PD-L1 mAb CK-301," American Association for Cancer Research Annual Meeting (AACR), Abstract 4606, American Association for Cancer Research, United States (Apr. 2016).

Fiedler, U., et al., "MP0250, a VEGF and HGF neutralizing DARPin® molecule shows high anti-tumor efficacy in mouse xenograft and patient-derived tumor models," Oncotarget 8:98371-98383, Impact Journals, United States (Oct. 2017).

Chen, S., et al., "Combination of 4-1BB agonist and PD-1 antagonist promotes antitumor effector/memory CD8 T cells in a poorly immunogenic tumor model," Cancer Immunology Research 3(2):149-160, Springer Science+Business Media, United States (Feb. 2015).

Hai, J., et al., "Generation of Genetically Engineered Mouse Lung Organoid Models for Squamous Cell Lung Cancers Allows for the Study of Combinatorial Immunotherapy," Clinical Cancer Research 26(13):3431-3442, American Association for Cancer Research, United States (Jul. 2020).

Du, W., et al., "Sitravatinib potentiates immune checkpoint blockade in refractory cancer models," JCI Insight 3(21):e124184, American Society for Clinical Investigation, United States (Nov. 2018).

Ladanyi, A., et al., "Adipocyte-induced CD36 expression drives ovarian cancer progression and metastasis," Oncogene 37(17):2285-2301, Springer, Germany (Apr. 2018).

Abdiche, Y.N., et al., "Exploring Blocking Assays using Octet, Proteon, and Biacore Biosensors," Analytical Biochemistry 386(2):172-180, Elsevier, United States (2009).

Almagro, J.C. and Fransson, J., "Humanization of Antibodies," Frontiers in Bioscience 13:1619-1633, Frontiers in Bioscience Publications, United States (Jan. 2008).

Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).

Bricogne, G., "[23] Bayesian Statistical Viewpoint on Structure Determination: Basic Concepts and Examples," Methods in Enzymology 276:361-423, Academic Press, United States (1997).

Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).

Brinkmann, U., et al., "Phage Display of Disulfide-stabilized Fv Fragments," Journal of Immunological Methods 182(1):41-50, Elsevier, Netherlands (1995).

Bruggemann, M., et al., "Comparison of the Effector Functions of Human Immunoglobulins Using a Matched Set of Chimeric Antibodies," The Journal of Experimental Medicine, 166:1351-1361, Rockefeller University Press, United States (Nov. 1987).

Burton, D.R. and Barbas, C.F. 3rd., "Human Antibodies From Combinatorial Libraries," Advances in Immunology 57:191-280, Academic Press, United States (1994).

Champe, M., et al., "Monoclonal Antibodies that Block the Activity of Leukocyte Function—Associated Antigen 1 Recognize Three Discrete Epitopes in the Inserted Domain of CD11a," The Journal of Biological Chemistry 270 (3):1388-1394, Elsevier Inc. on behalf of American Society for Biochemistry and Molecular Biology, United States (Jan. 1995).

Chayen, N.E., "The Role of Oil in Macromolecular Crystallization," Structure 5(10):1269-1274, Cell Press, United States (Oct. 1997).

Cheung, R.C., et al., "Epitope-specific Antibody Response to the Surface Antigen of Duck Hepatitis B Virus in Infected Ducks," Virology 176(2):546-552, Academic Press, United States (1990).

Chothia, C. and Lesk, A. M., "Canonical Structures for the Hypervariable Regions of Immunoglobulins," Journal of Molecular Biology 196(4):901-917, Elsevier, United Kingdom (Aug. 1987).

Clynes, R., et al., "Fc Receptors are Required in Passive and Active Immunity to Melanoma," Proceedings of the National Academy of Sciences of the USA 95(2):652-656, National Academy of Sciences, United States (1998).

Coales, S.J., et al., "Epitope Mapping by Amide Hydrogen/Deuterium Exchange Coupled With Immobilization of Antibody, On-Line Proteolysis, Liquid Chromatography and Mass Spectrometry," Rapid Communications in Mass Spectrometry, 23(5):639-647, John Wiley and Sons Ltd, United Kingdom (Mar. 2009).

Cole, S.P.C., et al., "The EBV-Hybridoma Technique and its Application to Human Lung Cancer," in Monoclonal Antibodies and Cancer Therapy, Reisfeld, R.A. and Sell, S., eds., pp. 77-96, Alan R. Liss, Inc., United States (1985).

Cote, R.J., et al., "Generation of Human Monoclonal Antibodies Reactive with Cellular Antigens," Proceedings of the National Academy of Sciences of the United States of America, 80(7):2026-2030, National Academy of Sciences, United States (1983).

Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).

Duncan, A,R. and Winter, G., "The Binding Site for C1q on IgG," Nature, 332(6166):738-740, Nature Publishing Group, United Kingdom (Apr. 1988).

Freeman, G.J., et al., "Protect the Killer: CTLs Need Defenses against the Tumor," Nature Medicine 8(8):787-789, Nature Publishing Company, United States (Aug. 2002).

Giege, R., et al., "Crystallogenesis of biological macromolecules: facts and perspectives," Acta Crystallographica. Section D, Biological Crystallography 50(Pt4):339-350, Wiley-Blackwell, United States (Jul. 1994).

Giudicelli, V., et al., "IMGT/LIGM-DB, the IMGT Comprehensive Database of Immunoglobulin and T Cell Receptor Nucleotide Sequences," Nucleic Acids Research 34(Database issue):D781-D784, Oxford University Press, United Kingdom (Jan. 2006).

Guyer, R.L., et al., "Immunoglobulin Binding by Mouse Intestinal Epithelial Cell Receptors," Journal of Immunology 117(2):587-93, American Association of Immunologists, United States (Aug. 1976).

Hellstrom, I., et al., "Strong Antitumor Activities of IgG3 Antibodies to a Human Melanoma-Associated Ganglioside," Proceedings of the National Academy of Sciences of the United States of America, 82:1499-1502 (Mar. 1985 ).

Hellstrom, I., et al., "Antitumor Effects of L6, An IgG2a Antibody That Reacts With Most Human Carcinomas," Proceedings of the National Academy of Sciences of the United States of America, 83:7059-7063. (Sep. 1986).

Imai-Nishiya, H., et al., "Double Knockdown of Alpha 1,6-Fucosyltransferase (FUT8) and GDP-Mannose 4,6-Dehydratase (GMD) in AntibodyPproducing Cells: a New Strategy for Generating Fully Non-Fucosylated Therapeutic Antibodies With Enhanced ADCC," BMC Biotechnology 7:84, BioMed Central, United Kingdom (2007).

International Search Report and Written Opinion for International Application No. PCT/IB2021/051881, European Patent Office, Netherlands, mailed on Jun. 8, 2021, 9 pages.

Jones, P.T., et al., "Replacing the Complementarity-determining Regions in a Human Antibody with those from a Mouse," Nature 321(6069):522-525, Nature Publishing Group, United Kingdom (May 1986).

Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).

Kim, J.K., et al., "Localization of the Site of the Murine IgG1 Molecule That is Involved in Binding to the Murine Intestinal Fc Receptor," European Journal of Immunology, 24:2429-2434, Wiley-VCH, Germany (Oct. 1994).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).

(56) References Cited

OTHER PUBLICATIONS

Kohler, G. and Milstein, C., "Continuous Cultures of Fused Cells Secreting Antibody of Predefined Specificity," Nature 256(5517):495-497, Nature Publishing Group, United Kingdom (Aug. 1975).

Kuroki, M., et al., "Biochemical Characterization of 25 Distinct Carcinoembryonic Antigen (CEA) Epitopes Recognized by 57 Monoclonal Antibodies and Categorized Into Seven Groups in Terms of Domain Structure of the CEA Molecule," Hybridoma 11(4):391-407, Mary Ann Liebert, United States (1992).

Kuroki, M., et al., "Determination of Epitope Specificities of a Large Number of Monoclonal Antibodies by Solid-phase Mutual Inhibition Assays Using Biotinylated Antigen," Immunological Investigations 21(6):523-538, Informa Healthcare, United Kingdom (1992).

Kuroki, M., et al., "Serological Mapping of the TAG-72 Tumor-Associated Antigen Using 19 Distinct Monoclonal Antibodies," Cancer Research 50 (16):4872-4879, American Association for Cancer Research, United States (1990).

Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

Liu, S.Y. and Wu, Y.L., "Ongoing Clinical Trials of PD-1 and PD-L1 Inhibitors for Lung Cancer in China," Journal of Hematology & Oncology 10(1):136, Biomed Central, United Kingdom (Jul. 2017).

Longmore, G.E., et al., "Product-Identification and Substrate-Specificity Studies of the GDP-L-Fucose:2-Acetamido-2-Deoxy-Beta-d-Glucoside (FUC→Asn-Linked GlcNAc) 6-Alpha-1-Fucosyltransferase in a Golgi-Rich Fraction From Porcine Liver," Carbohydrate Research 100:365-392, Elsevier, Netherlands (1982).

McPherson, A., "Crystallization of Proteins From Polyethylene Glycol," The Journal of Biological Chemistry 251(20):6300-6303, Elsevier Inc. on behalf of American Society for Biochemistry and Molecular Biology, United States (Oct. 1976).

McPherson, A., "Current Approaches to Macromolecular Crystallization," European Journal of Biochemistry 189(1):1-23, Blackwell Science Ltd, United Kingdom (Apr. 1990).

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, United Kingdom (1990).

Morel, G.A., et al., "Monoclonal Antibodies to Bovine Serum Albumin: Affinity and Specificity Determinations," Molecular Immunology 25(1):7-15, Pergamon Press, United Kingdom (1988).

Niwa R., et al., "Enhanced Natural Killer Cell Binding and Activation by Low-fucose IgG1 Antibody Results in Potent Antibody-dependent Cellular Cytotoxicity Induction at Lower Antigen Density," Clinical Cancer Research, 11(6):2327-2336, Denville, United States , (Mar. 2005).

Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).

Raju, T.S., "Glycosylation Variations with Expression Systems and their Impact on Biological Activity of Therapeutic Immunoglobulins," BioProcess International 44-53 (2003).

Riechmann, L., et al., "Reshaping Human Antibodies for Therapy," Nature 332(6162):323-327, Nature Publishing Group, United Kingdom (Mar. 1988).

Roguska, M.A., et al., "A Comparison of Two Murine Monoclonal Antibodies Humanized by CDR-grafting and Variable Domain Resurfacing," Protein Engineering 9(10):895-904, Oxford University Press, United Kingdom (Oct. 1996).

Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).

Routier, F.H., et al., "The Glycosylation Pattern of a Humanized IgGI Antibody (D1.3) Expressed in CHO Cells," Glycoconjugate Journal 14(2):201-207, Springer, United States (1997).

Roversi, P., et al., "Modelling Prior Distributions of Atoms for Macromolecular Refinement and Completion," Acta Crystallographica. Section D, Biological Crystallography 56(Pt10):1316-1323, Wiley-Blackwell, United States (Oct. 2000).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

Stahli, C., et al., "Distinction of Epitopes by Monoclonal Antibodies," Methods in Enzymology 92:242-253, Academic Press, United States (1983).

Stubenrauch, K., et al., "Impact of Molecular Processing in the Hinge Region of Therapeutic IgG4 Antibodies on Disposition Profiles in Cynomolgus Monkeys," Drug Metabolism and Disposition 38(1):84-91, American Society for Pharmacology and Experimental Therapeutics, United States (Jan. 2010).

UniProt Accession No. P16671, "Platelet glycoprotein 4," retrieved from https://www.uniprot.org/uniprotkb/P16671/entry , accessed on Feb. 7, 2023, 20 pages.

UniProt Accession No. Q07969, "Platelet glycoprotein 4," retrieved from https://www.uniprot.org/uniprotkb/Q07969/entry , accessed on Feb. 7, 2023, 15 pages.

UniProt Accession No. Q08857, "Platelet glycoprotein 4," retrieved from https://www.uniprot.org/uniprotkb/Q08857/entry , accessed on Feb. 7, 2023, 15 pages.

UniProt Accession No. Q4R6B4, "Platelet glycoprotein 4," retrieved from https://www.uniprot.org/uniprotkb/Q4R6B4/entry , accessed on Feb. 7, 2023, 11 pages.

UniProt Accession No. Q6J512, "Platelet glycoprotein 4," retrieved from https://www.uniprot.org/uniprotkb/Q6J512/entry , accessed on Feb. 7, 2023, 11 pages.

Verhoeyen, M., et al., "Reshaping Human Antibodies: Grafting an Antilysozyme Activity," Science 239(4847): 1534-1536, American Association for the Advancement of Science, United States (Mar. 1988).

Wagener, C., et al., "Monoclonal Antibodies for Carcinoembryonic Antigen and Related Antigens as a Model System: a Systematic Approach for the Determination of Epitope Specificities of Monoclonal Antibodies.," Journal of Immunology 130(5):2308-2315, American Association of Immunologists, United States (1983).

Wagener, C., et al., "Use of Biotin-Labeled Monoclonal Antibodies and Avidin-Peroxidase Conjugates for the Determination of Epitope Specificities in a Solid-phase Competitive Enzyme Immunoassay," Journal of Immunological Methods 68 (1-2):269-274, Elsevier, Netherlands (1984).

* cited by examiner

**Randomization &
Start treatment:**
- Abs 1 mg/Kg, daily
- Cisplatin 2mg/Kg, 2X/week Orthotopic
injection Detroit
562 Luc

T0     T9     T16     T23     T29

End Point
Organs and
tissues
collection

**Monitorization by IVIS every week
BW 2 times/week**

| Groups | Abs daily | Cisplatin 2x/week |
|---|---|---|
| IgA | 1 mg/kg | PBS |
| Cisplatin + IgA | 1 mg/kg | 2 mg/kg |
| Commercial anti-CD36 Ab | 1 mg/kg | PBS |
| Cisplatin + JC63.1 | 1 mg/kg | 2 mg/kg |

PRIMARY TUMOR

Tongue 4.4. F A Small to medium area of necrosis (right and middle)

FIGURE 3
LUNG METS
IgA Isotype Control
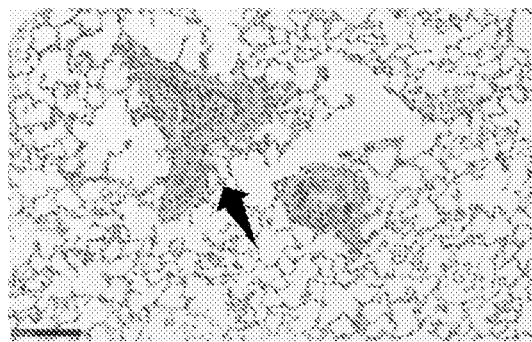
IgA Isotype Control + Cisplatin
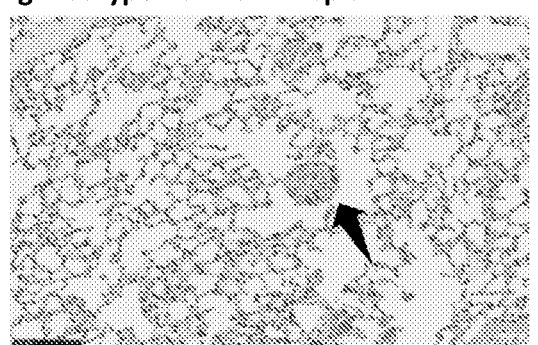
Commercial anti-CD36 Ab
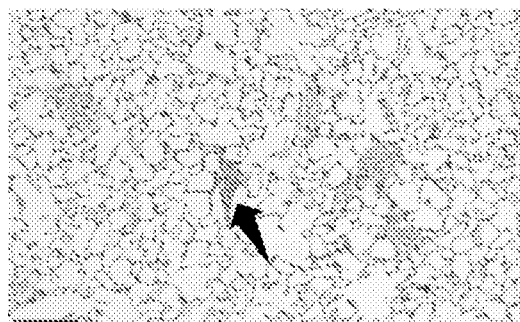
Commercial anti-CD36 Ab + Cisplatin
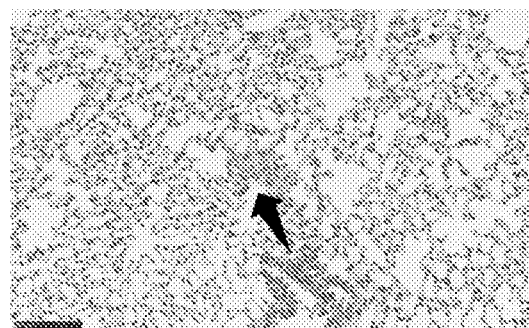

FIGURE 5
Murine ONA-0 Antibodies
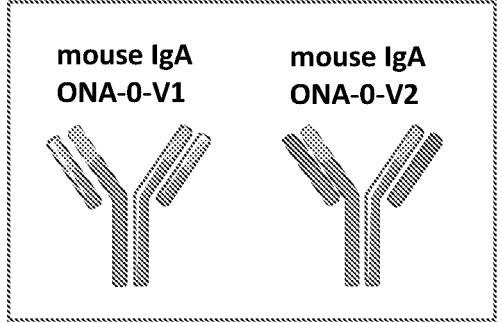
mouse IgA
ONA-0-V1
mouse IgA
ONA-0-V2
Chimeric ONA-0 Antibodies
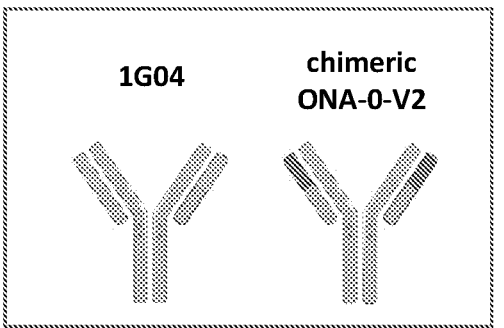
1G04
chimeric
ONA-0-V2
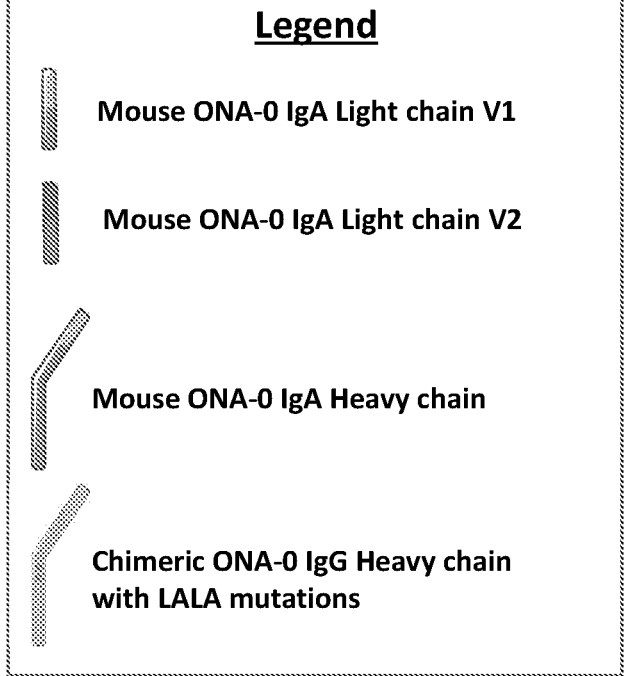
Legend
Mouse ONA-0 IgA Light chain V1
Mouse ONA-0 IgA Light chain V2
Mouse ONA-0 IgA Heavy chain
Chimeric ONA-0 IgG Heavy chain
with LALA mutations

FIGURE 6
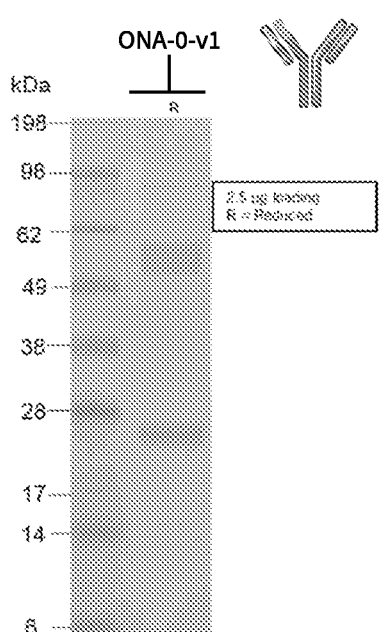
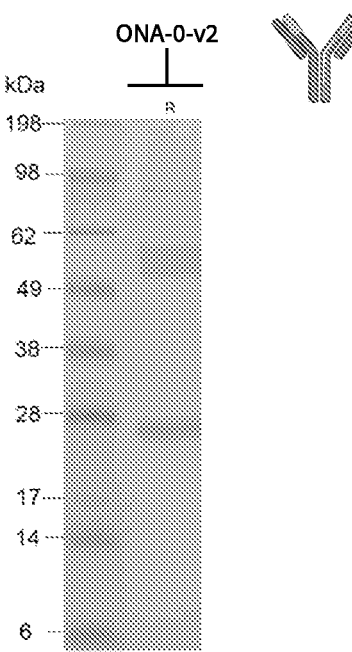
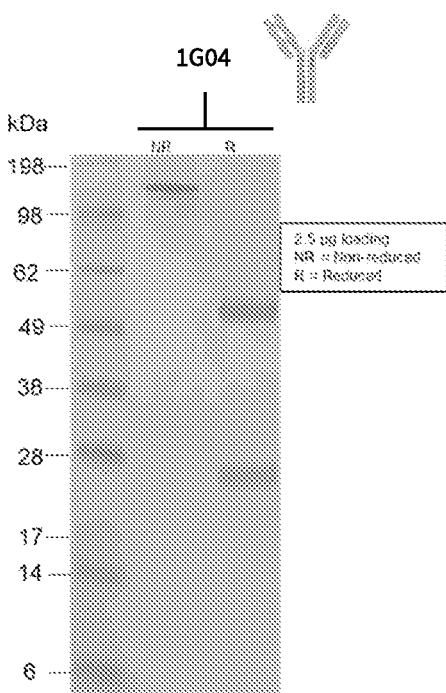
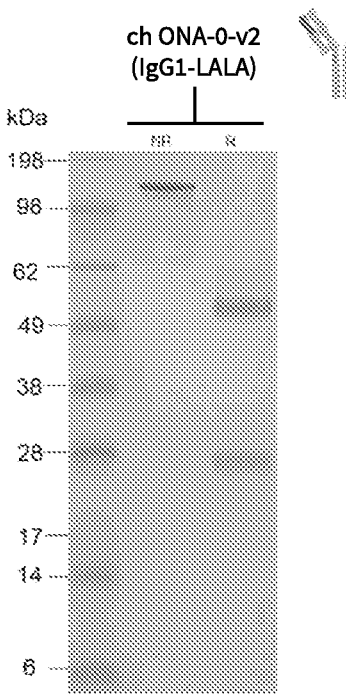

FIGURE 7
ELISA Analysis of 1G04 and Chimeric ONA-0-v2
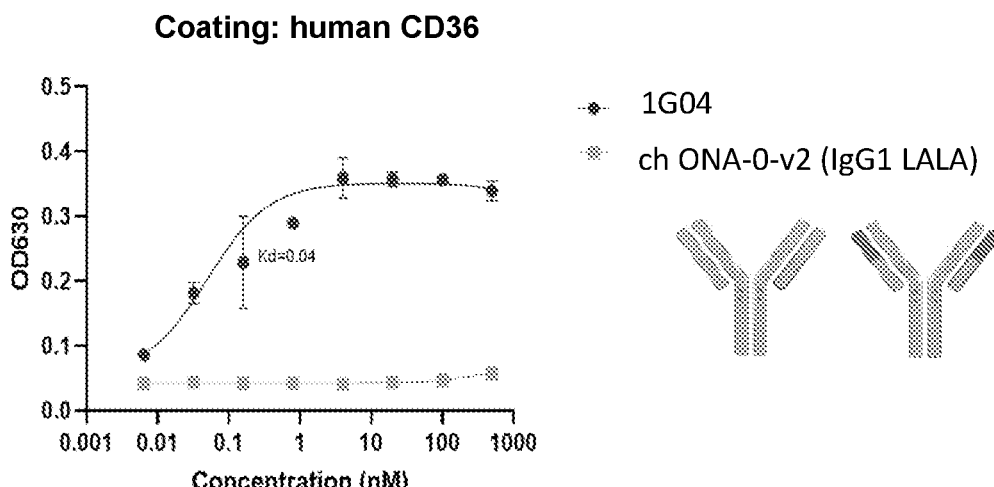
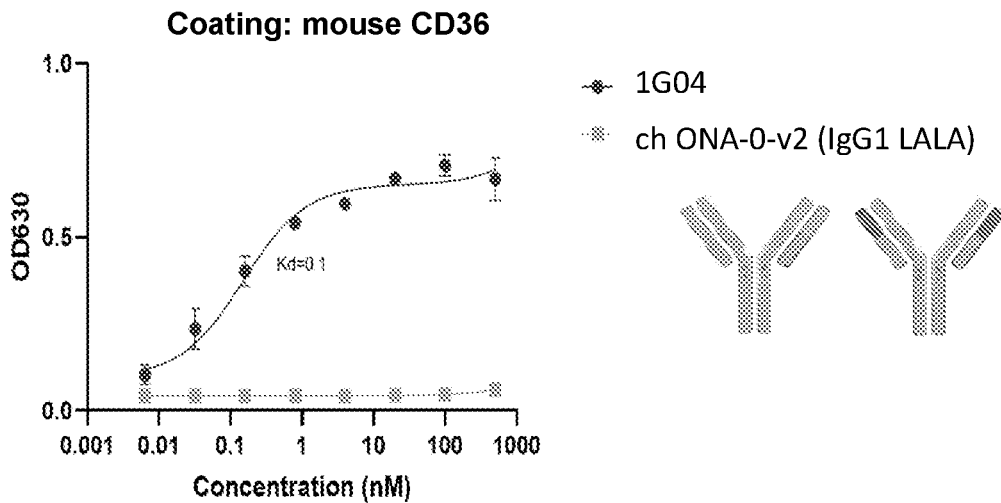

FIGURE 8
ELISA Comparison of ONA-0-v1 and Commercial Anti-CD36 Antibody
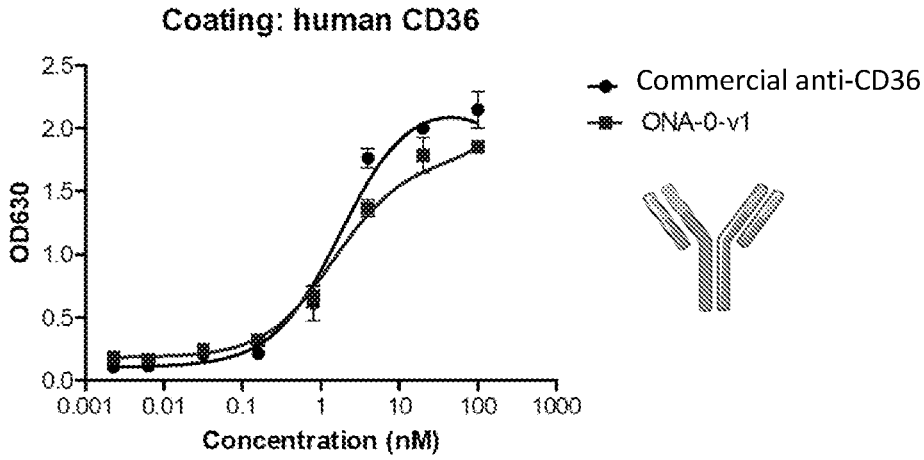
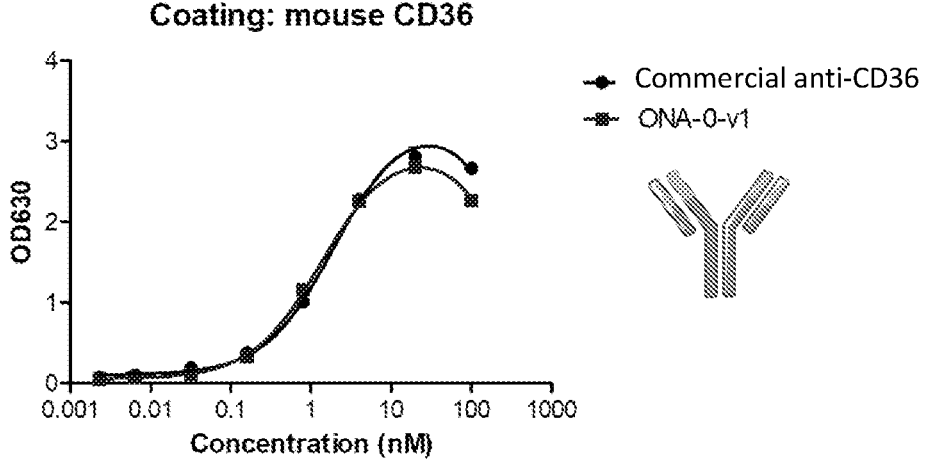

FACS Analysis of Antibody Binding to Cells Overexpressing Human CD36

ONA-0-v1
Commercial anti-CD36 Antibody
1G04

1G04
ch ONA-0-v2 (IgG1 LALA)

SCC-25 CD36 OE

All antibodies used at 100 nM

| Groups | Abs daily | Cisplatin 2x/week | n |
|---|---|---|---|
| IgA | 1 mg/kg | PBS | 7 |
| Cisplatin + IgA | 1 mg/kg | 2 mg/kg | 8 |
| ONA-0-v1 | 1 mg/kg | PBS | 8 |
| Cisplatin + ONA-0-v1 | 1 mg/kg | 2 mg/kg | 8 |

FIGURE 12A
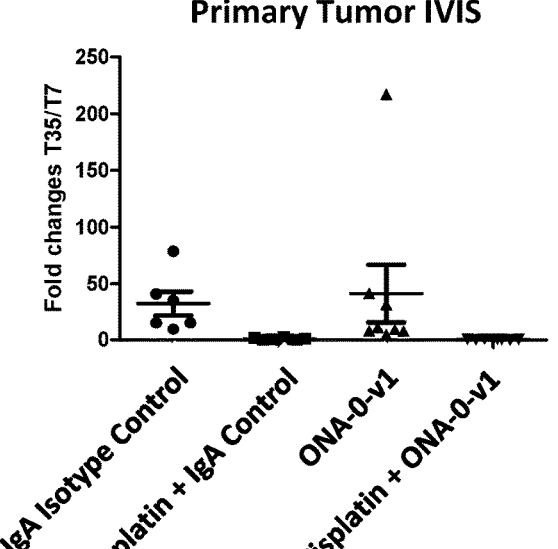
Primary Tumor IVIS
FIGURE 12B
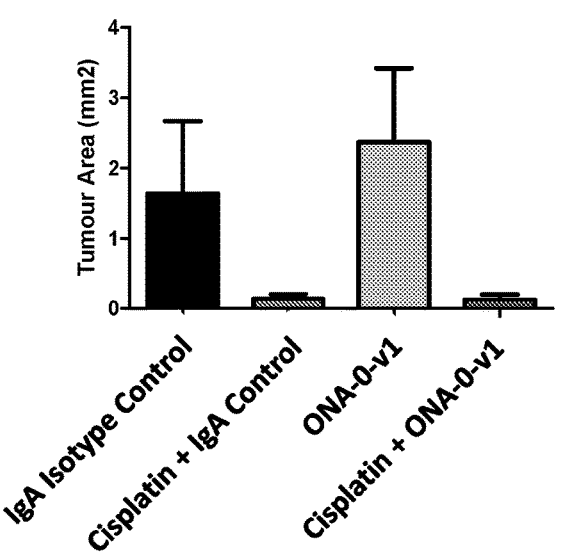
Primary Tumor H&E
FIGURE 13A
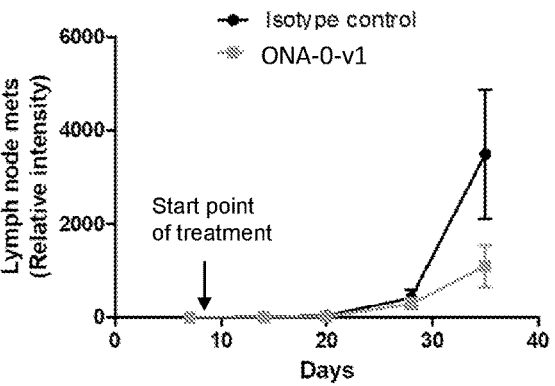
FIGURE 13B
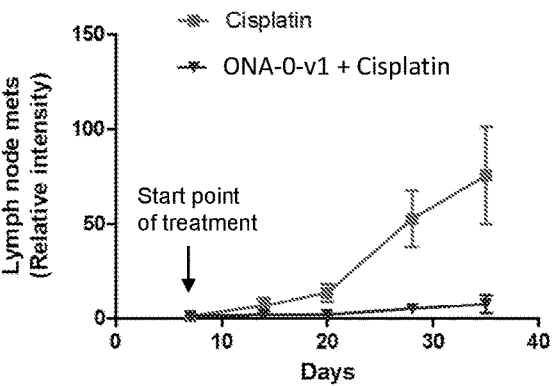

FIGURE 14
Cervical Lymph Node Metastases At The Start of Treatment
Day 7
post orthotopic injection
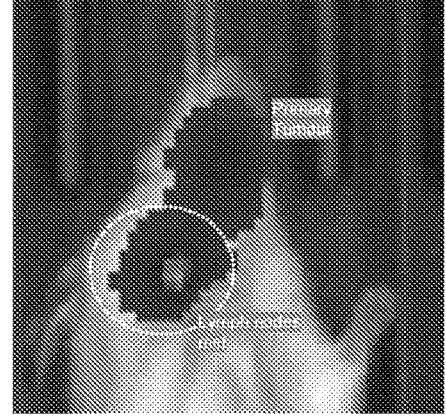
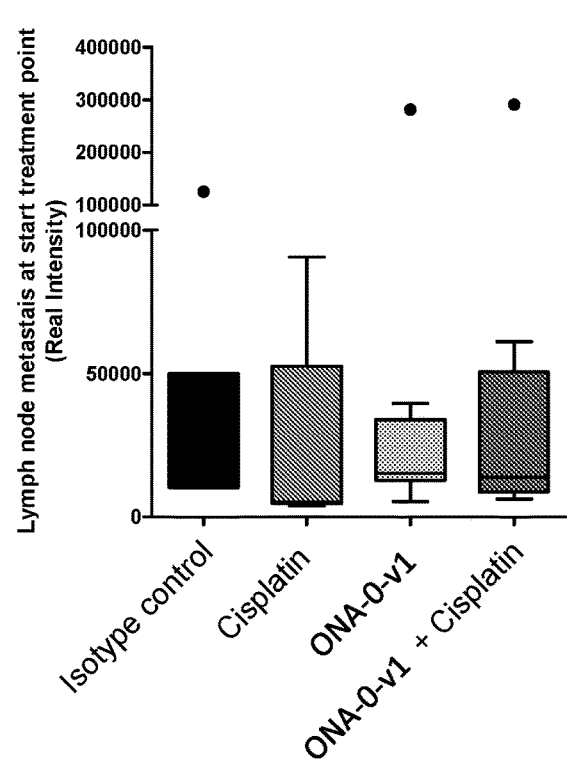

FIGURE 15
Cervical Lymph Node Metastases At End Point Day
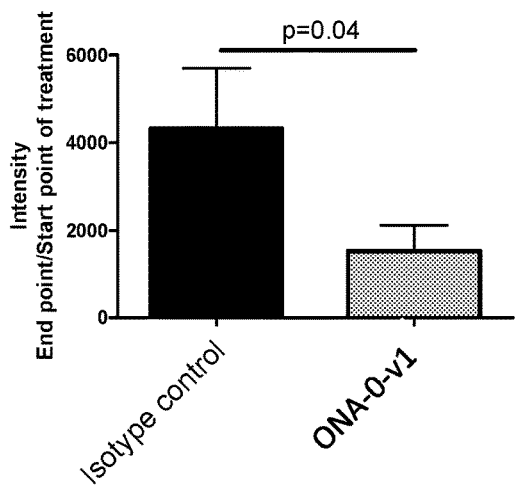
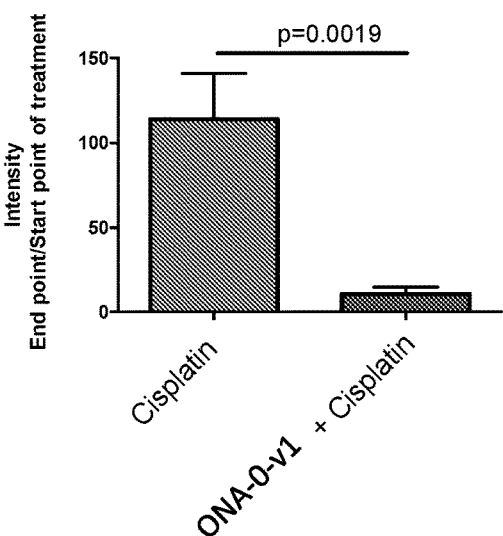

Penetrance of Lymph Node Metastases

Orthotopic injection of OVCAR-3 cells

T0

Randomization
Start treatment

T23

T42

End Point
Necropsy and
Histopathology

Primary tumors

Vehicle

ONA-0-v1
3mg/kg daily

Peritoneal Wall Metastases

Liver Metastases

Tumor Bioluminescence (in vivo BLI)

Tumor Bioluminescence (ex vivo BLI)

FIGURE 22A                     FIGURE 22B
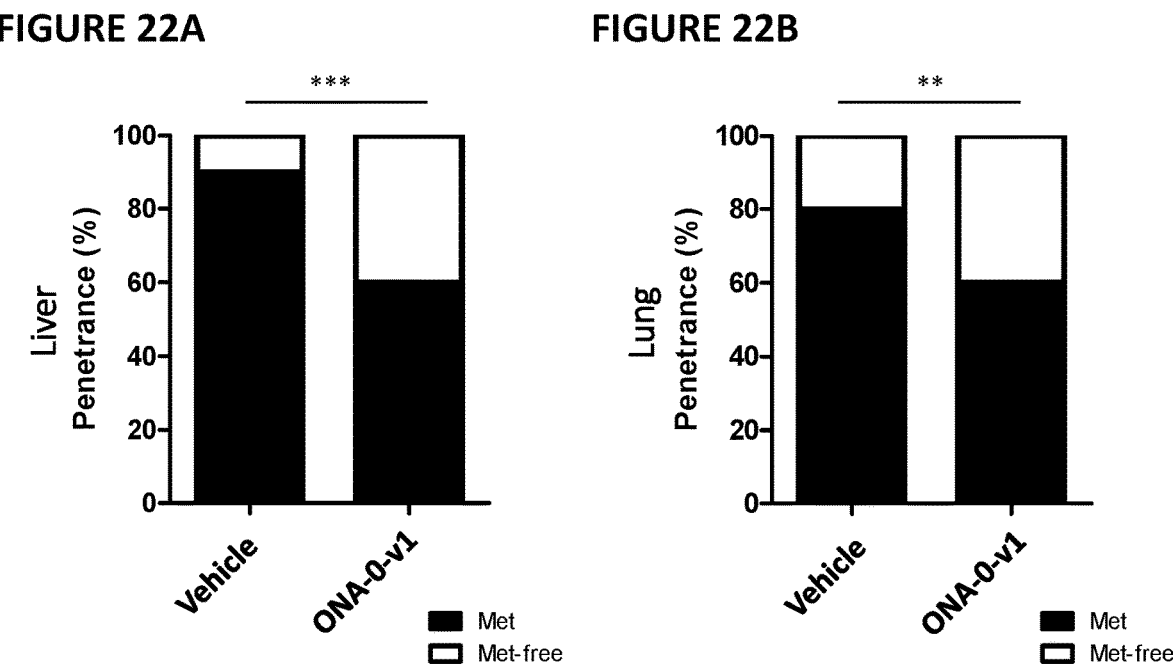
FIGURE 22C                     FIGURE 22D
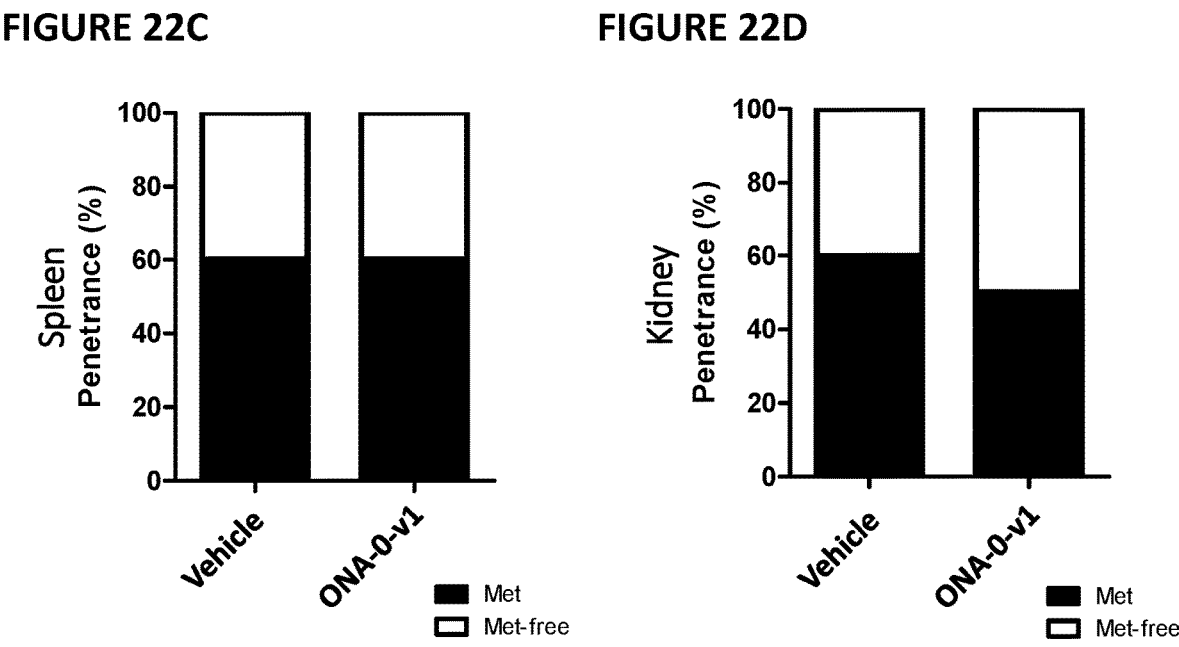

Orthotopic injection of OVCAR-3 cells

Randomization
Start treatment

End Point
Necropsy and
Histopathology

T0                    T7                              T28

Treatment Groups

Group 1. Vehicle

Group 2. ONA-0-v1 3mg/kg daily

Group 3. 1G04 10mg/kg TIW

Vehicle
ONA-0-v1
1G04

Orthotopic injection of HCT-116-luc 2x10⁶ cells

End Point
Necropsy, Ex vivo IVIS, and Histopathology

Treatment Groups

| |
|---|
| Group 1. Vehicle |
| Group 2. 1G04 10mg/kg TIW |

FACS Analysis of Antibody Binding to
Cells Overexpressing Human CD36

Intravenous injection
A549-luc    T0    T8    ⋯⋯⋯    IVIS weekly    ⋯⋯    T61

Randomization & Treatment

End Point Ex-vivo IVIS + organs collection

| Groups | Abs TIW |
|--------|---------|
| Vehicle | -- |
| 1G04 | 10 mg/kg |

| Groups | Abs TIW |
|--------|---------|
| Vehicle | -- |
| 1G04 | 10 mg/kg |

FIGURE 31C
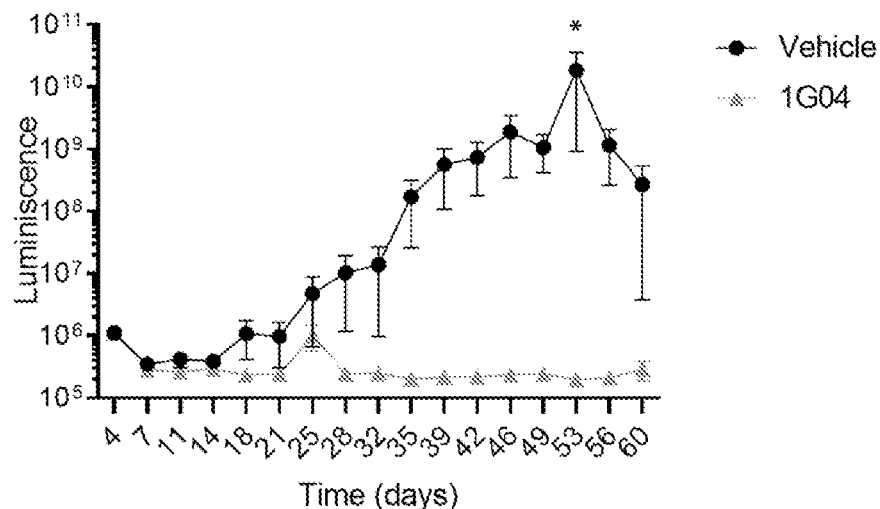
FIGURE 31D    FIGURE 31E
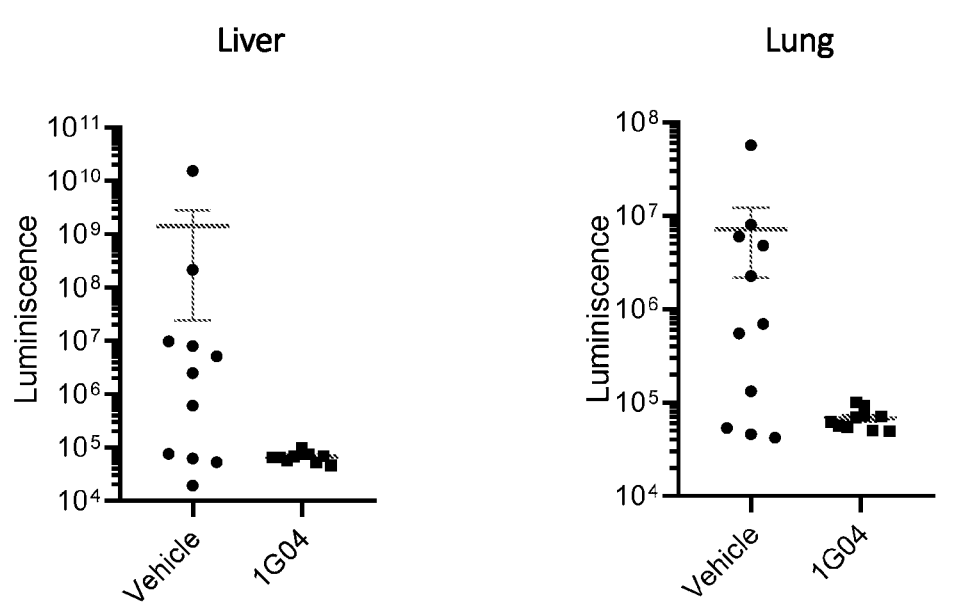

Mamary fat pad
injection
4T1 luc

Randomization &
Treatment

TO   T5 T6 T7 T11   T14   T18 T21 T22

End Point Ex-vivo IVIS +
organs collection

| Groups | Abs TIW |
|---------|---------|
| Vehicle | -- |
| 1G04 | 10 mg/kg |

ANTI-CD36 ANTIBODIES AND THEIR USE TO TREAT CANCER

CROSS-REFERENCE TO RELATED APPLICATIONS

This application is a 35 U.S.C. § 371 National Phase Application of International Application No. PCT/IB2021/051881, filed Mar. 5, 2021, which claims priority benefit of U.S. Provisional Application No. 62/986,174, filed Mar. 6, 2020, and U.S. Provisional Application No. 63/117,529, filed Nov. 24, 2020, each of which is incorporated by reference herein in its entirety.

REFERENCE TO SEQUENCE LISTING SUBMITTED ELECTRONICALLY

The content of the electronically submitted sequence listing (Name: 4427_0050003_Seqlisting_ST25.txt; Size: 72,761 bytes; and Date of Creation: Sep. 1, 2022) is herein incorporated by reference in its entirety.

TECHNICAL FIELD

The disclosure relates to the treatment of cancer, particularly cancer metastases, and the control of said disease. More specifically, the disclosure relates to the use of anti-CD36 antibodies for the treatment of cancer. The disclosure also relates to the use of anti-CD36 antibodies for the treatment of primary cancers, cancer metastases, or both. The treatments relate to the use of both full-length antibodies and fragments thereof.

BACKGROUND

CD36 (HGNC:1663, EntrezGene:948, Ensembl: ENSG00000135218, OMIM: 173510, UniProtKB: P16671) is a receptor protein with several different known functions, as it is indicated by the different alternative names that it receives: it is known, among others, as cluster determinant 36, thrombospondin receptor, collagen type I receptor, leukocyte differentiation antigen CD36, platelet glycoprotein 4 or fatty acid translocase. The Entrez Gene and UniProt/SwissProt Summaries for CD36 gene, as recapitulated by GeneCards (http://www.genecards.org/cgi-bin/carddisp.pl?gene=CD36) describe the protein as the fourth major glycoprotein of the platelet surface that serves as a receptor for thrombospondin in platelets and various cell lines. Since thrombospondins are widely distributed proteins involved in a variety of adhesive processes, this protein may play a role as a cell adhesion molecule. It binds to collagen and thrombospondin, mediating the antiangiogenic effect of the latter, as well as to anionic phospholipids and oxidized LDL. It directly mediates cytoadherence of *Plasmodium falciparum* parasitized erythrocytes and it binds long chain fatty acids. It is a co-receptor for the TLR4-TLR6 heterodimer that promotes inflammation in monocytes/macrophages. When CD36 binds a ligand such as oxLDL or amyloid-beta 42, CD36 rapidly induces the formation of a heterodimer of TLR4 and TLR6. The TLR4-TLR6 heterodimer is internalized and triggers an inflammatory response that leads to NF-kappa-B-dependent production of CXCL1, CXCL2 and CCL9 cytokines (via the MYD88 signalling pathway), production of CCL5 cytokine (via the TICAMI signalling pathway), and IL1b secretion. CD36 is also at the top of the signalling cascade that uptakes lipids from the extracellular environment and triggers their beta-oxidation to obtain energy in the form of ATP (Cobum et al., 2000; Ibrahimi et al., 1999; Pepino et al., 2014).

CD36 has been previously linked to cancer, but its implication for therapy and mechanism of action were not clear. WO 03/032813 discloses assays where it is shown that CD36 is one of the genes upregulated in renal cell carcinoma. Although no assays are presented for other types of cancer, CD36 is presented in said application as a useful target for the diagnosis and/or treatment, and even prevention, of certain cancers, being also considered as a predictor of the prognosis of the tumor treatment. SCC is mentioned as one of the possible cancer types where the treatment with CD36 antibodies, or antagonists such as antisense RNA, can be of use, but without providing any evidence of changes of CD36 expression in SCC or, particularly, of the efficacy of CD36 antibodies or other antagonists for preventing or treating either primary tumors or metastases. Spontaneous animal tumors are proposed for testing the efficacy of antibodies specifically binding the proteins that are overexpressed in renal cell carcinoma according to the assays shown in WO 03/032813, and, given that it is a highly invasive and malignant tumor, feline oral SCC is proposed as a suitable model. However, again, such proposal is done without providing examples of the actual utility of said approach and moreover, without showing any evidence that any of the genes overexpressed in renal cell carcinoma are also overexpressed in feline oral SCC and, particularly, not showing either any data about changes (increase or decrease) in the level of expression of CD36 in feline oral SCC or any evidence about a possible involvement of CD36 in the initiation, development or spread of metastasis in such type of cancer. Moreover, it is commented that feline oral SCC exhibits low incidence of metastasis, but also mentioning that this might be due to the short survival times of cats with this tumor.

With regard to metastasis, it has been previously shown that inhibition of CD36 (both by antibodies neutralizing its activity or by shRNAs) has a dramatic effect regarding metastasis initiation and progression, decreasing metastatic penetrance and growth of all cell lines and patient-derived tumours tested. See, U.S. Publ. No. 2019-0106503, which is incorporated herein by reference in its entirety.

SUMMARY

The disclosure of this application is directed to anti-CD36 antibodies, and the use of such antibodies for the treatment of cancer. In some embodiments, the anti-CD36 antibodies are used to treat cancer metastases. In some embodiments, the anti-CD36 antibodies are used to treat both primary tumors and cancer metastases. In some embodiments, the anti-CD36 antibody is an isolated antibody comprising one or more complementarity determining region (CDR) sequences from SEQ ID NO: 5 and SEQ ID NO: 7 (i.e., from the ONA-0-v1 antibody). In some embodiments, the anti-CD36 antibody is a chimeric antibody comprising one or more CDR sequences from SEQ ID NO: 5 and SEQ ID NO: 7. In some embodiments, the anti-CD36 antibody is a humanized antibody comprising one or more CDR sequences from SEQ ID NO: 5 and SEQ ID NO: 7. In some embodiments, the anti-CD36 antibody comprises a VH having at least 80%, at least 85%, at least 90%, at least 95%, at least 96%, at least 97%, at least 98%, at least 99%, or 100% identity with the amino acid sequence of the VH in the ONA-0-v1 antibody (SEQ ID NO: 11). In some embodiments, the anti-CD36 antibody comprises a VL having at least 80%, at least 85%, at least 90%, at least 95%, at least 96%, at least 97%, at least 98%, at least 99%, or 100% identity with the amino acid sequence of the VL in the ONA-0-v1 antibody (SEQ ID NO: 13). In some embodiments, the anti-CD36 antibody is ONA-0-v1, which comprises the heavy chain listed as SEQ ID NO: 5 and the light chain listed as SEQ ID NO: 7. In some embodiments, the anti-CD36 antibody is the chimeric ONA-0-v1 IgG1 LALA antibody that comprises the heavy chain listed in SEQ ID NO: 21 and the light chain listed in SEQ ID NO: 23 (i.e., the heavy chain and light chain from the 1G04 antibody). In some embodiments, the anti-CD36 antibody is the chimeric ONA-0-v1 IgG1 antibody that comprises the heavy chain listed in SEQ ID NO: 64 and the light chain listed in SEQ ID NO: 23 (i.e., the heavy chain and light chain from the 1G06 antibody).

In some embodiments, the anti-CD36 antibody comprises a heavy chain and a light chain, wherein the heavy chain CDR1 region comprises SEQ ID NO: 27, the heavy chain CDR2 region comprises SEQ ID NO: 28, the heavy chain CDR3 region comprises SEQ ID NO: 29, the light chain CDR1 region comprises SEQ ID NO: 30, the light chain CDR2 region comprises SEQ ID NO: 31, and the light chain CDR3 region comprises SEQ ID NO: 32. In some embodiments, the anti-CD36 antibody comprises a heavy chain and a light chain, wherein the heavy chain CDR1 region comprises SEQ ID NO: 37, the heavy chain CDR2 region comprises SEQ ID NO: 38, the heavy chain CDR3 region comprises SEQ ID NO: 29, the light chain CDR1 region comprises SEQ ID NO: 30, the light chain CDR2 region comprises SEQ ID NO: 31, and the light chain CDR3 region comprises SEQ ID NO: 32. In some embodiments, the anti-CD36 antibody comprises a heavy chain and a light chain, wherein the heavy chain CDR1 region comprises SEQ ID NO: 39, the heavy chain CDR2 region comprises SEQ ID NO: 40, the heavy chain CDR3 region comprises SEQ ID NO: 41, the light chain CDR1 region comprises SEQ ID NO: 42, the light chain CDR2 region comprises SEQ ID NO: 43, and the light chain CDR3 region comprises SEQ ID NO: 32.

In some embodiments, the anti-CD36 antibody is a humanized antibody in which the heavy chain CDR regions comprise (a) SEQ ID NOs: 37, 38, and 29; (b) SEQ ID NOs: 44, 46, and 29; or (c) SEQ ID NOs: 45, 47, and 29. In some of these embodiments, the light chain CDR regions comprise SEQ ID NOs: 30, 31, and 32. In some of these embodiments, the light chain CDR regions comprise SEQ ID NOs: 48, 31, and 32. In some of these embodiments, the light chain CDR regions comprise SEQ ID NOs: 48, 49, and 32. In some of these embodiments, the light chain CDR regions comprise SEQ ID NOs: 30, 50, and 32. In some of these embodiments, the heavy chain variable region comprises SEQ ID NO: 51, SEQ ID NO: 52, SEQ ID NO: 53, or SEQ ID NO: 54; and the light chain variable region comprises SEQ ID NO: 55, SEQ ID NO: 56, SEQ ID NO: 57, or SEQ ID NO: 58.

In some embodiments, the anti-CD36 antibody is a humanized antibody that comprises: (a) a heavy chain variable region comprising SEQ ID NO: 51 and a light chain variable region comprising SEQ ID NO: 55, SEQ ID NO: 56, SEQ ID NO: 57, or SEQ ID NO: 58; (b) a heavy chain variable region comprising SEQ ID NO: 52 and a light chain variable region comprising SEQ ID NO: 55, SEQ ID NO: 56, SEQ ID NO: 57, or SEQ ID NO: 58; (c) a heavy chain variable region comprising SEQ ID NO: 53 and a light chain variable region comprising SEQ ID NO: 55, SEQ ID NO: 56, SEQ ID NO: 57, or SEQ ID NO: 58; or (d) a heavy chain variable region comprising SEQ ID NO: 54 and a light chain variable region comprising SEQ ID NO: 55, SEQ ID NO: 56, SEQ ID NO: 57, or SEQ ID NO: 58.

In certain embodiments, the anti-CD36 antibody is an isolated, chimeric, or humanized antibody that binds to the same epitope of human CD36 as an antibody comprising the heavy chain in SEQ ID NO: 5 and the light chain in SEQ ID NO: 7. In certain embodiments, the anti-CD36 antibody is an isolated, chimeric, or humanized antibody that competes for binding to human CD36 with an antibody comprising the heavy chain in SEQ ID NO: 5 and the light chain in SEQ ID NO: 7.

In some embodiments, the antibody is substantially free of antibodies that do not specifically bind to CD36. In some embodiments, the antibody is substantially free of a light chain comprising the light chain CDR1 region, the light chain CDR2 region, and the light chain CDR3 region present in SEQ ID NO: 9.

In certain embodiments, the anti-CD36 antibody binds to human CD36. In some embodiments, the anti-CD36 antibody binds to human CD36 with an affinity of greater than 10 nM.

In certain embodiments, the anti-CD36 antibody further comprises a heavy chain constant region. In some embodiments, the antibody comprises an IgA or IgG heavy chain constant region. In some embodiments, the heavy chain constant region is selected from the group consisting of human immunoglobulin IgA1, IgA2, IgG1, IgG2, IgG3, or IgG4 heavy chain constant regions. In some embodiments, the heavy chain constant region comprises a constant region containing one or more mutations at amino acid positions E233, L234, L235, G236, N297, P331 and P329. In some embodiments, the heavy chain constant region comprises an IgG constant region containing a LALA mutation—which consists of leucine to alanine alterations at amino acid positions 234 and 235.

In some embodiments, the heavy chain constant region comprises an IgG constant region containing mutations at amino acid positions L234, L235, and/or G236. In some embodiments, the heavy chain constant region comprises an IgG constant region containing a set of mutations selected from the group consisting of L234A, L235S, and G236R; L234G, L235S, and G236R; L234Q, L235S, and G236R; L234S, L235G, and G236R; L234S, L235T, and G236R; L234S, L235V, and G236R; L234T, L235Q, and G236R; L234T, L235S, and G236R; L234T, L235T, and G236R; L234A and L235A; L234A, L235A, and P329G; G236R and L328R; L234A and G237A; L234A, L235A, and G237A; L234A and L235E; L235V, F243L, R292P, Y300L, and P396L; D265A and P329A; L234A, L235A, and K322A; L234F, L235E, and P331S; L234F, L235Q, and K322Q; L234A, L235A, G237A, P238S, H268A, A330S, and P331S; E233P, L234V, L235A, G236A, A327G, A330S, and P331S; L235A and G236R; L235S and G236R; G236R; L234Q and L235S; L235G and G236R; L234Q, L235S. and A236R; L234 Qand L235S; L234Q, L235S, and G236R; L234Q, L235S, and G236R; L234Q, L235S, and G236R; L234Q, L235S, and G236R; L234Q, L235S, and G236R, M252Y, S254T, and T256E; and L234Q, L235S, G236R, T250Q, and M428L. In some embodiments, the heavy chain constant region comprises an IgG constant region containing the L234G, L235S, and G236R mutations. In some embodiments, the heavy chain constant region comprises an IgG constant region containing the L234S, L235T, and G236R mutations. In some embodiments, the heavy chain constant region comprises an IgG constant region containing the L234S, L235V, and G236R mutations. In some embodiments, the heavy chain constant region comprises an IgG constant region containing the L234T, L235Q, and G236R mutations. In some embodiments, the heavy chain constant region comprises an IgG constant region containing the L234T, L235T, and G236R mutations. In some embodiments, the heavy chain constant region comprises an IgG constant region containing the L234A and L235A mutations. In some embodiments, the heavy chain constant region comprises an IgG constant region containing the L234A, L235A, and P329G mutations.

In certain embodiments, the anti-CD36 antibody further comprises a light chain constant region. In some embodiments, the light chain constant region is selected from the group consisting of human immunoglobulins kappa (κ) and lambda (λ) light chain constant regions. In some embodiments, the antibody comprises a heavy chain constant region and a light chain constant region, wherein the heavy chain constant region is a human IgG1 heavy chain constant region, and wherein the light chain constant region is a human κ light chain constant region.

In certain embodiments, the antibody is an antigen-binding fragment. In some embodiments, the antigen binding fragment comprises a Fab, Fab', F(ab')$_2$, single chain Fv (scFv), disulfide linked Fv, V-NAR domain, IgNar, intrabody, IgGΔCH2, minibody, F(ab')$_3$, tetrabody, triabody, diabody, single-domain antibody, DVD-Ig, Fcab, mAb2, (scFv)$_2$, or scFv-Fc.

Certain embodiments are pharmaceutical compositions comprising an anti-CD36 antibody described herein and a pharmaceutically acceptable excipient. In some embodiments, at least 95% of the antibodies in the pharmaceutical composition are afucosylated. In some embodiments, the pharmaceutical composition further comprises one or more other therapeutic agents. In some embodiments, the pharmaceutical composition further comprises a PD-1 inhibitor. Suitable PD-1 inhibitors include the anti-PD-1 antibodies pembrolizumab, pidilizumab, or nivolumab. In some embodiments, the pharmaceutical composition further comprises a PD-L1 inhibitor such as the anti-PD-L1 antibodies atezolizumab, durvalumab, avelumab, or BMS-936559. In some embodiments, the pharmaceutical composition further comprises a CTLA-4 inhibitor such as the anti-CTLA-4 antibody ipilimumab. In some embodiments, the pharmaceutical composition further comprises a chemotherapeutic agent such as cisplatin.

Certain embodiments are methods of administering the anti-CD36 antibodies and pharmaceutical compositions containing anti-CD36 antibodies described herein. Some embodiments are directed to methods of treating cancer in a patient comprising administering to a subject in need thereof a therapeutically effective amount of an antibody disclosed herein, or a therapeutically effective amount of a pharmaceutical composition disclosed herein. In some embodiments, the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma. Some embodiments are methods of treating one or more metastatic tumors in a patient comprising administering to a subject in need thereof a therapeutically effective amount of an antibody disclosed herein or a therapeutically effective amount of the pharmaceutical composition disclosed herein. In some embodiments, the metastatic tumors developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma. In some embodiments, the metastatic tumors are in the cervical lymph nodes, liver, lung, spleen, kidney, or peritoneal wall. In some embodiments, the treatment reduces the size of metastatic tumors, as measured by IVIS imaging or H&E staining. In some embodiments, the treatment reduces the size of the metastatic tumors in the cervical lymph nodes, liver, lung, spleen, kidney, or peritoneal wall. In some embodiments, the treatment prevents or inhibits the formation or development of metastatic tumors, as measured by IVIS imaging or H&E staining. In some embodiments, the treatment prevents or inhibits the formation or development of metastatic tumors in the cervical lymph nodes, liver, lung, spleen, kidney, or peritoneal wall. In some embodiments, the treatment reduces the number of metastatic tumors. In some embodiments, the patient is a human patient. In some embodiments, the treatment is effective in treating both a primary tumor and a metastatic tumor.

In certain embodiments, the method includes administering an anti-CD36 antibody that is a full length antibody, a single chain antibody, a scFv, a Fab fragment, or a F(ab')$_2$ fragment. In some embodiments, the method includes administering an anti-CD36 antibody that is a full length antibody. In some embodiments, the method includes administering an anti-CD36 that antibody comprises the heavy chain in SEQ ID NO: 21 and the light chain in SEQ ID NO: 23. In some embodiments, the method includes administering an anti-CD36 antibody that comprises the heavy chain in SEQ ID NO: 64 and the light chain in SEQ ID NO: 23.

In certain embodiments, the method includes administering a second therapy in addition to the anti-CD36 antibody. In some embodiments, the second therapy administered is an immunotherapy. In some embodiments, the administered immunotherapy is a PD-1 inhibitor such as the anti-PD-1 antibodies pembrolizumab, pidilizumab, or nivolumab. In some embodiments, the administered immunotherapy is a PD-L1 inhibitor such as the anti-PD-L1 antibodies atezolizumab, durvalumab, avelumab, or BMS-936559. In some embodiments, the administered immunotherapy is a CTLA-4 inhibitor such as the anti-CTLA-4 antibody ipilimumab. In some embodiments, the second therapy is a chemotherapeutic agent. In some embodiments, the administered chemotherapeutic agent is cisplatin.

In certain embodiments, metastasis is reduced or inhibited in the subject. In some embodiments, metastasis to the cervical lymph nodes, liver, lung, spleen, kidney, or peritoneal wall is reduced or inhibited in the subject. In some embodiments in which the method involves administering a second therapy in addition to the anti-CD36 antibody, the two therapies are administered sequentially. In some embodiments in which the method involves administering a second therapy in addition to the anti-CD36 antibody, the two therapies are administered simultaneously.

Certain embodiments are isolated polynucleotides that encode the antibodies disclosed herein. In some embodiments, the isolated polynucleotide encodes the heavy chain in SEQ ID NO: 5 and the light chain in SEQ ID NO: 7. In some embodiments, the isolated polynucleotide comprises SEQ ID NO: 6. In some embodiments, the isolated polynucleotide comprises SEQ ID NO: 8. In some embodiments, the isolated polynucleotide encodes the heavy chain in SEQ ID NO: 21 and the light chain in SEQ ID NO: 23. In some embodiments, the isolated polynucleotide encodes the heavy chain in SEQ ID NO: 64 and the light chain in SEQ ID NO: 23. In some embodiments, the isolated polynucleotide comprises SEQ ID NO: 22. In some embodiments, the isolated polynucleotide comprises SEQ ID NO: 24.

Certain embodiments are vectors comprising the isolated polynucleotides disclosed herein. Certain other embodiments are cells comprising the isolated polynucleotides or vectors disclosed herein. In some embodiments, the cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture. In some embodiments, the cell lacks a functional alpha-1,6-fucosyltransferase gene (FUT8) gene.

Certain embodiments are methods of making the antibodies disclosed herein. In some embodiments, the method of making an antibody comprises expressing the antibody using cells comprising the isolated polynucleotides or vectors disclosed herein. In some embodiments, the method of making an antibody comprises culturing a cell containing an isolated polynucleotide or vector disclosed herein under conditions suitable for expression of the antibody and isolating the antibody expressed therein.

BRIEF DESCRIPTION OF THE FIGURES

FIG. 2A shows the quantitation of IVIS imaging of the primary tumor during the course of treatment with the anti-CD36 antibody and/or cisplatin. FIG. 2B shows a representative image of an H&E stained primary tumor from the tongue of an orthotopically-injected mouse. And FIG. 2C presents the surface area of the primary tumors in at the end of the treatment regimen. These figures illustrate that the tested anti-CD36 Ab had at least additive anti-tumor activity with cisplatin on suppressing the growth of a primary tumor in oral cancer.

FIG. 3 contains representative H&E stained images of lung metastases at the end of the course of treatment with an anti-CD36 antibody and/or cisplatin in the Detroit-562 mouse model of oral cancer metastasis. This figure illustrates that mice treated with cisplatin (top right), anti-CD36 antibody (bottom left), or cisplatin and anti-CD36 antibody (bottom right) have fewer and smaller metastases than control treated mice (top left).

FIG. 5 is a schematic showing the structure of the ONA-0-v1 antibody, the ONA-0-v2 antibody, the 1G04 antibody (i.e., a chimeric IgG1 version of the ONA-0-v1 antibody with the LALA Fc alteration), and the chimeric ONA-0-v2 IgG LALA antibody. In this schematic, the green portions represent murine IgA constant region sequences present in both ONA-0-v1 and ONA-0-v2. The grey portions represent human IgG1 sequences used in the chimeric antibodies, and the red dots within the grey region are the Leucine to alanine mutations at amino acid positions 234 and 245 within the IgG1 sequence (i.e., the "LALA" alteration). The yellow portions represent the ONA-0-v1 variable regions. And the blue portion represents the light chain variable region in ONA-0-v2 that differs from ONA-0-v1's light chain variable region.

FIG. 6 depicts protein gels containing either reduced or non-reduced ONA-0 antibodies, with 2.5 µg antibody loaded in each lane. Separate gels are shown for the ONA-0-v1, ONA-0-v2, 1G04, and chimeric ONA-0-v2 IgG LALA antibodies.

FIG. 7 depicts data from an ELISA assay testing the ability of the 1G04 and chimeric ONA-0-v2 IgG LALA antibodies to bind to human CD36 and mouse CD36 protein coated in microwell plates. These data show that 1G04, but not the chimeric ONA-0-v2 IgG1 LALA antibody, specifically bound to human and mouse CD36.

FIG. 8 depicts data from an ELISA assay testing the ability of the ONA-0-v1 antibody and a commercial anti-CD36 antibody to bind to human CD36 and mouse CD36 protein coated in microwell plates. These data show that the two antibodies specifically bound to human and mouse CD36 in a similar manner.

Figure 9A:
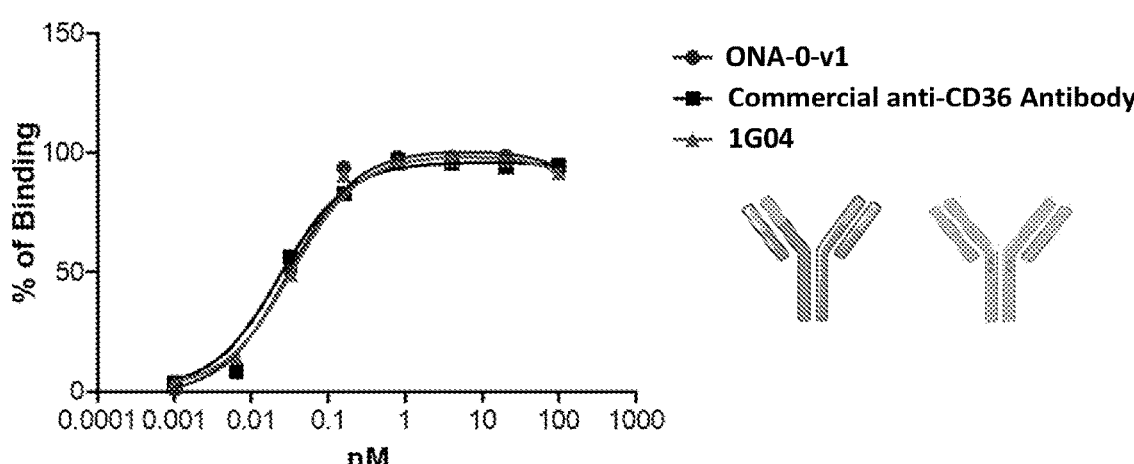
Figure 9B:
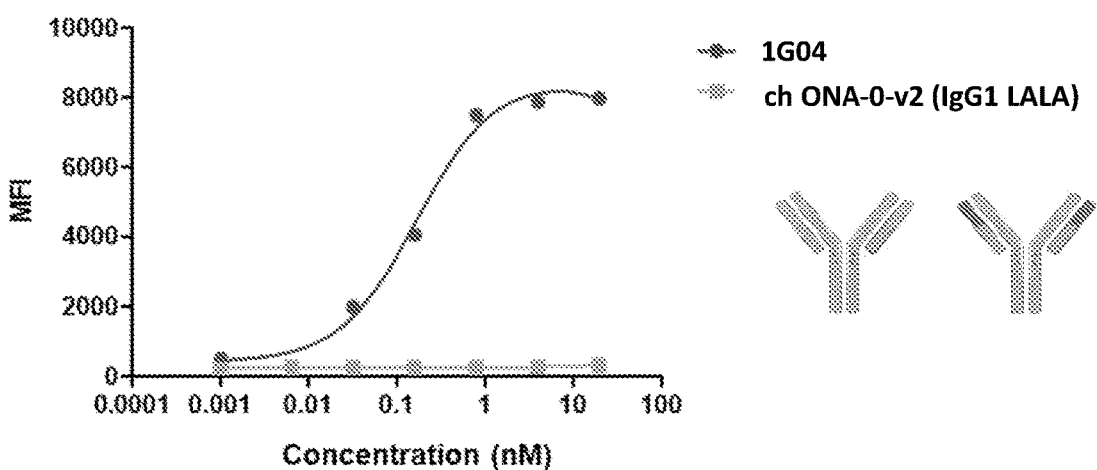

FIGS. 9A and 9B depict data from an FACS analysis of the ability of the ONA-0-v1, 1G04, and chimeric ONA-0-v2 IgG LALA antibodies to bind to cells overexpressing human CD36 relative to a commercially-available anti-CD36 antibody. These data show that ONA-0-v1, 1G04, and the commercial anti-CD36 antibody, but not the chimeric ONA-0-v2 IgG1 LALA antibody, specifically bound to human CD36.

Figure 10:
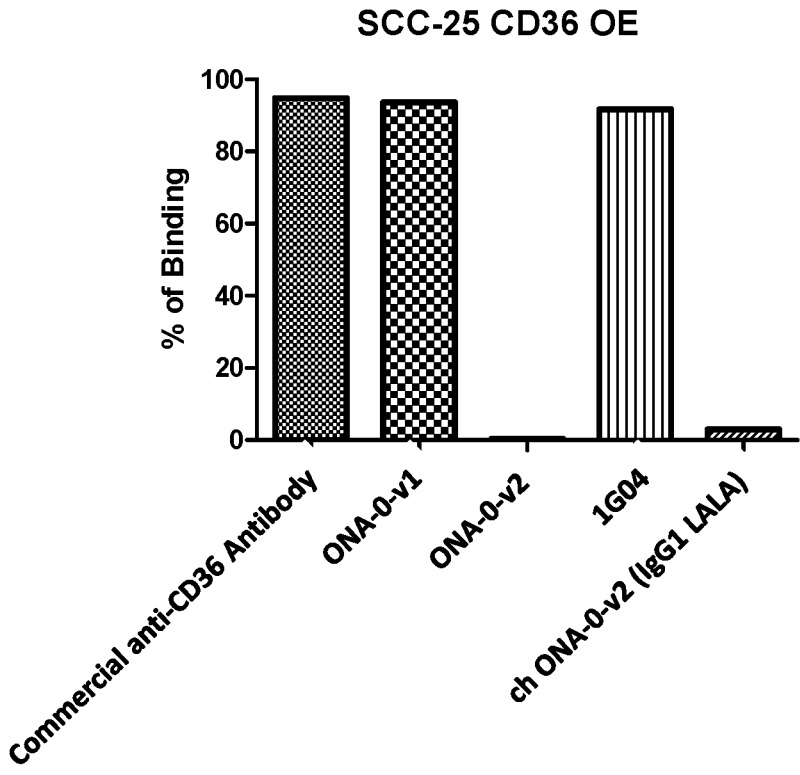

FIG. 10 depicts data from an FACS analysis of the ability of the ONA-0-v1, ONA-0-v2, 1G04, and chimeric ONA-0-v2 IgG LALA antibodies to bind to cells overexpressing human CD36 relative to a commercially-available anti-CD36 antibody. These data show that the switch to the chimeric antibody form did not alter the binding of the ONO-0 antibodies when they were tested at a 100 nM concentration.

Figures 11A, 11B:
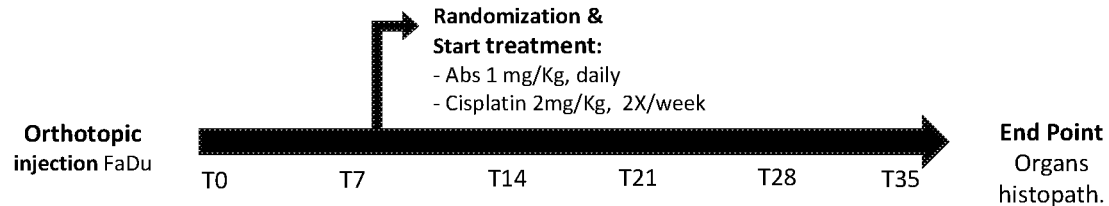

FIG. 11A is a schematic showing an experimental overview of a study of the effects of the ONA-0-v1 anti-CD36 antibody in a mouse model of oral cancer metastasis using FaDu cells, both with and without cisplatin. FIG. 11B details the study groups tested in that study, particularly the therapeutics and doses given to each group.

FIGS. 12A and 12B show the results of IVIS imaging (FIG. 12A) and H&E staining (FIG. 12B) of primary tumors from the study of the effects of the ONA-0-v1 anti-CD36 antibody in a mouse model of oral cancer metastasis using FaDu cells. In both assays, while cisplatin inhibited tumor growth, treatment with the administered dose of ONA-0-v1 did not have a statistically significant effect on the primary tumor relative to treatment with an isotype control antibody in this model.

FIGS. 13A and 13B shows the results of IVIS imaging of metastases from the study of the effects of the ONA-0-v1 anti-CD36 antibody in a mouse model of oral cancer metastasis using FaDu cells. These results show that treatment with ONA-0-v1 was able to inhibit growth of metastases.

FIG. 14 and FIG. 15 show the results of IVIS imaging of lymph node metastases from the study of the effects of the ONA-0-v1 anti-CD36 antibody in a mouse model of oral cancer metastasis using FaDu cells. Treatment with ONA-0-v1 antibody inhibited metastatic tumor growth by greater than 50% relative to the IgA isotype control, and addition of ONA-0-v1 to cisplatin enhanced cisplatin's ability to inhibit metastatic tumor growth.

Figure 16:
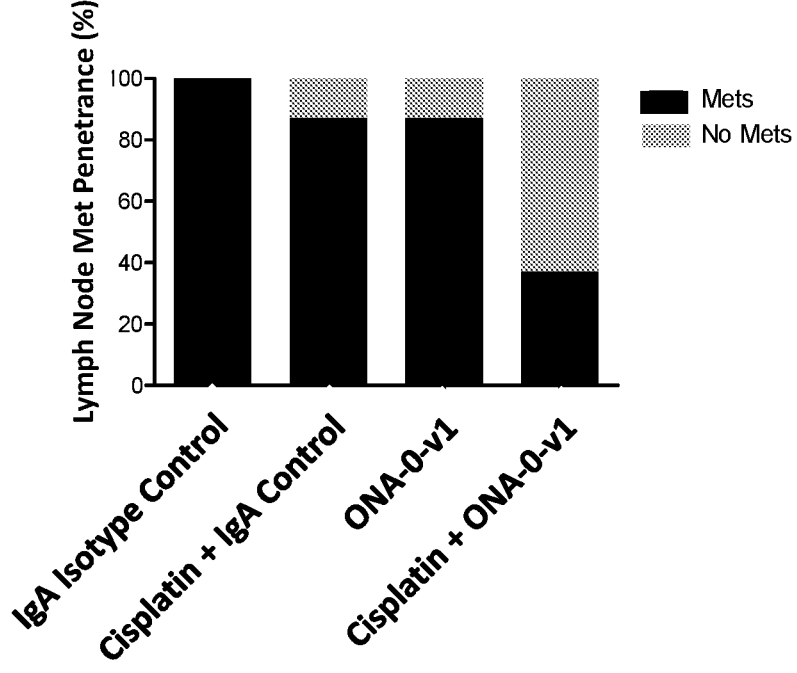

FIG. 16 shows the results of IVIS imaging of lymph node metastases from the study of the effects of the ONA-0-v1 anti-CD36 antibody in a mouse model of oral cancer metastasis using FaDu cells. Treatment with either cisplatin or ONA-0-v1 reduced metastasis into the lymph nodes, and ONA-0-v1's inhibition of penetrance was synergistic with that of cisplatin.

Figure 17A:
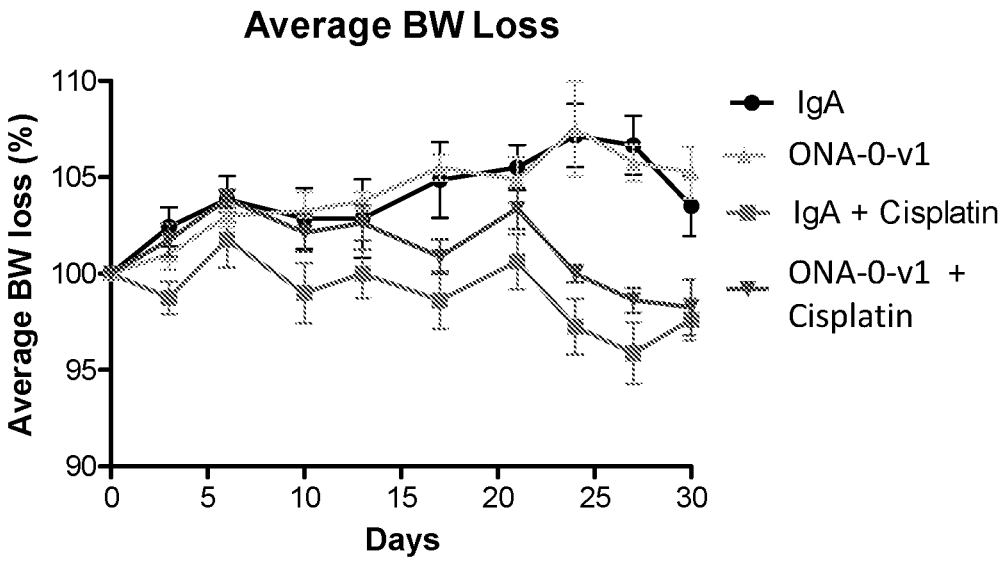
Figure 17B:
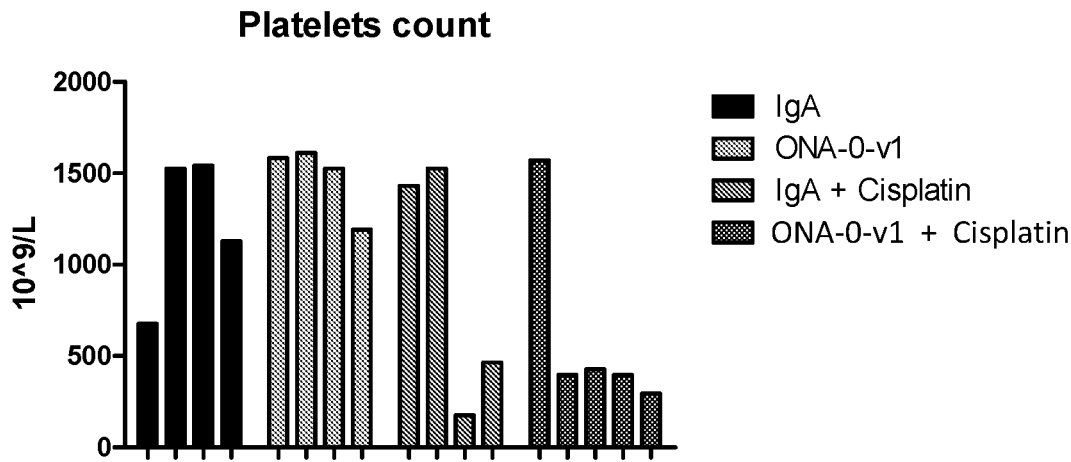

FIG. 17A and FIG. 17B contain measurements of body weight and platelet count during the course of treatment with ONA-0-v1 and/or cisplatin. These data show that, unlike cisplatin, ONA-0-v1 treatment alone did not have any effects on mouse body weight or platelet count relative to isotype control-treated mice.

Figure 18A:
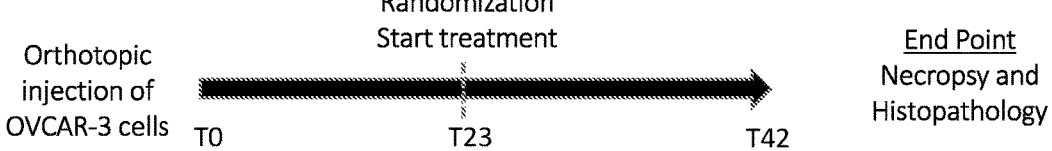
Figure 18B:
Figure 18C:
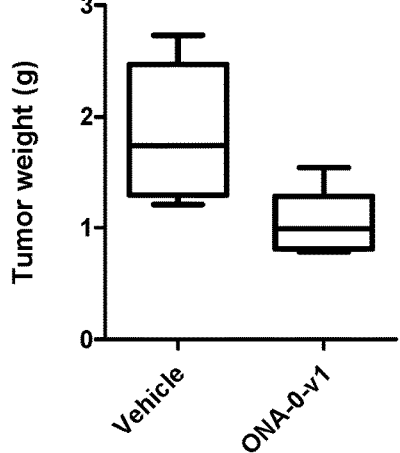
Figure 18D:
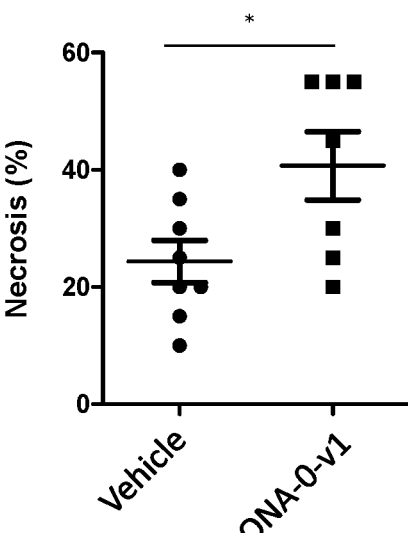
Figure 18E:
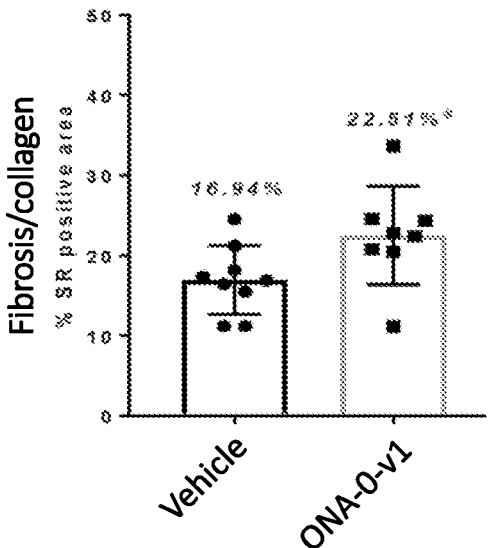

FIG. 18A is a schematic showing an experimental overview of a study of the effects of the ONA-0-v1 anti-CD36 antibody in a mouse model of ovarian cancer using OVCAR-3 cells. FIG. 18B is an image of the primary tumors excised from mice tested in this model, with tumors from vehicle-injected mice on the top row and tumors from mice injected with ONA-0-v1 on the bottom row. FIG. 18C presents the quantification of the weight of these primary tumors, and shows that treatment with ONA-0-v1 resulted in a relative decrease in the weight of the primary tumors (** indicates unpaired t test p=0.033). FIG. 18D and FIG. 18E show the results of histological analysis of the OVCAR-3 primary tumors for percent necrosis and fibrosis/collagen, respectively (* indicates unpaired t test p=0.0287). FIGS. 18D and 18E show that treatment with ONA-0-v1 results in increased necrosis and fibrosis occur in the analyzed tumors.

Figure 19A:
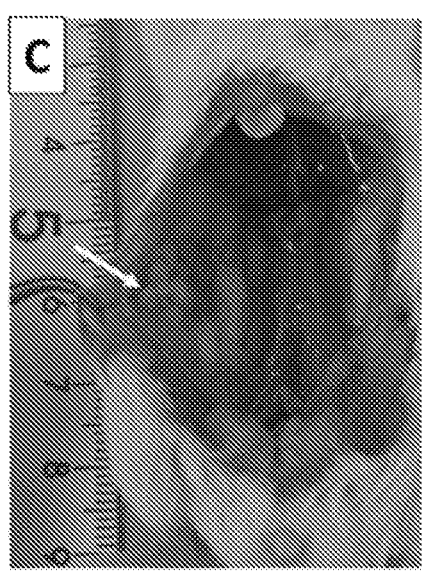
Figure 19B:
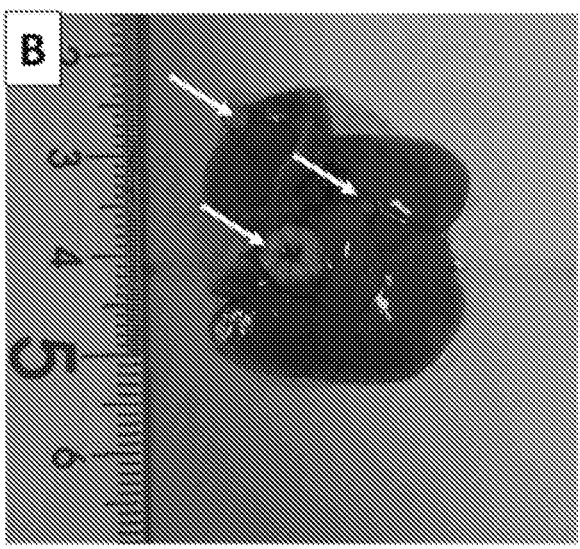

FIGS. 19A and 19B show representative images of metastases formed in the mouse model of ovarian cancer using OVCAR-3 cells. FIG. 19A shows exemplary metastases in the peritoneal wall, and FIG. 19B shows exemplary liver metastases. Each image includes a centimeter-marked ruler for scale, and white arrows that point to the metastases.

Figures 20A, 20B, 20C:
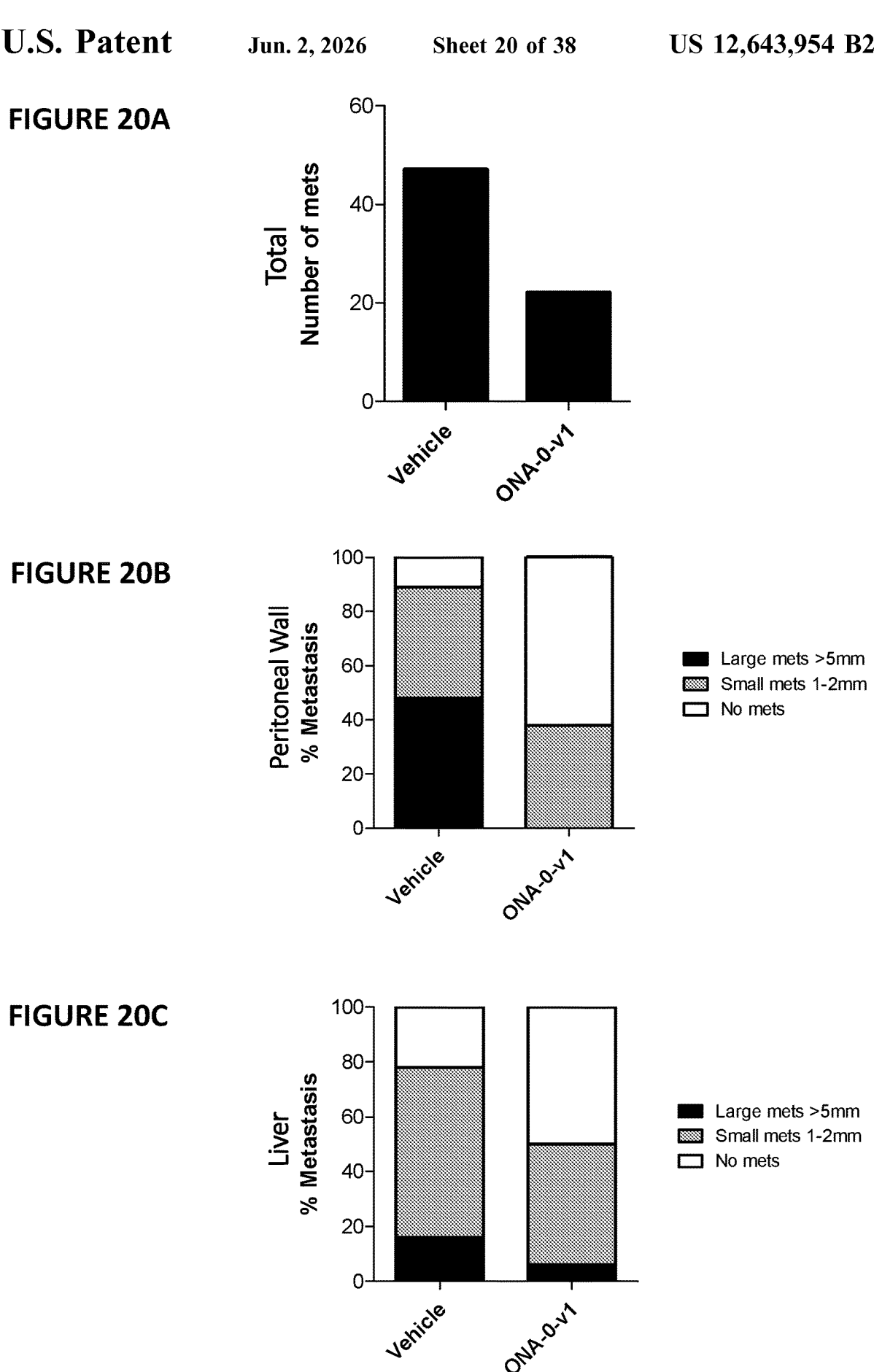

FIGS. 20A, 20B and 20C depict the quantification of the number and size of metastases in the OVCAR-3 mouse model of ovarian cancer in control-treated mice and mice treated with ONA-0-v1. FIG. 20A shows the total number of macroscopic metastases that were observed in any organ in control ("vehicle") mice (sum from all vehicle mice; n=9) and in mice treated with ONA-0-v1 (sum from all treated mice; n=8), and that treatment with ONA-0-v1 reduced the number of metastases by more than 50%. FIGS. 20B and 20C show the macroscopic quantification of the size of metastases in the peritoneal wall and liver, respectively. Collectively, FIGS. 20A, 20B, and 20C show that treating with ONA-0-v1 decreases the size and number of metastases in the OVCAR-3 mouse model of ovarian cancer.

Figure 21A:
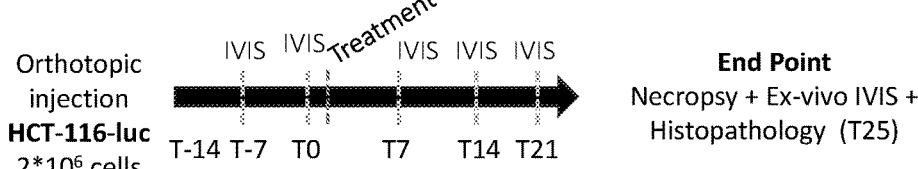

FIG. 21A is a schematic showing an experimental overview of a study of the effects of the ONA-0-v1 anti-CD36 antibody in a mouse model of colon cancer using HCT-116 cells. The luciferase luminescence from within the HCT-116 cells was quantified in vivo during the course of treatment (shown in FIG. 21B; * indicates Mann Whitney test p=0.0288), and ex vivo after the termination of the experiment (shown in FIG. 21C). These data show that treatment with ONA-0-V1 reduced the size of the primary tumor in this colon cancer model.

FIGS. 22A, 22B, 22C, and 22D show the effects of ONA-0-v1 treatment on the penetrance of metastases into various organs in the HCT-116 mouse model of colon cancer, as measured by ex vivo luminiscence analysis of the organs. FIGS. 22A and 22B show that treatment with ONA-0-v1 reduces the percentage of liver and lungs that were observed to contain metastases as more organs were measured as being metastasis-free (* indicates p<0.0001;  indicates p=0.0032 two tailed Fisher exact test).

Figure 23A:
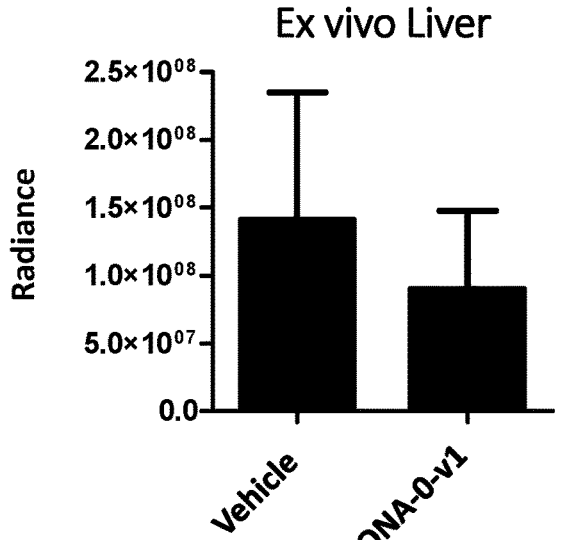
Figure 23B:
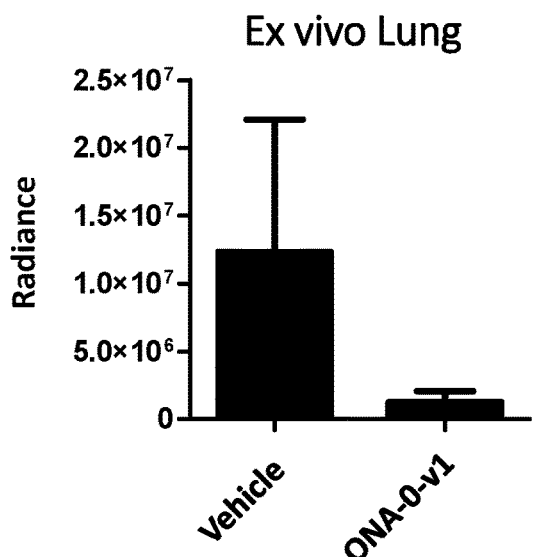
Figure 23C:
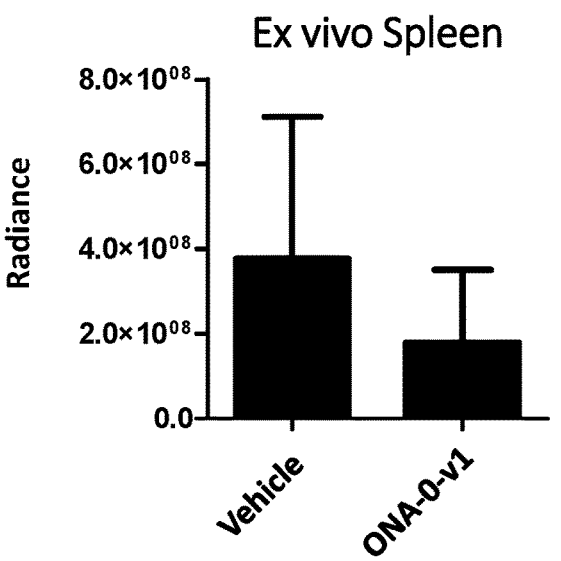
Figure 23D:
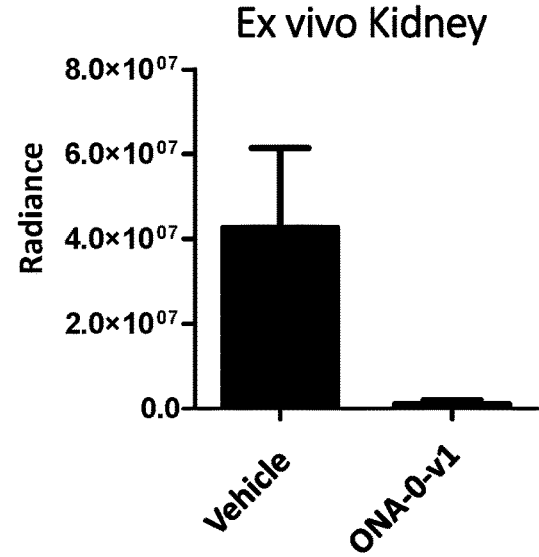

FIGS. 23A, 23B, 23C, and 23D show the effects of ONA-0-v1 treatment on the number of HCT-116 cells in particular organs (i.e., in metastases) in the mouse model of colon cancer, as measured by ex vivo analysis of luciferase luminescence. These data show that treating with ONA-0-v1 resulted in decreased luminescence in the liver (FIG. 23A), lungs (FIG. 23B), spleen (FIG. 23C), and kidney (FIG. 23D).

Figure 24:
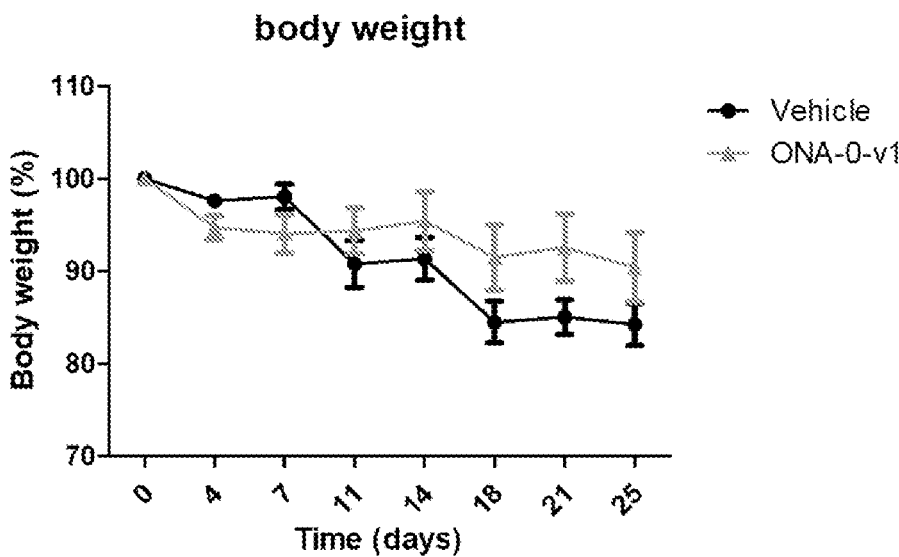

FIG. 24 shows the effect of ONA-0-v1 treatment on the body weight of mice in the HCT-116 mouse model of colon cancer. Over time, mice treated with ONA-0-v1 were better able to maintain body weight.

Figure 25A:
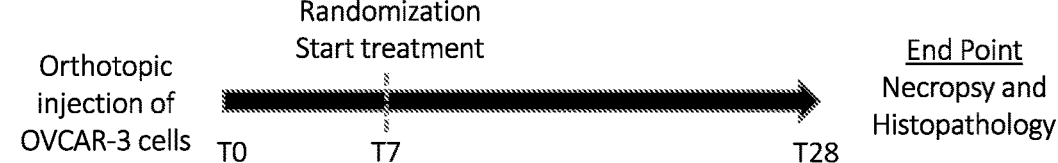
Figure 25B:
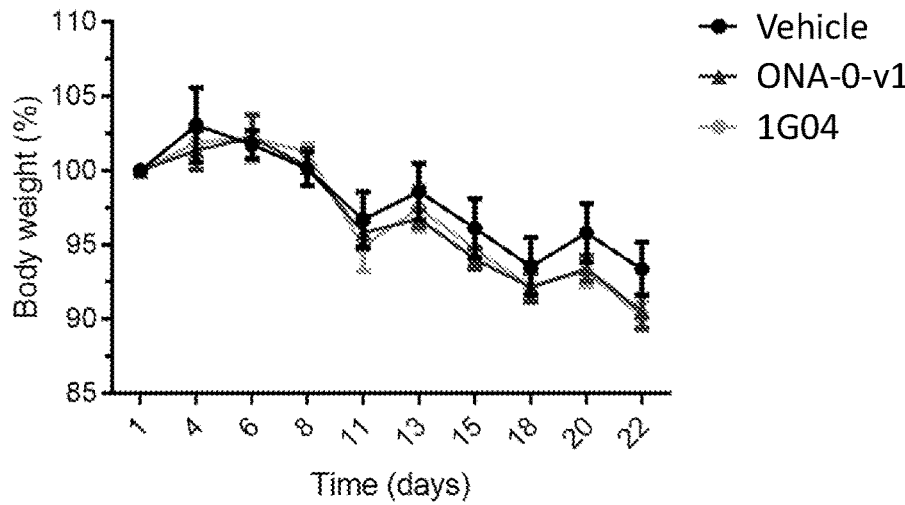

FIGS. 25A, 25B, 25C, 25D, 25E, 25F, and 25G show the results of testing the effects of the ONA-0-v1 and 1G04 anti-CD36 antibodies in the OVCAR-3 mouse model of ovarian cancer, relative to control-treated mice. FIG. 25A is a schematic showing an experimental overview of this study. FIG. 25B depicts the change in body weight of treated mice over time. FIGS. 25C-25G show that both ONA-0-v1 and 1G04 reduce both the number and size of metastases in the treated mice.

Figure 26A:
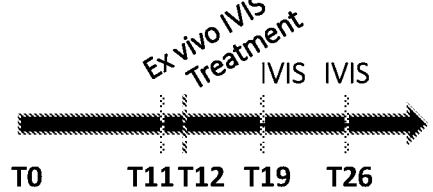

FIGS. 26A, 26B, 26C, 26D, 26E, 26F, and 26G show the effects of 1G04 treatment on the number of HCT-116 cells in particular organs (i.e., in metastases) in the mouse model of colon cancer, as measured by ex vivo analysis of luciferase luminescence. FIG. 26A is a schematic showing an experimental overview of this study.

Figure 26B:
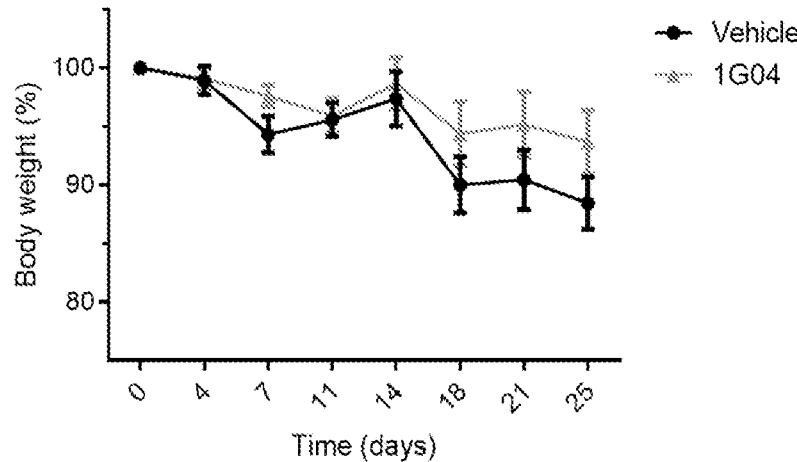
Figure 26C:
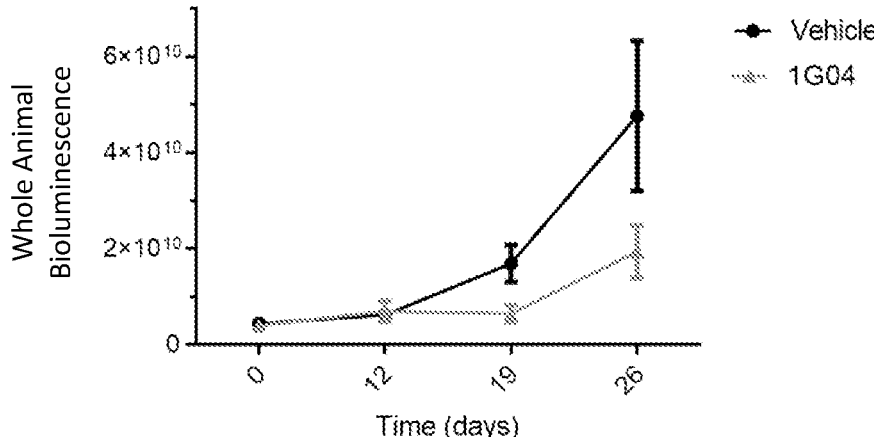
Figure 26D:
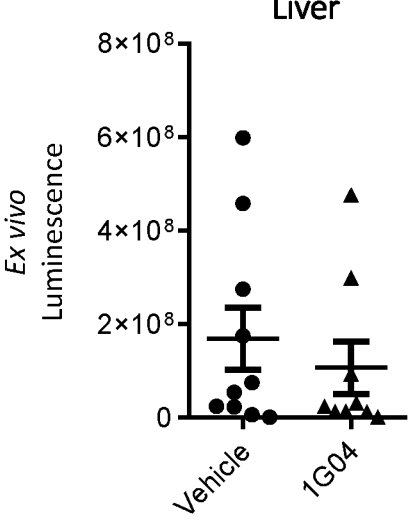
Figure 26E:
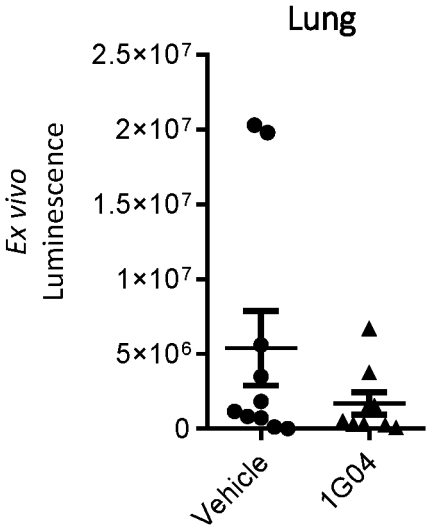
Figure 26F:
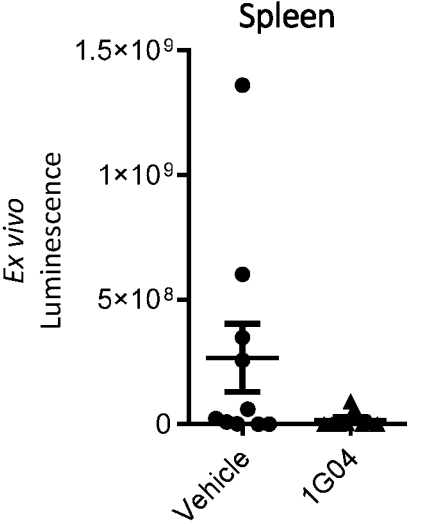
Figure 26G:
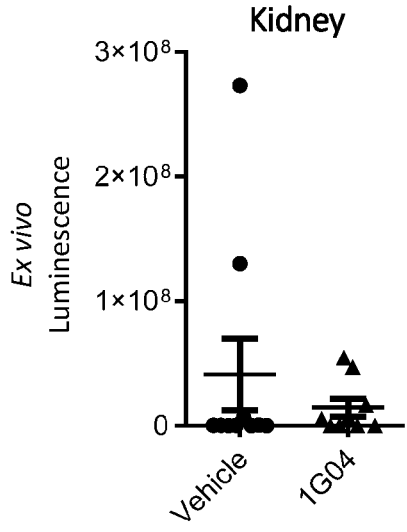

FIG. 26B depicts the change in body weight of treated mice over time. FIG. 26C shows that 1G04 reduces overall cancer cell burden in treated mice, and FIGS. 26D-26G show that treating with ONA-0-v1 resulted in decreased luminescence in the liver (FIG. 26D), lungs (FIG. 26E), spleen (FIG. 26F), and kidney (FIG. 26G).

Figure 27A:
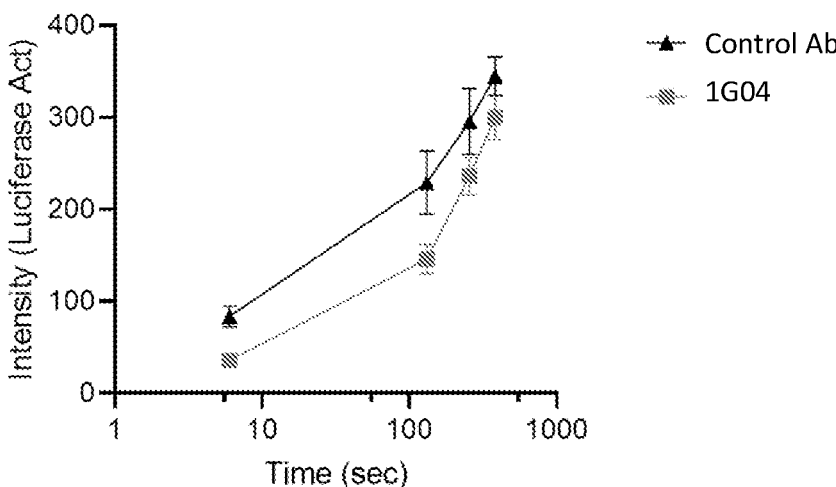
Figure 27B:
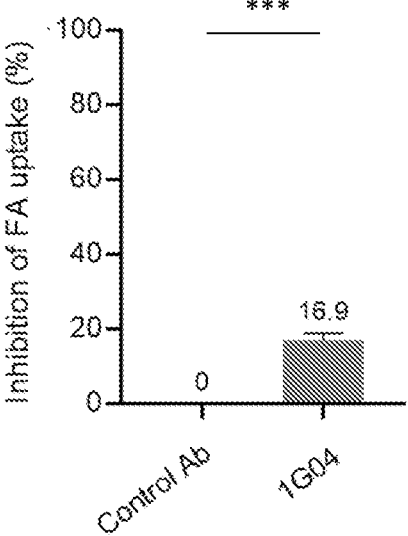

FIGS. 27A and 27B depict data from a luminescence-based fatty acid uptake assay using an isotype control antibody and 1G04. Kinetics of fatty acid uptake over time (FIG. 27A) and inhibition of fatty acid uptake at a given time (FIG. 27B) are shown.

Figures 28A, 28B:
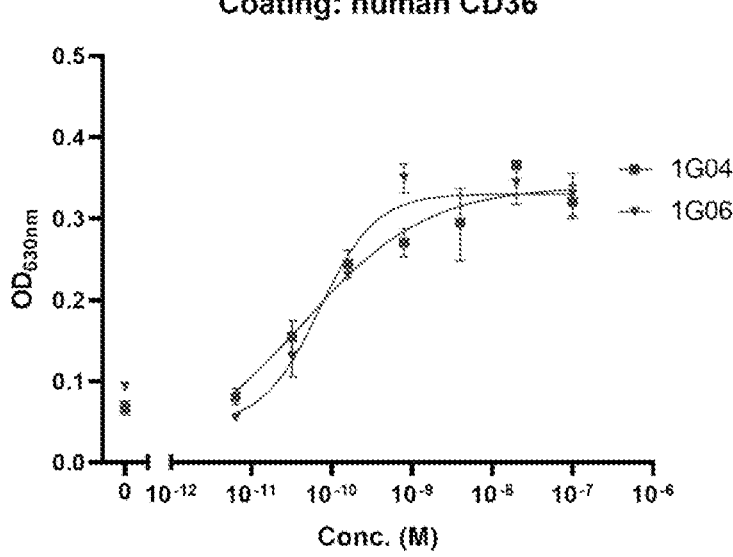

FIGS. 28A and 28B depict data from ELISA assays testing the ability of the 1G04 and 1G06 anti-CD36 antibodies to bind to mouse CD36 (FIG. 28A) and human CD36 (FIG. 28B) protein coated in microwell plates. These data show that the two antibodies specifically bound to human and mouse CD36 in a similar manner.

Figure 29:
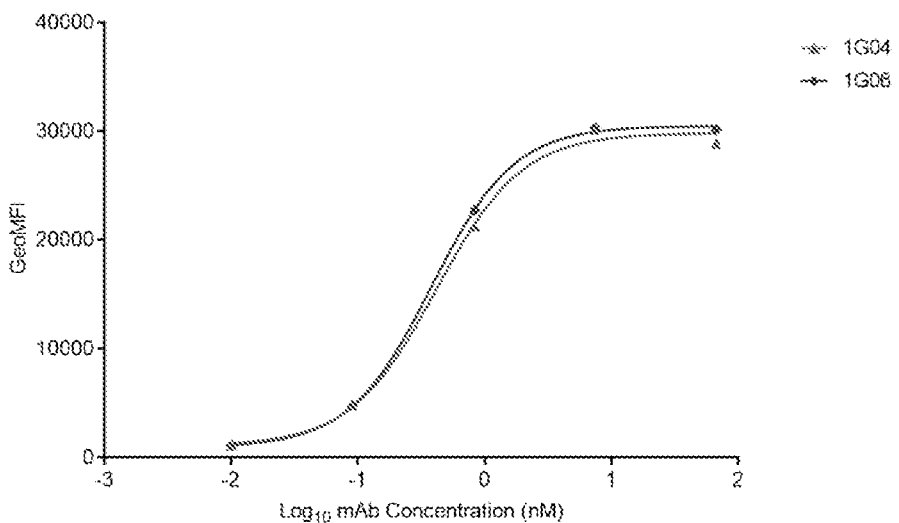

FIG. 29 shows binding of the 1G04 and 1G06 anti-CD36 antibodies to cells overexpressing human CD36, as measured by FACS analysis. These data show that the two antibodies specifically bound to human CD36 in a similar manner.

Figures 30A, 30B:
Figure 30C:
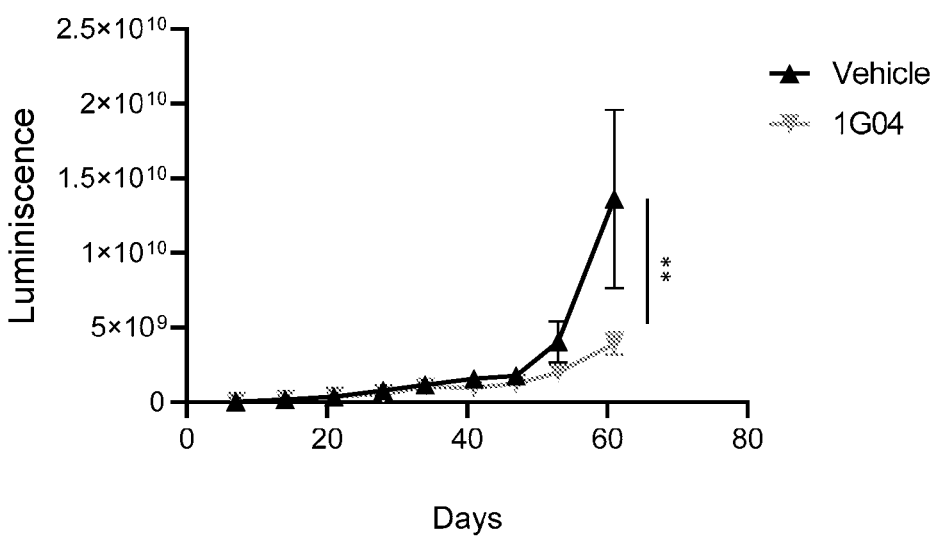
Figure 30D:
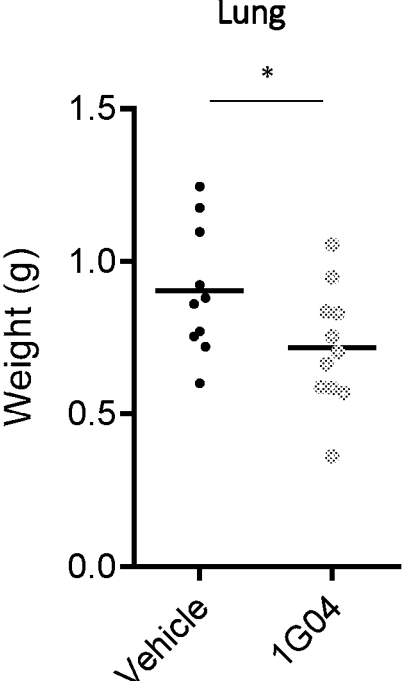
Figure 30E:
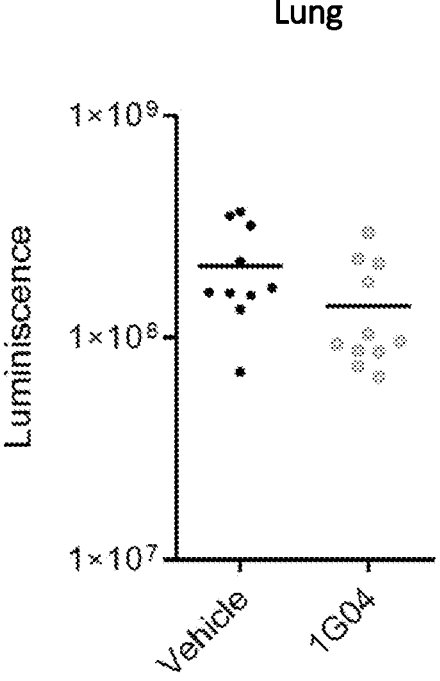

FIGS. 30A, 30B, 30C, 30D, and 30E show the results of testing the 1G04 anti-CD36 antibody in the A549 model of metastatic lung cancer, relative to vehicle-treated mice. FIG. 30A is a schematic showing an experimental overview of this study. FIG. 30B details the study groups tested in that study, particularly the therapeutics and dose given to each group. FIG. 30C shows that 1G04 reduces overall cancer cell burden in treated mice, as measured by luminescence. FIGS. 30D and 30E show that lung weight and lung luminescence ex vivo, respectively, are decreased after treatment with 1G04.

Figures 31A, 31B:
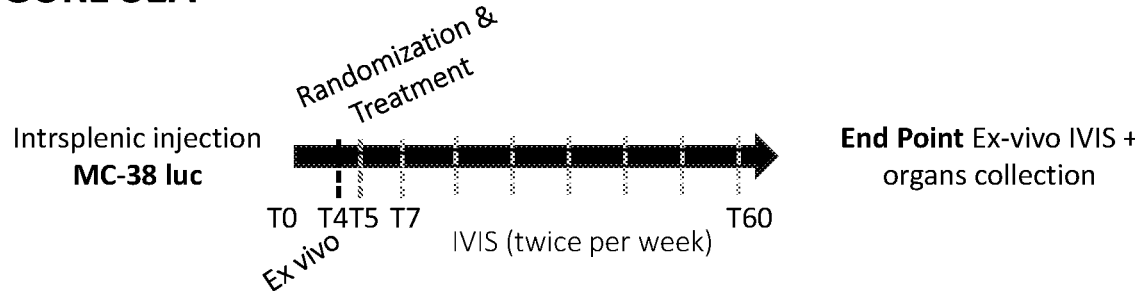

FIGS. 31A, 31B, 31C, 31D, and 31E show the effect of 1G04 treatment in the MC38 syngeneic colon cancer model. FIG. 31A is a schematic showing an experimental overview of this study. FIG. 31B details the study groups tested in that study, particularly the therapeutics and dose given to each group. FIG. 31C shows that 1G04 reduces overall cancer cell burden in treated mice, as measured by luminescence.

FIG. 31D shows that liver luminescence is reduced after 1G04 treatment, indicating a reduced level of metastasis in the liver. Similarly, FIG. 31E shows that lung luminescence is reduced after 1G04 treatment, indicating a reduced level of metastasis in the lung.

Figures 32A, 32B:
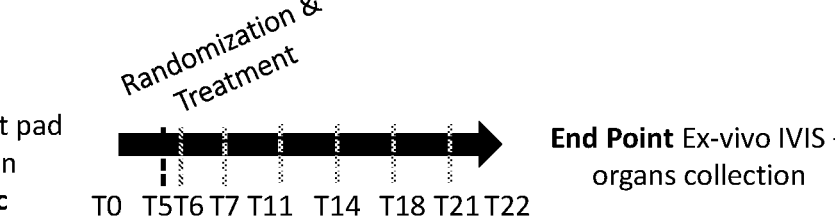
Figure 32C:
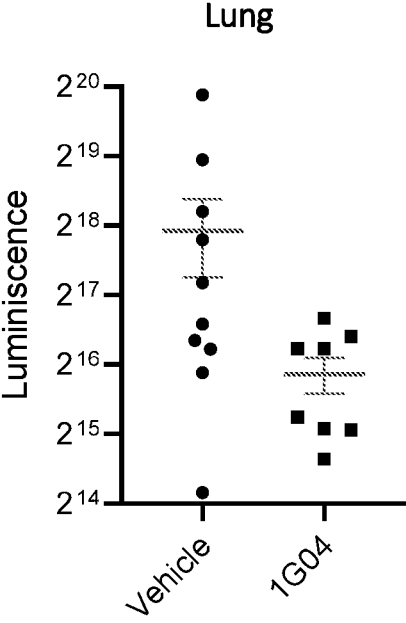

FIGS. 32A, 32B and 32C show the effect of treating mice bearing 4T1 breast cancer tumors with 1G04 anti-CD36 antibody. FIG. 32A is a schematic showing an experimental overview of this study. FIG. 32B details the study groups tested in that study, particularly the therapeutics and dose given to each group. FIG. 32C shows that luminescence in the lung is decreased after 1G04 treatment compared to vehicle treatment, indicating a reduced level of metastasis in the lung.

DETAILED DESCRIPTION

The present disclosure related to anti-CD36 antibodies, nucleotides encoding anti-CD36 antibodies, pharmaceutical compositions comprising anti-CD36 antibodies, and methods of treating (e.g., reducing and/or inhibiting) cancer, particularly cancer metastases, using anti-CD36 antibodies. The anti-CD36 antibodies disclosed include both IgA and IgG antibodies, both of which are effective in the disclosed methods of treating cancer. The disclosed anti-CD36 antibodies are effective at treating primary tumors, metastatic cancer, or both primary tumors and metastatic cancer.

Definitions of General Terms and Expressions

In order that the present disclosure can be more readily understood, certain terms are first defined. As used in this application, except as otherwise expressly provided herein, each of the following terms shall have the meaning set forth below. Additional definitions are set forth throughout the application.

The term "antibody" means an immunoglobulin molecule that recognizes and specifically binds to a target, such as a protein, polypeptide, peptide, carbohydrate, polynucleotide, lipid, or combinations of the foregoing. As used herein, the term "antibody" encompasses polyclonal antibodies, monoclonal antibodies, chimeric antibodies, humanized antibodies, fully human antibodies, recombinant antibodies, bispecific antibodies, fusion proteins comprising a full length antibody or fragments thereof, fragments of such antibodies, and any other modified immunoglobulin molecule so long as it exhibits the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')$_2$, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-CD36 antibody," "CD36 antibody" and "antibody that binds to CD36" refer to an antibody that is capable of binding CD36 with sufficient affinity such that the antibody is useful as a diagnostic and/or therapeutic agent in targeting CD36. The extent of binding of an anti-CD36 antibody to an unrelated, non-CD36 protein can be less than about 10% of the binding of the antibody to CD36 as measured, e.g., by a radioimmunoassay (RIA).

The terms "anti-PD-1 antibody," "PD-1 antibody" and "antibody that binds to PD-1" refer to an antibody that is capable of binding PD-1 with sufficient affinity such that the antibody is useful as a diagnostic and/or therapeutic agent in targeting PD-1. The extent of binding of an anti-PD-1 antibody to an unrelated, non-PD-1 protein can be less than about 10% of the binding of the antibody to PD-1 as measured, e.g., by a radioimmunoassay (RIA).

An "isolated antibody" refers to an antibody population that comprises a single species of antibody. For example, a particular isolated anti-CD36 antibody consists of an antibody population having a single heavy chain amino acid sequence and a single light chain amino acid sequence, which binds to a single CD36 epitope. An isolated antibody that binds specifically to CD36 can, however, have cross-reactivity to other antigens, such as CD36 molecules from different species. Also, a population of antibodies may still be an "isolated antibody" when contaminated by small amounts of other antibody species. In particular, an isolated antibody may contain less than 5%, less than 4%, less than 3%, less than 2%, less than 1%, or no other antibody species.

A "monoclonal antibody" refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody encompasses intact and full length monoclonal antibodies, as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal" antibody refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

The AbM hypervariable regions represent a compromise between the Kabat CDRs and Chothia structural loops, and are used by Oxford Molecular's AbM antibody modeling software. In specific embodiments, the CDRs of the antibodies described herein have been determined according to the Chothia numbering scheme or the AbM numbering scheme.

TABLE 1

| CDR Numbering | | | |
|---|---|---|---|
| Loop | Kabat | AbM | Chothia |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 (Kabat Numbering) |

14

TABLE 1-continued

| CDR Numbering | | | |
|---|---|---|---|
| Loop | Kabat | AbM | Chothia |
| H1 | H31-H35 | H26-H35 | H26-H32 (Chothia Numbering) |
| H2 | H50-H65 | H50-H58 | H52-H56 |
| H3 | H95-H102 | H95-H102 | H95-H102 |

In some aspects, the CDR regions CDRs can be determined according to the IMGT numbering system (see, e.g., Guidicelli et al., Nucl. Acids Res. 34:D781-D784 (2006); Lefranc et al., Dev. Comp. Immunol. 27:55-77 (2003)). This numbering scheme unifies numbering across antibody lambda and kappa light chains, heavy chains and T-cell receptor chains.

As used herein, the terms "constant region" and "constant domain" are interchangeable and have their common meaning in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG (e.g., IgG1, IgG2, IgG3, and IgG4) and subclasses of IgA (e.g., IgA1 and IgA2). Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "chimeric antibody" refers to a full length antibody or an antigen-binding fragment thereof wherein the amino acid sequence is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in derived from another (usually human) to avoid eliciting an immune response in that species.

A "humanized antibody" refers to a chimeric antibody, or antigen-binding fragment thereof, comprising amino acid residues from non-human CDRs and amino acid residues from human framework regions and constant regions. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Typically, humanized antibodies are human immunoglobulins in which residues from the CDRs are replaced by residues from the CDRs of a non-human species (e.g. mouse, rat, rabbit, hamster) that have the desired specificity, affinity, and capability (Jones et al., Nature 321:522-525 (1986); Riechmann et al., Nature 332: 323-327 (1988); Verhoeyen et al., Science 239:1534-1536 (1988)). Accordingly, humanized antibodies are also referred to as "CDR grafted" antibodies. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996).

A "human antibody" refers to a full length antibody or fragment thereof having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

An "afucosylated" antibody or antigen-binding fragment thereof, or an antibody or antigen-binding fragment thereof "lacking fucose," refers to an IgG1 or IgG3 isotype antibody or antigen-binding fragment thereof that lacks any fucose residues in the constant region glycosylation on at least 50% of the antibody population. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 (a 1,6 or a 1,3), or G2 glycan residues, depending on the amount of terminal Gal residues. See, e.g., Raju, T. S., BioProcess Int. 1: 44-53 (2003). CHO type glycosylation of antibody Fc is described, e.g., in Routier, F. FL, Glycoconjugate J. 14: 201-207 (1997).

Methods of measuring fucose include any methods known in the art. For purposes herein, fucose can be detected by the method described in Example 1 of WO2015/017600, which is herein incorporated by reference in its entirety. Briefly, glycan analysis can be performed by releasing glycans from the antibody (e.g., by enzymatic release), labeling the glycans with anthranilic acid (2-AA), and then purifying the labeled glycans. Normal phase HPLC with fluorescent detection is used to separate the glycans and measure the relative amount of each glycan in the antibody. The glycans may be positively identified as lacking or including fucose by mass spectrometry. In some embodiments, fucose is undetectable in a composition comprising a plurality of afucosylated antibodies. In some embodiments, an afucosylated antibody has enhanced ADCC activity, which may be measured by the assay provided in Example 12 herein. In some embodiments, an afucosylated antibody has enhanced affinity for Fc gamma RIIIA. In some embodiments, an afucosylated antibody has enhanced affinity for Fc gamma RIIIA(V158). In some embodiments, an afucosylated antibody has enhanced affinity for Fc gamma RIIIA(F158).

Affinity for Fc gamma RIIIA or its alleles may be measure by the assay provided in Example 10 herein.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Crystals of an antibody bound to antigen can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

A CD36 antibody that "binds to the same epitope" as a reference CD36 antibody refers to an antibody that binds to the same CD36 amino acid residues as the reference CD36 antibody. The ability of a CD36 antibody to bind to the same epitope as a reference CD36 antibody can be determined by a hydrogen/deuterium exchange assay (see Coales et al. Rapid Commun. Mass Spectrom. 2009; 23: 639-647), FACS analysis combined with alanine scanning, crosslinking-coupled mass spectrometry (XL-MS), peptide scanning, or mutagenesis.

As used herein, the terms "immunospecifically binds," "immunospecifically recognizes," "specifically binds," and "specifically recognizes" are analogous terms in the context of antibodies. These terms indicate that the antibody binds to an epitope via its antigen-binding domain and that the binding entails some complementarity between the antigen binding domain and the epitope. Accordingly, an antibody that "specifically binds" to human CD36 (SEQ ID NO: 1) may also bind to CD36 from other species (e.g., non-human primate, mouse, and/or rat CD36) and/or CD36 proteins produced from other human alleles, but the extent of binding to an un-related, non-CD36 protein is less than about 10% of the binding of the antibody to CD36 as measured, e.g., by a radioimmunoassay (RIA).

In a specific embodiment, provided herein is an antibody that binds to human, cynomolgus monkey, mouse, and rat CD36.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays or competition FACS. An antibody may be said to competitively inhibit binding of the reference antibody to a given epitope by at least 90%, at least 80%, at least 70%, at least 60%, or at least 50%.

As used herein, the characteristic of being "substantially free" of a substance refers to a near complete or complete lack of that substance. For example, a pharmaceutical composition that is substantially free of a particular antibody species has a near-complete or complete lack of that antibody species in the pharmaceutical composition in question. In this context, substantially free can refer to having less than 5%, less than 4%, less than 3%, less than 2%, less than 1%, or none of the antibody in the pharmaceutical composition be the antibody species in question. Moreover, "substantially free" of contaminants can refer to being purified such that it contains little other cellular material and/or chemicals (e.g., less than 5%, less than 4%, less than 3%, less than 2%, less than 1%, or no other cellular material and/or chemicals).

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm-.nih.gov).

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The terms "pharmaceutical composition" and "pharmaceutical formulation" refer to a preparation which is in such form as to permit the biological activity of the active ingredient to be therapeutically effective, and which contains no additional components which are unacceptably toxic to a subject to which the composition or formulation would be administered. The composition or formulation can be sterile.

The terms "administer", "administering", "administration", and the like, as used herein, refer to methods that may be used to enable delivery of a drug, e.g., an anti-CD36 antibody, to the desired site of biological action. Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa. Administration refers to the physical introduction of a composition comprising a therapeutic agent to a subject, using any of the various methods and delivery systems known to those skilled in the art. Preferred routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

Administration "in combination with" one or more further therapeutic agents includes simultaneous (concurrent) or consecutive administration in any order.

The combination therapy can provide "synergy," i.e., the effect achieved when the active agents used together is greater than the sum of the effects that result from using the active agents separately. A synergistic effect can be attained when the active agents are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the active agents are administered or delivered sequentially, e.g., by different injections in separate syringes. A "synergistic combination" produces an effect that is greater than the sum of the effects of the individual active agents of the combination.

The combination therapy can provide an "additive" effect, i.e., the effect achieved when the active agents used together is equal to the sum of the effects the result from using the active agents separately.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a cynomolgus monkey. In some embodiments, the subject is a human.

The term "therapeutically effective amount" refers to an amount of a drug, e.g., an anti-CD36 antibody, effective to achieve the desired therapeutic or prophylactic result. In some instances, the desired result is treating a disease or disorder in a subject. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof. In the context of metastatic cancer, treatment also refers to preventing the development of new metastatic tumors, reducing the size of metastatic tumors, or eliminating existing metastatic tumors.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor. Such distal tumors are also referred to as "metastatic tumors" or "metastases."

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Any compositions or methods provided herein can be combined with one or more of any of the other compositions and methods provided herein.

Anti-CD36 Antibodies

In a specific aspect, provided herein are full length antibodies (e.g., monoclonal antibodies, such as chimeric, humanized, or human antibodies) and antigen-binding fragments thereof which specifically bind to CD36 (e.g., human CD36). The amino acid sequences for human, cynomolgus monkey, rhesus macaque, murine, and rat CD36 are known in the art and are also provided herein as represented by SEQ ID NOs: 1-4, as shown below.

```
Human CD36 (SEQ ID NO: 1; UNIPROT P16671):
MGCDRNCGLIAGAVIGAVLAVFGGILMPVGDLLIQKTIKKQVVLEEGTI

AFKNWVKTGTEVYRQFWIFDVQNPQEVMMNSSNIQVKQRGPYTYRVRFL

AKENVTQDAEDNTVSFLQPNGAIFEPSLSVGTEADNFTVLNLAVAAASH

IYQNQFVQMILNSLINKSKSSMFQVRTLRELLWGYRDPFLSLVPYPVTT

TVGLFYPYNNTADGVYKVFNGKDNISKVAIIDTYKGKRNLSYWESHCDM

INGTDAASFPPFVEKSQVLQFFSSDICRSIYAVFESDVNLKGIPVYRFV

LPSKAFASPVENPDNYCFCTEKIISKNCTSYGVLDISKCKEGRPVYISL

PHFLYASPDVSEPIDGLNPNEEEHRTYLDIEPITGFTLQFAKRLQVNLL

VKPSEKIQVLKNLKRNYIVPILWLNETGTIGDEKANMFRSQVTGKINLL

GLIEMILLSVGVVMFVAFMISYCACRSKTIK

Cynomolgus monkey/Rhesus macaque CD36 (SEQ ID
NO: 2; UNIPROT Q4R6B4 and Q6J512, respectively):
MGCDRNCGLITGAVIGAVLAVFGGILMPVGDMLIQKTIKKEVVLEEGTI

AFKNWVKTGTEIYRQFWIFDVQNPQEVMMNSSNIQVKQRGPYTYRVRFL

AKENITQDPKDNTVSFLQPNGAIFEPSLSVGTEADNFTVLNLAVAAASH

IYPNPFVQVVLNSLINKSKSSMFQVRTLRELLWGYTDPFLSLVPYPVST

RVGMFYPYNNTADGVYKVFNGKDSISKVAIIDTYKGKRNLSYWESYCDM

INGTDAASFPPFVEKSQVLQFFSSDICRSIYAVFESDVNLKGIPVYRFV

LPSKAFASPVQNPDNHCFCTEKIISKNCTSYGVLDISKCKEGKPVYISL

PHFLYASPDVSETIDGLNPNEEEHRTYLDIEPITGFTLQFAKRLQVNLL

VKPSNKIQVLKRLKRNYIVPILWLNETGTIGDEKAKMFRSQVTGKINLL

GLIEMILLSVGVVMFVAFMISYCACRSKTIK

Murine CD36 (SEQ ID NO: 3; UNIPROT Q08857):
MGCDRNCGLIAGAVIGAVLAVFGGILMPVGDMLIEKTIKREVVLEEGTT

AFKNWVKTGTTVYRQFWIFDVQNPDDVAKNSSKIKVKQRGPYTYRVRYL

AKENITQDPEDHTVSFVQPNGAIFEPSLSVGTEDDNFTVLNLAVAAAPH

IYQNSFVQVVLNSLIKKSKSSMFQTRSLKELLWGYKDPFLSLVPYPIST

TVGVFYPYNDTVDGVYKVFNGKDNISKVAIIESYKGKRNLSYWPSYCDM

INGTDAASFPPFVEKSRTLRFFSSDICRSIYAVFGSEIDLKGIPVYRFV

LPANAFASPLQNPDNHCFCTEKVISNNCTSYGVLDIGKCKEGKPVYISL
```

```
-continued
PHFLHASPDVSEPIEGLHPNEDEHRTYLDVEPITGFTLQFAKRLQVNIL

VKPARKIEALKNLKRPYIVPILWLNETGTIGDEKAEMFKTQVTGKIKLL

GMVEMALLGIGVVMFVAFMISYCACKSKNGK

Rat CD36 (SEQ ID NO: 4; UNIPROT Q07969):
MGCDRNCGLITGAVIGAVLAVFGGILMPVGDLLIEKTIKREVVLEEGTI

AFKNWVKTGTTVYRQFWIFDVQNPEEVAKNSSKIKVKQRGPYTYRVRYL

AKENITQDPKDSTVSFVQPNGAIFEPSLSVGTENDNFTVLNLAVAAAPH

IYTNSFVQGVLNSLIKKSKSSMFQTRSLKELLWGYKDPFLSLVPYPIST

TVGVFYPYNNTVDGVYKVFNGKDNISKVAIIDTYKGKRNLSYWESYCDM

INGTDAASFPPFVEKSQTLRFFSSDICRSIYAVFESEVNLKGIPVYRFV

LPANAFASPLQNPDNHCFCTEKVISNNCTSYGVLDIGKCKEGKPVYISL

PHFLHASPDVSEPIEGLNPNEDEHRTYLDVEPITGFTLQFAKRLQVNIL

VKPARKIEALKNLKRPYIVPILWLNETGTIGDEKAEMFRNQVTGKIKLL

GLVEMVLLGVGVVMFVAFMISYCACRSKNGK
```

In certain embodiments, an antibody described herein binds to human CD36. In certain embodiments, an antibody binds to human and cynomolgus monkey CD36. In certain embodiments, an antibody binds to human and murine CD36. In certain embodiments, an antibody binds to human, murine, and rat CD36. In certain embodiments, an antibody binds to human, cynomolgus monkey, murine, and rat CD36.

Anti-CD36 antibodies of the invention include a full length antibody, a single chain antibody, and a scFv, Fab or F(ab')$_2$ fragment. In some embodiments, the anti-CD-36 inhibitor is a full length antibody. In some embodiments, the CD36 inhibitor is a humanized antibody. In some embodiments, the CD36 inhibitor is a human antibody. In some embodiments, the anti-CD36 antibody is ONA-0-v1 or ONA-0-v2. The amino acid sequence of ONA-0-v1 is provided as SEQ ID NO: 5 (heavy chain) and SEQ ID NO: 7 (light chain). The amino acid sequence of ONA-0-v2 is provided as SEQ ID NO: 5 (heavy chain) and SEQ ID NO: 9 (light chain). The ONA-0-v1 and ONA-0-v2 antibodies share the same constant regions and the same heavy chain variable region, but differ in that they contain different light chain variable regions. Schematic diagrams of ONA-0-v1 and ONA-0-v2 are provided in FIG. 5.

Embodiments of the invention also include antibody fragments derived from ONA-0-v1 or ONA-0-v2, including but not limited to Fab, Fab', F(ab')$_2$, single chain Fv (scFv), disulfide linked Fv, V-NAR domain, IgNar, intrabody, IgG∆CH2, minibody, F(ab')$_3$, tetrabody, triabody, diabody, single-domain antibody, DVD-Ig, Fcab, mAb2, (scFv)$_2$, or scFv-Fc. An antibody fragment can be produced by any technique known to those of skill in the art. In certain embodiments, the antibody fragment further comprises a moiety that extends the half-life of the antibody in vivo. The moiety is also termed a "half-life extending moiety." Any moiety known to those of skill in the art for extending the half-life of an antibody fragment in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain embodiments, the Fab, Fab', F(ab')$_2$, or scFv can be modified by the addition of one or more C-terminal amino acids for attachment of the half-life extending moiety. In certain embodiments the half-life extending moiety is polyethylene glycol or human serum albumin. In certain embodiments, the Fab, Fab', F(ab')$_2$, or scFv is fused to a Fc region.

In certain embodiments, an antibody binds to CD36 and comprises one or more of the CDRs of ONA-0-v1, as identified by the Chothia, Kabat, or IMGT antibody numbering schemes. In some embodiments, the antibody thereof is a humanized antibody comprising one or more of the six CDRs in SEQ ID NOs 27-32. In some embodiments, the antibody thereof is a humanized antibody comprising one or more of the six CDRs in SEQ ID NOs 37, 38, and 29-32. In some embodiments, the antibody thereof is a humanized antibody comprising one or more of the six CDRs in SEQ ID NOs 39-43 and 32. In some embodiments, the heavy chain sequence contains the CDR regions GYTFTDY (heavy chain CDR1; SEQ ID NO: 27), YPGSGN (heavy chain CDR2; SEQ ID NO: 28), and GIGGGFGMDY (heavy chain CDR3; SEQ ID NO: 29). In some embodiments, the heavy chain sequence contains the CDR regions DYYIN (heavy chain CDR1; SEQ ID NO: 37), RIYPGSGNTYYNEKFKG (heavy chain CDR2; SEQ ID NO: 38), and GIGGGFGMDY (heavy chain CDR3; SEQ ID NO: 29). In some embodiments, the heavy chain sequence contains the CDR regions GYTFTDYY (heavy chain CDR1; SEQ ID NO: 39), IYPGSGNT (heavy chain CDR2; SEQ ID NO: 40), and ARGIGGGFGMDY (heavy chain CDR3; SEQ ID NO: 41). In some embodiments, the light chain variable region contains the CDR regions KASQSVSDDVA (light chain CDR1; SEQ ID NO: 30), YASNRYT (light chain CDR2; SEQ ID NO: 31), and QQDYSSPLT (light chain CDR3; SEQ ID NO: 32). In some embodiments, the light chain variable region contains the CDR regions QSVSDD (light chain CDR1; SEQ ID NO: 42), YAS (light chain CDR2; SEQ ID NO: 43), and QQDYSSPLT (light chain CDR3; SEQ ID NO: 32).

In certain embodiments, an antibody binds to CD36 and comprises a variant of one or more of the CDRs of ONA-0-v1, as identified by the Chothia, Kabat, or IMGT antibody numbering schemes. In some embodiments, the antibody contains DYYMH (SEQ ID NO: 44) or DYYMN (SEQ ID NO: 45) as a variant of the ONA-0-v1 heavy chain CDR1 region. In some embodiments, the antibody contains RIYPGSGNTYYNEKFQG (SEQ ID NO: 46) or RIYPGSGNTYYNEKFTG (SEQ ID NO: 47) as a variant of the ONA-0-v1 heavy chain CDR2 region. In some embodiments, the antibody contains QASQSVSDDVA (SEQ ID NO: 48) as a variant of the ONA-0-v1 light chain CDR1 region. In some embodiments, the antibody contains YASNLYT (SEQ ID NO: 49) or YASNRYS (SEQ ID NO: 50) as a variant of the ONA-0-v1 light chain CDR2 region.

In some embodiments, the antibody thereof is a humanized antibody comprising one or more of the CDRs of ONA-0-v1 or variants of the CDRs of ONA-0-v1, as identified by the Chothia, Kabat, or IMGT antibody numbering schemes. Exemplary embodiments of antibodies comprising one or more of the CDRs of ONA-0-v1 or variants of the CDRs of ONA-0-v1 (as identified according to the Kabat numbering scheme) are provided in Table 2 below.

TABLE 2

| | CDRs in ONA-0-1 and Humanized Variants of ONA-0-v1 | | | | | |
| --- | --- | --- | --- | --- | --- | --- |
| | CDR-H1 SEQ ID NO | CDR-H2 SEQ ID NO | CDR-H3 SEQ ID NO | CDR-L1 SEQ ID NO | CDR-L2 SEQ ID NO | CDR-L3 SEQ ID NO |
| ONA-0-v1 | 37 | 38 | 29 | 30 | 31 | 32 |
| ONA-0-v1 Humanized v1 | 37 | 38 | 29 | 48 | 31 | 32 |
| ONA-0-v1 Humanized v2 | 37 | 38 | 29 | 48 | 49 | 32 |
| ONA-0-v1 Humanized v3 | 37 | 38 | 29 | 30 | 31 | 32 |
| ONA-0-v1 Humanized v4 | 37 | 38 | 29 | 30 | 50 | 32 |
| ONA-0-v1 Humanized v5 | 44 | 46 | 29 | 48 | 31 | 32 |
| ONA-0-v1 Humanized v6 | 44 | 46 | 29 | 48 | 49 | 32 |
| ONA-0-v1 Humanized v7 | 44 | 46 | 29 | 30 | 31 | 32 |
| ONA-0-v1 Humanized v8 | 44 | 46 | 29 | 30 | 50 | 32 |
| ONA-0-v1 Humanized v9 | 37 | 38 | 29 | 48 | 31 | 32 |
| ONA-0-v1 Humanized v10 | 37 | 38 | 29 | 48 | 49 | 32 |
| ONA-0-v1 Humanized v11 | 37 | 38 | 29 | 30 | 31 | 32 |
| ONA-0-v1 Humanized v12 | 37 | 38 | 29 | 30 | 50 | 32 |
| ONA-0-v1 Humanized v13 | 45 | 47 | 29 | 48 | 31 | 32 |
| ONA-0-v1 Humanized v14 | 45 | 47 | 29 | 48 | 49 | 32 |
| ONA-0-v1 Humanized v15 | 45 | 47 | 29 | 30 | 31 | 32 |
| ONA-0-v1 Humanized v16 | 45 | 47 | 29 | 30 | 50 | 32 |

In some embodiments, the antibody thereof is a humanized antibody comprising humanized variants of the ONA-0-v1 antibody. In some embodiments, the humanized variant of the ONA-0-v1 antibody comprises a humanized heavy chain variable region comprising SEQ ID NO: 51, SEQ ID NO: 52, SEQ ID NO: 53, or SEQ ID NO: 54. In some embodiments, the humanized variant of the ONA-0-v1 antibody comprises a humanized light chain variable region comprising SEQ ID NO: 55, SEQ ID NO: 56, SEQ ID NO: 57, or SEQ ID NO: 58. In some embodiments, the humanized variant of the ONA-0-v1 antibody comprises a humanized heavy chain variable region comprising SEQ ID NO: 51 and a humanized light chain variable region comprising SEQ ID NO: 55, SEQ ID NO: 56, SEQ ID NO: 57, or SEQ ID NO: 58. In some embodiments, the humanized variant of the ONA-0-v1 antibody comprises a humanized heavy chain variable region comprising SEQ ID NO: 52 and a humanized light chain variable region comprising SEQ ID NO: 55, SEQ ID NO: 56, SEQ ID NO: 57, or SEQ ID NO: 58. In some embodiments, the humanized variant of the ONA-0-v1 antibody comprises a humanized heavy chain variable region comprising SEQ ID NO: 53 and a humanized light chain variable region comprising SEQ ID NO: 55, SEQ ID NO: 56, SEQ ID NO: 57, or SEQ ID NO: 58. In some embodiments, the humanized variant of the ONA-0-v1 antibody comprises a humanized heavy chain variable region comprising SEQ ID NO: 54 and a humanized light chain variable region comprising SEQ ID NO: 55, SEQ ID NO: 56, SEQ ID NO: 57, or SEQ ID NO: 58.

In certain embodiments, an antibody binds to CD36 and comprises one or more of the six CDRs of ONA-0-v2, as identified by the Chothia, Kabat, or IMGT antibody numbering schemes. In some embodiments, the antibody is a humanized antibody comprising one or more of the six CDRs listed in SEQ ID NOs 27-29 and 33-35. In some embodiments, the heavy chain sequence contains the CDR regions GYTFTDY (heavy chain CDR1; SEQ ID NO: 27), YPGSGN (heavy chain CDR2; SEQ ID NO: 28), and GIGGGFGMDY (heavy chain CDR3; SEQ ID NO: 29). In some embodiments, the light chain variable region contains the CDR regions KASENVVTYVS (light chain CDR1; SEQ ID NO: 33), GASNRYT (light chain CDR2; SEQ ID NO: 34), and GQGYSYPYT (light chain CDR3; SEQ ID NO: 35). In some embodiments, the antibody is a humanized antibody comprising one or more of the six CDRs of ONA-0-v2.

In certain embodiments, an antibody described herein binds to human CD36 and comprises the ONA-0-v1 VH sequence provided as SEQ ID NO: 11. In certain embodiments, an antibody binds to human CD36 and comprises the ONA-0-v1 VL sequence provided as SEQ ID NO: 13. In certain embodiments, an antibody binds to human CD36 and comprises the VL provided as SEQ ID NO: 20. In some embodiments, the antibody is a chimeric antibody comprising the VH sequence provided as SEQ ID NO: 11 and the VL provided as SEQ ID NO: 13. In some embodiments, the antibody is a chimeric antibody comprising the heavy chain sequence provided as SEQ ID NO: 21 and the light chain provided as SEQ ID NO: 23, such as the 1G04 antibody. In some embodiments, the antibody is a chimeric antibody comprising the heavy chain sequence provided as SEQ ID NO: 64 and the light chain provided as SEQ ID NO: 23, such as the 1G06 antibody.

In certain embodiments, the anti-CD36 antibody is a bispecific antibody. The term "bispecific" means that the antibody in question is able to specifically bind to at least two distinct epitopes or antigens. Typically, a bispecific antibody comprises two antigen binding sites, each of which is specific for a different epitope or antigen. Accordingly, in some embodiments the bispecific anti-CD36 antibody also binds to a second epitope or antigen. In some embodiments, the bispecific antibody specifically binds to CD36 and specifically binds to a T-cell receptor antigen. In some embodiments, the bispecific antibody specifically binds to CD36 and specifically binds to CD3. In some embodiments, the bispecific anti-CD36 antibody comprises one or more CDRs from the ONA-0-v1 antibody. Embodiments of the invention include methods of using such bispecific antibodies to recruit T cells to tumors. In some embodiments of these methods, the recruited T cells lyse tumor cells while bypassing antigen presentation through the major histocompatibility complex. Exemplary methods for preparing and using bispecific antibodies can be found in WO 2016/141287 A1, which is incorporated herein by reference in its entirety.

Amino acid sequences relating to the ONA-0-v1 antibody, ONA-0-v2 antibody, and other embodiments are provided below in Table 3.

TABLE 3

| | | |
|---|---|---|
| | | Amino Acid Sequences |
| Name | SEQ ID NO: | Sequence |
| ONA-0-v1 heavy chain | 5 | QVQLKQSGADLVRPGASVKLSCKASGYTFTDYYIN WVKQRPGQGLEWIARIYPGSGNTYYNEKFKGKATL TAEKSSSTAYMQLSSLTSEDSAVYFCARGIGGGFGM DYWGQGTSVTVSSESARNPTIYPLTLPPVLCSDPVIIG CLIHDYFPFGTMNVTWGKSGKDITTVNFPPALASGG RYTMSSQLTLPAVECPEGESVKCSVQHDSNPVQELD VNCSPTPPPPITIPSCQPSLSLQRPALEDLLLGSDASIT CTLNGLRNPEGAAFTWEPSTGKDAVQKKAAQNSCG CYSVSSVLPGCAERWNSGASFKCTVTHPESGTLTGTI AKVTVNTFPPQVHLLPPPSEELALNELLSLTCLVRAF NPKEVLVRWLHGNEELSPESYLVFEPLKEPGEGATT YLVTSVLRVSAETWKQGDQYSCMVGHEALPMNFT QKTIDRLSGKPTNVSVSVIMSEGDGICY |
| ONA-0-v1 light chain | 7 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLEIKRA DAAPTVSIFPPSSEQLTSGGASVVCFLNNFYPKDINV KWKIDGSERQNGVLNSWTDQDSKDSTYSMSSTLTL |

TABLE 3-continued

Amino Acid Sequences

| Name | SEQ ID NO: | Sequence |
|------|------------|----------|
| | | TKDEYERHNSYTCEATHKTSTSPIVKSFNRNEC |
| ONA-0-v2 light chain | 9 | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK RADAAPTVSIFPPSSEQLTSGGASVVCFLNNFYPKDI NVKWKIDGSERQNGVLNSWTDQDSKDSTYSMSSTL TLTKDEYERHNSYTCEATHKTSTSPIVKSFNRNEC |
| ONA-0-v1 VH | 11 | QVQLKQSGADLVRPGASVKLSCKASGYTFTDYYIN WVKQRPGQGLEWIARIYPGSGNTYYNEKFKGKATL TAEKSSSTAYMQLSSLTSEDSAVYFCARGIGGGFGM DYWGQGTSVTVSS |
| ONA-0-v1 VL | 13 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLEIK |
| ONA-0-v2 VL | 15 | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK |
| ONA-0-v1B heavy chain | 17 | QVQLKQSGADLVRPGASVKLSCKASGYTFTDYYIN WVKQRPGQGLEWIARIYPGSGNTYYNEKFKGKATL TAEKSSSTAYMQLSSLTSEDSAVYFCARGIGGGFGM DYWGQGTSVTVSSESARNPTIYPLTLPRALSSDPVIIG CLIHDYFPSGTMNVTWGKSGKDITTVNFPPALASGG GYTMSSQLTLPAVECPEGESVKCSVQHDSNAVQEL DVKCSGPPPPCPPCPPSCHPSLSLQRPALEDLLLGSD ASLTCTLNGLRNPEGAVFTWEPSTGKDAVQKKAVQ NSCGCYSVSSVLPGCAERWNSGASFKCTVTHPESDT LTGTIAKITVNTFPPQVHLLPPPSEELALNELVSLTCL VRAFNPKEVLVRWLHGNEELSPESYLVFEPLKEPGE GATTYLVTSVLRVSAELWKQGDQYSCMVGHEALP MNFTQKTIDRLSGKPTNVSVSVIMSEGDGICY |
| ONA-0-v1B light chain | 18 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLELKR ADAAPTVSIFPPSSEQLTSGGASVVCFLNNFYPKDIN VKWKIDGSERQNGVLNSWTDQDSKDSTYSMSSTLT LTKDEYERHNSYTCEATHKTSTSPIVKSFNRNEC |
| ONA-0-v2B light chain | 19 | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK RADAAPTVSIFPPSSEQLTSGGASVVCFLNNFYPKDI NVKWKIDGSERQNGVLNSWTDQDSKDSTYSMSSTL TLTKDEYERHNSYTCEATHKTSTSPIVKSFNRNEC |
| ONA-0-v1B VL | 20 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLELK |
| 1G04 heavy chain | 21 | QVQLKQSGADLVRPGASVKLSCKASGYTFTDYYIN WVKQRPGQGLEWIARIYPGSGNTYYNEKFKGKATL TAEKSSSTAYMQLSSLTSEDSAVYFCARGIGGGFGM DYWGQGTSVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK KVEPKSCDKTHTCPPCPAPEAAGGPSVFLFPPKPKDT LMISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSRD ELTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 1G04 light chain | 23 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |

TABLE 3-continued

Amino Acid Sequences

| Name | SEQ ID NO: | Sequence |
|------|-----------|----------|
| ONA-0-v2 ch IgG1 LALA light chain | 25 | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK RTVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| ONA-0-v1 VH CDR1 Chothia | 27 | GYTFTDY |
| ONA-0-v1 VH CDR2 Chothia | 28 | YPGSGN |
| ONA-0-v1 VH CDR3 Chothia | 29 | GIGGGFGMDY |
| ONA-0-v1 VL CDR1 Chothia | 30 | KASQSVSDDVA |
| ONA-0-v1 VL CDR2 Chothia | 31 | YASNRYT |
| ONA-0-v1 VL CDR3 Chothia | 32 | QQDYSSPLT |
| ONA-0-v2 VL CDR1 Chothia | 33 | KASENVVTYVS |
| ONA-0-v2 VL CDR2 Chothia | 34 | GASNRYT |
| ONA-0-v2 VL CDR3 Chothia | 35 | GQGYSYPYT |
| ONA-0-v1 VH CDR1 Kabat | 37 | DYYIN |
| ONA-0-v1 VH CDR2 Kabat | 38 | RIYPGSGNTYYNEKFKG |
| ONA-0-v1 VH CDR3 Kabat | 29 | GIGGGFGMDY |
| ONA-0-v1 VL CDR1 Kabat | 30 | KASQSVSDDVA |
| ONA-0-v1 VL CDR2 Kabat | 31 | YASNRYT |
| ONA-0-v1 VL CDR3 Kabat | 32 | QQDYSSPLT |
| ONA-0-v1 VH CDRI IMGT | 39 | GYTFTDYY |
| ONA-0-v1 VH CDR2 IMGT | 40 | IYPGSGNT |

TABLE 3-continued

| | | |
|---|---|---|
| | | Amino Acid Sequences |

| Name | SEQ ID NO: | Sequence |
|---|---|---|
| ONA-0-v1 VH CDR3 IMGT | 41 | ARGIGGGFGMDY |
| ONA-0-v1 VL CDRI IMGT | 42 | QSVSDD |
| ONA-0-v1 VL CDR2 IMGT | 43 | YAS |
| ONA-0-v1 VL CDR3 IMGT | 32 | QQDYSSPLT |
| VH CDR1 Humanized variant Kabat | 44 | DYYMH |
| VH CDR1 Humanized variant Kabat | 45 | DYYMN |
| VH CDR2 Humanized variant Kabat | 46 | RIYPGSGNTYYNEKFQG |
| VH CDR2 Humanized variant Kabat | 47 | RIYPGSGNTYYNEKFTG |
| VL CDR1 Humanized variant Kabat | 48 | QASQSVSDDVA |
| VL CDR2 Humanized variant Kabat | 49 | YASNLYT |
| VL CDR2 Humanized variant Kabat | 50 | YASNRYS |
| Humanized ONA-0-v1 VH variant 1 | 51 | QVQLVQSGAEVKKPGASVKVSCKASGYTFTDYYIN WVRQAPGQGLEW1AR1YPGSGNTYYNEKFKGRVTL TAEKSTSTAYMELSSLRSEDTAVYFCARGIGGGFGM DYWGQGTTVTVSS |
| Humanized ONA-0-v1 VH variant 2 | 52 | QVQLVQSGAEVKKPGASVKVSCKASGYTFTDYYM HWVRQAPGQGLEWMARIYPGSGNTYYNEKFQGRV TMTADKSTSTAYMELSSLRSEDTAVYYCARGIGGGF GMDYWGQGTTVTVSS |
| Humanized ONA-0-v1 VH variant 3 | 53 | QVQLVQSGSELKKPGASVKVSCKASGYTFTDYYIN WVRQAPGQGLEWIARIYPGSGNTYYNEGFKGRFVL SAEKSVSTAYLQISSLKAEDTAVYFCARGIGGGFGM DYWGQGTTVTVSS |
| Humanized ONA-0-v1 VH variant 4 | 54 | QVQLVQSGSELKKPGASVKVSCKASGYTFTDYYMN WVRQAPGQGLEWMARIYPGSGNTYYNEGFTGRFVF SADKSVSTAYLQISSLKAEDTAVYYCARGIGGGFGM DYWGQGTTVTVSS |
| Humanized ONA-0-v1 VL variant 1 | 55 | SIQMTQSPSSLSASVGDRVTITCQASQSVSDDVAWY QQKPGKAPKLLIYYASNRYTGVPSRFSGSGYGTDFT FTISSLQPEDIATYFCQQDYSSPLTFGGGTKLEIK |
| Humanized ONA-0-v1 VL variant 2 | 56 | DIQMTQSPSSLSASVGDRVTITCQASQSVSDDVAWY QQKPGKAPKLLIYYASNLYTGVPSRFSGSGSGTDFTF TISSLQPEDIATYYCQQDYSSPLTFGGGTKLEIK |
| Humanized ONA-0-v1 VL variant 3 | 57 | SIVMTQSPDSLAVSLGERATINCKASQSVSDDVAWY QQKPGQPPKLLIYYASNRYTGVPDRFSGSGYGTDFT LTISSLQAEDVAVYFCQQDYSSPLTFGGGTKLEIK |

TABLE 3-continued

Amino Acid Sequences

| Name | SEQ ID NO: | Sequence |
|------|------------|----------|
| Humanized ONA-0-v1 VL variant 4 | 58 | DIVMTQSPDSLAVSLGERATINCKASQSVSDDVAWY QQKPGQPPKLLIYYASNRYSGVPDRFSGSGSGTDFTL TISSLQAEDVAVYYCQQDYSSPLTFGGGTKLEIK |
| 1G06 heavy chain | 59 | QVQLKQSGADLVRPGASVKLSCKASGYTFTDYYIN WVKQRPGQGLEWIARIYPGSGNTYYNEKFKGKATL TAEKSSSTAYMQLSSLTSEDSAVYFCARGIGGGFGM DYWGQGTSVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK KVEPKSCDKTHTCPPCPAPESTRGPSVFLFPPKPKDT LMISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSRD ELTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 1G06 light chain | 23 | SIVMTQTPKFLLVSAGDRITITCKASQSVSDDVAWY QQKPGQSPKLLIYYASNRYTGVPDRFTGSGYGTDFT FTISTVQAEDLAVYFCQQDYSSPLTFGAGTKLEIKRT VAAPSVFIFPPSDEQLKSGTASVVCLLNNFYPREAKV QWKVDNALQSGNSQESVTEQDSKDSTYSLSSTLTLS KADYEKHKVYACEVTHQGLSSPVTKSFNRGEC |

In certain embodiments, an antibody described herein binds to CD36, comprises the six CDRs of ONA-0-v1 (i.e., SEQ ID Nos: 27-32), and comprises a VH comprising a sequence at least 80% identical to the VH sequence of ONA-0-v1 (SEQ ID NO: 11) and a VL comprising a sequence at least 80% identical to the VL sequence of ONA-0-v1 (SEQ ID NO: 13). In some of these embodiments, the antibody comprises a VH comprising at least 85%, at least 90%, at least 95%, at least 96%, at least 97%, at least 98%, or at least 99% identity to the VH sequence of ONA-0-v1 (SEQ ID NO: 11). In some of these embodiments, the antibody comprises a VL comprising at least 85%, at least 90%, at least 95%, at least 96%, at least 97%, at least 98%, or at least 99% identity to the VL sequence of ONA-0-v1 (SEQ ID NO: 13).

In certain embodiments, an antibody described herein binds to CD36, comprises the six CDRs of ONA-0-v1 (i.e., SEQ ID Nos: 27-32), and comprises a heavy chain comprising a sequence at least 80% identical to the heavy chain sequence of ONA-0-v1 (SEQ ID NO: 5) and a light chain comprising a sequence at least 80% identical to the light chain sequence of ONA-0-v1 (SEQ ID NO: 7). In some of these embodiments, the antibody comprises a heavy chain comprising at least 85%, at least 90%, at least 95%, at least 96%, at least 97%, at least 98%, or at least 99% identity to the heavy chain sequence of ONA-0-v1 (SEQ ID NO: 5). In some of these embodiments, the antibody comprises a light chain comprising at least 85%, at least 90%, at least 95%, at least 96%, at least 97%, at least 98%, or at least 99% identity to the light chain sequence of ONA-0-v1 (SEQ ID NO: 7).

In another aspect, provided herein are antibodies that bind the same epitope of CD36 (e.g., an epitope of human CD36) as an antibody described herein (e.g., ONA-0-v1).

Competition binding assays can be used to determine whether two antibodies bind to overlapping epitopes. Competitive binding can be determined in an assay in which the immunoglobulin under test inhibits specific binding of a reference antibody to a common antigen, such as CD36.

Numerous types of competitive binding assays are known, for example: competition FACS; solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., CD36 such as human CD36) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one embodiment, a competition assay is performed using surface plasmon resonance (BIAcore®), e.g., by an 'in tandem approach' such as that described by Abdiche Y N et al., (2009) Analytical Biochem 386: 172-180, whereby CD36 antigen is immobilized on the chip surface, for example, a CM5 sensor chip and the anti-CD36 antibodies are then run over the chip. To determine if an antibody competes with an anti-CD36 antibody described herein, the anti-CD36 antibody is first run over the chip surface to achieve saturation and then the potential, competing antibody is added. Binding of the competing antibody can then be determined and quantified relative to a non-competing control.

In one embodiment, Fortebio Octet competition binding is used to determine that a CD36 antibody competitively inhibits the binding of another CD36 antibody to CD36.

In another aspect, provided herein are antibodies that competitively inhibit (e.g., in a dose dependent manner) an antibody described herein (e.g., ONA-0-v1) from binding to CD36 (e.g., human CD36), as determined using assays known to one of skill in the art or described herein (e.g., ELISA competitive assays, or suspension array, or surface plasmon resonance assay).

It is preferred that the anti-CD36 antibody modulates the activity of CD36, antagonizing or blocking it. The antibody that blocks or inhibits CD36 activity can be a full length antibody. It is also possible to use analogues or fragments of antibodies, such as single chain antibodies, single chain variable domain fragments (scFv), F(ab')$_2$ fragments (which can be obtained by pepsin digestion of an antibody molecule), or Fab fragments (which can be obtained by reducing the disulphide bridges of the F(ab')$_2$ fragments. Humanized antibodies can be used when the subject is a human being.

As CD36 has several known functions, the antibody can be selected so that it inhibits all known functions of CD36, including its interaction with thrombospondin, collagens and fatty acids, or so that it inhibits only specific functions of CD36 (e.g., blocking only fatty acid and oxidised-LDL uptake). Therefore, in some embodiments, the anti-CD36 antibody blocks the CD36-mediated uptake of fatty acids and/or oxidised-LDL. In some embodiments, the anti-CD36 antibody blocks the CD36-mediated uptake of fatty acids and/or oxLDL while having little to no effect on CD36's binding to TSP-1. And in some embodiments, the anti-CD36 antibody blocks the CD36-mediated uptake of fatty acids and/or oxLDL while having no little to no effect on CD36's role as the ligand for TSP-1. In some embodiments, the anti-CD36 antibody blocks the CD36-mediated uptake of fatty acids and/or oxidised-LDL by at least about 10%, at least about 15%, at least about 20%, at least about 25%, or at least about 30% relative to untreated controls. In some embodiments, the anti-CD36 antibody blocks the CD36-mediated uptake of fatty acids and/or oxidised-LDL by at least about 17%.

When the subject to be treated is a human being, any known anti-CD36 antibody can be used or the antibody can be prepared for being administered to human beings. For antibodies that have been generated in a non-human immune system (as those used in the assays of the present application), such as in mice, humanization can be necessary to enable their administration to human beings, in order to avoid adverse reactions. Humanized antibodies are antibodies, usually monoclonal antibodies, initially generated in a non-human species and whose protein sequences have been modified to increase their similarity to antibody variants produced naturally in humans, so that minimal sequence derived from non-human immunoglobulins remain. Even after humanization, the amino acid sequence of humanized antibodies is partially distinct from antibodies occurring naturally in human beings. Several processes are known for those skilled in the art for antibody humanization, as it has been reviewed, for instance, by Almagro and Fransson (2008), including: humanizing through production of a mouse-human (mouse Fab spliced to human Fc) chimera, which chimera might be further humanized by selective alteration of the amino acid sequence of the Fab portion; insertion of one or more CDR segments of the "donor" (non-human antibody) by replacing the corresponding segments of a human antibody, which can be done using recombinant DNA techniques to create constructs capable of expression in mammalian cell culture, or even avoiding the use of non-human mammals by creating antibody gene libraries usually derived from human RNA isolated from peripheral blood and displayed by micro-organisms or viruses (as in phage display) or even cell free extracts (as in ribosome display), selection of the appropriate intermediate product (usually, antibody fragments such as Fab or scFv) and obtaining full antibodies for instance, again, recombinant DNA techniques. Several patent documents have been dedicated to humanization methods like, for instance U.S. Pat. No. 6,054,297, assigned to Genentech; U.S. Pat. Nos. 5,225,539 and 4,816,397 are also useful references, and are incorporated herein by reference in their entirety.

The method for obtaining monoclonal antibodies is well known for those skilled in the art. In general, antibodies against CD36 receptor can be raised according to known methods, such as those mentioned in classic laboratory manuals as "Antibodies: A Laboratory Manual, Second edition", edited by E. A. Greenfield in 2014, by administering CD36 whole protein or a fragment or epitope thereof to a host animal which is a different from the mammal where a therapeutic effect is sought. Monoclonal antibodies in particular can be prepared and isolated by any technique that provides for the production of antibody molecules by continuous cell lines in culture, such as the hybridoma technique originally described by Kohler and Milstein (1975), the human B-cell hybridoma technique (Cote et al., 1983), or the EBV-hybridoma technique (Cole et al., 1985). Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra). Alternatively, as commented above, Fab and/or scFv expression libraries can be constructed to allow rapid identification of fragments having the desired specificity to the CD36 receptor. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

For the design of antibodies with a particular specificity, it is advantageous to resource to annotated NCBI Reference Sequence (NC_000007.14, *Homo sapiens* annotation release: 107, which is the current release on 29 Sep. 2015)

or UniProtKB P16671, in order to choose as immunogen, if wished, a particular domain or region of the antibody to be targeted or mutated before generating the antibodies.

For achieving a therapeutic effect, the anti-CD36 antibody, which is a blocker of activity of CD36, will be administered preferably in therapeutically effective amounts. The precise determination of what would be considered an effective dose may be based on factors individual to each patient, including their size, age, cancer stage, and nature of the blocker (e.g. expression construct, antisense oligonucleotide, antibody or fragment thereof, etc.). Therefore, dosages can be readily ascertained by those of ordinary skill in the art from this disclosure and the knowledge in the art. Multiple doses can be also administered to the subject over a particular treatment period, for instance, daily, weekly, monthly, every two months, every three months, or every six months. Therapeutically effective plasma levels may also be achieved by administering multiple doses each day. In certain dose schedules, the subject receives an initial dose at a first time point that is higher than one or more subsequent or maintenance doses. For repeated administrations over several days or longer, depending on the condition, the treatment would generally be sustained until a desired effect occurs. The progress of this therapy is easily monitored by conventional techniques and assays.

Depending on the type and severity of the disease, about 1 µg/kg to 15 mg/kg (e.g. 0.1 mg/kg-10 mg/kg) of the anti-CD36 antibody can be an initial candidate dosage for administration to the patient. The dosage may be administered for example, by one or more separate administrations, or by continuous infusion. A daily dosage might range from about 1 µg/kg to 100 mg/kg or more. One exemplary dosage of the anti-CD36 antibody would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data. Dosage amount and interval may be adjusted individually to provide plasma levels of the anti-CD36 antibody which are sufficient to maintain therapeutic effect. Levels in plasma may be measured, for example, by HPLC.

An anti-CD36 antibody can be fused or conjugated (e.g., covalently or noncovalently linked) to a detectable label or substance. Examples of detectable labels or substances include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin. Such labeled antibodies can be used to detect CD36 (e.g., human CD36) protein.

Antibodies with reduced fucose content have been reported to have an increased affinity for Fc receptors, such as, e.g., FcγRIIIA. Accordingly, in certain embodiments, an antibody described herein has reduced fucose content or lacks fucose (i.e., is "afucosylated"). Such antibodies can be produced using techniques known to one skilled in the art. For example, they can be expressed in cells deficient or lacking the ability to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content. Alternatively, antibodies with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies thereof with no fucose content or reduced fucose content.

In some embodiments, the CD36 antibody has enhanced ADCC activity in vitro compared to fucosylated CD36 antibodies having the same amino acid sequence. In some embodiments, the afucosylated CD36 antibodies cause specific lysis that is at least 10, at least 15, at least 20, at least 25, at least 30, at least 35, at least 40, at least 45, at least 50, at least 60, at least 65, at least 70, or at least 75 percentage points greater than specific lysis with fucosylated CD36 antibodies.

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions. In some embodiments, the Fc domain comprises one or more amino acid substitution that reduces binding to an Fc receptor, in particular towards Fcγ receptor. In some embodiments, the Fc domain is of human IgG1 subclass with the amino acid mutations L234A, L235A and/or P329G (numbering according to Kabat EU index. In some embodiments, the Fc domain is of human IgG1 subclass with the amino acid mutations L234G, L235S, and G236R. In some embodiments, the Fc domain is of human IgG1 subclass with the amino acid mutations L234S, L235T, and G236R. In some embodiments, the Fc domain is of human IgG1 subclass with the amino acid mutations L234S, L235V, and G236R. In some embodiments, the Fc domain is of human IgG1 subclass with the amino acid mutations L234T, L235Q, and G236R. In some embodiments, the Fc domain is of human IgG1 subclass with the amino acid mutations L234T, L235T, and G236R. In some embodiments, the Fc domain is of human IgG1 subclass with the amino acid mutations L234A and L235A.

The Fc domain confers favorable pharmacokinetic properties to the antibodies of the invention, including a long serum half-life which contributes to good accumulation in the target tissue and a favorable tissue-blood distribution ratio. At the same time it may, however, lead to undesirable targeting of the antibodies of the invention to cells expressing Fc receptors rather than to the preferred antigen-bearing cells. Accordingly, in particular embodiments the Fc domain of the antibodies of the invention exhibits reduced binding affinity to an Fc receptor and/or reduced effector function, as compared to a native IgG Fc domain, in particular an IgG1 FC domain or an IgG4 Fc domain. More particularly, the Fc domain is an IgG1 FC domain.

In a particular aspect, the Fc domain is engineered to have reduced binding affinity to an Fc receptor and/or reduced effector function, as compared to a non-engineered Fc domain. In one such embodiment the Fc domain exhibits less than 50%, preferably less than 20%, more preferably less than 10% and most preferably less than 5% of the binding affinity to an Fc receptor, as compared to a native IgG1 Fc domain, and/or less than 50%, preferably less than 20%, more preferably less than 10% and most preferably less than 5% of the effector function, as compared to a native IgG1 Fc domain. In one embodiment, the Fe domain does not substantially bind to an Fe receptor and/or induce effector function. In a particular embodiment the Fc receptor is an Fcγ receptor. In one embodiment, the Fc receptor is a human Fc receptor. In one embodiment, the Fc receptor is an activating Fc receptor. In a specific embodiment, the Fc receptor is an activating human Fcγ receptor, more specifically human FcγRIIIa, FcγRI or FcγRIIa, most specifically human FcγRIIIa. In one embodiment, the Fc receptor is an inhibitory Fc receptor. In a specific embodiment, the Fc receptor is an inhibitory human Fcγ receptor, more specifically human FcγRIIIB. In one embodiment the effector function is one or more of CDC, ADCC, ADCP, and cytokine secretion. In a particular embodiment, the effector function is ADCC. In one embodiment, the Fc domain exhibits substantially similar binding affinity to neonatal Fc receptor (FcRn), as compared to a native IgG1 Fc domain. Substantially similar binding to FcRn is achieved when the Fc domain exhibits greater than about 70%, particularly greater than about 80%, more particularly greater than about 90% of the binding affinity of a native IgG1 Fc domain to FcRn. In some embodiments, binding affinity to a complement component, specifically binding affinity to C1q, is also reduced. In one aspect, binding affinity to neonatal Fc receptor (FcRn) is not reduced.

In certain embodiments the Fc domain of the antibody of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc domain comprises an amino acid substitution at one or more of positions E233, L234, L235, G236, N297, P331 and P329. In some aspects, the Fc domain comprises the amino acid substitutions L234A and L235A ("LALA"). In one such embodiment, the Fc domain is an IgG1 Fc domain, particularly a human IgG1 Fc domain. In one aspect, the Fc domain comprises an amino acid substitution at position P329. In a more specific aspect, the amino acid substitution is P329A or P329G, particularly P329G. In one embodiment the Fc domain comprises an amino acid substitution at position P329 and a further amino acid substitution selected from the group consisting of E233P, L234A, L235A, L235E, N297A, N297D or P331S. In more particular embodiments the Fc domain comprises the amino acid mutations L234A, L235A and P329G ("P329G LALA"). The "P329G LALA" combination of amino acid substitutions almost completely abolishes Fcγ receptor binding of a human IgG1 Fc domain, as described in PCT Patent Application No. WO 2012/130831 A1. Said document also describes methods of preparing such mutant Fc domains and methods for determining its properties such as Fc receptor binding or effector functions. Such an antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, Md., 1991).

In some aspects of the invention, the heavy chain constant region comprises an IgG constant region containing mutations at amino acid positions L234, L235, and/or G236. Sets of mutations that can be particularly beneficial for use with anti-CD36 antibodies include embodiments in which the heavy chain constant region comprises an IgG constant region containing a set of mutations selected from the group consisting of L234A, L235S, and G236R; L234G, L235S, and G236R; L234Q, L235S, and G236R; L234S, L235G, and G236R; L234S, L235T, and G236R; L234S, L235V, and G236R; L234T, L235Q, and G236R; L234T, L235S, and G236R; L234T, L235T, and G236R; L234A and L235A; L234A, L235A, and P329G; G236R and L328R; L234A and G237A; L234A, L235A, and G237A; L234A and L235E; L235V, F243L, R292P, Y300L, and P396L; D265A and P329A; L234A, L235A, and K322A; L234F, L235E, and P331S; L234F, L235Q, and K322Q; L234A, L235A, G237A, P238S, H268A, A330S, and P331S; E233P, L234V, L235A, G236A, A327G, A330S, and P331S; L235A and G236R; L235S and G236R; G236R; L234Q and L235S; L235G and G236R; L234Q, L235S. and A236R; L234Q and L235S; L234Q, L235S, and G236R; L234Q, L235S, and G236R; L234Q, L235S, and G236R; L234Q, L235S, G236R, M252Y, S254T, and T256E; and L234Q, L235S, G236R, T250Q, and M428L. In some embodiments, the heavy chain constant region comprises an IgG constant region containing the L234G, L235S, and G236R mutations. In some embodiments, the heavy chain constant region comprises an IgG constant region containing the L234S, L235T, and G236R mutations. In some embodiments, the heavy chain constant region comprises an IgG constant region containing the L234S, L235V, and G236R mutations. In some embodiments, the heavy chain constant region comprises an IgG constant region containing the L234T, L235Q, and G236R mutations. In some embodiments, the heavy chain constant region comprises an IgG constant region containing the L234T, L235T, and G236R mutations. In some embodiments, the heavy chain constant region comprises an IgG constant region containing the L234A and L235A mutations. In some embodiments, the heavy chain constant region comprises an IgG constant region containing the L234A, L235A, and P329G mutations.

In one aspect, the antibody of the invention comprises (all positions according to EU index of Kabat) (i) a homodimeric Fc-region of the human IgG1 subclass optionally with the mutations P329G, L234A and L235A, or (ii) a homodimeric Fc-region of the human IgG4 subclass optionally with the mutations P329G, S228P and L235E, or (iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or (iv) a heterodimeric Fc-region wherein one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C, or (v) a heterodimeric Fc-region of the human IgG1 subclass wherein both Fc-region polypeptides comprise the mutations P329G, L234A and L235A and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

In one aspect, the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)). Thus, in one aspect, provided is an antibody, comprising (all positions according to EU index of Kabat) a heterodimeric Fc-region of the human IgG4 subclass wherein both Fc-region polypeptides comprise the mutations P329G, S228P and L235E and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fe region variants.

Binding to Fe receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating antibodies comprising an Fc domain for Fc receptors may be evaluated using cell lines known to express particular Fc receptors, such as human NK cells expressing FcγIIIa receptor. Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96@ non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

Nucleotides Encoding Anti-CD36 Antibodies

In certain aspects, provided herein are polynucleotides comprising a nucleotide sequence encoding an antibody described herein or a domain thereof (e.g., a variable light chain region and/or variable heavy chain region) that immunospecifically binds to a CD36 (e.g., human CD36) antigen, and vectors, e.g., vectors comprising such polynucleotides for recombinant expression in host cells (e.g., E. coli and mammalian cells).

In particular aspects, provided herein are polynucleotides comprising nucleotide sequences encoding antibodies that immunospecifically bind to a CD36 polypeptide (e.g., human CD36) and comprise an amino acid sequence as described herein, as well as antibodies that compete with such antibodies for binding to a CD36 polypeptide (e.g., in a dose-dependent manner), or which bind to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a heavy chain comprising the VHs or CDRs of antibodies described herein. The polynucleotides can comprise nucleotide sequences encoding a light chain comprising the VLs or CDRs of antibodies described herein.

In particular embodiments, provided herein are polynucleotides comprising a nucleotide sequence encoding an anti-CD36 antibody comprising three VH chain CDRs, e.g., containing VH CDR1, VH CDR2, VH CDR3 of any one of antibodies described herein. In specific embodiments, provided herein are polynucleotides comprising three VL chain CDRs, e.g., containing VL CDR1, VL CDR2, and VL CDR3 of any one of antibodies described herein. In specific embodiments, provided herein are polynucleotides comprising a nucleotide sequence encoding an anti-CD36 antibody comprising three VH chain CDRs, e.g., containing VH CDR1, VH CDR2, and VH CDR3 of any one of antibodies described herein and three VL chain CDRs, e.g., containing VL CDR1, VL CDR2, and VL CDR3 of any one of antibodies described herein.

In particular embodiments, provided herein are polynucleotides comprising a nucleotide sequence encoding an anti-CD36 antibody or a fragment thereof comprising a VH domain, e.g., containing FR1-CDR1-FR2-CDR2-FR3-CDR3-FR4, comprising an amino acid sequence described herein. In specific embodiments, provided herein are polynucleotides comprising a nucleotide sequence encoding an anti-CD36 antibody or a fragment thereof comprising a VL domain, e.g., containing FR1-CDR1-FR2-CDR2-FR3-CDR3-FR4, comprising an amino acid sequence described herein.

Also provided herein are polynucleotides encoding an anti-CD36 antibody described herein or a domain thereof that are optimized, e.g., by codon/RNA optimization, replacement with heterologous signal sequences, and elimination of mRNA instability elements. Methods to generate optimized nucleic acids encoding an anti-CD36 antibody or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

In some embodiments, provided herein are polynucleotides encoding any of the antibodies or antibody fragments described in this application. Exemplary nucleotide sequences encoding the ONA-0-v1 antibody, ONA-0-v2 antibody, and other embodiments are provided below in Table 4.

TABLE 4

| Nucleotide Sequences | | |
|---|---|---|
| Name | SEQ ID NO: | Sequence |
| ONA-0 heavy chain | 6 | CAAGTGCAGCTGAAGCAGTCCGGAGCTGATCTGG<br>TGAGACCCGGAGCCAGCGTGAAGCTGAGCTGCAA<br>GGCCAGCGGCTACACCTTCACCGACTACTACATCA<br>ACTGGGTGAAGCAGAGGCCCGGCCAAGGACTGGA<br>GTGGATCGCTAGAATCTACCCCGGCTCCGGCAAT<br>ACATACTACAACGAGAAGTTCAAAGGCAAGGCCA<br>CACTGACCGCCGAGAAGAGCAGCAGCACCGCCTA<br>CATGCAGCTGAGCTCTCTGACCTCCGAGGACAGC<br>GCCGTGTACTTTTGCGCCAGAGGCATCGGAGGCG<br>GATTCGGCATGGATTACTGGGGCCAAGGCACCTC<br>CGTGACCGTCTCGAGCGAATCGGCCAGAAACCCC<br>ACTATCTACCCTCTGACCCTGCCTCCTGTCCTGTGT<br>TCCGACCCCGTGATCATCGGATGCCTGATCCACGA<br>CTACTTCCCTTTCGGCACCATGAACGTGACCTGGG<br>GGAAGTCGGGAAAGGACATTACTACCGTGAACTT<br>CCCACCGGCCCTGGCGTCGGGGGGTCGCTACACC<br>ATGTCCAGCCAGCTTACTCTGCCCGCTGTGGAGTG<br>CCCCGAAGGAGAGTCAGTGAAGTGCTCCGTGCAA<br>CATGACTCCAACCCGGTCCAGGAATTGGACGTCA<br>ATTGCTCCCCGACTCCGCCTCCGCCTATCACGATC<br>CCAAGCTGCCAGCCCTCCCTGAGCCTCCAGCGGCC<br>AGCCCTGGAGGATCTTCTGCTGGGCTCCGACGCCT<br>CCATTACATGCACTCTGAACGGCCTGAGAAACCCC<br>GGAAGGGGCGGCCTTTACTTGGGAGCCCTCCACC<br>GGGAAGGATGCGGTCCAGAAGAAGGCAGCCCAA<br>AATTCCTGCGGATGCTACTCAGTGTCTAGCGTGCT<br>GCCTGGTTGTGCCGAACGGTGGAACTCCGGAGCG<br>TCATTCAAGTGTACCGTGACCCACCCTGAGTCCGG<br>AACTCTGACCGGCACCATCGCCAAGGTCACCGTG<br>AACACCTTTCCGCCACAAGTGCACCTCCTGCCGCC<br>GCCGTCGGAGGAACTCGCTCTGAACGAGTTGCTCT<br>CGCTGACTTGTCTCGTGCGCGCCTTCAACCCTAAG<br>GAGGTGCTCGTGCGCTGGCTGCATGGCAACGAAG<br>AACTGTCCCCCGAATCGTACCTGGTGTTCGAACCG<br>CTGAAAGAGCCCGGAGAGGGTGCAACCACCTACC<br>TTGTGACGAGCGTGCTCCGGGTGTCCGCCGAAAC<br>CTGGAAGCAGGGCGACCAGTACAGCTGCATGGTC<br>GGCCACGAGGCCCTCCCCATGAACTTCACTCAGA<br>AAACCATTGATAGGTTGTCGGAAAGCCCACCAA<br>CGTGTCAGTGTCCGTGATTATGAGCGAAGGAGAT<br>GGAATCTGCTAT |

TABLE 4-continued

| Nucleotide Sequences | | |
| --- | --- | --- |
| Name | SEQ ID NO: | Sequence |
| ONA-0-v1 light chain | 8 | TCCATCGTGATGACCCAGACCCCCAAGTTTCTGCT<br>GGTGTCCGCCGGAGACAGAATCACCATCACATGC<br>AAGGCCAGCCAGAGCGTGAGCGATGACGTGGCTT<br>GGTACCAGCAGAAGCCCGGCCAGAGCCCTAAGCT<br>GCTGATCTACTACGCCAGCAATAGATACACCGGA<br>GTGCCCGATAGATTCACCGGCAGCGGCTACGGCA<br>CCGACTTCACCTTCACAATCTCCACCGTGCAAGCC<br>GAGGATCTGGCCGTGTACTTCTGTCAGCAAGACTA<br>CTCCAGCCCTCTGACCTTCGGAGCCGGCACCAAGC<br>TCGAGATCAAGCGCGCAGATGCTGCTCCTACCGT<br>GAGCATCTTCCCGCCGTCCAGCGAACAACTCACTA<br>GCGGAGGCGCGTCAGTGGTCTGCTTCCTTAACAAT<br>TTCTACCCTAAGGACATCAACGTCAAGTGGAAGA<br>TTGACGGATCGGAACGCCAGAACGGAGTGCTGAA<br>CTCATGGACTGATCAGGATTCCAAAGACTCGACTT<br>ACTCCATGTCCAGCACCCTGACCCTGACCAAAGA<br>CGAGTACGAAAGGCACAACTCGTACACGTGCGAA<br>GCCACCCACAAGACTTCCACCTCGCCCATCGTGAA<br>GTCCTTCAATCGCAATGAGTGC |
| ONA-0-v2 light chain | 10 | AACATCGTGATGACCCAAAGCCCCAAGAGCATGA<br>GCATGTCCGTGGGCGAGAGAGTGACACTGACATG<br>CAAGGCCAGCGAGAACGTGGTGACCTACGTGAGC<br>TGGTACCAGCAGAAGCCCGAACAGAGCCCTAAGC<br>TGCTGATCTACGGAGCCTCCAATAGATATACCGGC<br>GTGCCCGACAGATTCACCGGCAGCGGCAGCGCCA<br>CCGATTTCACACTGACCATCAGCAGCGTGCAAGC<br>CGAGGATCTGGCTGACTACCACTGCGGCCAAGGC<br>TACAGCTACCCCTACACCTTCGGCGGCGGCACCA<br>AGCTCGAGATCAAGCGCGCAGATGCTGCTCCTAC<br>CGTGAGCATCTTCCCGCCGTCCAGCGAACAACTCA<br>CTAGCGGAGGCGCGTCAGTGGTCTGCTTCCTTAAC<br>AATTTCTACCCTAAGGACATCAACGTCAAGTGGA<br>AGATTGACGGATCGGAACGCCAGAACGGAGTGCT<br>GAACTCATGGACTGATCAGGATTCCAAAGACTCG<br>ACTTACTCCATGTCCAGCACCCTGACCCTGACCAA<br>AGACGAGTACGAAAGGCACAACTCGTACACGTGC<br>GAAGCCACCCACAAGACTTCCACCTCGCCCATCGT<br>GAAGTCCTTCAATCGCAATGAGTGC |
| ONA-0-v1 VH | 12 | CAAGTGCAGCTGAAGCAGTCCGGGAGCTGATCTGG<br>TGAGACCCGGAGCCAGCGTGAAGCTGAGCTGCAA<br>GGCCAGCGGCTACACCTTCACCGACTACTACATCA<br>ACTGGGTGAAGCAGAGGCCCGGCCAAGGACTGGA<br>GTGGATCGCTAGAATCTACCCCGGCTCCGGCAAT<br>ACATACTACAACGAGAAGTTCAAAGGCAAGGCCA<br>CACTGACCGCCGAGAAGAGCAGCAGCACCGCCTA<br>CATGCAGCTGAGCTCTCTGACCTCCGAGGACAGC<br>GCCGTGTACTTTTGCGCCAGAGGCATCGGAGGCG<br>GATTCGGCATGGATTACTGGGGCCAAGGCACCTC<br>CGTGACCGTCTCGAGC |
| ONA-0-v1 VL | 14 | TCCATCGTGATGACCCAGACCCCCAAGTTTCTGCT<br>GGTGTCCGCCGGAGACAGAATCACCATCACATGC<br>AAGGCCAGCCAGAGCGTGAGCGATGACGTGGCTT<br>GGTACCAGCAGAAGCCCGGCCAGAGCCCTAAGCT<br>GCTGATCTACTACGCCAGCAATAGATACACCGGA<br>GTGCCCGATAGATTCACCGGCAGCGGCTACGGCA<br>CCGACTTCACCTTCACAATCTCCACCGTGCAAGCC<br>GAGGATCTGGCCGTGTACTTCTGTCAGCAAGACTA<br>CTCCAGCCCTCTGACCTTCGGAGCCGGCACCAAGC<br>TCGAGATCAAG |
| ONA-0-v2 VL | 16 | AACATCGTGATGACCCAAAGCCCCAAGAGCATGA<br>GCATGTCCGTGGGCGAGAGAGTGACACTGACATG<br>CAAGGCCAGCGAGAACGTGGTGACCTACGTGAGC<br>TGGTACCAGCAGAAGCCCGAACAGAGCCCTAAGC<br>TGCTGATCTACGGAGCCTCCAATAGATATACCGGC<br>GTGCCCGACAGATTCACCGGCAGCGGCAGCGCCA<br>CCGATTTCACACTGACCATCAGCAGCGTGCAAGC<br>CGAGGATCTGGCTGACTACCACTGCGGCCAAGGC<br>TACAGCTACCCCTACACCTTCGGCGGCGGCACCA<br>AGCTCGAGATCAAG |
| 1G04 heavy chain | 22 | CAAGTGCAGCTGAAGCAGTCCGGAGCTGATCTGG<br>TGAGACCCGGAGCCAGCGTGAAGCTGAGCTGCAA |

TABLE 4-continued

Nucleotide Sequences

| Name | SEQ ID NO: | Sequence |
|------|-----------|----------|
| | | GGCCAGCGGCTACACCTTCACCGACTACTACATCA |
| | | ACTGGGTGAAGCAGAGGCCCGGCCAAGGACTGGA |
| | | GTGGATCGCTAGAATCTACCCCGGCTCCGGCAAT |
| | | ACATACTACAACGAGAAGTTCAAAGGCAAGGCCA |
| | | CACTGACCGCCGAGAAGAGCAGCAGCACCGCCTA |
| | | CATGCAGCTGAGCTCTCTGACCTCCGAGGACAGC |
| | | GCCGTGTACTTTTGCGCCAGAGGCATCGGAGGCG |
| | | GATTCGGCATGGATTACTGGGGCCAAGGCACCTC |
| | | CGTGACCGTCTCGAGCGCCAGCACCAAAGGTCCA |
| | | TCCGTGTTTCCGCTCGCCCCGTCCTCAAAGTCGAC |
| | | CTCCGGAGGCACTGCCGCCCTGGGCTGCCTTGTCA |
| | | AGGACTATTTCCCCGAACCTGTCACGGTGTCCTGG |
| | | AACAGCGGCGCTCTGACTTCCGGAGTGCACACCTT |
| | | CCCCGCCGTCCTGCAATCCAGCGGCCTGTACTCAC |
| | | TGTCATCCGTTGTGACTGTCCCGTCGTCCAGCCTG |
| | | GGAACCCAAACCTACATTTGCAACGTGAATCACA |
| | | AACCATCGAATACCAAGGTCGATAAGAAAGTCGA |
| | | GCCGAAGTCATGCGACAAGACTCACACCTGTCCG |
| | | CCTTGCCCGGCGCCAGAAGCGGCCGGCGGCCCTT |
| | | CGGTGTTTTTGTTTCCGCCGAAGCCGAAGGACACT |
| | | CTGATGATCTCACGCACTCCAGAGGTGACTTGCGT |
| | | GGTGGTCGATGTTTCGCACGAGGACCCGGAAGTG |
| | | AAATTCAACTGGTATGTCGACGGGGTGGAAGTGC |
| | | ATAATGCCAAGACGAAGCCGAGGGAGGAACAGT |
| | | ACAACTCCACCTACAGAGTGGTTTCAGTCCTTACC |
| | | GTCCTCCATCAAGATTGGCTGAACGGAAAGGAGT |
| | | ACAAATGTAAGGTGTCGAACAAAGCGTTGCCGGC |
| | | CCCTATCGAAAAGACTATCAGCAAGGCCAAAGGA |
| | | CAGCCGCGGGAGCCGCAAGTGTACACCCTCCCGC |
| | | CTTCGCGGGACGAGCTGACCAAGAATCAGGTGTC |
| | | CCTTACTTGCCTGGTGAAGGGATTCTACCCCTCGG |
| | | ATATCGCAGTCGAATGGGAATCGAATGGACAGCC |
| | | AGAAAACAACTACAAGACCACTCCCCCGGTGCTC |
| | | GACTCCGACGGTTCCTTCTTCCTGTACTCGAAGCT |
| | | GACCGTGGACAAATCACGCTGGCAGCAGGGAAAC |
| | | GTGTTTAGCTGCAGCGTGATGCATGAGGCGCTGC |
| | | ATAATCACTACACCCAGAAGTCACTCTCGCTCAGC |
| | | CCAGGGAAG |
| 1G04 light chain | 24 | TCCATCGTGATGACCCAGACCCCCAAGTTTCTGCT |
| | | GGTGTCCGCCGGAGACAGAATCACCATCACATGC |
| | | AAGGCCAGCCAGAGCGTGAGCGATGACGTGGCTT |
| | | GGTACCAGCAGAAGCCCGGCCAGAGCCCTAAGCT |
| | | GCTGATCTACTACGCCAGCAATAGATACACCGGA |
| | | GTGCCCGATAGATTCACCGGCAGCGGCTACGGCA |
| | | CCGACTTCACCTTCACAATCTCCACCGTGCAAGCC |
| | | GAGGATCTGGCCGTGTACTTCTGTCAGCAAGACTA |
| | | CTCCAGCCCTCTGACCTTCGGAGCCGGCACCAAGC |
| | | TCGAGATCAAGAGAACTGTGGCCGCGCCGTCAGT |
| | | GTTTATCTTCCCTCCATCGGATGAACAGCTTAAGT |
| | | CCGGCACGGCGTCTGTGGTCTGCCTGCTCAATAAC |
| | | TTTTACCCTAGGGAAGCTAAAGTCCAATGGAAAG |
| | | TGGATAACGCCCTGCAGTCAGGAAACAGCCAGGA |
| | | ATCGGTTACCGAACAGGACAGCAAGGACAGCACT |
| | | TACTCCTTGTCGTCGACTCTTACTCTGAGCAAGGC |
| | | CGATTACGAGAAGCACAAGGTCTACGCCTGCGAG |
| | | GTCACCCATCAGGGACTCTCGTCCCCGGTGACCAA |
| | | ATCCTTCAATAGAGGCGAATGC |
| ONA-0-v2 ch IgG1 LALA light chain | 26 | AACATCGTGATGACCCAAAGCCCCAAGAGCATGA |
| | | GCATGTCCGTGGGCGAGAGAGTGACACTGACATG |
| | | CAAGGCCAGCGAGAACGTGGTGACCTACGTGAGC |
| | | TGGTACCAGCAGAAGCCCGAACAGAGCCCTAAGC |
| | | TGCTGATCTACGGAGCCTCCAATAGATATACCGGC |
| | | GTGCCCGACAGATTCACCGGCAGCGGCAGCGCCA |
| | | CCGATTTCACACTGACCATCAGCAGCGTGCAAGC |
| | | CGAGGATCTGGCTGACTACCACTGCGGCCAAGGC |
| | | TACAGCTACCCCTACACCTTCGGCGGCGGCACCA |
| | | AGCTCGAGATCAAGAGAACTGTGGCCGCGCCGTC |
| | | AGTGTTTATCTTCCCTCCATCGGATGAACAGCTTA |
| | | AGTCCGGCACGGCGTCTGTGGTCTGCCTGCTCAAT |
| | | AACTTTTACCCTAGGGAAGCTAAAGTCCAATGGA |
| | | AAGTGGATAACGCCCTGCAGTCAGGAAACAGCCA |
| | | GGAATCGGTTACCGAACAGGACAGCAAGGACAGC |
| | | ACTTACTCCTTGTCGTCGACTCTTACTCTGAGCAA |
| | | GGCCGATTACGAGAAGCACAAGGTCTACGCCTGC |

TABLE 4-continued

Nucleotide Sequences

| Name | SEQ ID NO: | Sequence |
|------|-----------|----------|
| | | GAGGTCACCCATCAGGGACTCTCGTCCCCGGTGA |
| | | CCAAATCCTTCAATAGAGGCGAATGC |

A polynucleotide encoding an antibody described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In certain embodiments, the polynucleotide is a cDNA or a DNA lacking one more endogenous introns. In certain embodiments, a polynucleotide is a non-naturally occurring polynucleotide. In certain embodiments, a polynucleotide is recombinantly produced. In certain embodiments, the poly-nucleotides are isolated. In certain embodiments, the poly-nucleotides are substantially pure. In certain embodiments, a polynucleotide is purified from natural components.

Antibody Production

Antibodies that immunospecifically bind to CD36 (e.g., human CD36) can be produced by any method known in the art for the synthesis of full length antibodies or antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucle-otides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody that immunospecifically binds to CD36 (e.g., human CD36) comprising culturing a cell or host cell described herein. In a certain aspect, provided herein is a method of making an antibody which immunospecifically binds to CD36 (e.g., human CD36) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucle-otides have been introduced into the cell. In a particular embodiment, the method further comprises the step of purifying the antibody obtained from the cell or host cell.

Pharmaceutical Compositions

Provided herein are compositions comprising an anti-CD36 antibody described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed.

In various embodiments, compositions comprising an anti-CD36 antibody are provided in formulations with a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)).

Pharmaceutical compositions described herein can be useful in blocking CD36 activity. Pharmaceutical compositions described herein can be useful in treating a condition such as cancer. Examples of cancer that can be treated in accordance with the methods described herein include, but are not limited to, solid cancers and metastases thereof. In some embodiments, the pharmaceutical compositions described herein can be useful in treating an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma. In some embodiments, the pharmaceutical compositions described herein can be useful in treating metastases developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma. In some embodiments, the pharmaceutical compositions described herein can be useful in treating both the primary tumor and metastases developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

The pharmaceutical compositions described herein are in one embodiment for use as a medicament. The pharmaceutical compositions described herein are in one embodiment for use as a diagnostic, e.g., to detect the presence of CD36 in a sample obtained from a patient (e.g., a human patient).

The compositions to be used for in vivo administration can be sterile. This is readily accomplished by filtration through, e.g., sterile filtration membranes.

In some embodiments, the pharmaceutical compositions comprise an isolated antibody. In some embodiments, the pharmaceutical compositions are substantially free of other antibodies. In some embodiments, the pharmaceutical compositions are substantially free of the ONA-0-v2 antibody.

In some embodiments, pharmaceutical compositions are provided, wherein the pharmaceutical composition comprises anti-CD36 antibodies described herein and a pharmaceutically acceptable carrier. In some embodiments, pharmaceutical compositions are provided, wherein the pharmaceutical composition comprises afucosylated anti-CD36 antibodies described herein and a pharmaceutically acceptable carrier.

In specific embodiments, such pharmaceutical composition comprises afucosylated anti-CD36 antibodies e.g., wherein at least 80% of the antibodies in the composition are afucosylated. Antibodies with Fc regions having reduced fucose content in glycan moieties may exhibit higher ADCC activity compared to a fully fucosylated antibody because of an increased affinity for Fc receptors, such as, e.g., FcγRIIIA (Niwa R et al., Clinical Cancer Research 11(6):2327-36 (2005)). In some embodiments, the CD36 antibody has enhanced ADCC activity in vitro compared to fucosylated CD36 antibodies having the same amino acid sequence. In specific embodiments, such pharmaceutical composition comprises afucosylated anti-CD36 antibodies e.g., wherein at least 50% of the antibodies in the composition are afucosylated. In specific embodiments, such pharmaceutical composition comprises afucosylated anti-CD36 antibodies e.g., wherein at least 60% of the antibodies in the composition are afucosylated. In specific embodiments, such pharmaceutical composition comprises afucosylated anti-CD36 antibodies e.g., wherein at least 70% of the antibodies in the composition are afucosylated. In specific embodiments, such pharmaceutical composition comprises afucosylated anti-CD36 antibodies e.g., wherein at least 80% of the antibodies in the composition are afucosylated. In specific embodiments, such pharmaceutical composition comprises afucosylated anti-CD36 antibodies e.g., wherein at least 85% of the antibodies in the composition are afucosylated. In specific embodiments, such pharmaceutical composition comprises afucosylated anti-CD36 antibodies e.g., wherein at least 90% of the antibodies in the composition are afucosylated. In specific embodiments, such pharmaceutical composition comprises afucosylated anti-CD36 antibodies e.g., wherein at least 95% of the antibodies in the composition are afucosylated. In specific embodiments, such pharmaceutical composition comprises afucosylated anti-CD36 antibodies e.g., wherein at least 96% of the antibodies in the composition are afucosylated. In specific embodiments, such pharmaceutical composition comprises afucosylated anti-CD36 antibodies e.g., wherein at least 97% of the antibodies in the composition are afucosylated. In specific embodiments, such pharmaceutical composition comprises afucosylated anti-CD36 antibodies e.g., wherein at least 98% of the antibodies in the composition are afucosylated. In specific embodiments, such pharmaceutical composition comprises afucosylated anti-CD36 antibodies e.g., wherein at least 99% of the antibodies in the composition are afucosylated. In specific embodiments, such pharmaceutical composition comprises afucosylated anti-CD36 antibodies wherein fucose is undetectable in the composition.

Methods of the Disclosure

In some embodiments, the present invention provides methods of treating cancer in a mammal using a combination of an anti-CD36 antibody and a second therapy. In some embodiments, the cancer is selected from the group consisting of oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, and lymphoma. In embodiments, the cancer is oral squamous cell carcinoma. In some embodiments, the cancer is ovarian cancer. In other embodiments, the cancer is melanoma. In a further embodiment, the cancer is any cancer disclosed herein. In some embodiments, the cancer is metastatic cancer. In some embodiments, the cancer is both a primary tumor and metastatic cancer. In some embodiments, the mammal is a human.

In some embodiments, the anti-CD36 antibody is a full length antibody, a single chain antibody, or a scFv, Fab or F(ab')₂ fragment. In one embodiment, the CD36 inhibitor is an antibody. In an embodiment, the CD36 inhibitor is a humanized antibody. In certain embodiments, the CD36 inhibitor is an antibody disclosed herein. In certain embodiments, the CD36 inhibitor is a commercial anti-CD36 antibody, such as the antibody JC63.1. In one embodiment, the CD36 inhibitor is a shRNA or an iRNA, a siRNA, or an antisense RNA or DNA.

In some embodiments, the second therapy is an immunotherapy. In one embodiment, the immunotherapy is a PD-1 inhibitor. In an embodiment, the PD-1 inhibitor is an ant-PD-1 antibody. In one embodiment, the anti-PD-1 antibody is pembrolizumab (KEYTRUDA; MK-3475), pidilizumab (CT-011), or nivolumab (OPDIVO; BMS-936558). In an embodiment, the immunotherapy is a PD-L1 inhibitor. In one embodiment, PD-L1 inhibitor is an anti-PD-L1 antibody. In an embodiment, the anti-PD-L1 antibody is atezolizumab (Tecentriq or RG7446), durvalumab (Imfinzi or MEDI4736), avelumab (Bavencio) or BMS-936559 In one embodiment, the immunotherapy is a CTLA-4 inhibitor. In an embodiment, the CTLA-4 inhibitor is an anti-CTLA-4 antibody. In one embodiment, the anti-CTLA-4 antibody is ipilimmab or an antigen-binding fragment thereof.

In one embodiment, the second therapy is a chemotherapeutic agent. In an embodiment, the chemotherapeutic agent is cisplatin. In certain embodiments, the chemotherapeutic agent comprises one of the anti-cancer drugs or anti-cancer drug combinations listed in Table 5.

TABLE 5

| Chemotherapeutic Agents | | | |
| --- | --- | --- | --- |
| Abemaciclib | Abiraterone Acetate | Abraxane (Paclitaxel Albumin-stabilized Nanoparticle Formulation) | ABVD |
| ABVE | ABVE-PC | AC | Acalabrutinib |
| AC-T | Actemra (Tocilizumab) | Adcetris (Brentuximab Vedotin) | ADE |

TABLE 5-continued

| Chemotherapeutic Agents | | | |
| --- | --- | --- | --- |
| Abemaciclib | Abiraterone Acetate | Abraxane (Paclitaxel Albumin-stabilized Nanoparticle Formulation) | ABVD |
| Ado-Trastuzumab Emtansine | Adriamycin (Doxorubicin Hydrochloride) | Afatinib Dimaleate | Afinitor (Everolimus) |
| Akynzeo (Netupitant and Palonosetron Hydrochloride) | Aldara (Imiquimod) | Aldesleukin | Alecensa (Alectinib) |
| Alectinib | Alemtuzumab | Alimta (Pemetrexed Disodium) | Aliqopa (Copanlisib Hydrochloride) |
| Alkeran for Injection (Melphalan Hydrochloride) | Alkeran Tablets (Melphalan) | Aloxi (Palonosetron Hydrochloride) | Alunbrig (Brigatinib) |
| Ameluz (Aminolevulinic Acid) | Amifostine | Aminolevulinic Acid | Anastrozole |
| Apalutamide | Aprepitant | Aranesp (Darbepoetin Alfa) | Aredia (Pamidronate Disodium) |
| Arimidex (Anastrozole) | Aromasin (Exemestane) | Arranon (Nelarabine) | Arsenic Trioxide |
| Arzerra (Ofatumumab) | Asparaginase Erwinia chrysanthemi | Atezolizumab | Avastin (Bevacizumab) |
| Avelumab | Axicabtagene Ciloleucel | Axitinib | Azacitidine |
| Azedra (Iobenguane I 131) | Bavencio (Avelumab) | BEACOPP | Beleodaq (Belinostat) |
| Belinostat | Bendamustine Hydrochloride | Bendeka (Bendamustine Hydrochloride) | BEP |
| Besponsa (Inotuzumab Ozogamicin) | Bevacizumab | Bexarotene | Bicalutamide |
| BiCNU (Carmustine) | Binimetinib | Bleomycin | Blinatumomab |
| Blincyto (Blinatumomab) | Bortezomib | Bosulif (Bosutinib) | Bosutinib |
| Braftovi (Encorafenib) | Brentuximab Vedotin | Brigatinib | BuMel |
| Busulfan | Busulfex (Busulfan) | Cabazitaxel | Cabometyx (Cabozantinib-S-Malate) |
| Cabozantinib-S-Malate | CAF | Calquence (Acalabrutinib) | Campath (Alemtuzumab) |
| Camptosar (Irinotecan Hydrochloride) | Capecitabine | CAPOX | Carac (Fluorouracil - - - Topical) |
| Carboplatin | CARBOPLATIN-TAXOL | Carfilzomib | Carmustine |
| Carmustine Implant | Casodex (Bicalutamide) | CEM | Cemiplimab-rwlc |
| Ceritinib | Cerubidine (Daunorubicin Hydrochloride) | Cervarix (Recombinant HPV Bivalent Vaccine) | Cetuximab |
| CEV | Chlorambucil | CHLORAMBUCIL-PREDNISONE | CHOP |
| Cisplatin | Cladribine | Clofarabine | Clolar (Clofarabine) |
| CMF | Cobimetinib | Cometriq (Cabozantinib-S-Malate) | Copanlisib Hydrochloride |
| COPDAC | Copiktra (Duvelisib) | COPP | COPP-ABV |
| Cosmegen (Dactinomycin) | Cotellic (Cobimetinib) | Crizotinib | CVP |
| Cyclophosphamide | Cyramza (Ramucirumab) | Cytarabine | Cytarabine Liposome |
| Cytosar-U (Cytarabine) | Dabrafenib | Dacarbazine | Dacogen (Decitabine) |

TABLE 5-continued

| Chemotherapeutic Agents | | | |
|---|---|---|---|
| Abemaciclib | Abiraterone Acetate | Abraxane (Paclitaxel Albumin-stabilized Nanoparticle Formulation) | ABVD |
| Dacomitinib | Dactinomycin | Daratumumab | Darbepoetin Alfa |
| Darzalex (Daratumumab) | Dasatinib | Daunorubicin Hydrochloride | Daunorubicin Hydrochloride and Cytarabine Liposome |
| Decitabine | Defibrotide Sodium | Defitelio (Defibrotide Sodium) | Degarelix |
| Denileukin Diftitox | Denosumab | DepoCyt (Cytarabine Liposome) | Dexamethasone |
| Dexrazoxane Hydrochloride | Dinutuximab | Docetaxel | Doxil (Doxorubicin Hydrochloride Liposome) |
| Doxorubicin Hydrochloride | Doxorubicin Hydrochloride Liposome | Dox-SL (Doxorubicin Hydrochloride Liposome) | Durvalumab |
| Duvelisib | Efudex (Fluorouracil - - - Topical) | Eligard (Leuprolide Acetate) | Elitek (Rasburicase) |
| Ellence (Epirubicin Hydrochloride) | Elotuzumab | Eloxatin (Oxaliplatin) | Eltrombopag Olamine |
| Emend (Aprepitant) | Empliciti (Elotuzumab) | Enasidenib Mesylate | Encorafenib |
| Enzalutamide | Epirubicin Hydrochloride | EPOCH | Epoetin Alfa |
| Epogen (Epoetin Alfa) | Erbitux (Cetuximab) | Eribulin Mesylate | Erivedge (Vismodegib) |
| Erleada (Apalutamide) | Erlotinib Hydrochloride | Erwinaze (Asparaginase Erwinia chrysanthemi) | Ethyol (Amifostine) |
| Etopophos (Etoposide Phosphate) | Etoposide | Etoposide Phosphate | Evacet (Doxorubicin Hydrochloride Liposome) |
| Everolimus | Evista (Raloxifene Hydrochloride) | Evomela (Melphalan Hydrochloride) | Exemestane |
| 5-FU (Fluorouracil Injection) | 5-FU (Fluorouracil - - - Topical) | Fareston (Toremifene) | Farydak (Panobinostat) |
| Faslodex (Fulvestrant) | FEC | Femara (Letrozole) | Filgrastim |
| Firmagon (Degarelix) | Fludarabine Phosphate | Fluoroplex (Fluorouracil - - - Topical) | Fluorouracil Injection |
| Fluorouracil - - - Topical | Flutamide | FOLFIRI | FOLFIRI-BEVACIZUMAB |
| FOLFIRI-CETUXIMAB | FOLFIRINOX | FOLFOX | Folotyn (Pralatrexate) |
| Fostamatinib Disodium | FU-LV | Fulvestrant | Fusilev (Leucovorin Calcium) |
| Gardasil (Recombinant HPV Quadrivalent Vaccine) | Gardasil 9 (Recombinant HPV Nonavalent Vaccine) | Gazyva (Obinutuzumab) | Gefitinib |
| Gemcitabine Hydrochloride | GEMCITABINE-CISPLATIN | GEMCITABINE-OXALIPLATIN | Gemtuzumab Ozogamicin |
| Gemzar (Gemcitabine Hydrochloride) | Gilotrif (Afatinib Dimaleate) | Gleevec (Imatinib Mesylate) | Gliadel Wafer (Carmustine Implant) |
| Glucarpidase | Goserelin Acetate | Granisetron | Granisetron Hydrochloride |
| Granix (Filgrastim) | Halaven (Eribulin Mesylate) | Hemangeol (Propranolol Hydrochloride) | Herceptin (Trastuzumab) |
| HPV Bivalent Vaccine, Recombinant | HPV Nonavalent Vaccine, Recombinant | HPV Quadrivalent Vaccine, Recombinant | Hycamtin (Topotecan Hydrochloride) |
| Hydrea (Hydroxyurea) | Hydroxyurea | Hyper-CVAD | Ibrance (Palbociclib) |
| Ibritumomab Tiuxetan | Ibrutinib | ICE | Iclusig (Ponatinib Hydrochloride) |
| Idarubicin Hydrochloride | Idelalisib | Idhifa (Enasidenib Mesylate) | Ifex (Ifosfamide) |
| Ifosfamide | IL-2 (Aldesleukin) | Imatinib Mesylate | Imbruvica (Ibrutinib) |

TABLE 5-continued

| Chemotherapeutic Agents | | | |
| --- | --- | --- | --- |
| Abemaciclib | Abiraterone Acetate | Abraxane (Paclitaxel Albumin-stabilized Nanoparticle Formulation) | ABVD |
| Imfinzi (Durvalumab) | Imiquimod | Imlygic (Talimogene Laherparepvec) | Inlyta (Axitinib) |
| Inotuzumab Ozogamicin | Interferon Alfa-2b, Recombinant | Interleukin-2 (Aldesleukin) | Intron A (Recombinant Interferon Alfa-2b) |
| Iobenguane I 131 | Ipilimumab | Iressa (Gefitinib) | Irinotecan Hydrochloride |
| Irinotecan Hydrochloride Liposome | Istodax (Romidepsin) | Ivosidenib | Ixabepilone |
| Ixazomib Citrate | Ixempra (Ixabepilone) | Jakafi (Ruxolitinib Phosphate) | JEB |
| Jevtana (Cabazitaxel) | Kadcyla (Ado-Trastuzumab Emtansine) | Kepivance (Palifermin) | Keytruda (Pembrolizumab) |
| Kisqali (Ribociclib) | Kymriah (Tisagenlecleucel) | Kyprolis (Carfilzomib) | Lanreotide Acetate |
| Lapatinib Ditosylate | Larotrectinib Sulfate | Lartruvo (Olaratumab) | Lenalidomide |
| Lenvatinib Mesylate | Lenvima (Lenvatinib Mesylate) | Letrozole | Leucovorin Calcium |
| Leukeran (Chlorambucil) | Leuprolide Acetate | Levulan Kerastik (Aminolevulinic Acid) | Libtayo (Cemiplimab-rwlc) |
| LipoDox (Doxorubicin Hydrochloride Liposome) | Lomustine | Lonsurf (Trifluridine and Tipiracil Hydrochloride) | Lorbrena (Lorlatinib) |
| Lorlatinib | Lumoxiti (Moxetumomab Pasudotox-tdfk) | Lupron (Leuprolide Acetate) | Lupron Depot (Leuprolide Acetate) |
| Lutathera (Lutetium Lu 177-Dotatate) | Lutetium (Lu 177-Dotatate) | Lynparza (Olaparib) | Marqibo (Vincristine Sulfate Liposome) |
| Matulane (Procarbazine Hydrochloride) | Mechlorethamine Hydrochloride | Megestrol Acetate | Mekinist (Trametinib) |
| Mektovi (Binimetinib) | Melphalan | Melphalan Hydrochloride | Mercaptopurine |
| Mesna | Mesnex (Mesna) | Methotrexate | Methylnaltrexone Bromide |
| Midostaurin | Mitomycin C | Mitoxantrone Hydrochloride | Mogamulizumab-kpkc |
| Moxetumomab Pasudotox-tdfk | Mozobil (Plerixafor) | Mustargen (Mechlorethamine Hydrochloride) | MVAC |
| Myleran (Busulfan) | Mylotarg (Gemtuzumab Ozogamicin) | Nanoparticle Paclitaxel (Paclitaxel Albumin-stabilized Nanoparticle Formulation) | Navelbine (Vinorelbine Tartrate) |
| Necitumumab | Nelarabine | Neratinib Maleate | Nerlynx (Neratinib Maleate) |
| Netupitant and Palonosetron Hydrochloride | Neulasta (Pegfilgrastim) | Neupogen (Filgrastim) | Nexavar (Sorafenib Tosylate) |
| Nilandron (Nilutamide) | Nilotinib | Nilutamide | Ninlaro (Ixazomib Citrate) |
| Niraparib Tosylate Monohydrate | Nivolumab | Nplate (Romiplostim) | Obinutuzumab |
| Odomzo (Sonidegib) | OEPA | Ofatumumab | OFF |
| Olaparib | Olaratumab | Omacetaxine Mepesuccinate | Oncaspar (Pegaspargase) |
| Ondansetron Hydrochloride | Onivyde (Irinotecan Hydrochloride Liposome) | Ontak (Denileukin Diftitox) | Opdivo (Nivolumab) |

TABLE 5-continued

| Chemotherapeutic Agents | | | |
|---|---|---|---|
| Abemaciclib | Abiraterone Acetate | Abraxane (Paclitaxel Albumin-stabilized Nanoparticle Formulation) | ABVD |
| OPPA | Osimertinib | Oxaliplatin | Paclitaxel |
| Paclitaxel Albumin-stabilized Nanoparticle Formulation | PAD | Palbociclib | Palifermin |
| Palonosetron Hydrochloride | Palonosetron Hydrochloride and Netupitant | Pamidronate Disodium | Panitumumab |
| Panobinostat | Pazopanib Hydrochloride | PCV | PEB |
| Pegaspargase | Pegfilgrastim | Peginterferon Alfa-2b | PEG-Intron (Peginterferon Alfa-2b) |
| Pembrolizumab | Pemetrexed Disodium | Perjeta (Pertuzumab) | Pertuzumab |
| Plerixafor | Pomalidomide | Pomalyst (Pomalidomide) | Ponatinib Hydrochloride |
| Portrazza (Necitumumab) | Poteligeo (Mogamulizumab-kpkc) | Pralatrexate | Prednisone |
| Procarbazine Hydrochloride | Procrit (Epoetin Alfa) | Proleukin (Aldesleukin) | Prolia (Denosumab) |
| Promacta (Eltrombopag Olamine) | Propranolol Hydrochloride | Provenge (Sipuleucel-T) | Purinethol (Mercaptopurine) |
| Purixan (Mercaptopurine) | Radium 223 Dichloride | Raloxifene Hydrochloride | Ramucirumab |
| Rasburicase | R-CHOP | R-CVP | Recombinant Human Papillomavirus (HPV) Bivalent Vaccine |
| Recombinant Human Papillomavirus (HPV) Nonavalent Vaccine | Recombinant Human Papillomavirus (HPV) Quadrivalent Vaccine | Recombinant Interferon Alfa-2b | Regorafenib |
| Relistor (Methylnaltrexone Bromide) | R-EPOCH | Retacrit (Epoetin Alfa) | Revlimid (Lenalidomide) |
| Rheumatrex (Methotrexate) | Ribociclib | R-ICE | Rituxan (Rituximab) |
| Rituxan Hycela (Rituximab and Hyaluronidase Human) | Rituximab | Rituximab and Hyaluronidase Human | Rolapitant Hydrochloride |
| Romidepsin | Romiplostim | Rubidomycin (Daunorubicin Hydrochloride) | Rubraca (Rucaparib Camsylate) |
| Rucaparib Camsylate | Ruxolitinib Phosphate | Rydapt (Midostaurin) | Sancuso (Granisetron) |
| Sclerosol Intrapleural Aerosol (Talc) | Siltuximab | Sipuleucel-T | Somatuline Depot (Lanreotide Acetate) |
| Sonidegib | Sorafenib Tosylate | Sprycel (Dasatinib) | STANFORD V |
| Sterile Talc Powder (Talc) | Steritalc (Talc) | Stivarga (Regorafenib) | Sunitinib Malate |
| Sustol (Granisetron) | Sutent (Sunitinib Malate) | Sylatron (Peginterferon Alfa-2b) | Sylvant (Siltuximab) |
| Synribo (Omacetaxine Mepesuccinate) | Tabloid (Thioguanine) | TAC | Tafinlar (Dabrafenib) |
| Tagrisso (Osimertinib) | Talc | Talimogene Laherparepvec | Tamoxifen Citrate |
| Tarabine PFS (Cytarabine) | Tarceva (Erlotinib Hydrochloride) | Targretin (Bexarotene) | Tasigna (Nilotinib) |
| Tavalisse (Fostamatinib Disodium) | Taxol (Paclitaxel) | Taxotere (Docetaxel) | Tecentriq (Atezolizumab) |
| Temodar (Temozolomide) | Temozolomide | Temsirolimus | Thalidomide |

TABLE 5-continued

| | | | |
|---|---|---|---|
| Chemotherapeutic Agents | | | |
| Abemaciclib | Abiraterone Acetate | Abraxane (Paclitaxel Albumin-stabilized Nanoparticle Formulation) | ABVD |
| Thalomid (Thalidomide) | Thioguanine | Thiotepa | Tibsovo (Ivosidenib) |
| Tisagenlecleucel | Tocilizumab | Tolak (Fluorouracil - - - Topical) | Topotecan Hydrochloride |
| Toremifene | Torisel (Temsirolimus) | Totect (Dexrazoxane Hydrochloride) | TPF |
| Trabectedin | Trametinib | Trastuzumab | Treanda (Bendamustine Hydrochloride) |
| Trexall (Methotrexate) | Trifluridine and Tipiracil Hydrochloride | Trisenox (Arsenic Trioxide) | Tykerb (Lapatinib Ditosylate) |
| Unituxin (Dinutuximab) | Uridine Triacetate | VAC | Valrubicin |
| Valstar (Valrubicin) | Vandetanib | VAMP | Varubi (Rolapitant Hydrochloride) |
| Vectibix (Panitumumab) | VeIP | Velcade (Bortezomib) | Vemurafenib |
| Venclexta (Venetoclax) | Venetoclax | Verzenio (Abemaciclib) | Vidaza (Azacitidine) |
| Vinblastine Sulfate | Vincristine Sulfate | Vincristine Sulfate Liposome | Vinorelbine Tartrate |
| VIP | Vismodegib | Vistogard (Uridine Triacetate) | Vitrakvi (Larotrectinib Sulfate) |
| Vizimpro (Dacomitinib) | Voraxaze (Glucarpidase) | Vorinostat | Votrient (Pazopanib Hydrochloride) |
| Vyxeos (Daunorubicin Hydrochloride and Cytarabine Liposome) | Xalkori (Crizotinib) | Xeloda (Capecitabine) | XELIRI |
| XELOX | Xgeva (Denosumab) | Xofigo (Radium 223 Dichloride) | Xtandi (Enzalutamide) |
| Yervoy (Ipilimumab) | Yescarta (Axicabtagene Ciloleucel) | Yondelis (Trabectedin) | Zaltrap (Ziv-Aflibercept) |
| Zarxio (Filgrastim) | Zejula (Niraparib Tosylate Monohydrate) | Zelboraf (Vemurafenib) | Zevalin (Ibritumomab Tiuxetan) |
| Zinecard (Dexrazoxane Hydrochloride) | Ziv-Aflibercept | Zofran (Ondansetron Hydrochloride) | Zoladex (Goserelin Acetate) |
| Zoledronic Acid | Zolinza (Vorinostat) | Zometa (Zoledronic Acid) | Zydelig (Idelalisib) |
| Zykadia (Ceritinib) | Zytiga (Abiraterone Acetate) | | |

In some embodiments, the present invention provides methods of treating cancer in a mammal using a combination of a CD36 inhibitor and anti-PD-1 antibody. In some embodiments, the cancer is selected from the group consisting of oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, and lymphoma. In some embodiments, the cancer is oral squamous cell carcinoma. In some embodiments, the cancer is ovarian cancer. In other embodiments, the cancer is melanoma. In a further embodiment, the cancer is any other cancer disclosed herein. In one embodiment, the cancer is metastatic cancer. In some embodiments, the cancer is both a primary tumor and a metastatic cancer. In embodiments, the CD36 inhibitor is an antibody, a single chain antibody, or a scFv, Fab or F(ab')$_2$ fragment. In one embodiment, the CD36 inhibitor is an antibody. In an embodiment, the CD36 inhibitor is a humanized antibody. In certain embodiments, the CD36 inhibitor is an antibody disclosed herein. In certain embodiments, the CD36 inhibitor is a commercial anti-CD36 antibody such as the antibody JC63.1. In one embodiment, the CD36 inhibitor is a shRNA or an iRNA, a siRNA, or an antisense RNA or DNA. In one embodiment, the anti-PD-1 antibody is pembrolizumab (KEYTRUDA; MK-3475), pidilizumab (CT-011), or nivolumab (OPDIVO; BMS-936558).

Examples of cancers and/or malignant tumors that may be treated using the methods of the invention, include liver cancer, hepatocellular carcinoma (HCC), bone cancer, pancreatic cancer, skin cancer, oral cancer, cancer of the head or neck, breast cancer, lung cancer, small cell lung cancer, NSCLC, cutaneous or intraocular malignant melanoma, Merkel cell carcinoma (MCC), cutaneous squamous cell carcinoma (cSCC), renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, squamous cell carcinoma of the head and neck (SCCHN), non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, urothelial carcinoma, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers. In embodiments, the cancer is oral squamous cell carcinoma. In some embodiments, the cancer is ovarian cancer. In other embodiments, the cancer is melanoma.

In embodiments, the antibodies can be administered systemically, for instance, intraperitoneally, and can be in the form of an appropriate suspension, for instance an aqueous suspension, in water or another appropriate liquid such as saline solution.

For administration of the antibodies, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. In certain embodiments, the antibodies are administered at a flat or fixed dose. In embodiments, the antibodies are administered at any dosage described for the antibody in the art.

Anti-PD-1 and Anti-PD-L1 Antibodies

As used herein, the terms "Programmed Death 1," "Programmed Cell Death 1," "Protein PD-1," "PD-1," "PD1," "PDCD1," "hPD-1" and "hPD-I" are used interchangeably, and include variants, isoforms, species homologs of human PD-1, and analogs having at least one common epitope with PD-1. The complete PD-1 sequence can be found under GenBank Accession No. U64863.

Programmed Cell Death 1 (PD-1) is a cell surface signaling receptor that plays a critical role in the regulation of T cell activation and tolerance (Keir M. E., et al., Annu. Rev. Immunol. 2008; 26:677-704). It is a type I transmembrane protein and together with BTLA, CTLA-4, ICOS and CD28, comprise the CD28 family of T cell co-stimulatory receptors. PD-1 is primarily expressed on activated T cells, B cells, and myeloid cells (Dong H., et al., Nat. Med. 1999; 5:1365-1369; Agata et al., supra; Okazaki et al. (2002) Curr. Opin. Immunol. 14: 391779-82; Bennett et al. (2003) J Immunol 170:711-8). It is also expressed on natural killer (NK) cells (Terme M., et al., Cancer Res. 2011; 71:5393-5399). Binding of PD-1 by its ligands, PD-L1 and PD-L2, results in phosphorylation of the tyrosine residue in the proximal intracellular immune receptor tyrosine inhibitory domain, followed by recruitment of the phosphatase SHP-2, eventually resulting in down-regulation of T cell activation. One important role of PD-1 is to limit the activity of T cells in peripheral tissues at the time of an inflammatory response to infection, thus limiting the development of autoimmunity (Pardoll D. M., Nat. Rev. Cancer 2012; 12:252-264). Evidence of this negative regulatory role comes from the finding that PD-1-deficient mice develop lupus-like autoimmune diseases including arthritis and nephritis, along with cardiomyopathy (Nishimura H., et al., Immunity, 1999; 11:141-151; and Nishimura H., et al., Science, 2001; 291: 319-322). In the tumor setting, the consequence is the development of immune resistance within the tumor microenvironment. PD-1 is highly expressed on tumor-infiltrating lymphocytes, and its ligands are up-regulated on the cell surface of many different tumors (Dong H., et al., Nat. Med. 2002; 8:793-800). Multiple murine cancer models have demonstrated that binding of ligand to PD-1 results in immune evasion. In addition, blockade of this interaction results in anti-tumor activity (Topalian S. L., et al. NEJM 2012; 366(26):2443-2454; Hamid O., et al., NEJM 2013; 369:134-144). Moreover, it has been shown that inhibition of the PD-1/PD-L1 interaction mediates potent antitumor activity in preclinical models (U.S. Pat. Nos. 8,008,449 and 7,943,743).

The initial members of the PD-1 family, CD28 and ICOS, were discovered by functional effects on augmenting T cell proliferation following the addition of monoclonal antibodies (Hutloff et al. Nature (1999); 397:263-266; Hansen et al. Immunogenics (1980); 10:247-260). PD-1 was discovered through screening for differential expression in apoptotic cells (Ishida et al. EMBO J (1992); 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Although structurally similar to CTLA-4, PD-1 lacks the MYPPPY motif (SEQ ID NO: 36) that is critical for B7-1 and B7-2 binding. Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

Consistent with PD-1 being an inhibitory member of the CD28 family, PD-1 deficient animals develop various auto-immune phenotypes, including autoimmune cardiomyopa-thy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78; Prokunina and Alarcon-Riquelme (2004) Hum Mol Genet 13:R143; Nielsen et al. (2004) Lupus 13:510). In a murine B cell tumor line, the ITSM of PD-1 was shown to be essential to block BCR-mediated Ca.sup.2+-flux and tyrosine phosphorylation of downstream effector molecules (Okazaki et al. (2001) PNAS 98:13866-71).

"Programmed Death Ligand-1 (PD-L1)" is one of two cell surface glycoprotein ligands for PD-1 (the other being PD-L2) that down-regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

Some embodiments of the invention include an anti-PD-1 antibody, or an anti-PD-L1 antibody, in combination with an anti-CD36 antibody. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies (HuMAbs) that bind spe-cifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication Nos. WO2012/145493 and WO2016/168716. Each of the anti-PD-1 HuMAbs disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reac-tion (MLR) assay; (d) increases interferon-$\gamma$ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and (j) inhibits tumor cell growth in vivo.

Anti-PD-1 antibodies useful for the present invention include mAbs that bind specifically to human PD-1 and exhibit at least one, preferably at least five, of the preceding characteristics.

Anti-human-PD-1 antibodies (or VH and/or VL domains derived therefrom) suitable for use in the invention can be generated using methods well known in the art. Alterna-tively, art recognized anti-PD-1 antibodies can be used. For example, monoclonal antibodies 5C4 (referred to herein as Nivolumab or BMS-936558), 17D8, 2D3, 4H1, 4A11, 7D3, and 5F4, described in WO 2006/121168, the teachings of which are hereby incorporated by reference, can be used. Other known PD-1 antibodies include lambrolizumab (MK-3475) described in WO 2008/156712, and AMP-514 described in WO 2012/145493. Further known anti-PD-1 antibodies and other PD-1 inhibitors include those described in WO 2009/014708, WO 03/099196, WO 2009/114335 and WO 2011/161699. Another known anti-PD-1 antibody is pidilizumab (CT-011). Antibodies that compete with any of these antibodies or inhibitors for binding to PD-1 also can be used.

In one embodiment, the anti-PD-1 antibody is nivolumab. Nivolumab (also known as "OPDIVO®"; BMS-936558; formerly designated 5C4, BMS-936558, MDX-1106, or ONO-4538) is a fully human IgG4 (S228P) PD-1 immune checkpoint inhibitor antibody that selectively prevents inter-action with PD-1 ligands (PD-L1 and PD-L2), thereby blocking the down-regulation of antitumor T-cell functions (U.S. Pat. No. 8,008,449; Wang et al., 2014 Cancer Immunol Res. 2(9):846-56). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody is pem-brolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

In another embodiment, the anti-PD-1 antibody cross-competes with pembrolizumab. In some embodiments, the anti-PD-1 antibody binds to the same epitope as pembroli-zumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (pro-grammed death-1 or programmed cell death-1). Pembroli-zumab is described, for example, in U.S. Pat. Nos. 8,354,509 and 8,900,587; see also http://www.cancer.gov/drugdiction-ary?cdrid=695789 (last accessed: May 25, 2017). Pembroli-zumab has been approved by the FDA for the treatment of relapsed or refractory melanoma.

In other embodiments, the anti-PD-1 antibody thereof cross-competes with MEDI0608. In still other embodiments, the anti-PD-1 antibody binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089 or in http://www.cancer.gov/drugdictionary?cdrid=756047 (last accessed May 25, 2017).

In other embodiments, the anti-PD-1 antibody cross-competes with BGB-A317. In some embodiments, the anti-PD-1 antibody binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies useful for the disclosed compositions also include isolated antibodies that bind specifically to human PD-1 and cross-compete for binding to human PD-1 with nivolumab (see, e.g., U.S. Pat. Nos. 8,008,449 and 8,779,105; Int'l Pub. No. WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., Int'l Pub. No. WO 2013/173223).

In certain embodiments, antibodies that cross-compete for binding to human PD-1 with, or bind to the same epitope region of human PD-1 as, nivolumab are mAbs. For administration to human subjects, these cross-competing antibodies can be chimeric antibodies, or humanized or human antibodies. Such chimeric, humanized or human mAbs can be prepared and isolated by methods well known in the art.

Anti-PD-1 antibodies useful for the compositions of the disclosed invention also include antigen-binding portions of the above antibodies. It has been amply demonstrated that the antigen-binding function of an antibody can be performed by fragments of a full length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; and (iv) a Fv fragment consisting of the VL and VH domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody cross-competes with nivolumab for binding to human PD-1. In other embodiments, the anti-PD-1 antibody is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody comprises a heavy chain constant region which is of a human IgG1 or IgG4 isotype. In certain other embodiments, the sequence of the IgG4 heavy chain constant region of the anti-PD-1 antibody contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or Pidilizumab (CT-011). Other known PD-1 antibodies include lambrolizumab (MK-3475) described in, for example, WO 2008/156712, and AMP-514 described in, for example, WO 2012/145493. Further known anti-PD-1 antibodies and other PD-1 inhibitors include those described in, for example, WO 2009/014708, WO 03/099196, WO 2009/114335 and WO 2011/161699. In one embodiment, the anti-PD-1 antibody is REGN2810. In one embodiment, the anti-PD-1 antibody is PDR001. Another known anti-PD-1 antibody is pidilizumab (CT-011). Each of the above references are incorporated by reference. Antibodies that compete with any of these antibodies or inhibitors for binding to PD-1 also can be used.

Other anti-PD-1 monoclonal antibodies have been described in, for example, U.S. Pat. Nos. 6,808,710, 7,488, 802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540, each of which are herein incorporated by reference.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., J. Hematol. Oncol. 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., J. Hematol. Oncol. 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., J. Hematol. Oncol. 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), and IBI308 (Innovent; see WO 2017/024465, WO 2017/025016, WO 2017/132825, and WO 2017/133540). Each of the above references are herein incorporated by reference.

In embodiments, the anti-PD-1 antibody is a bispecific antibody. In embodiments, the second therapy is a PD-1 inhibitor. In embodiments, the PD-1 inhibitor is a small molecule.

Because anti-PD-1 antibodies and anti-PD-L1 antibodies target the same signaling pathway and have been shown in clinical trials to exhibit similar levels of efficacy in a variety of cancers, an anti-PD-L1 antibody can be substituted for an anti-PD-1 antibody in any of the therapeutic methods or compositions disclosed herein.

Anti-human-PD-L1 antibodies (or VH and/or VL domains derived therefrom) suitable for use in the invention can be generated using methods well known in the art. Alternatively, art recognized anti-PD-L1 antibodies can be used. For example, human anti-PD-L1 antibodies disclosed in U.S. Pat. No. 7,943,743, the contents of which are hereby incorporated by reference, can be used. Such anti-PD-L1 antibodies include 3G10, 12A4 (also referred to as BMS-936559), 10A5, 5F8, 10H10, 1B12, 7H1, 11E6, 12B7, and 13G4. Other art recognized anti-PD-L1 antibodies which can be used include those described in, for example, U.S. Pat. Nos. 7,635,757 and 8,217,149, U.S. Publication No. 2009/0317368, and PCT Publication Nos. WO 2011/066389 and WO 2012/145493, each of which are herein incorporated by reference. Other examples of an anti-PD-L1 antibody include atezolizumab (TECENTRIQ; RG7446), or durvalumab (IMFINZI; MEDI4736). Antibodies that compete with any of these art-recognized antibodies or inhibitors for binding to PD-L1 also can be used.

Examples of anti-PD-L1 antibodies useful in the methods of the present disclosure include the antibodies disclosed in U.S. Pat. No. 9,580,507, which is herein incorporated by reference. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1 \times 10^{-7}$ M or less, as determined by surface plasmon resonance using a Biacore biosensor system; (b) increase T-cell proliferation in a Mixed Lymphocyte Reaction (MLR) assay; (c) increase interferon-$\gamma$ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. 2013 J Clin Oncol 31(suppl):3000; U.S. Pat. No. 8,217,149), MEDI4736 (Khleif, 2013, In: Proceedings from the European Cancer Congress 2013; Sep. 27-Oct. 1, 2013; Amsterdam, The Netherlands. Abstract 802), or MSB0010718C (also called Avelumab; see US 2014/0341917). In certain embodiments, antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art. In certain embodiments, the anti-PD-L1 antibody is selected from the group consisting of BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see, e.g., WO 2011/066389), avelumab (Pfizer; also known as BAVENCIO®, MSB-0010718C; see, e.g., WO 2013/079174), STI-1014 (Sorrento; see, e.g., WO2013/181634), CX-072 (Cytomx; see, e.g., WO2016/149201), KN035 (3D Med/Alphamab; see Zhang et al., Cell Discov. 7:3 (March 2017), LY3300054 (Eli Lilly Co.; see, e.g., WO 2017/034916), and CK-301 (Checkpoint Therapeutics; see Gorelik et al., AACR:Abstract 4606 (April 2016)). The above references are herein incorporated by reference.

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™) Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and upregulating the immune system. In certain embodiments, the anti-PD-L1 antibody cross-competes with atezolizumab, durvalumab, and/or avelumab for binding to human PD-L1.

Anti-CTLA-4 Antibodies

In certain embodiments, an embodiment encompasses use of an anti-CTLA-4 antibody. In one embodiment, the anti-CTLA-4 antibody binds to and inhibits CTLA-4. In some embodiments, the anti-CTLA-4 antibody is ipilimumab (YERVOY), tremelimumab (ticilimumab; CP-675,206), AGEN-1884, or ATOR-1015.

Further Embodiments

An isolated antibody that binds to CD36, which comprises a light chain CDR1 region, a light chain CDR2 region, a light chain CDR3 region, a heavy chain CDR1 region, a heavy chain CDR2 region, and a heavy chain CDR3 region; wherein the heavy chain CDR3 region is the heavy chain CDR3 region present in SEQ ID NO: 5 as identified according to the Kabat numbering scheme.

1. A chimeric antibody that binds to CD36, which comprises a light chain CDR1 region, a light chain CDR2 region, a light chain CDR3 region, a heavy chain CDR1 region, a heavy chain CDR2 region, and a heavy chain CDR3 region; wherein the heavy chain CDR3 region is the heavy chain CDR3 region present in SEQ ID NO: 5 as identified according to the Kabat numbering scheme.

2. A humanized antibody that binds to CD36, which comprises a light chain CDR1 region, a light chain CDR2 region, a light chain CDR3 region, a heavy chain CDR1 region, a heavy chain CDR2 region, and a heavy chain CDR3 region, wherein the heavy chain CDR3 region is the heavy chain CDR3 region present in SEQ ID NO: 5 as identified according to the Kabat numbering scheme.

3. An isolated antibody that binds to CD36, which comprises a light chain CDR1 region, a light chain CDR2 region, a light chain CDR3 region, a heavy chain CDR1 region, a heavy chain CDR2 region, and a heavy chain CDR3 region, wherein the light chain CDR1 region, the light chain CDR2 region, and the light chain CDR3 region are the light chain CDR1 region, the light chain CDR2 region, and the light chain CDR3 region present in SEQ ID NO: 7 as identified according to the Kabat numbering scheme; and wherein the heavy chain CDR1 region, the heavy chain CDR2 region, and the heavy chain CDR3 region are the heavy chain CDR1 region, the heavy chain CDR2 region, and the heavy chain CDR3 region present in SEQ ID NO: 5 as identified according to the Kabat numbering scheme.

4. A chimeric antibody that binds to CD36, which comprises a light chain CDR1 region, a light chain CDR2 region, a light chain CDR3 region, a heavy chain CDR1 region, a heavy chain CDR2 region, and a heavy chain CDR3 region, wherein the light chain CDR1 region, the light chain CDR2 region, and the light chain CDR3 region are the light chain CDR1 region, the light chain CDR2 region, and the light chain CDR3 region present in SEQ ID NO: 7 as identified according to the Kabat numbering scheme; and wherein the heavy chain CDR1 region, the heavy chain CDR2 region, and the heavy chain CDR3 region are the heavy chain CDR1 region, the heavy chain CDR2 region, and the heavy chain CDR3 region present in SEQ ID NO: 5 as identified according to the Kabat numbering scheme.

5. A humanized antibody that binds to CD36, which comprises a light chain CDR1 region, a light chain CDR2 region, a light chain CDR3 region, a heavy chain CDR1 region, a heavy chain CDR2 region, and a heavy chain CDR3 region, wherein the light chain CDR1 region, the light chain CDR2 region, and the light chain CDR3 region are the light chain CDR1 region, the light chain CDR2 region, and the light chain CDR3 region present in SEQ ID NO: 7 as identified according to the Kabat numbering scheme; and wherein the heavy chain CDR1 region, the heavy chain CDR2 region, and the heavy chain CDR3 region are the heavy chain CDR1 region, the heavy chain CDR2 region, and the heavy chain CDR3 region present in SEQ ID NO: 5 as identified according to the Kabat numbering scheme.

6. The antibody of any one of embodiments 1 to 3, wherein the heavy chain CDR1 region comprises SEQ ID NO: 27, the heavy chain CDR2 region comprises SEQ ID NO: 28, the heavy chain CDR3 region comprises SEQ ID NO: 29, the light chain CDR1 region comprises SEQ ID NO: 30, the light chain CDR2 region comprises SEQ ID NO: 31, and the light chain CDR3 region comprises SEQ ID NO: 32.

7. The antibody of any one of embodiments 1 to 3, wherein the heavy chain CDR1 region comprises SEQ ID NO: 37, the heavy chain CDR2 region comprises SEQ ID NO: 38, the heavy chain CDR3 region comprises SEQ ID NO: 29, the light chain CDR1 region comprises SEQ ID NO: 30, the light chain CDR2 region comprises SEQ ID NO: 31, and the light chain CDR3 region comprises SEQ ID NO: 32.

8. The antibody of any one of embodiments 1 to 3, wherein the heavy chain CDR1 region comprises SEQ ID NO: 39, the heavy chain CDR2 region comprises SEQ ID NO: 40, the heavy chain CDR3 region comprises SEQ ID NO: 41, the light chain CDR1 region comprises SEQ ID NO: 42, the light chain CDR2 region comprises SEQ ID NO: 43, and the light chain CDR3 region comprises SEQ ID NO: 32.

9. The humanized antibody of embodiment 3, wherein the heavy chain CDR regions comprise:

(a) SEQ ID NOs: 37, 38, and 29;

(b) SEQ ID NOs: 44, 46, and 29; or (c) SEQ ID NOs: 45, 47, and 29.

10. The humanized antibody of embodiment 3 or embodiment 10, wherein the light chain CDR regions comprise SEQ ID NOs: 30, 31, and 32.

11. The humanized antibody of embodiment 3 or embodiment 10, wherein the light chain CDR regions comprise SEQ ID NOs: 48, 31, and 32.

12. The humanized antibody of embodiment 3 or embodiment 10, wherein the light chain CDR regions comprise SEQ ID NOs: 48, 49, and 32.

13. The humanized antibody of embodiment 3 or embodiment 10, wherein the light chain CDR regions comprise SEQ ID NOs: 30, 50, and 32.

14. The humanized antibody of any one of embodiments 3 and 10-14, wherein the heavy chain variable region comprises SEQ ID NO: 51, SEQ ID NO: 52, SEQ ID NO:

53, or SEQ ID NO: 54; and wherein the light chain variable region comprises SEQ ID NO: 55, SEQ ID NO: 56, SEQ ID NO: 57, or SEQ ID NO: 58.

15. The humanized antibody of embodiment 15, wherein the humanized antibody comprises:

(a) a heavy chain variable region comprising SEQ ID NO: 51 and a light chain variable region comprising SEQ ID NO: 55, SEQ ID NO: 56, SEQ ID NO: 57, or SEQ ID NO: 58;

(b) a heavy chain variable region comprising SEQ ID NO: 52 and a light chain variable region comprising SEQ ID NO: 55, SEQ ID NO: 56, SEQ ID NO: 57, or SEQ ID NO: 58;

(c) a heavy chain variable region comprising SEQ ID NO: 53 and a light chain variable region comprising SEQ ID NO: 55, SEQ ID NO: 56, SEQ ID NO: 57, or SEQ ID NO: 58; or (d) a heavy chain variable region comprising SEQ ID NO: 54 and a light chain variable region comprising SEQ ID NO: 55, SEQ ID NO: 56, SEQ ID NO: 57, or SEQ ID NO: 58.

16. An isolated antibody that binds to the same epitope of human CD36 as an antibody comprising the light chain in SEQ ID NO: 7 and the heavy chain in SEQ ID NO: 5.

17. An isolated antibody that competes for binding to human CD36 with an antibody comprising the light chain in SEQ ID NO: 7 and the heavy chain in SEQ ID NO: 5.

18. The antibody of any one of embodiments 1 to 18, wherein the antibody is substantially free of antibodies that do not specifically bind to CD36.

19. The antibody of any one of embodiments 1 to 19, wherein the antibody is substantially free of a light chain comprising the light chain CDR1 region, the light chain CDR2 region, and the light chain CDR3 region present in SEQ ID NO: 9 as identified according to the Kabat numbering scheme.

20. The antibody of any one of embodiments 1 to 20, wherein the antibody binds to human CD36.

21. The antibody of any one of embodiments 1 to 21, wherein the antibody binds to human CD36 with a $K_D$ of less than 10 nM, as measured using SPR data fitted with a 1-to-1 model.

22. The antibody of any one of embodiments 1, 2, 4, 5, 7 to 9, or 19 to 22, wherein the antibody comprises a VH having at least 80%, at least 85%, at least 90%, at least 95%, at least 96%, at least 97%, at least 98%, at least 99%, or 100% identity with the amino acid sequence of SEQ ID NO: 11.

23. The antibody of embodiment 23, wherein the antibody comprises a VH comprising the amino acid sequence of SEQ ID NO: 11.

24. The antibody of any one of embodiments 1, 2, 4, 5, 7 to 9, or 19 to 22, wherein the antibody comprises a VL having at least 80%, at least 85%, at least 90%, at least 95%, at least 96%, at least 97%, at least 98%, at least 99%, or 100% identity with the amino acid sequence of SEQ ID NO: 13.

25. The antibody of embodiment 25, wherein the antibody comprises a VL comprising the amino acid sequence of SEQ ID NO: 13.

26. The antibody of any one of embodiments 1 to 26, which further comprises a heavy chain constant region.

27. The antibody of embodiment 27, wherein the heavy chain constant region is selected from the group consisting of human immunoglobulin IgA1, IgA2, IgG1, IgG2, IgG3, or IgG4 heavy chain constant regions.

28. The antibody of embodiment 28, which comprises an IgG1 heavy chain constant region.

29. The antibody of embodiment 29, wherein the heavy chain constant region comprises an IgG constant region containing the amino acid substitutions L234A and L235A ("LALA").

30. The antibody of embodiment 29, wherein the heavy chain constant region comprises an IgG constant region containing a set of amino acid substitutions selected from the group consisting of L234G, L235S, and G236R; L234S, L235T, and G236R; L234S, L235V, and G236R; L234T, L235Q, and G236R; L234T, L235T, and G236R; L234A and L235A; and L234A, L235A, and P329G.

31. The antibody of embodiment 28, which comprises an IgG4 heavy chain constant region.

32. The antibody of embodiment 31, wherein the heavy chain constant region comprises an IgG constant region containing the amino acid substitution S228P.

33. The antibody of any one of embodiments 1 to 33, wherein the antibody further comprises a light chain constant region.

34. The antibody of embodiment 34, wherein the light chain constant region is selected from the group consisting of human immunoglobulins κ and λ light chain constant regions.

35. The antibody of any one of embodiments 1 to 35, wherein the antibody further comprises a heavy chain constant region and a light chain constant region, wherein the heavy chain constant region is a human IgG1 heavy chain constant region, and wherein the light chain constant region is a human κ light chain constant region.

36. The antibody of any one of embodiments 1-2, 4-5, or 17 to 36, wherein the antibody comprises the light chain in SEQ ID NO: 23 and the heavy chain in SEQ ID NO: 21.

37. The antibody of any one of embodiments 1-2, 4-5, or 17 to 36, wherein the antibody comprises the light chain in SEQ ID NO: 23 and the heavy chain in SEQ ID NO: 64.

38. The antibody of any one of embodiments 1-36, which is an antigen binding fragment.

39. The antigen binding fragment of embodiment 39, wherein the antigen binding fragment comprises a Fab, Fab', F(ab')$_2$, single chain Fv (scFv), disulfide linked Fv, V-NAR domain, IgNar, intrabody, IgGΔCH2, minibody, F(ab')$_3$, tetrabody, triabody, diabody, single-domain antibody, DVD-Ig, Fcab, mAb2, (scFv)$_2$, or scFv-Fc.

40. A pharmaceutical composition comprising the antibody of any one of embodiments 1 to 40 and a pharmaceutically acceptable excipient.

41. The pharmaceutical composition of embodiment 41, wherein at least 95% of the antibodies in the composition are afucosylated.

42. The pharmaceutical composition of embodiment 41 or embodiment 42, which further comprises a PD-1 inhibitor.

43. The pharmaceutical composition of embodiment 43, wherein the PD-1 inhibitor is an anti-PD-1 antibody.

44. The pharmaceutical composition of embodiment 44, wherein the anti-PD-1 antibody is pembrolizumab, pidilizumab, or nivolumab.

45. The pharmaceutical composition of any one of embodiments 41 to 45, which further comprises a PD-L1 inhibitor 46. The pharmaceutical composition of embodiment 46, wherein the PD-L1 inhibitor is an anti-PD-L1 antibody.

47. The pharmaceutical composition of embodiment 47, wherein the anti-PD-L1 antibody is atezolizumab, durvalumab, avelumab, or BMS-936559.

48. The pharmaceutical composition of any one of embodiments 41 to 48, which further comprises a CTLA-4 inhibitor.

49. The pharmaceutical composition of embodiment 49, wherein the CTLA-4 inhibitor is an anti-CTLA-4 antibody.

50. The pharmaceutical composition of embodiment 50, wherein the anti-CTLA-4 antibody is ipilimumab.

51. The pharmaceutical composition of any one of embodiments 41 to 51, wherein the composition further comprises a chemotherapeutic agent.

52. The pharmaceutical composition of embodiment 52, wherein the chemotherapeutic agent is cisplatin.

53. The pharmaceutical composition of any one of embodiments 41 to 53, wherein the antibody is substantially free of a light chain comprising the light chain CDR1 region, the light chain CDR2 region, and the light chain CDR3 region present in SEQ ID NO: 9 as identified according to the Kabat numbering scheme.

54. A method of treating cancer in a patient comprising administering to a subject in need thereof a therapeutically effective amount of the antibody of any one of embodiments 1 to 40, or a therapeutically effective amount of the pharmaceutical composition of any one of embodiments 41 to 54.

55. The method of embodiment 55, wherein the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

56. A method of treating one or more metastatic tumors in a patient comprising administering to a subject in need thereof a therapeutically effective amount of the antibody of any one of embodiments 1 to 40, or a therapeutically effective amount of the pharmaceutical composition of any one of embodiments 41 to 54.

57. The method of embodiment 57, wherein the metastatic tumors developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

58. The method of embodiment 58, wherein the treatment reduces the size of metastatic tumors, as measured by IVIS imaging or H&E staining.

59. The method of any one of embodiments 57 to 59, wherein the treatment inhibits the formation or development of metastatic tumors, as measured by IVIS imaging or H&E staining.

60. The method of any one of embodiments 55 to 60, wherein the anti-CD36 antibody blocks the CD36-mediated uptake of fatty acids and/or oxLDL while having little to no effect on CD36's binding to TSP-1.

61. The method of any one of embodiments 55 to 61, wherein the patient is a human patient.

62. The method of any one of embodiments 55 to 62, wherein the anti-CD36 antibody is a full length antibody, a single chain antibody, a scFv, a Fab fragment, or a F(ab')₂ fragment.

63. The method of any one of embodiments 55 to 63, wherein the anti-CD36 antibody is a full length antibody.

64. The method of embodiment 64, wherein the anti-CD36 antibody comprises the light chain in SEQ ID NO: 23 and the heavy chain in SEQ ID NO: 21.

65. The method of embodiment 64, wherein the anti-CD36 antibody comprises the light chain in SEQ ID NO: 23 and the heavy chain in SEQ ID NO: 64.

66. The method of any one of embodiments 55-66, wherein the method further comprises administering a second therapy.

67. The method of embodiment 67, wherein the second therapy is an immunotherapy.

68. The method of embodiment 68, wherein the immunotherapy is a PD-1 inhibitor.

69. The method of embodiment 69, wherein the PD-1 inhibitor is an anti-PD-1 antibody.

70. The method of embodiment 70, wherein the anti-PD-1 antibody is pembrolizumab, pidilizumab, or nivolumab.

71. The method of embodiment 68, wherein the immunotherapy is a PD-L1 inhibitor.

72. The method of embodiment 72, wherein the PD-L1 inhibitor is an anti-PD-L1 antibody.

73. The method of embodiment 73, wherein the anti-PD-L1 antibody is atezolizumab, durvalumab, avelumab, or BMS-936559.

74. The method of embodiment 68, wherein the immunotherapy is a CTLA-4 inhibitor.

75. The method of embodiment 75, wherein the CTLA-4 inhibitor is an anti-CTLA-4 antibody.

76. The method of embodiment 76, wherein the anti-CTLA-4 antibody is ipilimumab.

77. The method embodiment 67, wherein the second therapy is a chemotherapeutic agent.

78. The method of embodiment 78, wherein the chemotherapeutic agent is cisplatin.

79. The method of any one of embodiments 55-79, wherein metastasis is reduced or inhibited in the subject.

80. The method of any one of embodiments 67-80, wherein the two therapies are administered sequentially.

81. The method of any one of embodiments 67-80, wherein the two therapies are administered simultaneously.

82. The antibody of any one of embodiments 1 to 40, for use in a method of treating a subject having a cancer that expresses CD36, the method comprising administering to the subject a therapeutically effective amount of the anti-CD36 antibody according to the invention.

83. The antibody for use of embodiment 83, wherein the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

84. The antibody for use of embodiment 83 or embodiment 84, wherein the cancer is a metastatic cancer.

85. The antibody for use of any one of embodiments 83 to 85, wherein the treatment reduces the size of metastatic tumors, as measured by IVIS imaging or H&E staining.

86. The antibody for use of any one of embodiments 83 to 86, wherein the treatment inhibits the formation or development of metastatic tumors, as measured by IVIS imaging or H&E staining.

87. The antibody for use of any one of embodiments 83 to 87, wherein the anti-CD36 antibody blocks the CD36-mediated uptake of fatty acids and/or oxLDL while having little to no effect on CD36's binding to TSP-1.

88. The antibody for use of any one of embodiments 83 to 88, wherein the use is in combination with a second therapy.

89. The antibody for use of embodiment 89, wherein the second therapy is an immunotherapy.

90. The antibody for use of embodiment 90, wherein the immunotherapy is an anti-PD-1 antibody, an anti-PL-L1 antibody, or an anti-CTLA-4 antibody.

91. The antibody for use of embodiment 89, wherein the second therapy is a chemotherapeutic agent.

92. The antibody for use of embodiment 92, wherein the chemotherapeutic agent is cisplatin.

93. Use of the antibody of any one of embodiments 1 to 40 in the manufacture of a medicament for treating a subject having a cancer that expresses CD36.

94. The use of the antibody according to embodiment 94, wherein the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

95. The use of the antibody according to embodiment 94 or embodiment 95, wherein the cancer is a metastatic cancer.

96. The use of the antibody according to any one of embodiments 94 to 96, wherein the treatment reduces the size of metastatic tumors, as measured by IVIS imaging or H&E staining.

97. The use of the antibody according to any one of embodiments 94 to 97, wherein the treatment inhibits the formation or development of metastatic tumors, as measured by IVIS imaging or H&E staining.

98. The use of the antibody according to any one of embodiments 94 to 98, wherein the anti-CD36 antibody blocks the CD36-mediated uptake of fatty acids and/or oxLDL while having little to no effect on CD36's binding to TSP-1.

99. The use of the antibody according to any one of embodiments 94 to 99, wherein the use is in combination with a second therapy.

100. The use of the antibody according to embodiment 100, wherein the second therapy is an immunotherapy.

101. The use of the antibody according to embodiment 101, wherein the immunotherapy is an anti-PD-1 antibody, an anti-PL-L1 antibody, or an anti-CTLA-4 antibody.

102. The use of the antibody according to embodiment 100, wherein the second therapy is a chemotherapeutic agent.

103. The use of the antibody according to embodiment 103, wherein the chemotherapeutic agent is cisplatin.

104. An isolated polynucleotide that encodes the antibody of any one of embodiments 1 to 40.

105. The isolated polynucleotide of embodiment 105, which encodes the light chain in SEQ ID NO: 7 and the heavy chain in SEQ ID NO: 5.

106. The isolated polynucleotide of embodiment 105 or 106, which comprises SEQ ID NO: 8.

107. The isolated polynucleotide of any one of embodiments 105 to 107, which comprises SEQ ID NO: 6.

108. The isolated polynucleotide of embodiment 105 or 106, which comprises SEQ ID NO: 24.

109. The isolated polynucleotide of any one of embodiments 105 to 107, which comprises SEQ ID NO: 22.

110. A vector comprising the isolated polynucleotide of any one of embodiments 105 to 110.

111. A cell comprising the isolated polynucleotide of any one of embodiments 105 to 110 or the vector of embodiment 111.

112. The cell of embodiment 112, which is selected from the group consisting of *E. coli, Pseudomonas, Bacillus, Streptomyces,* yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

113. The cell of embodiment 112 or 113, wherein the cell lacks a functional alpha-1,6-fucosyltransferase gene (FUT8) gene.

114. A method of making an antibody that is capable of specifically binding CD36, comprising expressing the antibody in the cell of any one of embodiments embodiment 112 to 114.

115. A method of making an antibody that is capable of specifically binding CD36, comprising culturing the cell of any one of embodiments 112 to 115 and isolating the antibody expressed therein.

116. The use of an antibody of any one of embodiments 1 to 40, for the manufacture of a pharmaceutical composition.

117. The use of an antibody of any one of embodiments 1 to 40 and a pharmaceutically acceptable excipient or carrier for the manufacture of a pharmaceutical composition.

118. The method of any one of embodiments 57 to 82, wherein the metastatic tumors are present in one or more of the liver, lung, spleen, kidney, cervical lymph nodes, or peritoneal wall.

119. The antibody for use of any one of embodiments 83 to 93, wherein the metastatic cancer comprises metastatic tumors in one or more of the liver, lung, spleen, kidney, cervical lymph nodes, or peritoneal wall.

120. The use of the antibody of any one of embodiments 94-104, wherein the metastatic cancer comprises metastatic tumors in one or more of the liver, lung, spleen, kidney, vervical lymph nodes, or peritoneal wall.

121. A method of treating both a primary tumor and metastatic tumors in a patient comprising administering to a subject in need thereof a therapeutically effective amount of the antibody of any one of embodiments 1 to 40, or a therapeutically effective amount of the pharmaceutical composition of any one of embodiments 41 to 54.

122. The method of embodiment 122, wherein the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

123. The method of embodiment 122 or 123, wherein the metastatic tumors developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

124. The method of any one of embodiments 122 to 124, wherein the treatment reduces the size of metastatic tumors, as measured by IVIS imaging or H&E staining.

125. The method of any one of embodiments 122 to 125, wherein the treatment reduces the size of a primary tumor.

126. The method of any one of embodiments 122 to 126, wherein the treatment inhibits the formation or development of metastatic tumors, as measured by IVIS imaging or H&E staining.

127. The method of any one of embodiments 122 to 127, wherein the anti-CD36 antibody blocks the CD36-mediated uptake of fatty acids and/or oxLDL while having little to no effect on CD36's binding to TSP-1.

128. The method of any one of embodiments 122 to 128, wherein the patient is a human patient.

129. The method of any one of embodiments 122 to 129, wherein the anti-CD36 antibody is a full length antibody, a single chain antibody, a scFv, a Fab fragment, or a F(ab')$_2$ fragment.

130. The method of any one of embodiments 122 to 130, wherein the anti-CD36 antibody is a full length antibody.

131. The method of embodiment 131, wherein the anti-CD36 antibody comprises the light chain in SEQ ID NO: 23 and the heavy chain in SEQ ID NO: 21.

132. The method of embodiment 131, wherein the anti-CD36 antibody comprises the light chain in SEQ ID NO: 23 and the heavy chain in SEQ ID NO: 64.

133. The method of any one of embodiments 122 to 133, wherein the method further comprises administering a second therapy.

134. The method of embodiment 134, wherein the second therapy is an immunotherapy.

135. The method of embodiment 135, wherein the immunotherapy is a PD-1 inhibitor.

136. The method of embodiment 136, wherein the PD-1 inhibitor is an anti-PD-1 antibody.

137. The method of embodiment 137, wherein the anti-PD-1 antibody is pembrolizumab, pidilizumab, or nivolumab.

138. The method of embodiment 135, wherein the immunotherapy is a PD-L1 inhibitor.

139. The method of embodiment 139, wherein the PD-L1 inhibitor is an anti-PD-L1 antibody.

140. The method of embodiment 140, wherein the anti-PD-L1 antibody is atezolizumab, durvalumab, avelumab, or BMS-936559.

141. The method of embodiment 135, wherein the immunotherapy is a CTLA-4 inhibitor.

142. The method of embodiment 142, wherein the CTLA-4 inhibitor is an anti-CTLA-4 antibody.

143. The method of embodiment 143, wherein the anti-CTLA-4 antibody is ipilimumab.

144. The method embodiment 134, wherein the second therapy is a chemotherapeutic agent.

145. The method of embodiment 145, wherein the chemotherapeutic agent is cisplatin.

146. The method of any one of embodiments 122 to 146, wherein metastasis is reduced or inhibited in the subject.

147. The method of any one of embodiments 134-147, wherein the two therapies are administered sequentially.

148. The method of any one of embodiments 134-147, wherein the two therapies are administered simultaneously.

EXAMPLES

Example 1: Animal Studies

Unless otherwise indicated, the animal studies disclosed in the Examples below were carried out using the following materials and methodologies.

NOD scid gamma (NSG) (NOD.Cg-Prkdc$^{scid}$Il2rg$^{tm1 Wjl}$/SzJ) mice were purchased from Charles River and crossed in-house. All mice were housed under a regimen of 12h light/12h dark cycles and SPF conditions, and all procedures were evaluated and approved by the CEEA (Ethical Committee for Animal Experimentation) from the Government of Catalunya. SCC intra-tongue injection was performed as previously described (Oskarsson et al., 2014; Nieman et al., 2011). Briefly, mice were anesthetized by intraperitoneal injection with a mixture of 50 mg per kg of ketamine and 0.5 mg per kg of medetomidin, and SCC cells resuspended in 30 µl PBS were injected into each mouse tongue with a BD ultra-fine 6 mm needle. Mice were monitored for the luciferase bioluminescent signal immediately after injection (TO) and once weekly thereafter with a Xenogen IVIS Imaging System-100 (Caliper Life Sciences). Briefly, animals were injected by retro-orbital injection with 50 µl of D-luciferin (Promega) diluted in 1×PBS at 5 mg ml$^{-1}$. Continuous administration of isofluorane gas was provided to ensure anesthetizing animals during imaging. Data was quantified with the Living Image software version 4.4 (Caliper Life Sciences). Quantifications were calculated with unsaturated pixels. Color scale minimum and maximum values are shown in pictures.

To treat mice in vivo with neutralizing anti-CD36 antibodies, mice were injected intraperitoneally with 100 µl of physiological serum containing 5 µg, 10 µg or 20 µg of the neutralizing monoclonal anti-CD36 antibody JC63.1 (CAYMAN, CAY-10009893-500); 5 µg, 10 µg or 20 µg of neutralizing monoclonal anti-CD36 ONA-0-v1 (either IgA or IgG isotype); or 5 µg, 10 µg or 20 µg of the corresponding control IgA (mouse IgA, kappa [S107], Abcam, ab37322) or IgG antibody. These doses corresponded to 0.25, 0.5, and 1 mg/kg, respectively. All antibodies were azide-free with no added preservative compound.

For each experiment, mice were sacrificed at the same time, once an experimental group reached the humane endpoint according to the approved CEEA protocol (4-6 weeks after the orthotopic injection as soon as mice started to lose weight due to the growth of the oral lesion), and subsequent cell analysis was performed.

Total blood samples from mice were collected from the inferior vena cava and then processed in the Experimental Toxicology and Ecotoxicology Unit (PCB) following standard procedures.

Animal tissue was collected and fixed with 4% paraformaldehyde (PFA) for overnight at room temperature (RT) and then either embedded in OCT and frozen at −80° C. or dehydrated and embedded in paraffin. Toxicological study was performed at the Histopathology Facility according to standard procedures.

Histological Analysis. For analysis, cryo- or de-paraffinized antigen retrieved sections (10 min in boiling 0.01M citric acid, pH 6.0) of 8 µm were permeabilized for 25 min in 0.25% Triton X-100/PBS and blocked for 90 min in 0.25% gelatin/PBS. Hematoxilin and eosin (H&E) staining was done according to the standard protocol. Images were acquired using a Nikon E600+Olympus DP72, Leica SPE and a Leica TCS SP5 confocal microscope. Representative pictures were selected in each case.

For all the experiments, adequate sample size was determined based on results of pilot studies. No statistical method was used to determine sample size. All the animals that fulfilled proper experimental conditions during the experimental procedures were included in the analysis. Based on results of pilot studies, homogeneous groups of males and females between 8 and 12 weeks and their control littermates were used for the experimental studies. Animals were randomized at day 7 post-injection based on luminescence intensity of the primary tumours or of the cervical lymph nodes metastasis. Data are generally shown as the mean±s.e.m. Statistical significance was analyzed using Prism 6 software (GraphPad) by using a two-tailed t-test, Mann-Whitney U test, Fisher exact test or hypergeometric test. Significance was considered at P< or equal 0.05.

Example 2: Treatment of Cancer Using an Anti-CD36 Antibody, with or without Cisplatin Studies of the effects of an anti-CD36 antibody, both with and without cisplatin, were performed in NSG mice (immuno-deficient). An experimental overview of these studies is provided in FIG. 1A. The studies included only male mice, though similar trends (data not reported) were observed using female mice. All mice were inoculated with commercially available Detroit 562 (ATCC) cancer cells, transduced with a retroviral vector expressing luciferase and the green fluorescent protein (Luc-GFP). Detroit 562 cells were derived from the metastatic site of a pharyngeal carcinoma (i.e., from an oral cancer). Prior to inoculation, the Detroit 562 cells were cultured in a humidified incubator at 37° C. with 5% $CO_2$, and were grown in EMEM (LONZA) supplemented with 5 µg ml$^{-1}$ penicillin/streptomycin and 10% FBS (GIBCO).

For each mouse, 50,000 Detroit 562 cells were inoculated via orthotopic injection. Previous testing revealed that, in untreated NSG mice, 100% of mice inoculated with Detroit 562 cells formed a large primary tumor and 81% of inoculated mice were observed to develop lymph node metastases within one week of inoculation.

Figures 1A, 1B:
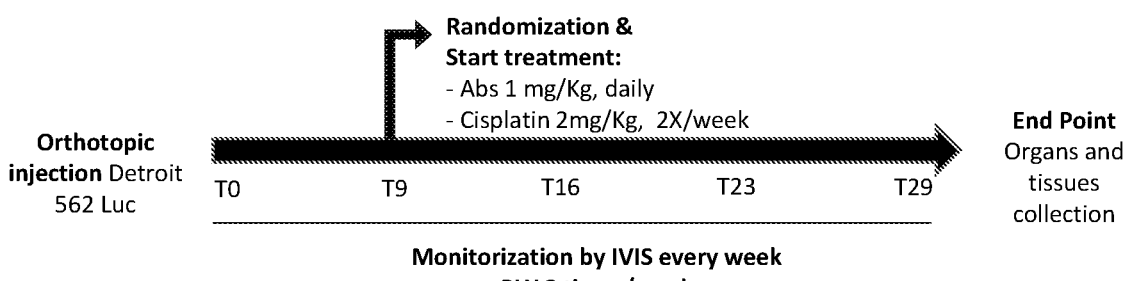
FIG. 1A is a schematic showing an experimental overview of a study of the effects of a commercial anti-CD36 antibody in a mouse model of oral cancer metastasis using Detroit-562 cells, both with and without cisplatin.
FIG. 1B details the study groups tested in that study, particularly the therapeutics and doses given to each group.

Treatment of the inoculated mice began nine days after inoculation with the cancer cells. Inoculated mice were divided into four distinct treatment groups. As can be seen in FIG. 1B, the treatment groups were:

Group 1: IgA isotype control (n=9 on days 1 through 23; n=6 on day 29);

Group 2: IgA isotype control plus cisplatin (n=5);

Group 3: commercial anti-CD36 antibody (JC63.1) (n=6 on days 1 through 23; n=4 on day 29);

Group 4: commercial anti-CD36 antibody (JC63.1) plus cisplatin (n=5).

Antibody treatments were administered via intraperitoneal (i.p.) injection daily at a dose of 1 mg/kg. Cisplatin was administered twice weekly at a dose of 2 mg/kg (Groups 2 and 4). Mice that did not receive cisplatin (Groups 1 and 3) instead received a volume equivalent injection of PBS. During the course of treatment, mice were observed once weekly using an in vivo imaging system (IVIS). Further, mouse body weight was measured twice weekly to update appropriate dosage amounts. Mice were sacrificed either when their bodyweight dropped under the ethical approved guidelines or at the end of the treatment period. Upon sacrifice, organs and tissues were collected for performance of immunohistochemistry analysis.

Figure 2A:
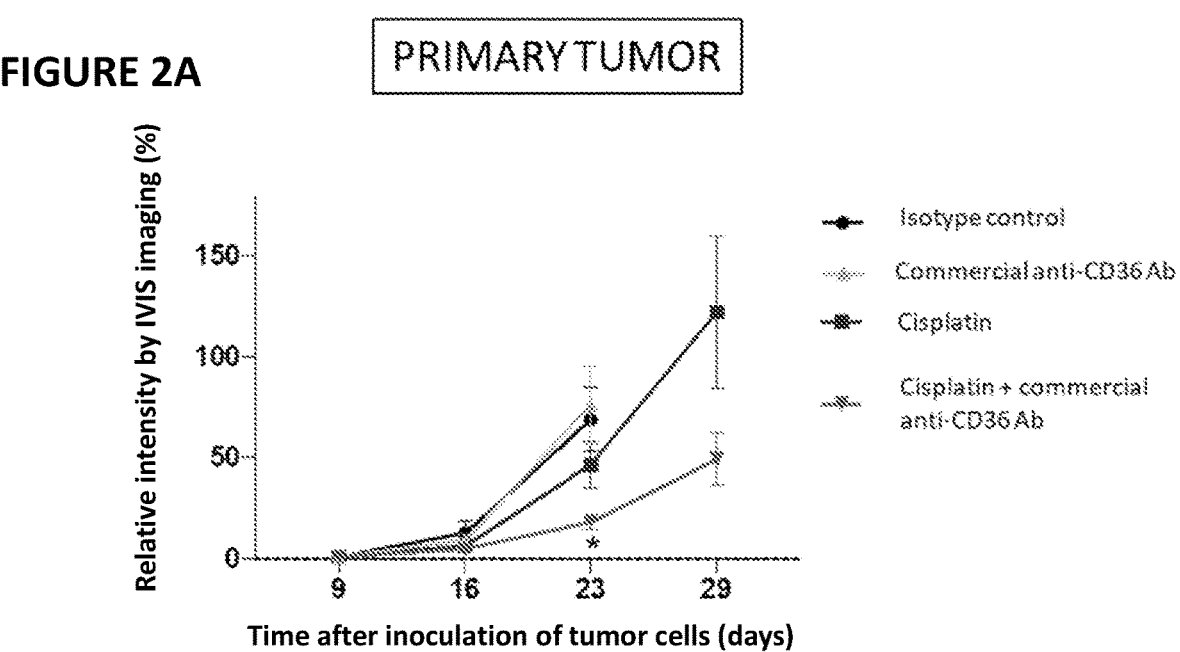
FIGS. 2A-2C provide results relating to the effects of an anti-CD36 antibody and/or cisplatin on the primary tumor in the Detroit-562 mouse model of oral cancer metastasis.
Figure 2B:
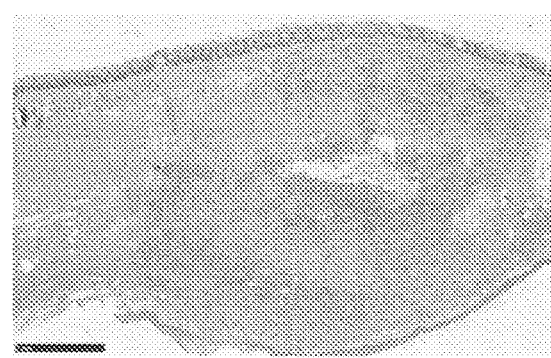
Figure 2C:
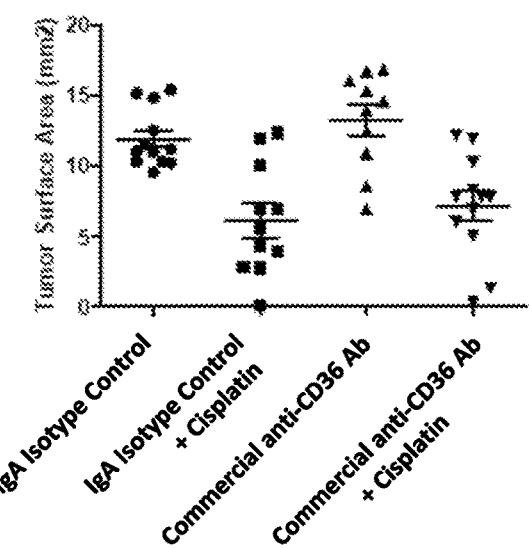

As can be seen in FIGS. 2A-2C, anti-CD36 Ab treatment has at least additive anti-tumor activity with cisplatin on suppressing the growth of a primary tumor in oral cancer. FIG. 2A shows that mice treated with both anti-CD36 antibody and cisplatin were better able to suppress tumor growth than mice treated with control antibody (IgA) and cisplatin, as measured by the relative intensity of luciferase-induced luminescence in treated mice relative to control mice. FIG. 2B shows a representative image of a primary tumor developed in the tongue after orthotopic injection of the Detroit 562 cells. FIG. 2C shows that mice treated with both anti-CD36 antibody or with control antibody (IgA) and cisplatin had primary tumors with reduced tumor surface area.

Figure 4A:
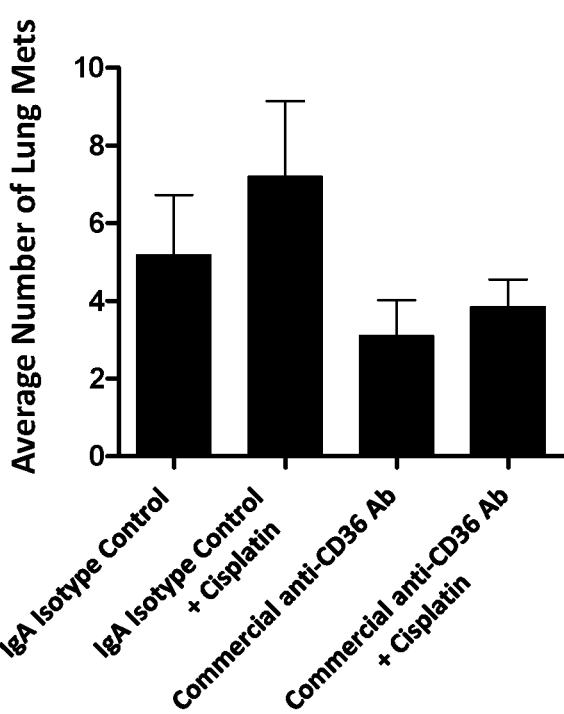
FIGS. 4A and 4B contain quantitation of the number and size of lung metastasis, respectively, in the Detroit-562 mouse model of oral cancer metastasis. These figures illustrate that mice treated with an anti-CD36 antibody alone had smaller and fewer metastases than control mice. Mice treated with cisplatin alone had similar numbers of metastases to control mice, though cisplatin did reduce the size of the metastatic tumors. Treatment with both anti-CD36 antibody and cisplatin resulted in mice with similar numbers of metastases than treatment with anti-CD36 antibody alone. However, treatment with both the anti-CD36 antibody and cisplatin resulted in reduction of metastatic tumor size to a greater extent than either the anti-CD36 antibody or cisplatin alone.
Figure 4B:
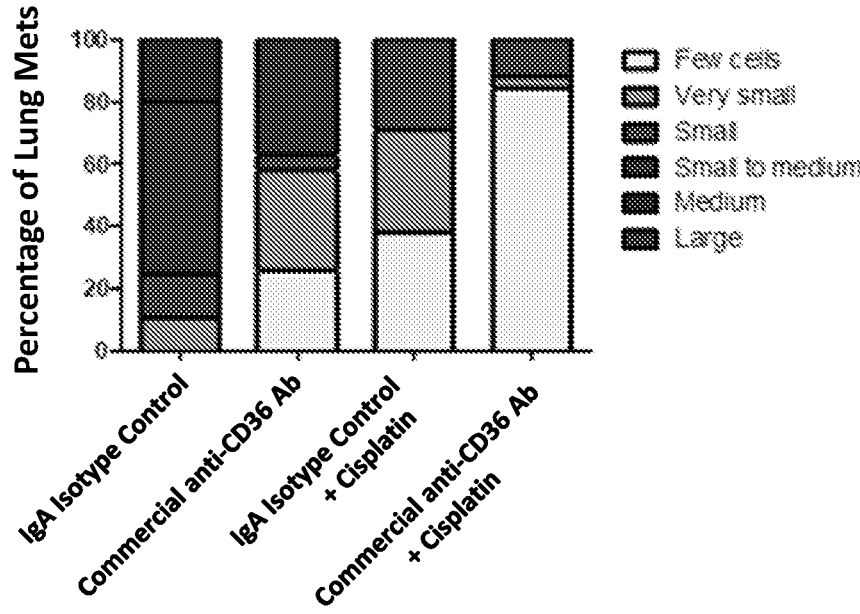

FIG. 3 shows representative images of lung metastases present in mice inoculated with Detroit 562 cancer cells and treated as described above. These images illustrate that mice treated with cisplatin (top right), a commercial anti-CD36 antibody (JC63.1; bottom left), or cisplatin and JC63.1 (bottom right) have fewer and smaller metastases than control treated mice (top left). Further, the quantitation of the number (FIG. 4A) and size (FIG. 4B) of lung metastases shows that mice treated with JC63.1 alone had smaller and fewer metastases than control-treated mice. Mice treated with cisplatin alone had similar numbers of metastases to control cells, though cisplatin did reduce the size of the metastatic tumors. Treatment with both JC63.1 and cisplatin resulted in mice with similar numbers of metastases as treatment with JC63.1 alone. However, treatment with both JC63.1 and cisplatin resulted in reduction of metastatic tumor size to a greater extent than either JC63.1 or cisplatin alone.

Example 3: Construction of Chimeric Antibodies

New chimeric antibodies were generated based on the ONA-0-v1 and ONA-0-v2 antibodies using standard molecular biology techniques. Briefly, the ONA-0-v1 and ONA-0-v2 antibody variable domains were codon optimized for expression in human cells and designed with NheI and AvaI restriction sites at the 5' and 3' ends. Variable domains were synthesized and then cloned into expression vectors containing the constant domain sequences of the respective human IgG1-LALA heavy chain, mouse IgA heavy chain or human kappa light chain. Following sequence verification, plasmids were prepared in sufficient quantity for transfection using Plasmid Plus purification kits (Qiagen).

The chimeric ONA-0-v1 IgG1 LALA antibody comprises the heavy chain in SEQ ID NO: 21 and the light chain in SEQ ID NO: 23, and was given the name 1G04. The analogous chimeric ONA-0-v2 IgG1 LALA antibody comprises the heavy chain in SEQ ID NO: 21 and the light chain in SEQ ID NO: 25. Exemplary polynucleotides encoding 1G04 are provided as SEQ ID NO: 22 (encoding the heavy chain) and SEQ ID NO: 24 (encoding the light chain). Exemplary polynucleotides encoding the chimeric ONA-0-v2 IgG1 LALA antibody are SEQ ID NO: 22 (encoding the heavy chain) and SEQ ID NO: 26 (encoding the light chain).

FIG. 5 presents a schematic diagram of the sequence and structure of the ONA-0-v1, ONA-0-v2, 1G04, and chimeric ONA-0-v2 IgG1 LALA antibodies. This schematic illustrates that the light chain variable region (shown in blue) is the only region of difference between ONA-0-v1 and ONA-0-v2. And this schematic further illustrates that the chimeric version of the ONA-0 antibodies contain a human IgG1 Fc tail with a LALA mutation (shown in red) in place of the murine IgA Fc tail.

Example 4: Characterizing Anti-CD36 Antibodies

HEK 293 (human embryonic kidney 293) mammalian cells were passaged to the optimum stage for transient transfection. Cells were transiently transfected with heavy and light chain expression vectors and cultured for a further 6 days.

Culture media was harvested by centrifugation at 4000 rpm and filtered through a 0.22 µm filter. For IgG antibodies, the first step of purification was performed by Protein A affinity chromatography with elution using citrate pH 3.0 buffer. For mouse IgA antibodies, the first step of purification was ConA sepharose affinity chromatography with elution using a 0.1M Tris, 0.1M NaCl, 0.5M glucopyranoside pH 7.6 buffer. Purified antibodies were then buffer exchanged into phosphate buffered saline (PBS) using a PD10 desalting column (GE Healthcare). Antibody concentration was determined by UV spectroscopy and the antibodies concentrated as necessary. Antibody purity was determined by SDS-PAGE (sodium dodecyl sulphate polyacrylamide gel electrophoresis) using an X-cell Sure-Lock system with 4-12% Bis-Tris NuPAGE gels and NuPAGE MES buffer (Thermo). Where required samples were reducing using NuPAGE sample reducing agent. The stained protein gels showing purified ONA-0-v1, ONA-0-v2, 1G04, and chimeric ONA-0-v2 (IgG1-LALA) are shown in FIG. 6.

To perform ELISA assays, 96-well ELISA plates were coated over night with human CD36 (Sino Biological, reference 10752-H08H) or mouse CD36 (Sino Biological, reference 50422-M08H) recombinant proteins at a concentration of 0.25 mg/ml. After two washes with PBS, plates were blocked with 4% skimmed milk in PBS for 1 hour at 37° C. Blocking solution was discarded and plates were washed five times with 200 μl/well PBS-Tween20 (0.5%). Primary antibodies were either omitted (control blocking solution treatment) or mixed in blocking solution at several dilutions ranging from 0.01 nM to 0.5 μM. The primary antibody solutions were added to the wells and incubated over night at 4° C. After 5 washes with 200 ul/well of PBS-Tween20 (0.5%), plates were incubated for 1 hour at room temperature with a goat anti-mouse HRP-conjugated antibody (Abcam, reference ab97235) diluted 1:2000 in blocking solution. Plates were then washed 5 times with 200 μl/well of PBS-Tween20 (0.5%), incubated with 100 μl/well TMB and detected after 10 minutes, 30 minutes, or 60 minutes with a spectrophotometer at a wave length of 630 nm.

As shown in the ELISA assays in FIG. 7, ONA-0-v1 was able to specifically bind to both human CD36 (top panel; magenta circles) and mouse CD36 (bottom panel; magenta circles). Based on this ELISA assay data, ONA-0-v1 was estimated to have a $K_D$ of approximately 0.04 nM for human CD36 and 0.1 nM for mouse CD36. In contrast, FIG. 7 also shows that ONA-0-v2 did not interact with either human CD36 (top panel; grey squares) or mouse CD36 (bottom panel; grey squares) in the same ELISA assay.

As shown in the ELISA assays in FIG. 8, the ONA-0-v1 antibody and a commercially-available anti-CD36 antibody (JC63.1) displayed similar affinity and binding characteristics for both human CD36 (top panel) and mouse CD36 (bottom panel).

As shown in the ELISA assays in FIG. 28A and FIG. 28B, 1G04 antibody and 1G06 antibody displayed similar affinity and binding characteristics for both human CD36 and mouse CD36.

For FACS analysis, cells were trypsinized, collected in a 15 mL tube and diluted in washing buffer (2% FBS in PBS). Cells were then centrifuged at 1500 rpm for 5 min at 4° C., supernatant was discarded, and cells were resuspended in fresh washing buffer. Anti-CD36 antibodies were either omitted (control wash buffer treatment) or serially diluted in washing buffer (dilution range up to 100 nM), and then added to the cells. Incubation was performed on ice for 1 hour. Cells were then centrifuged at 1500 rpm for 5 min at 4° C., supernatant was discarded, and cells were resuspended in fresh washing buffer. Finally, cells were incubated with a goat anti-mouse IgA (BV421 Rat Anti-Mouse IgA, Becton Dickinson, reference 743293) diluted 1:100 in washing buffer, washed and analysed by FACS.

As shown in the FACS assays in FIGS. 9A and 9B, both ONA-0-v1 and 1G04 specifically bound to cells overexpressing human CD36 (FIG. 9A). A commercial anti-CD36 antibody (JC63.1) similarly bound to cells overexpressing human CD36. However, analogous to what was observed in ELISA assays, the chimeric ONA-0-v2 IgG1 LALA antibody was not observed to interact with cells overexpressing human CD36 in the FACS assay (FIG. 9B).

As shown in the FACS assay in FIG. 10, ONA-0-v1 and 1G04 bound equivalently to cells overexpressing human CD36 when the antibodies were used at a 100 nM concentration.

As shown in the FACS assay in FIG. 29, 1G04 antibody and 1G06 antibody bound equivalently to cells overexpressing human CD36.

The affinity of ONA-0-v1, 1G04, and a commercial anti-CD36 antibody (JC63.1) for human CD36 was also measured by surface plasmon resonance (SPR) using a Biacore T200. 1G04 was analysed using a protein A capture surface, with a capture range of 100-150 RU and an antigen titration range of 3.3-333 nM. The mouse antibodies ONA-0-V1 and the commercial anti-CD36 antibody were analysed using an anti-mouse IgA capture surface, with a capture range of 160-180 RU and an antigen titration range of 3.3-333 nM. For each single analysis cycle a titration of five antigen concentrations were injected over the captured antibody and then the dissociation of the complex was measured. A double referencing method was employed in which data from the reference surfaces where no antibody was captured (fc 1 and 3 respectively) were subtracted from the antibody bound capture surface (fc 2 and 4). Blank injections of buffer were run for every antigen titration cycle and then subtracted from analyte injection cycles, to correct for small changes in the antibody capture surface density. All analysis was performed at 25° C., and the sample rack was kept at 6° C. during experimental runs. Each experiment was run at least three times with the mean binding constants generated from at least two independent assays reported. All analysis was performed in PBS-T running buffer at 40 μL/min.

In the SPR analysis, the commercial anti-CD36 antibody and ONA-0-V1 displayed similar $K_D$ values, while 1G04 displayed the tightest binding. The SPR results are presented in Table 6, Table 7, and Table 8 below.

TABLE 6

Mean kinetic data for the SPR-measured interaction of antibodies with CD36 fitted with the 1-to-1 model

| Antibody | $k_a$ (1/Ms) | $k_d$ (1/s) | $K_D$ (M) |
|---|---|---|---|
| Commercial anti-CD36 | 4.18E+05 | 1.96E−03 | 4.71E−09 |
| ONA-0-v1 (IgA) | 6.32E+05 | 3.54E−03 | 5.85E−09 |
| 1G04 (IgG1) | 1.00E+05 | 1.59E−04 | 1.74E−09 |

TABLE 7

Mean kinetic data for the SPR-measured interaction with CD36 fitted with the 2-state model

| Antibody | $k_a1$ (1/Ms) | $k_d1$ (1/s) | $k_a2$ (1/s) | $k_d2$ (1/s) | $K_D$ (M) |
|---|---|---|---|---|---|
| Commercial anti-CD36 | 8.69E+04 | 1.80E−03 | 5.72E−04 | 3.32E−04 | 7.61E−09 |
| ONA-O-v1 (IgA) | 1.08E+05 | 2.30E−03 | 5.58E−04 | 3.93E−04 | 8.72E−09 |
| 1G04 (IgG1) | 1.57E+05 | 3.24E−03 | 1.31E−03 | 1.64E−04 | 2.78E−09 |

TABLE 8

| | | | Mean kinetic data for the SPR-measured interaction with CD36 fitted with the bivalent model | | | | |
|---|---|---|---|---|---|---|---|
| Antibody | $k_a1$ (1/Ms) | $k_d1$ (1/s) | $k_a2$ (1/RUs) | $k_d2$ (1/s) | $k_a1$ (1/Ms) | $K_D1$ (M) | $K_D2$ (M) |
| Commercial anti-CD36 | 2.72E+04 | 2.06E−03 | 5.50E−05 | 3.99E−04 | 4.13E+02 | 7.65E−08 | 9.56E−07 |
| ONA-0-v1 (IgA) | 3.34E+04 | 2.59E−03 | 6.74E−05 | 5.27E−04 | 5.06E+02 | 7.73E−08 | 9.86E−07 |
| 1G04 (IgG1) | 5.23E+04 | 6.69E−04 | 6.41E−02 | 5.48E−02 | 4.81E+05 | 1.56E−08 | 1.14E−07 |

To measure the ability of anti-CD36 antibodies to alter fatty-acid uptake driven by CD36, commercially available SCC-25 cells (ATCC) were modified by stable transduction with a retroviral vector expressing CD36 and a lentiviral vector expressing luciferase. These cells, derived from a squamous cell carcinoma of the tongue, were grown were grown in keratinocyte serum-free medium (KSFM) supplemented with 5 g/ml penicillin/streptomycin, 0.025 mg/ml bovine pituitary extract and 0.2 μg/ml hEGF. Fatty acid uptake was evaluated using a commercially available bioluminescent-labelled long chain fatty acid analogue (SwissLumix) as a substrate. To perform the assay, cells were plated in 96-well plates and, starting the following day, were stimulated with 100 uM palmitic acid for 48 hours. Isotype control antibody or 1G04 were added at 10 ug/ml prior to palmitic stimulation and refreshed on the following days. To quantify uptake kinetics, substrate was added to plates after washing with PBSIX, and readings were taken over time using a Synergy HIM plate reader. This analysis showed that treatment with 1G04 blocked fatty acid uptake over time, as shown in FIG. 27A. Comparison of fatty acid uptake 256 seconds after addition of substrate showed that 1G04 inhibited approximately 17% of fatty acid uptake, relative to control cells (FIG. 27B; ***=p value of 0.0010).

Example 5: Treatment of Cancer Using the ONA-0-v1 Anti-CD36 Antibody, with or without Cisplatin Studies on the combination of the effects of the ONA-0-v1 anti-CD36 antibody, both with and without cisplatin, were performed in NSG mice (immuno-deficient). An experimental overview of these studies is provided in FIG. 11A. The studies included both male and female mice. All mice were inoculated with commercially available FaDu (ATCC) cancer cells, transduced with a retroviral vector expressing luciferase and the green fluorescent protein (Luc-GFP). FaDu cells were derived from a squamous cell carcinoma (i.e., from an oral cancer). Prior to inoculation, the FaDu cells were cultured in a humidified incubator at 37° C. with 5% $CO_2$, and were grown in EMEM (LONZA) supplemented with 5 μg ml$^{-1}$ penicillin/streptomycin and 10% FBS (GIBCO).

For each mouse, 100,000 FaDu cells were inoculated via orthotopic injection. Previous testing revealed that, in untreated NSG mice, 100% of mice inoculated with FaDu cells formed a large primary tumor and 91% of inoculated mice were observed to develop lymph node metastases within one week of inoculation.

Treatment of the inoculated mice began nine days after inoculation with the cancer cells. Inoculated mice were divided into four distinct treatment groups. As can be seen in FIG. 11B, the treatment groups were:

Group 1: IgA isotype control (n=7);
Group 2: IgA isotype control plus cisplatin (n=8);
Group 3: anti-CD36 antibody ONA-0-v1 (n=8);
Group 4: anti-CD36 antibody ONA-0-v1 plus cisplatin (n=8).

Antibody treatments were administered via intraperitoneal (i.p.) injection daily at a dose of 1 mg/kg. Cisplatin was administered twice weekly at a dose of 2 mg/kg (Groups 2 and 4). Mice that did not receive cisplatin (Groups 1 and 3) instead received a volume equivalent injection of PBS. During the course of treatment, mice were observed once weekly using an in vivo imaging system (IVIS). Further, mouse body weight was measured twice weekly to update appropriate dosage amounts. At the end of the treatment period, the mice were sacrificed, and organs and tissues were collected for performance of immunohistochemistry analysis.

As can be seen in FIGS. 12A and 12B, treating with the anti-CD36 antibody ONA-0-v1 in combination with cisplatin had similar effects to treating with cisplatin alone as measured by IVIS imaging and H&E staining of the primary tumor. Treatment with ONA-0-v1 alone at a 1 mg/kg dose in this model did not have a statistically significant effect on the primary tumor relative to treatment with an isotype control antibody. In contrast, FIGS. 13A and 13B show that treatment with ONA-0-v1 alone was able to inhibit growth of lymph node metastases, as measured by relative intensity in IVIS imaging. Moreover, treatment with ONA-0-v1 in combination with cisplatin resulted in almost complete inhibition of lymph node metastasis growth, as measured by relative intensity in IVIS imaging.

Treatment with the ONA-0-v1 antibody inhibited growth of lymph node metastases. FIG. 14 shows a representative IVIS image of an inoculated NSG mouse on day 7 postorthotopic injection of FaDu cells, immediately prior to the start of treatment. The lymph node metastasis in that mouse is indicated by the circled area, with the intensity of the luciferase signalling indicated by the heat map. FIG. 14 also shows the quantitation of the lymph node metastases present in all groups of mice on day 7. That initial intensity was the same in all groups. Further IVIS imaging was performed at the end-point of treatment, As shown in FIG. 15 (left panel), treatment with ONA-0-v1 antibody inhibited metastatic tumor growth by greater than 50% relative to the IgA isotype control, as measured by the ratio of IVIS imaging intensity between the ending and starting points of treatment. Further, also as shown in FIG. 15 (right panel), addition of ONA-0-v1 to cisplatin enhanced cisplatin's ability to inhibit metastatic tumor growth. The ONA-0-v1 and cisplatin combination resulted in almost complete inhibition of tumor growth in lymph node metastases.

Treatment with the ONA-0-v1 antibody also inhibited penetrance of metastases into lymph nodes, as shown in FIG. 16. All control mice presented with lymph node metastases. Treatment with either cisplatin or ONA-0-v1 prevented metastasis into the lymph nodes in one of the eight tested mice in each respective treatment group. Moreover, ONA-0-v1's inhibition of penetrance was synergistic with that of cisplatin, as the combination of cisplatin and ONA-0-v1 prevented any metastasis in five of the eight tested mice.

Treatment with the ONA-0-v1 antibody was well-tolerated by NSG mice over the course of treatment. As shown in FIG. 17A and FIG. 17B, ONA-0-v1 treatment alone did not have any effects on mouse body weight or platelet count relative to isotype control-treated mice. ONA-0-v1 treatment also did not significantly enhance cisplatin-mediated weight loss or the cisplatin-mediated decrease in platelet count.

Example 6: Antitumor Efficacy of Anti-CD36 Antibodies in Combination with PD1 Inhibition in C57B16/J Mice Bearing YUMM1.7 Cells-Derived Melanoma Tumors 250,000 YUMM1.7 cells are suspended in PBS and are injected subcutaneously in the flank of 8-12 week-old C57B16/J mice. When tumors reach a mean volume of 50-100 mm³, mice are randomized and the treatment is started.

The experimental groups are as shown in Table 9 below.

TABLE 9

Treatment Groups for Treating with anti-CD36
and anti-PD-1 Antibodies

| Group | No. Mice | Treatment |
|---|---|---|
| 1 | 10 | anti-PD1 isotype control (rat IgG2a, clone 2A3 ) |
| 2 | 10 | anti-mouse PD-1 (clone RMP1-14) |
| 3 | 10 | anti-CD36 isotype control |
| 4 | 10 | anti-CD36 |
| 5 | 10 | anti-mouse PD-1 + anti-CD36 |

All antibodies are injected IP at the concentration of 10 mg/kg, 3 times/week. Mice are monitored three times per week for body weight and tumour volume and daily for behaviour and survival. When tumour reaches a maximum volume of 1.500 mm³, mice are euthanized and tissues collected. Primary tumours are weighted and measured again with a caliper. Lung and liver are embedded in paraffin for H&E staining and a blinded analysis for metastatic lesions. Results of the study are expected to show that anti-CD36 antibodies (e.g., 1G04) and anti-PD-1 antibodies have additive or synergistic effects in treating cancer in the YUMM1.7 mouse model of melanoma.

Example 7: Treatment of Ovarian Cancer Using the ONA-0-v1 Anti-CD36 Antibody Studies of the effects of the ONA-0-v1 anti-CD36 antibody on ovarian cancer were performed in NSG mice (immuno-deficient). An experimental overview of these studies is provided in FIG. 18A. The studies included only female mice. All mice were inoculated with commercially available OVCAR-3 (ATCC) cancer cells. OVCAR-3 cells were derived from a human progressive adenocarcinoma of the ovary (i.e., from an ovarian cancer). Prior to inoculation, the OVCAR-3 cells were cultured in a humidified incubator at 37° C. with 5% CO₂, and were grown in RPMI-1640 supplemented with 5 µg ml⁻¹ penicillin/streptomycin, 0.01 mg/ml bovine inulin and 20% FBS (GIBCO).

For each mouse, a piece of an OVCAR-3 xenograft was implanted orthotopically. As shown in FIG. 18B, NSG mice implanted with OVCAR-3 cells form a large primary tumor. Mice implanted with OVCAR-3 also develop metastases in both the peritoneal wall and liver. Exemplary metastases from inoculated mice are shown in FIGS. 19A and 19B.

Treatment of the implanted mice began 23 days after implantation with the OVCAR-3 tumor pieces. Inoculated mice were divided into one of two treatment groups: vehicle injection control (n=9) or ONA-0-v1 treatment (n=9). Antibody treatments were administered via intraperitoneal (i.p.) injection daily at a dose of 3 mg/kg, while control mice received an equal volume of vehicle on the same schedule. Mice were sacrificed at the end of the treatment period. Upon sacrifice, organs and tissues were collected for performance of immunohistochemistry analysis.

As can be seen in FIGS. 18B and 18C, treatment with ONA-0-v1 results in smaller tumors in the OVCAR-3 mouse model of ovarian cancer. The quantification of this effect in FIG. 18C shows that treatment with OVCAR-3 reduced tumor weight from an average of 1.844 g to an average of 1.058, a decrease of 43% percent. These data indicate that ONA-0-v1 inhibited tumor growth and/or promoted tumor cell destruction during the treatment period.

Histological analysis of the primary tumors in vehicle-treated and ONA-0-v1-treated mice was also performed. First, the tumors were analysed to determine percent necrosis by visual inspection and quantification of a pathologist. The results of this analysis are shown in FIG. 18D, which shows that ONA-0-v1 increased from approximately 24.4% to approximately 40.71% (*=p value of 0.0287). This increase indicates that treated tumors present higher cell death. The primary tumors of treated and ONA-0-v1-treated mice were also analysed to determine the percent of collagenous and fibrotic areas by Sirius red staining. The results of this analysis are shown in FIG. 18E, which shows that ONA-0-v1 increased the SR positive area from 16.9% to 22.5% (*=p value of 0.0457). This increase indicates that treatment with ONA-0-v1 increases fibrosis and, together with the increased necrosis, indicates that the treated tumors and not only smaller, but also they are composed of fewer tumoral cells.

FIGS. 20A, 20B, and 20C show the results of quantifying metastatic tumors in ONA-0-v1 treated mice. FIG. 20A shows that the total number of metastases decreased by over 50% in the ONA-0-v1-treated mice relative to vehicle-treated mice. The total number of metastases was determined by visual inspection of the organs. FIG. 20B and FIG. 20C show the results of macroscopic analysis of the size of metastases in the peritoneal wall and liver, respectively. The size of the metastases was measured by visual inspection. In the vehicle-treated group, 48% of the animals had large metastasis (>5 mm), 41% small metastasis (1-2 mm), and 11% no metastasis in the peritoneal wall. In the ONA-0-v1 treated animals, no large metastasis were detected, 38% of the animals had small metastasis, and 63% presented no metastasis. In the liver, the percentage of mice without metastasis increased from 22% in the vehicle group to 50% in the treated group. Among the animals with liver metastasis, the number of large ones was reduced from 16% to 6% and small ones from 62% to 44%. Treating with ONA-0-v1 shifted the size of peritoneal wall metastases such that large metastases disappeared entirely, and more mice did not have peritoneal metastases at all (FIG. 20B). Similarly, treating with ONA-0-v1 shifted the size of liver metastases such that fewer large metastases were found, and more mice did not have liver metastases at all (FIG. 20C). Collectively, FIGS. 20A, 20B, and 20C show that ONA-0-v1 is effective at reducing the formation and growth of metastases from ovarian cancer.

Example 8: Treatment of Colon Cancer Using the ONA-0-v1 Anti-CD36 Antibody

Studies of the effects of the ONA-0-v1 anti-CD36 antibody on colon cancer were performed in BALB/c nude mice (immuno-deficient). An experimental overview of these studies is provided in FIG. 21A. The studies included only female mice. All mice were inoculated with commercially available HCT-116 (ATCC) cancer cells, transduced with a retroviral vector expressing luciferase. HCT-116 cells were derived from a human colorectal carcinoma (i.e., from a colon cancer). Prior to inoculation, the HCT-116 cells were cultured in a humidified incubator at 37° C. with 5% $CO_2$, and were grown in McCoy's 5A medium supplemented with 5 $\mu g$ $ml^{-1}$ penicillin/streptomycin and 10% FBS (GIBCO).

For each mouse, $2 \times 10^6$ HCT-116 cells were inoculated via orthotopic injection. Each mouse was imaged after inoculation and one week later and liver metastasis were confirmed by ex vivo luminescence prior to start of treatment. Treatment began 14 days after inoculation with the HCT-116 cells. Inoculated mice were divided into one of two treatment groups: vehicle injection control (n=10) or ONA-0-v1 treatment (n=10). Antibody treatments were administered via intraperitoneal (i.p.) injection daily at a dose of 3 mg/kg, while control mice received an equal volume of vehicle on the same schedule. At 7, 14, and 21 days after start of treatment, all mice were imaged via IVIS. Mice were sacrificed at the end of the treatment period (day 25). Upon sacrifice, organs and tissues were collected for performance of necropsy, ex-vivo IVIS, and histopathology.

Figure 21B:
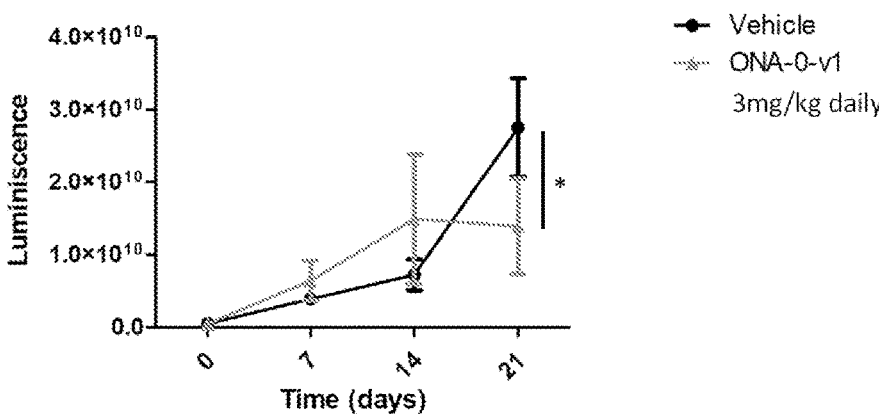
Figure 21C:
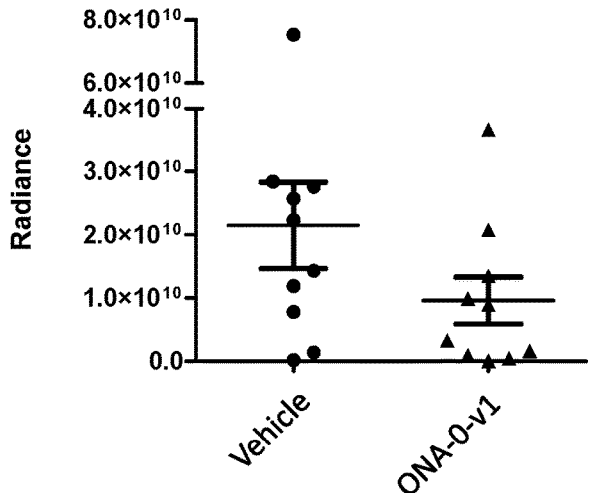

FIG. 21B and FIG. 21C show IVIS imaging of the primary tumor formed at the site of HCT-116 inoculation. FIG. 21B shows the change in in vivo total tumor biolumi-nescence over time, and shows that by day 21 treatment with ONA-0-v1 had reduced the growth of the tumor relative to the vehicle-treated control (*=p value of 0.0288). FIG. 21C shows the bioluminescence of the tumor on day 25, as measured by ex vivo imaging after sacrifice of the mice. ONA-0-v1 treatment again was observed to have reduced the growth of the tumor (average radiance $1.51 \times 10^{10}$) relative to the vehicle-treated control (average radiance $2.15 \times 10^{10}$).

FIGS. 22A, 22B, 22C, and 22D show the results of quantifying metastatic tumors in the ONA-0-v1 and vehicle treated mice. The penetrance of metastatic tumors in the liver, lung, spleen, and kidney were quantified by ex vivo luminescence, where organs that showed no luminescence were characterized as being metastasis-free. FIG. 22A shows that treatment with ONA-0-v1 reduced the percentage of mice with tumors in their liver from 90% to 60% (*=p value less than 0.0001). Similarly, FIG. 22B shows that treatment with ONA-0-v1 reduced the percentage of mice with tumors in their lungs from 80% to 60% (*=p value of 0.0032).

The luminescence of the metastatic tumors in the liver, lung, spleen, and kidney was also quantified, and FIGS. 23A, 23B, 23C, and 23D show the results of that quantification. After the organs to be examined were removed from the mice, they were examined by IVIS. FIGS. 23B and 23D show that treatment with ONA-0-v1 led to almost complete elimination of the luminescence in the ex vivo lung (1.23*107 to $1.24 \times 10^6$) (FIG. 23B) and kidney (FIG. 23D) from treated mice ($4.26 \times 10^6$ to $1.08 \times 10^6$), reflecting a complete or nearly complete elimination of metastases in those organs. Similarly, FIGS. 23A and 23C show that treatment with ONA-0-v1 led to a reduction in the luminescence in the ex vivo liver (1.41*108 to $9.02 \times 10^7$) and spleen (3.77*108 to $1.79 \times 10^8$) from treated mice, reflecting a reduction in the size and/or number of metastases in the lung. These data indicate that ONA-0-v1 is a potent inhibitor of metastasis spread and growth in colon cancer.

The body weight of the mice inoculated with HCT-116 was also tracked through the course of the experiment. FIG. 24 shows that, from day 18 onward, mice treated with ONA-0-v1 on average had a higher body weight than the control mice. For example, on day 18 the control mice had a body weight of 84.3% of their starting body weight, while mice treated with ONA-0-v1 had a body weight of 91.1% of their starting body weight. This is reflective of the ONA-0-v1 mice being healthier and being better able to fight the colon cancer tumors.

Example 9: Treatment of Ovarian Cancer Using the ONA-0-v1 and 1G04 Anti-CD36 Antibodies Studies of the effects of the ONA-0-v1 and 1G04 anti-CD36 antibodies on ovarian cancer were performed in NSG mice (immuno-deficient). An experimental overview of these studies is provided in FIG. 25A. The studies included only female mice. All mice were inoculated with commercially available OVCAR-3 (ATCC) cancer cells. OVCAR-3 cells were derived from a human progressive adenocarci-noma of the ovary (i.e., from an ovarian cancer). For each mouse, a piece of an OVCAR-3 xenograft was implanted orthotopically. Prior to inoculation, the OVCAR-3 cells were cultured in a humidified incubator at 37° C. with 5% $CO_2$, and were grown in RPMI-1640 supplemented with 5 $\mu g$ $ml^{-1}$ penicillin/streptomycin, 0.01 mg/ml bovine insulin and 20% FBS (GIBCO).

Treatment of the implanted mice began 7 days after implantation with the OVCAR-3 tumor pieces. Inoculated mice were divided into one of three treatment groups: vehicle injection control (n=9), ONA-0-v1 treatment (n=9), or 1G04 treatment (n=9). ONA-0-v1 antibody treatments were administered via intraperitoneal (i.p.) injection daily at a dose of 3 mg/kg. 1G04 antibody treatments were administered via i.p. injection TIW (three-times weekly) at a dose of 10 mg/kg. Control mice received an equal volume of vehicle daily. As can be seen in FIG. 25B, the weight of mice in all three treatment groups remained the same throughout the treatment period. Mice were sacrificed at the end of the treatment period. Upon sacrifice, organs and tissues were collected for performance of necropsy and histopathology analysis.

Figure 25C:
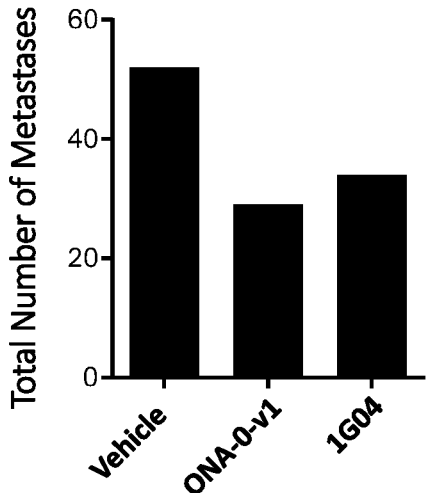

FIGS. 25C-25G show the results of quantifying metastatic tumors in treated mice. FIG. 25C shows the total number of metastases for each treatment condition. The total number of metastases was determined by visual inspection of the organs. This analysis revealed that the number of metastases decreased by approximately 45% in the ONA-0-v1-treated mice, relative to vehicle-treated mice (52 metastasis counted in vehicle and 29 in treated group). The total number of metastases also decreased by approximately 35% in the 1G04-treated mice, relative to vehicle-treated mice (52 metastasis counted in vehicle and 34 in treated group).

Figure 25D:
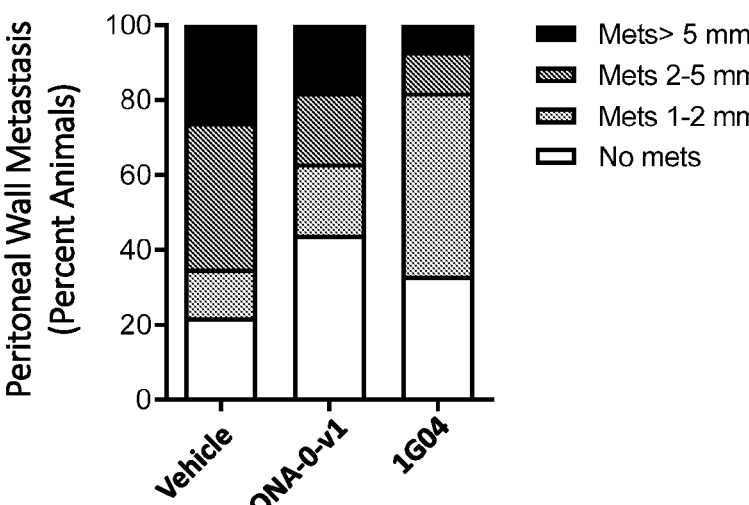
Figure 25E:
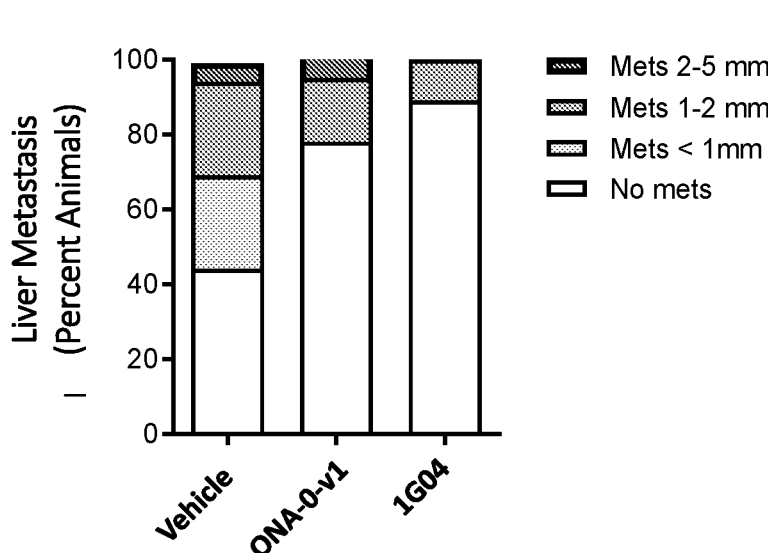

FIG. 25D and FIG. 25E show the results of macroscopic analysis of the size of metastases in the peritoneal wall and liver, respectively. The size of the metastases was measured by visual inspection. Treating with either ONA-0-v1 or 1G04 reduced the observed size of metastases such that fewer large (>5 mm) and medium (1-2 mm) sized metastases were observed. Vehicle-treated animals presented with 26% of the mice having >5 mm metastasis, 39% having 2-5 mm metastasis, and 13% having 1-2 mm metastasis in the peritoneal wall. ONA-0-v1 treated animals presented with 19% of mice having >5 mm metastasis, 19% having 2-5 mm metastasis, and 19% having 1-2 mm metastasis in the peritoneal wall. 1G04-treated animals presented with 7% of mice having >5 mm metastasis, 11% with 2-5 mm metastasis, and 49% with 1-2 mm metastasis in the peritoneal wall. In addition, the livers of treated mice showed an analogous pattern. Vehicle-treated animals presented with 5% of the mice having 2-5 mm metastasis, 25% having 1-2 mm metastasis, and 25% having <1 mm metastasis in the liver. ONA-0-v1 treated animals presented with 6% of the mice having 2-5 mm metastasis, 17% having 1-2 mm metastasis, and none having <1 mm metastasis in the liver. 1G04-treated none with 2-5 mm metastasis, 11% with 1-2 mm metastasis and none with <1 mm metastasis. Moreover, treatment with either ONA-0-v1 or 1G04 increased the percentage of animals that were free of metastases in the peritoneal wall and liver. 22% of the vehicle-treated mice, 44% of the ONA-0-v1-treated mice, and 33% of the 1G04-treated mice were metastasis-free in the peritoneal wall. 44% of vehicle-treated mice, 78% of the ONA-0-v1-treated mice, and 89% of the 1G04-treated mice were free of metastasis in the liver.

Figure 25F:
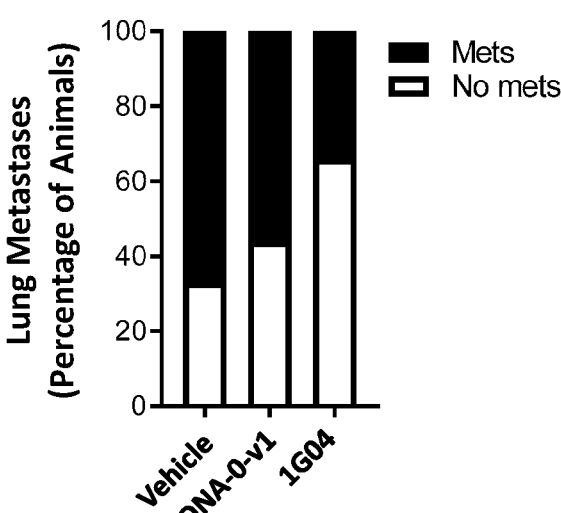
Figure 25G:
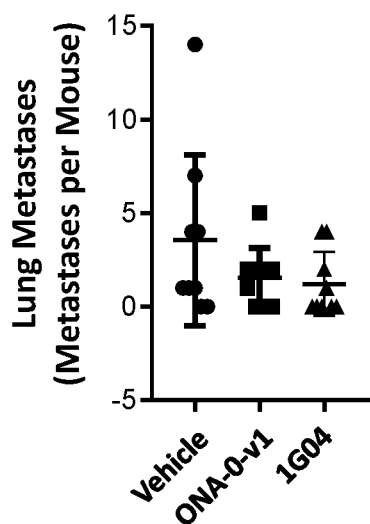

FIG. 25F shows the results of microscopic analysis of the penetrance of metastases in the lung. As with the peritoneal wall and liver, treatment with either ONA-0-v1 or 1G04 increased the percentage of animals that were free of metastases in the lung (from 33% in vehicle to 44% and 66% in ONA-0-v1 and 1G04 groups respectively). Moreover, as quantified in FIG. 25G, treatment with either ONA-0-v1 or 1G04 reduced the number of metastases in the lungs per mouse (mean metastasis number 3.6 in vehicle-treated, 1.6 in ONA-0-v1 and 1.2 in 1G04 groups).

Collectively, FIGS. 25C-25G show that both ONA-0-v1 (a murine IgA antibody) and 1G04 (a chimeric IgG1 antibody) are effective at reducing the formation and growth of metastases from ovarian cancer.

Example 10: Treatment of Colon Cancer Using the 1G04 Anti-CD36 Antibody

Studies of the effects of the 1G04 anti-CD36 antibody on colon cancer were performed in BALB/c nude mice (immuno-deficient). An experimental overview of these studies is provided in FIG. 26A. The studies included only female mice. All mice were inoculated with commercially available HCT-116 (ATCC) cancer cells, transduced with a retroviral vector expressing luciferase. HCT-116 cells were derived from a human colorectal carcinoma (i.e., from a colon cancer). Prior to inoculation, the HCT-116 cells were cultured in a humidified incubator at $37°$ C. with 5% $CO_2$, and were grown in McCoy's 5A medium supplemented with 5 $\mu g\ ml^{-1}$ penicillin/streptomycin and 10% FBS (GIBCO).

For each mouse, $2 \times 10^6$ HCT-116 cells were inoculated via orthotopic injection. Each mouse was imaged after inoculation and one week later and liver metastasis were confirmed by ex vivo luminescence prior to start of treatment. Treatment began 12 days after inoculation with the HCT-116 cells. Inoculated mice were divided into one of two treatment groups: vehicle injection control (n=10) or 1G04 treatment (n=10). Antibody treatments were administered via intraperitoneal (i.p.) injection at a dose of 10 mg/kg three times per week, while control mice received an equal volume of vehicle on the same schedule. One day prior to the start of treatment, and at 7, 14, and 21 days after the start of treatment, all mice were imaged via IVIS. Mice were sacrificed at the end of the treatment period (day 25). Upon sacrifice, organs and tissues were collected for performance of necropsy, ex-vivo IVIS, and histopathology.

As can be seen in FIG. 26B, mice treated with 1G04 were better able to maintain weight during the course of treatment. FIG. 26C shows the results of whole-animal bioluminescence imaging over time, which is a readout for the growth of luciferase-containing tumor cells in the mouse. The bioluminescence imaging showed that 1G04 decreased whole animal luminescence, and thus slowed the growth of the injected HCT-116 tumor cells in vivo.

FIGS. 26D, 26E, 26F, and 26G show the results of quantifying metastatic tumors in the 1G04 and vehicle treated mice. After the organs to be examined were removed from the mice, the luminescence of the metastatic tumors in the liver (FIG. 26D), lung (FIG. 26E), spleen (FIG. 26F), and kidney (FIG. 26G) was quantified by ex vivo luminescence using IVIS. In each organ, 1G04 treatment decreases the luminescence, reflecting a reduction in the size and/or number of metastases. The observed mean luminescence values for liver, lung, spleen and kidney of vehicle-treated mice were 1.69*108, 5.38*$10^6$, 2.66*108, and 4.11*107, respectively. The observed mean luminiscence values for liver, lung, spleen and kidney of 1G04-treated mice were 1.07*108, 1.68*$10^6$, 1.83*107, and 1.46*107, respectively. These data indicate that 1G04 is a potent inhibitor of metastasis spread and growth in colon cancer.

Collectively, FIGS. 26D-26G show that 1G04 is effective at reducing the formation and growth of metastases from colon cancer.

Example 11: Treatment of Lung Cancer Using the 1G04 Anti-CD36 Antibody

Studies of the effects of the 1G04 anti-CD36 antibody on lung cancer were performed in NSG mice (immuno-deficient). An experimental overview of these studies is provided in FIG. 30A. The studies included only female mice. All mice were inoculated with commercially available A549-luc2 (ATCC) cancer cells, a modified version of A549 cells generated by stable transduction with a lentiviral vector expressing luciferase. A549 cells are cells derived from a lung carcinoma (i.e. from a lung cancer), and therefore were used as part of a mouse model of lung cancer. Prior to inoculation, the A549 cells were cultured in a humidified incubator at $37°$ C. with 5% $CO_2$, and were grown in F-12K medium supplemented with 5 $\mu g\ ml^{-1}$ penicillin/streptomycin and 10% FBS (GIBCO).

For each mouse, $1 \times 10^6$ A549 cells were inoculated intravenously via tail vein injection. Each mouse was imaged after inoculation and one week later and lung metastasis was confirmed by luminescence prior to start of treatment. Treatment began 8 days after inoculation with the A549 cells. As detailed in FIG. 30B, inoculated mice were divided into one of two treatment groups: vehicle injection control (n=11) or 1G04 treatment (n=11). Antibody treatments were administered via intraperitoneal (i.p.) injection at a dose of 10 mg/kg three times per week, while control mice received an equal volume of vehicle on the same schedule. One day prior to the start of treatment, and once weekly after the start of treatment, all mice were imaged via IVIS. Mice were sacrificed at the end of the treatment period (day 61). Upon sacrifice, organs and tissues were collected for performance of necropsy and ex-vivo IVIS.

FIG. 30C shows the results of imaging whole-animal bioluminescence over time, with decreased fluorescence observed in 1G04 treated mice. This indicates that 1G04 treatment reduced the growth of the injected A549 tumor cells in vivo (=p value of p=0.0002). At endpoint, lungs of mice treated with 1G04 antibody were smaller than lungs from control vehicle-treated mice (FIG. 30**D), indicating that less tumor growth occurred. The observed mean lung weight was 0.90 g in vehicle-treated mice and 0.72 g in 1G04-treated mice (20% reduction). Animals treated with 1G04 also presented less luminescence in the lung at endpoint (2.11*108 to 1.39*108) as presented in FIG. 30E. These results indicate that 1G04 inhibits metastasis growth in lung cancer.

Example 12: Treatment of Colon Cancer Using the 1G04 Anti-CD36 Antibody

Studies of the effects of the 1G04 anti-CD36 antibody on lung cancer were performed in C57BL/6 mice (immunocompetent). An experimental overview of these studies is provided in FIG. 31A. The studies included only female mice. All mice were inoculated with commercially available MC-38 cancer cells, transduced with a vector expressing luciferase. MC-38 cells are cells derived from a mouse colon adenocarcinoma (i.e. from a colon cancer). Prior to inoculation, MC-38 cells were cultured in a humidified incubator at 37° C. with 5% $CO_2$ and were grown in DMEM medium supplemented with 5 ug $ml^{-1}$ penicillin/streptomycin and 10% FBS (GIBCO).

For each mouse, $1 \times 10^6$ MC-38 cells were inoculated intrasplenically. Each mouse was imaged 4 days later, and liver metastasis was confirmed by ex vivo luminescence prior to start of treatment on day 5 after inoculation. As detailed in FIG. 31B, inoculated mice were divided into one of two treatment groups: vehicle injection control (n=13) or 1G04 treatment (n=10). Antibody treatments were administered via intraperitoneal (i.p.) injection at a dose of 10 mg/kg three times per week, while control mice received an equal volume of vehicle on the same schedule. One day prior to the start of treatment, and twice weekly after the start of treatment, all mice were imaged via IVIS. Mice were sacrificed at the end of the treatment period (day 60). Upon sacrifice, organs and tissues were collected for performance of necropsy and ex-vivo IVIS.

Whole-animal bioluminescence imaging during the study showed that 1G04-treatment decreases luminescence, indicating a reduction in tumoral growth (*=p value of 0.003, FIG. 31C). Ex vivo analysis of luminescence showed that mice treated with 1G04 present lower luminescence in both liver ($1.41 \times 10^9$ to $6.67 \times 10^4$) and lungs ($7.23 \times 10^6$ to 6.78*104) (FIGS. 31D and 31E, respectively). In conclusion, 1G04 showed efficacy decreasing metastasis size in colon cancer.

Example 13: Treatment of Breast Cancer Using the 1G04 Anti-CD36 Antibody

Studies of the effects of the 1G04 anti-CD36 antibody on breast cancer were performed in BALB/c mice (immunocompetent). An experimental overview of these studies is provided in FIG. 32A. The studies included only female mice. All mice were inoculated with commercially available 4T1 cancer cells (ATCC), transduced with a vector expressing luciferase. 4T1 cells were derived from murine mammary gland tissue (i.e. from a breast cancer). Prior to inoculation, 4T1 cells were cultured in a humidified incubator at 37° C. with 5% $CO_2$, and were grown in RPMI medium supplemented with 5 μg $ml^{-1}$ penicillin/streptomycin, 2 mM L-Glutamine and 10% FBS (GIBCO).

For each mouse, $4 \times 10^4$ 4T1 cells were inoculated orthotopically in the mammary fat pad. Treatment began 5 days after inoculation with 4T1 cells. Mice were divided into one of two treatment groups: vehicle injection control (n=10) or 1G04 treatment (n=10). Antibody treatments were administered via intraperitoneal (i.p.) injection at a dose of 10 mg/kg three times per week, while control mice received an equal volume of vehicle on the same schedule (FIG. 32B). Mice were sacrificed at the end of the treatment period (day 22). Upon sacrifice, organs and tissues were collected for performance of necropsy and ex-vivo IVIS.

Luminiscence in the lungs was reduced in 1G04-treated mice compared to vehicle-treated ones ($2.49 \times 10^5$ to $5.96 \times 10^4$, FIG. 32C), indicating that anti-CD36 treatment reduces the size of metastasis and/or metastatic spread to distant organs.

The invention claimed is:

1. An isolated antibody that binds to CD36, which comprises a light chain CDR1 region, a light chain CDR2 region, a light chain CDR3 region, a heavy chain CDR1 region, a heavy chain CDR2 region, and a heavy chain CDR3 region; wherein:
   (i) the heavy chain CDR1 region, the heavy chain CDR2 region, and the heavy chain CDR3 region are selected, respectively, from the group consisting of
      (a) SEQ ID NOs: 37, 38, and 29;
      (b) SEQ ID NOs: 44, 46, and 29;
      (c) SEQ ID NOs: 45, 47, and 29; and
   (ii) the light chain CDR1 region, the light chain CDR2 region, and the light chain CDR3 region are selected, respectively, from the group consisting of
      (a) SEQ ID NOs: 30, 31, and 32;
      (b) SEQ ID NOs: 48, 31, and 32;
      (c) SEQ ID NOs: 48, 49, and 32; and
      (d) SEQ ID NOs: 30, 50, and 32.

2. The isolated antibody of claim 1, wherein the antibody is a chimeric antibody.

3. The isolated antibody of claim 1, wherein the antibody is a humanized antibody.

4. The isolated antibody of claim 1, wherein the isolated antibody comprises:
   (a) a heavy chain variable region comprising SEQ ID NO: 51 and a light chain variable region comprising SEQ ID NO: 55, SEQ ID NO: 56, SEQ ID NO: 57, or SEQ ID NO: 58;
   (b) a heavy chain variable region comprising SEQ ID NO: 52 and a light chain variable region comprising SEQ ID NO: 55, SEQ ID NO: 56, SEQ ID NO: 57, or SEQ ID NO: 58;
   (c) a heavy chain variable region comprising SEQ ID NO: 53 and a light chain variable region comprising SEQ ID NO: 55, SEQ ID NO: 56, SEQ ID NO: 57, or SEQ ID NO: 58; or
   (d) a heavy chain variable region comprising SEQ ID NO: 54 and a light chain variable region comprising SEQ ID NO: 55, SEQ ID NO: 56, SEQ ID NO: 57, or SEQ ID NO: 58.

5. The isolated antibody of claim 1, wherein the isolated antibody-binds to an epitope of human CD36 that is the same as an antibody comprising the light chain in SEQ ID NO: 7 and the heavy chain in SEQ ID NO: 5.

6. The isolated antibody of claim 1, wherein the isolated antibody competes for binding to human CD36 with an antibody comprising the light chain in SEQ ID NO: 7 and the heavy chain in SEQ ID NO: 5.

7. The antibody of claim 1, wherein the antibody binds to human CD36 with a KD of less than 10 nM.

8. The antibody of claim 1, wherein the antibody comprises a VH having at least 80% identity with comprising the amino acid sequence of SEQ ID NO: 11 and a VL comprising the amino acid sequence of SEQ ID NO: 13.

9. The antibody of claim 8, wherein the antibody comprises a VH comprising the amino acid sequence of SEQ ID NO: 11.

10. The antibody of claim 1, which further comprises
(i) a heavy chain constant region selected from the group consisting of human immunoglobulin IgA1, IgA2, IgG1, IgG2, IgG3, or IgG4 heavy chain constant regions; and
(ii) a light chain constant region selected from the group consisting of human immunoglobulins K and λ light chain constant regions.

11. The antibody of claim 10, which comprises
(i) an IgG1 heavy chain constant region comprising a set of amino acid substitutions selected from the group consisting of
  (a) L234A and L235A; and
  (b) L234A, L235A, and P329G; or
(ii) an IgG4 heavy chain constant region comprising the amino acid substitution S228P.

12. The antibody of claim 10, wherein
(i) the heavy chain constant region is a human immunoglobulin IgG1 heavy chain constant region, and
(ii) the light chain constant region is a human immunoglobulin k light chain constant region.

13. The antibody of claim 1, wherein the antibody comprises
(i) the light chain of SEQ ID NO: 23; and
(ii) the heavy chain of SEQ ID NO: 21 or SEQ ID NO: 59.

14. The antibody of claim 1, which is an antigen binding fragment, wherein the antigen binding fragment comprises a Fab, Fab', F(ab')2, single chain Fv (scFv), disulfide linked Fv, intrabody, IgGΔCH2, F(ab')3, tetrabody, triabody, diabody, DVD-Ig, mAb2, (scFv) 2, or scFv-Fc.

15. A pharmaceutical composition comprising the antibody of claim 1 and a pharmaceutically acceptable excipient.

16. A method of treating a CD36-expressing cancer in a subject comprising administering to a subject in need thereof a therapeutically effective amount of the antibody of claim 1.

17. The method of claim 16, wherein the cancer is oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

18. A method of treating one or more CD36-expressing metastatic tumors in a subject comprising administering to a subject in need thereof a therapeutically effective amount of the antibody of claim 1.

19. The method of claim 18, wherein the metastatic tumors developed from an oral squamous cell carcinoma, head and neck cancer, esophageal cancer, gastric cancer, ovarian cancer, cervical cancer, lung cancer, breast cancer, colon cancer, renal cancer, prostate cancer, sarcoma, melanoma, leukemia, or lymphoma.

20. The method of claim 16, wherein the anti-CD36 antibody blocks the CD36-mediated uptake of fatty acids.

21. The method of claim 16, wherein the method further comprises administering a second therapy.

22. The method of claim 21, wherein the second therapy is an immunotherapy.

23. The method of claim 22, wherein the immunotherapy is a PD-1 inhibitor.

24. The method of claim 22, wherein the immunotherapy is a PD-L1 inhibitor.

25. The method claim 21, wherein the second therapy is a chemotherapeutic agent.

26. An isolated polynucleotide that encodes the antibody of claim 1 or a domain thereof.

27. A vector comprising the isolated polynucleotide of claim 26.

28. A host cell comprising the isolated polynucleotide of claim 26.

29. A method of making an antibody that is capable of specifically binding CD36, comprising
(i) culturing the host cell of claim 28 under conditions that express the antibody; and
(ii) recovering the expressed antibody.

30. A method of treating both a CD36-expressing primary tumor and a CD36-expressing metastatic tumor in a subject comprising administering to a subject in need thereof a therapeutically effective amount of the antibody of claim 1.

31. The pharmaceutical composition of claim 15, wherein the pharmaceutical composition is substantially free of antibodies that do not specifically bind to CD36.

32. The isolated antibody of claim 1, wherein the antibody is a bispecific antibody.

* * * * *

SEQUENCE LISTING

```
<160> NUMBER OF SEQ ID NOS: 59

<210> SEQ ID NO 1
<211> LENGTH: 472
<212> TYPE: PRT
<213> ORGANISM: Artificial Sequence
<220> FEATURE:
<223> OTHER INFORMATION: Human CD36

<400> SEQUENCE: 1

Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
        35                  40                  45

Ile Ala Phe Lys Asn Trp Val Lys Thr Gly Thr Glu Val Tyr Arg Gln
    50                  55                  60
```

```
Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
            115                 120                 125

Gly Thr Glu Ala Asp Asn Phe Thr Val Leu Asn Leu Ala Val Ala Ala
        130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
            195                 200                 205

Asp Gly Val Tyr Lys Val Phe Asn Gly Lys Asp Asn Ile Ser Lys Val
        210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
            275                 280                 285

Pro Val Tyr Arg Phe Val Leu Pro Ser Lys Ala Phe Ala Ser Pro Val
        290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu Glu His Arg
            355                 360                 365

Thr Tyr Leu Asp Ile Glu Pro Ile Thr Gly Phe Thr Leu Gln Phe Ala
        370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
            435                 440                 445

Leu Ser Val Gly Val Val Met Phe Val Ala Phe Met Ile Ser Tyr Cys
        450                 455                 460

Ala Cys Arg Ser Lys Thr Ile Lys
465                 470
```

-continued

```
<210> SEQ ID NO 2
<211> LENGTH: 472
<212> TYPE: PRT
<213> ORGANISM: Artificial Sequence
<220> FEATURE:
<223> OTHER INFORMATION: Cynomolgus monkey/Rhesus macaque CD36

<400> SEQUENCE: 2

Met Gly Cys Asp Arg Asn Cys Gly Leu Ile Thr Gly Ala Val Ile Gly
1               5                   10                  15

Ala Val Leu Ala Val Phe Gly Gly Ile Leu Met Pro Val Gly Asp Met
                20                  25                  30

Leu Ile Gln Lys Thr Ile Lys Lys Glu Val Val Leu Glu Glu Gly Thr
            35                  40                  45

Ile Ala Phe Lys Asn Trp Val Lys Thr Gly Thr Glu Ile Tyr Arg Gln
        50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Ile Thr Gln Asp Pro Lys Asp Asn Thr Val
            100                 105                 110

Ser Phe Leu Gln Pro Asn Gly Ala Ile Phe Glu Pro Ser Leu Ser Val
            115                 120                 125

Gly Thr Glu Ala Asp Asn Phe Thr Val Leu Asn Leu Ala Val Ala Ala
        130                 135                 140

Ala Ser His Ile Tyr Pro Asn Pro Phe Val Gln Val Val Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Thr Asp Pro Phe Leu Ser Leu Val Pro Tyr
            180                 185                 190

Pro Val Ser Thr Arg Val Gly Met Phe Tyr Pro Tyr Asn Asn Thr Ala
            195                 200                 205

Asp Gly Val Tyr Lys Val Phe Asn Gly Lys Asp Ser Ile Ser Lys Val
        210                 215                 220

Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
        290                 295                 300

Gln Asn Pro Asp Asn His Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Lys Pro Val Tyr Ile Ser Leu Pro His Phe Leu Tyr Ala Ser Pro Asp
            340                 345                 350

Val Ser Glu Thr Ile Asp Gly Leu Asn Pro Asn Glu Glu Glu His Arg
            355                 360                 365
```

```
Thr Tyr Leu Asp Ile Glu Pro Ile Thr Gly Phe Thr Leu Gln Phe Ala
    370             375             380

Lys Arg Leu Gln Val Asn Leu Leu Val Lys Pro Ser Asn Lys Ile Gln
385             390             395             400

Val Leu Lys Arg Leu Lys Arg Asn Tyr Ile Val Pro Ile Leu Trp Leu
            405             410             415

Asn Glu Thr Gly Thr Ile Gly Asp Glu Lys Ala Lys Met Phe Arg Ser
            420             425             430

Gln Val Thr Gly Lys Ile Asn Leu Leu Gly Leu Ile Glu Met Ile Leu
            435             440             445

Leu Ser Val Gly Val Val Met Phe Val Ala Phe Met Ile Ser Tyr Cys
    450             455             460

Ala Cys Arg Ser Lys Thr Ile Lys
465             470
```

```
<210> SEQ ID NO 3
<211> LENGTH: 472
<212> TYPE: PRT
<213> ORGANISM: Artificial Sequence
<220> FEATURE:
<223> OTHER INFORMATION: Murine CD36

<400> SEQUENCE: 3

Met Gly Cys Asp Arg Asn Cys Gly Leu Ile Ala Gly Ala Val Ile Gly
1               5               10              15

Ala Val Leu Ala Val Phe Gly Gly Ile Leu Met Pro Val Gly Asp Met
            20              25              30

Leu Ile Glu Lys Thr Ile Lys Arg Glu Val Val Leu Glu Glu Gly Thr
            35              40              45

Thr Ala Phe Lys Asn Trp Val Lys Thr Gly Thr Thr Val Tyr Arg Gln
    50              55              60

Phe Trp Ile Phe Asp Val Gln Asn Pro Asp Asp Val Ala Lys Asn Ser
65              70              75              80

Ser Lys Ile Lys Val Lys Gln Arg Gly Pro Tyr Thr Tyr Arg Val Arg
            85              90              95

Tyr Leu Ala Lys Glu Asn Ile Thr Gln Asp Pro Glu Asp His Thr Val
            100             105             110

Ser Phe Val Gln Pro Asn Gly Ala Ile Phe Glu Pro Ser Leu Ser Val
            115             120             125

Gly Thr Glu Asp Asp Asn Phe Thr Val Leu Asn Leu Ala Val Ala Ala
    130             135             140

Ala Pro His Ile Tyr Gln Asn Ser Phe Val Gln Val Val Leu Asn Ser
145             150             155             160

Leu Ile Lys Lys Ser Lys Ser Ser Met Phe Gln Thr Arg Ser Leu Lys
            165             170             175

Glu Leu Leu Trp Gly Tyr Lys Asp Pro Phe Leu Ser Leu Val Pro Tyr
            180             185             190

Pro Ile Ser Thr Thr Val Gly Val Phe Tyr Pro Tyr Asn Asp Thr Val
            195             200             205

Asp Gly Val Tyr Lys Val Phe Asn Gly Lys Asp Asn Ile Ser Lys Val
    210             215             220

Ala Ile Ile Glu Ser Tyr Lys Gly Lys Arg Asn Leu Ser Tyr Trp Pro
225             230             235             240

Ser Tyr Cys Asp Met Ile Asn Gly Thr Asp Ala Ala Ser Phe Pro Pro
            245             250             255
```

-continued

```
Phe Val Glu Lys Ser Arg Thr Leu Arg Phe Phe Ser Ser Asp Ile Cys
            260             265             270

Arg Ser Ile Tyr Ala Val Phe Gly Ser Glu Ile Asp Leu Lys Gly Ile
            275             280             285

Pro Val Tyr Arg Phe Val Leu Pro Ala Asn Ala Phe Ala Ser Pro Leu
            290             295             300

Gln Asn Pro Asp Asn His Cys Phe Cys Thr Glu Lys Val Ile Ser Asn
305             310             315             320

Asn Cys Thr Ser Tyr Gly Val Leu Asp Ile Gly Lys Cys Lys Glu Gly
            325             330             335

Lys Pro Val Tyr Ile Ser Leu Pro His Phe Leu His Ala Ser Pro Asp
            340             345             350

Val Ser Glu Pro Ile Glu Gly Leu His Pro Asn Glu Asp Glu His Arg
            355             360             365

Thr Tyr Leu Asp Val Glu Pro Ile Thr Gly Phe Thr Leu Gln Phe Ala
            370             375             380

Lys Arg Leu Gln Val Asn Ile Leu Val Lys Pro Ala Arg Lys Ile Glu
385             390             395             400

Ala Leu Lys Asn Leu Lys Arg Pro Tyr Ile Val Pro Ile Leu Trp Leu
            405             410             415

Asn Glu Thr Gly Thr Ile Gly Asp Glu Lys Ala Glu Met Phe Lys Thr
            420             425             430

Gln Val Thr Gly Lys Ile Lys Leu Leu Gly Met Val Glu Met Ala Leu
            435             440             445

Leu Gly Ile Gly Val Val Met Phe Val Ala Phe Met Ile Ser Tyr Cys
            450             455             460

Ala Cys Lys Ser Lys Asn Gly Lys
465             470
```

```
<210> SEQ ID NO 4
<211> LENGTH: 472
<212> TYPE: PRT
<213> ORGANISM: Artificial Sequence
<220> FEATURE:
<223> OTHER INFORMATION: Rat CD36

<400> SEQUENCE: 4
```

```
Met Gly Cys Asp Arg Asn Cys Gly Leu Ile Thr Gly Ala Val Ile Gly
1               5               10              15

Ala Val Leu Ala Val Phe Gly Gly Ile Leu Met Pro Val Gly Asp Leu
            20              25              30

Leu Ile Glu Lys Thr Ile Lys Arg Glu Val Val Leu Glu Glu Gly Thr
            35              40              45

Ile Ala Phe Lys Asn Trp Val Lys Thr Gly Thr Thr Val Tyr Arg Gln
            50              55              60

Phe Trp Ile Phe Asp Val Gln Asn Pro Glu Glu Val Ala Lys Asn Ser
65              70              75              80

Ser Lys Ile Lys Val Lys Gln Arg Gly Pro Tyr Thr Tyr Arg Val Arg
            85              90              95

Tyr Leu Ala Lys Glu Asn Ile Thr Gln Asp Pro Lys Asp Ser Thr Val
            100             105             110

Ser Phe Val Gln Pro Asn Gly Ala Ile Phe Glu Pro Ser Leu Ser Val
            115             120             125

Gly Thr Glu Asn Asp Asn Phe Thr Val Leu Asn Leu Ala Val Ala Ala
            130             135             140
```

```
Ala Pro His Ile Tyr Thr Asn Ser Phe Val Gln Gly Val Leu Asn Ser
145                 150                 155                 160

Leu Ile Lys Lys Ser Lys Ser Ser Met Phe Gln Thr Arg Ser Leu Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Tyr Pro Tyr Asn Asn Thr Val
            195                 200                 205

Asp Gly Val Tyr Lys Val Phe Asn Gly Lys Asp Asn Ile Ser Lys Val
        210                 215                 220

Ala Ile Ile Asp Thr Tyr Lys Gly Lys Arg Asn Leu Ser Tyr Trp Glu
225                 230                 235                 240

Ser Tyr Cys Asp Met Ile Asn Gly Thr Asp Ala Ala Ser Phe Pro Pro
                245                 250                 255

Phe Val Glu Lys Ser Gln Thr Leu Arg Phe Phe Ser Ser Asp Ile Cys
                260                 265                 270

Arg Ser Ile Tyr Ala Val Phe Glu Ser Glu Val Asn Leu Lys Gly Ile
            275                 280                 285

Pro Val Tyr Arg Phe Val Leu Pro Ala Asn Ala Phe Ala Ser Pro Leu
        290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                325                 330                 335

Lys Pro Val Tyr Ile Ser Leu Pro His Phe Leu His Ala Ser Pro Asp
            340                 345                 350

Val Ser Glu Pro Ile Glu Gly Leu Asn Pro Asn Glu Asp Glu His Arg
            355                 360                 365

Thr Tyr Leu Asp Val Glu Pro Ile Thr Gly Phe Thr Leu Gln Phe Ala
        370                 375                 380

Lys Arg Leu Gln Val Asn Ile Leu Val Lys Pro Ala Arg Lys Ile Glu
385                 390                 395                 400

Ala Leu Lys Asn Leu Lys Arg Pro Tyr Ile Val Pro Ile Leu Trp Leu
                405                 410                 415

Asn Glu Thr Gly Thr Ile Gly Asp Glu Lys Ala Glu Met Phe Arg Asn
                420                 425                 430

Gln Val Thr Gly Lys Ile Lys Leu Leu Gly Leu Val Glu Met Val Leu
            435                 440                 445

Leu Gly Val Gly Val Val Met Phe Val Ala Phe Met Ile Ser Tyr Cys
        450                 455                 460

Ala Cys Arg Ser Lys Asn Gly Lys
465                 470

<210> SEQ ID NO 5
<211> LENGTH: 462
<212> TYPE: PRT
<213> ORGANISM: Artificial Sequence
<220> FEATURE:
<223> OTHER INFORMATION: ONA-0-v1 heavy chain

<400> SEQUENCE: 5

Gln Val Gln Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
                20                  25                  30
```

```
Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Gly Gly Gly Phe Gly Met Asp Tyr Trp Gly Gln Gly
            100                 105                 110

Thr Ser Val Thr Val Ser Ser Glu Ser Ala Arg Asn Pro Thr Ile Tyr
            115                 120                 125

Pro Leu Thr Leu Pro Pro Val Leu Cys Ser Asp Pro Val Ile Ile Gly
    130                 135                 140

Cys Leu Ile His Asp Tyr Phe Pro Phe Gly Thr Met Asn Val Thr Trp
145                 150                 155                 160

Gly Lys Ser Gly Lys Asp Ile Thr Thr Val Asn Phe Pro Pro Ala Leu
                165                 170                 175

Ala Ser Gly Gly Arg Tyr Thr Met Ser Ser Gln Leu Thr Leu Pro Ala
            180                 185                 190

Val Glu Cys Pro Glu Gly Glu Ser Val Lys Cys Ser Val Gln His Asp
            195                 200                 205

Ser Asn Pro Val Gln Glu Leu Asp Val Asn Cys Ser Pro Thr Pro Pro
    210                 215                 220

Pro Pro Ile Thr Ile Pro Ser Cys Gln Pro Ser Leu Ser Leu Gln Arg
225                 230                 235                 240

Pro Ala Leu Glu Asp Leu Leu Leu Gly Ser Asp Ala Ser Ile Thr Cys
                245                 250                 255

Thr Leu Asn Gly Leu Arg Asn Pro Glu Gly Ala Ala Phe Thr Trp Glu
                260                 265                 270

Pro Ser Thr Gly Lys Asp Ala Val Gln Lys Lys Ala Ala Gln Asn Ser
            275                 280                 285

Cys Gly Cys Tyr Ser Val Ser Ser Val Leu Pro Gly Cys Ala Glu Arg
    290                 295                 300

Trp Asn Ser Gly Ala Ser Phe Lys Cys Thr Val Thr His Pro Glu Ser
305                 310                 315                 320

Gly Thr Leu Thr Gly Thr Ile Ala Lys Val Thr Val Asn Thr Phe Pro
                325                 330                 335

Pro Gln Val His Leu Leu Pro Pro Pro Ser Glu Glu Leu Ala Leu Asn
            340                 345                 350

Glu Leu Leu Ser Leu Thr Cys Leu Val Arg Ala Phe Asn Pro Lys Glu
            355                 360                 365

Val Leu Val Arg Trp Leu His Gly Asn Glu Glu Leu Ser Pro Glu Ser
    370                 375                 380

Tyr Leu Val Phe Glu Pro Leu Lys Glu Pro Gly Glu Gly Ala Thr Thr
385                 390                 395                 400

Tyr Leu Val Thr Ser Val Leu Arg Val Ser Ala Glu Thr Trp Lys Gln
                405                 410                 415

Gly Asp Gln Tyr Ser Cys Met Val Gly His Glu Ala Leu Pro Met Asn
            420                 425                 430

Phe Thr Gln Lys Thr Ile Asp Arg Leu Ser Gly Lys Pro Thr Asn Val
            435                 440                 445

Ser Val Ser Val Ile Met Ser Glu Gly Asp Gly Ile Cys Tyr
```

-continued

```
          450                455                460
```

<210> SEQ ID NO 6
<211> LENGTH: 1386
<212> TYPE: DNA
<213> ORGANISM: Artificial Sequence
<220> FEATURE:
<223> OTHER INFORMATION: ONA-0 heavy chain

<400> SEQUENCE: 6

```
caagtgcagc tgaagcagtc cggagctgat ctggtgagac ccggagccag cgtgaagctg        60
agctgcaagg ccagcggcta caccttcacc gactactaca tcaactgggt gaagcagagg       120
cccggccaag gactggagtg gatcgctaga atctaccccg gctccggcaa tacatactac       180
aacgagaagt tcaaaggcaa ggccacactg accgccgaga gagcagcag caccgcctac       240 atgcagctga gctctctgac ctccgaggac agcgccgtgt acttttgcgc cagaggcatc       300
ggaggcggat cggcatgga ttactggggc caaggcacct ccgtgaccgt ctcgagcgaa       360
tcggccagaa accccactat ctaccctctg accctgcctc ctgtcctgtg ttccgacccc       420
gtgatcatcg gatgcctgat ccacgactac ttccctttcg gcaccatgaa cgtgacctgg       480
gggaagtcgg aaaggacat tactaccgtg aacttcccac cggccctggc gtcggggggt       540
cgctacacca tgtccagcca gcttactctg cccgctgtgg agtgccccga aggagagtca       600
gtgaagtgct ccgtgcaaca tgactccaac ccggtccagg aattggacgt caattgctcc       660
ccgactccgc ctccgcctat cacgatccca agctgccagc cctccctgag cctccagcgg       720
ccagccctgg aggatcttct gctgggctcc gacgcctcca ttacatgcac tctgaacggc       780
ctgagaaacc cggaaggggc ggcctttact tgggagccct ccaccgggaa ggatgcggtc       840
cagaagaagg cagcccaaaa ttcctgcgga tgctactcag tgtctagcgt gctgcctggt       900
tgtgccgaac ggtggaactc cggagcgtca ttcaagtgta ccgtgaccca ccctgagtcc       960
ggaactctga ccggcaccat cgccaaggtc accgtgaaca cctttccgcc acaagtgcac      1020
ctcctgccgc cgccgtcgga ggaactcgct ctgaacgagt tgctctcgct gacttgtctc      1080
gtgcgcgcct tcaaccctaa ggaggtgctc gtgcgctggc tgcatggcaa cgaagaactg      1140
tcccccgaat cgtacctggt gttcgaaccg ctgaaagagc ccggagaggg tgcaaccacc      1200
taccttgtga cgagcgtgct ccgggtgtcc gccgaaacct ggaagcaggg cgaccagtac      1260
agctgcatgg tcggccacga ggccctcccc atgaacttca ctcagaaaac cattgatagg      1320
ttgtccggaa agcccaccaa cgtgtcagtg tccgtgatta tgagcgaagg agatggaatc      1380
tgctat                                                                 1386
```

<210> SEQ ID NO 7
<211> LENGTH: 214
<212> TYPE: PRT
<213> ORGANISM: Artificial Sequence
<220> FEATURE:
<223> OTHER INFORMATION: ONA-0-v1 light chain

<400> SEQUENCE: 7

```
Ser Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asp Asp
            20                  25                  30

Val Ala Trp Tyr Gln Gln Lys Pro Gly Gln Ser Pro Lys Leu Leu Ile
        35                  40                  45
```

-continued

```
Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210
```

```
<210> SEQ ID NO 8
<211> LENGTH: 642
<212> TYPE: DNA
<213> ORGANISM: Artificial Sequence
<220> FEATURE:
<223> OTHER INFORMATION: ONA-0-v1 light chain

<400> SEQUENCE: 8
tccatcgtga tgacccagac ccccaagttt ctgctggtgt ccgccggaga cagaatcacc      60
atcacatgca aggccagcca gagcgtgagc gatgacgtgg cttggtacca gcagaagccc     120
ggccagagcc ctaagctgct gatctactac gccagcaata gatacaccgg agtgcccgat     180
agattcaccg gcagcggcta cggcaccgac ttcaccttca caatctccac cgtgcaagcc     240
gaggatctgg ccgtgtactt ctgtcagcaa gactactcca gccctctgac cttcggagcc     300
ggcaccaagc tcgagatcaa gcgcgcagat gctgctccta ccgtgagcat cttcccgccg     360
tccagcgaac aactcactag cggaggcgcg tcagtggtct gcttccttaa caatttctac     420
cctaaggaca tcaacgtcaa gtggaagatt gacggatcgg aacgccagaa cggagtgctg     480
aactcatgga ctgatcagga ttccaaagac tcgacttact ccatgtccag caccctgacc     540
ctgaccaaag acgagtacga aaggcacaac tcgtacacgt gcgaagccac ccacaagact     600
tccacctcgc ccatcgtgaa gtccttcaat cgcaatgagt gc                        642
```

```
<210> SEQ ID NO 9
<211> LENGTH: 214
<212> TYPE: PRT
<213> ORGANISM: Artificial Sequence
<220> FEATURE:
<223> OTHER INFORMATION: ONA-0-v2 light chain

<400> SEQUENCE: 9

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
```

-continued

```
                20                    25                    30
Val Ser Trp Tyr Gln Gln Lys Pro Glu Gln Ser Pro Lys Leu Leu Ile
        35                    40                    45

Tyr Gly Ala Ser Asn Arg Tyr Thr Gly Val Pro Asp Arg Phe Thr Gly
    50                    55                    60

Ser Gly Ser Ala Thr Asp Phe Thr Leu Thr Ile Ser Ser Val Gln Ala
65                    70                    75                    80

Glu Asp Leu Ala Asp Tyr His Cys Gly Gln Gly Tyr Ser Tyr Pro Tyr
                85                    90                    95

Thr Phe Gly Gly Gly Thr Lys Leu Glu Ile Lys Arg Ala Asp Ala Ala
            100                   105                   110

Pro Thr Val Ser Ile Phe Pro Pro Ser Ser Glu Gln Leu Thr Ser Gly
        115                   120                   125

Gly Ala Ser Val Val Cys Phe Leu Asn Asn Phe Tyr Pro Lys Asp Ile
        130                   135                   140

Asn Val Lys Trp Lys Ile Asp Gly Ser Glu Arg Gln Asn Gly Val Leu
145                   150                   155                   160

Asn Ser Trp Thr Asp Gln Asp Ser Lys Asp Ser Thr Tyr Ser Met Ser
            165                   170                   175

Ser Thr Leu Thr Leu Thr Lys Asp Glu Tyr Glu Arg His Asn Ser Tyr
            180                   185                   190

Thr Cys Glu Ala Thr His Lys Thr Ser Thr Ser Pro Ile Val Lys Ser
            195                   200                   205

Phe Asn Arg Asn Glu Cys
    210
```

```
<210> SEQ ID NO 10
<211> LENGTH: 642
<212> TYPE: DNA
<213> ORGANISM: Artificial Sequence
<220> FEATURE:
<223> OTHER INFORMATION: ONA-0-v2 light chain

<400> SEQUENCE: 10
aacatcgtga tgacccaaag ccccaagagc atgagcatgt ccgtgggcga gagagtgaca      60
ctgacatgca aggccagcga gaacgtggtg acctacgtga gctggtacca gcagaagccc     120
gaacagagcc ctaagctgct gatctacgga gcctccaata gatataccgg cgtgcccgac     180
agattcaccg gcagcggcag cgccaccgat ttcacactga ccatcagcag cgtgcaagcc     240
gaggatctgg ctgactacca ctgcggccaa ggctacagct acccctacac cttcggcggc     300
ggcaccaagc tcgagatcaa gcgcgcagat gctgctccta ccgtgagcat cttcccgccg     360
tccagcgaac aactcactag cggaggcgcg tcagtggtct gcttccttaa caatttctac     420
cctaaggaca tcaacgtcaa gtggaagatt gacggatcgg aacgccagaa cggagtgctg     480
aactcatgga ctgatcagga ttccaaagac tcgacttact ccatgtccag caccctgacc     540
ctgaccaaag acgagtacga aaggcacaac tcgtacacgt gcgaagccac ccacaagact     600
tccacctcgc ccatcgtgaa gtccttcaat cgcaatgagt gc                        642
```

```
<210> SEQ ID NO 11
<211> LENGTH: 119
<212> TYPE: PRT
<213> ORGANISM: Artificial Sequence
<220> FEATURE:
<223> OTHER INFORMATION: ONA-0-v1 VH

<400> SEQUENCE: 11
```

```
Gln Val Gln Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Gly Gly Gly Phe Gly Met Asp Tyr Trp Gly Gln Gly
            100                 105                 110

Thr Ser Val Thr Val Ser Ser
        115
```

<210> SEQ ID NO 12
<211> LENGTH: 357
<212> TYPE: DNA
<213> ORGANISM: Artificial Sequence
<220> FEATURE:
<223> OTHER INFORMATION: ONA-0-v1 VH

<400> SEQUENCE: 12

```
caagtgcagc tgaagcagtc cggagctgat ctggtgagac ccggagccag cgtgaagctg      60
agctgcaagg ccagcggcta caccttcacc gactactaca tcaactgggt gaagcagagg     120
cccggccaag gactggagtg gatcgctaga atctaccccg gctccggcaa tacatactac     180
aacgagaagt tcaaaggcaa ggccacactg accgccgaga gagcagcag caccgcctac      240 atgcagctga gctctctgac ctccgaggac agcgccgtgt actttttgcgc cagaggcatc     300 ggaggcggat tcggcatgga ttactggggc caaggcacct ccgtgaccgt ctcgagc        357
```

<210> SEQ ID NO 13
<211> LENGTH: 107
<212> TYPE: PRT
<213> ORGANISM: Artificial Sequence
<220> FEATURE:
<223> OTHER INFORMATION: ONA-0-v1 VL

<400> SEQUENCE: 13

```
Ser Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asp Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Ile Lys
            100                 105
```

```
<210> SEQ ID NO 14
<211> LENGTH: 321
<212> TYPE: DNA
<213> ORGANISM: Artificial Sequence
<220> FEATURE:
<223> OTHER INFORMATION: ONA-0-v1 VL

<400> SEQUENCE: 14
tccatcgtga tgacccagac ccccaagttt ctgctggtgt ccgccggaga cagaatcacc        60
atcacatgca aggccagcca gagcgtgagc gatgacgtgg cttggtacca gcagaagccc       120
ggccagagcc ctaagctgct gatctactac gccagcaata gatacaccgg agtgcccgat       180
agattcaccg gcagcggcta cggcaccgac ttcaccttca caatctccac cgtgcaagcc       240
gaggatctgg ccgtgtactt ctgtcagcaa gactactcca gccctctgac cttcggagcc       300
ggcaccaagc tcgagatcaa g                                                   321

<210> SEQ ID NO 15
<211> LENGTH: 107
<212> TYPE: PRT
<213> ORGANISM: Artificial Sequence
<220> FEATURE:
<223> OTHER INFORMATION: ONA-0-v2 VL

<400> SEQUENCE: 15

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 16
<211> LENGTH: 321
<212> TYPE: DNA
<213> ORGANISM: Artificial Sequence
<220> FEATURE:
<223> OTHER INFORMATION: ONA-0-v2 VL

<400> SEQUENCE: 16
aacatcgtga tgacccaaag ccccaagagc atgagcatgt ccgtgggcga gagagtgaca        60
ctgacatgca aggccagcga gaacgtggtg acctacgtga gctggtacca gcagaagccc       120
gaacagagcc ctaagctgct gatctacgga gcctccaata gatataccgg cgtgcccgac       180
agattcaccg gcagcggcag cgccaccgat ttcacactga ccatcagcag cgtgcaagcc       240
gaggatctgg ctgactacca ctgcggccaa ggctacagct acccctacac cttcggcggc       300
ggcaccaagc tcgagatcaa g                                                   321

<210> SEQ ID NO 17
<211> LENGTH: 463
<212> TYPE: PRT
<213> ORGANISM: Artificial Sequence
```

```
<220> FEATURE:
<223> OTHER INFORMATION: ONA-0-v1B heavy chain

<400> SEQUENCE: 17

Gln Val Gln Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Gly Gly Gly Phe Gly Met Asp Tyr Trp Gly Gln Gly
            100                 105                 110

Thr Ser Val Thr Val Ser Ser Glu Ser Ala Arg Asn Pro Thr Ile Tyr
            115                 120                 125

Pro Leu Thr Leu Pro Arg Ala Leu Ser Ser Asp Pro Val Ile Ile Gly
    130                 135                 140

Cys Leu Ile His Asp Tyr Phe Pro Ser Gly Thr Met Asn Val Thr Trp
145                 150                 155                 160

Gly Lys Ser Gly Lys Asp Ile Thr Thr Val Asn Phe Pro Pro Ala Leu
            165                 170                 175

Ala Ser Gly Gly Gly Tyr Thr Met Ser Ser Gln Leu Thr Leu Pro Ala
            180                 185                 190

Val Glu Cys Pro Glu Gly Glu Ser Val Lys Cys Ser Val Gln His Asp
            195                 200                 205

Ser Asn Ala Val Gln Glu Leu Asp Val Lys Cys Ser Gly Pro Pro Pro
    210                 215                 220

Pro Cys Pro Pro Cys Pro Ser Cys His Pro Ser Leu Ser Leu Gln
225                 230                 235                 240

Arg Pro Ala Leu Glu Asp Leu Leu Leu Gly Ser Asp Ala Ser Leu Thr
                245                 250                 255

Cys Thr Leu Asn Gly Leu Arg Asn Pro Glu Gly Ala Val Phe Thr Trp
            260                 265                 270

Glu Pro Ser Thr Gly Lys Asp Ala Val Gln Lys Lys Ala Val Gln Asn
            275                 280                 285

Ser Cys Gly Cys Tyr Ser Val Ser Ser Val Leu Pro Gly Cys Ala Glu
    290                 295                 300

Arg Trp Asn Ser Gly Ala Ser Phe Lys Cys Thr Val Thr His Pro Glu
305                 310                 315                 320

Ser Asp Thr Leu Thr Gly Thr Ile Ala Lys Ile Thr Val Asn Thr Phe
            325                 330                 335

Pro Pro Gln Val His Leu Leu Pro Pro Ser Glu Glu Leu Ala Leu
            340                 345                 350

Asn Glu Leu Val Ser Leu Thr Cys Leu Val Arg Ala Phe Asn Pro Lys
            355                 360                 365

Glu Val Leu Val Arg Trp Leu His Gly Asn Glu Glu Leu Ser Pro Glu
    370                 375                 380

Ser Tyr Leu Val Phe Glu Pro Leu Lys Glu Pro Gly Glu Gly Ala Thr
385                 390                 395                 400
```

```
Thr Tyr Leu Val Thr Ser Val Leu Arg Val Ser Ala Glu Leu Trp Lys
            405                 410                 415

Gln Gly Asp Gln Tyr Ser Cys Met Val Gly His Glu Ala Leu Pro Met
            420                 425                 430

Asn Phe Thr Gln Lys Thr Ile Asp Arg Leu Ser Gly Lys Pro Thr Asn
            435                 440                 445

Val Ser Val Ser Val Ile Met Ser Glu Gly Asp Gly Ile Cys Tyr
    450                 455                 460
```

```
<210> SEQ ID NO 18
<211> LENGTH: 214
<212> TYPE: PRT
<213> ORGANISM: Artificial Sequence
<220> FEATURE:
<223> OTHER INFORMATION: ONA-0-v1B light chain

<400> SEQUENCE: 18

Ser Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asp Asp
            20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
            85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210
```

```
<210> SEQ ID NO 19
<211> LENGTH: 214
<212> TYPE: PRT
<213> ORGANISM: Artificial Sequence
<220> FEATURE:
<223> OTHER INFORMATION: ONA-0-v2B light chain

<400> SEQUENCE: 19

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
```

-continued

```
                20              25              30

Val Ser Trp Tyr Gln Gln Lys Pro Glu Gln Ser Pro Lys Leu Leu Ile
            35              40              45

Tyr Gly Ala Ser Asn Arg Tyr Thr Gly Val Pro Asp Arg Phe Thr Gly
        50              55              60

Ser Gly Ser Ala Thr Asp Phe Thr Leu Thr Ile Ser Ser Val Gln Ala
65              70              75              80

Glu Asp Leu Ala Asp Tyr His Cys Gly Gln Gly Tyr Ser Tyr Pro Tyr
                85              90              95

Thr Phe Gly Gly Gly Thr Lys Leu Glu Ile Lys Arg Ala Asp Ala Ala
            100             105             110

Pro Thr Val Ser Ile Phe Pro Pro Ser Ser Glu Gln Leu Thr Ser Gly
            115             120             125

Gly Ala Ser Val Val Cys Phe Leu Asn Asn Phe Tyr Pro Lys Asp Ile
        130             135             140

Asn Val Lys Trp Lys Ile Asp Gly Ser Glu Arg Gln Asn Gly Val Leu
145             150             155             160

Asn Ser Trp Thr Asp Gln Asp Ser Lys Asp Ser Thr Tyr Ser Met Ser
            165             170             175

Ser Thr Leu Thr Leu Thr Lys Asp Glu Tyr Glu Arg His Asn Ser Tyr
            180             185             190

Thr Cys Glu Ala Thr His Lys Thr Ser Thr Ser Pro Ile Val Lys Ser
        195             200             205

Phe Asn Arg Asn Glu Cys
    210
```

```
<210> SEQ ID NO 20
<211> LENGTH: 107
<212> TYPE: PRT
<213> ORGANISM: Artificial Sequence
<220> FEATURE:
<223> OTHER INFORMATION: ONA-0-v1B VL

<400> SEQUENCE: 20

Ser Ile Val Met Thr Gln Thr Pro Lys Phe Leu Leu Val Ser Ala Gly
1               5               10              15

Asp Arg Ile Thr Ile Thr Cys Lys Ala Ser Gln Ser Val Ser Asp Asp
            20              25              30

Val Ala Trp Tyr Gln Gln Lys Pro Gly Gln Ser Pro Lys Leu Leu Ile
            35              40              45

Tyr Tyr Ala Ser Asn Arg Tyr Thr Gly Val Pro Asp Arg Phe Thr Gly
        50              55              60

Ser Gly Tyr Gly Thr Asp Phe Thr Phe Thr Ile Ser Thr Val Gln Ala
65              70              75              80

Glu Asp Leu Ala Val Tyr Phe Cys Gln Gln Asp Tyr Ser Ser Pro Leu
                85              90              95

Thr Phe Gly Ala Gly Thr Lys Leu Glu Leu Lys
            100             105
```

```
<210> SEQ ID NO 21
<211> LENGTH: 449
<212> TYPE: PRT
<213> ORGANISM: Artificial Sequence
<220> FEATURE:
<223> OTHER INFORMATION: 1G04 heavy chain

<400> SEQUENCE: 21
```

```
Gln Val Gln Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Gly Gly Gly Phe Gly Met Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
             420              425              430
Ala Leu His Asn His Tyr Thr Gln Lys Ser Leu Ser Leu Ser Pro Gly
         435              440              445

Lys
```

```
<210> SEQ ID NO 22
<211> LENGTH: 1347
<212> TYPE: DNA
<213> ORGANISM: Artificial Sequence
<220> FEATURE:
<223> OTHER INFORMATION: 1G04 heavy chain

<400> SEQUENCE: 22
caagtgcagc tgaagcagtc cggagctgat ctggtgagac ccggagccag cgtgaagctg      60
agctgcaagg ccagcggcta caccttcacc gactactaca tcaactgggt gaagcagagg     120
cccggccaag gactggagtg gatcgctaga atctaccccg gctccggcaa tacatactac     180
aacgagaagt tcaaaggcaa ggccacactg accgccgaga gagcagcag caccgcctac      240 atgcagctga gctctctgac ctccgaggac agcgccgtgt acttttgcgc cagaggcatc     300
ggaggcggat tcggcatgga ttactggggc caaggcacct ccgtgaccgt ctcgagcgcc     360
agcaccaaag gtccatccgt gtttccgctc gccccgtcct caaagtcgac ctccggaggc     420
actgccgccc tgggctgcct tgtcaaggac tatttccccg aacctgtcac ggtgtcctgg     480
aacagcggcg ctctgacttc cggagtgcac accttcsccg ccgtcctgca atccagcggc     540
ctgtactcac tgtcatccgt tgtgactgtc ccgtcgtcca gcctgggaac ccaaacctac     600
atttgcaacg tgaatcacaa accatcgaat accaaggtcg ataagaaagt cgagccgaag     660
tcatgcgaca gactcacac ctgtccgcct tgcccggcgc cagaagcggc cggcggccct      720
tcggtgtttt tgtttccgcc gaagccgaag gacactctga tgatctcacg cactccagag     780
gtgacttgcg tggtggtcga tgtttcgcac gaggacccgg aagtgaaatt caactggtat     840
gtcgacgggg tggaagtgca taatgccaag acgaagccga gggaggaaca gtacaactcc     900
acctacagag tggtttcagt ccttaccgtc ctccatcaag attggctgaa cggaaaggag     960
tacaaatgta aggtgtcgaa caaagcgttg ccggccccta tcgaaaagac tatcagcaag    1020
gccaaaggac agccgcggga ccgcaagtg tacaccctcc cgccttcgcg ggacgagctg     1080
accaagaatc aggtgtccct tacttgcctg gtgaagggat tctacccctc ggatatcgca    1140
gtcgaatggg aatcgaatgg acagccagaa aacaactaca gaccactcc ccggtgctc       1200 gactccgacg gttccttctt cctgtactcg aagctgaccg tggacaaatc acgctggcag    1260
cagggaaacg tgtttagctg cagcgtgatg catgaggcgc tgcataatca ctacacccag    1320
aagtcactct cgctcagccc agggaag                                        1347
```

```
<210> SEQ ID NO 23
<211> LENGTH: 214
<212> TYPE: PRT
<213> ORGANISM: Artificial Sequence
<220> FEATURE:
<223> OTHER INFORMATION: 1G04 light chain; 1G06 light chain

<400> SEQUENCE: 23

Ser Ile Val Met Thr Gln Thr Pro Lys Phe Leu Leu Val Ser Ala Gly
1               5                  10                 15

Asp Arg Ile Thr Ile Thr Cys Lys Ala Ser Gln Ser Val Ser Asp Asp
            20                 25                 30
```

-continued

```
Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210
```

```
<210> SEQ ID NO 24
<211> LENGTH: 642
<212> TYPE: DNA
<213> ORGANISM: Artificial Sequence
<220> FEATURE:
<223> OTHER INFORMATION: 1G04 light chain

<400> SEQUENCE: 24
tccatcgtga tgacccagac ccccaagttt ctgctggtgt ccgccggaga cagaatcacc      60
atcacatgca aggccagcca gagcgtgagc gatgacgtgg cttggtacca gcagaagccc     120
ggccagagcc ctaagctgct gatctactac gccagcaata gatacaccgg agtgcccgat     180
agattcaccg gcagcggcta cggcaccgac ttcaccttca caatctccac cgtgcaagcc     240
gaggatctgg ccgtgtactt ctgtcagcaa gactactcca gccctctgac cttcggagcc     300
ggcaccaagc tcgagatcaa gagaactgtg gccgcgccgt cagtgtttat cttccctcca     360
tcggatgaac agcttaagtc cggcacggcg tctgtggtct gcctgctcaa taactttttac    420 cctagggaag ctaaagtcca atggaaagtg gataacgccc tgcagtcagg aaacagccag     480
gaatcggtta ccgaacagga cagcaaggac agcacttact ccttgtcgtc gactcttact     540
ctgagcaagg ccgattacga gaagcacaag gtctacgcct gcgaggtcac ccatcaggga     600
ctctcgtccc cggtgaccaa atccttcaat agaggcgaat gc                       642
```

```
<210> SEQ ID NO 25
<211> LENGTH: 214
<212> TYPE: PRT
<213> ORGANISM: Artificial Sequence
<220> FEATURE:
<223> OTHER INFORMATION: ONA-0-v2 ch IgG1 LALA light chain

<400> SEQUENCE: 25

Asn Ile Val Met Thr Gln Ser Pro Lys Ser Met Ser Met Ser Val Gly
```

```
1                 5                   10                  15
Glu Arg Val Thr Leu Thr Cys Lys Ala Ser Glu Asn Val Val Thr Tyr
              20                  25                  30

Val Ser Trp Tyr Gln Gln Lys Pro Glu Gln Ser Pro Lys Leu Leu Ile
          35                  40                  45

Tyr Gly Ala Ser Asn Arg Tyr Thr Gly Val Pro Asp Arg Phe Thr Gly
      50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
              85                  90                  95

Thr Phe Gly Gly Gly Thr Lys Leu Glu Ile Lys Arg Thr Val Ala Ala
          100                 105                 110

Pro Ser Val Phe Ile Phe Pro Pro Ser Asp Glu Gln Leu Lys Ser Gly
          115                 120                 125

Thr Ala Ser Val Val Cys Leu Leu Asn Asn Phe Tyr Pro Arg Glu Ala
      130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
              165                 170                 175

Ser Thr Leu Thr Leu Ser Lys Ala Asp Tyr Glu Lys His Lys Val Tyr
          180                 185                 190

Ala Cys Glu Val Thr His Gln Gly Leu Ser Ser Pro Val Thr Lys Ser
          195                 200                 205

Phe Asn Arg Gly Glu Cys
      210
```

<210> SEQ ID NO 26
<211> LENGTH: 642
<212> TYPE: DNA
<213> ORGANISM: Artificial Sequence
<220> FEATURE:
<223> OTHER INFORMATION: ONA-0-v2 ch IgG1 LALA light chain

<400> SEQUENCE: 26

```
aacatcgtga tgacccaaag ccccaagagc atgagcatgt ccgtgggcga gagagtgaca      60
ctgacatgca aggccagcga gaacgtggtg acctacgtga ctggtacca gcagaagccc     120 gaacagagcc ctaagctgct gatctacgga gcctccaata gatataccgg cgtgcccgac     180
agattcaccg gcagcggcag cgccaccgat ttcacactga ccatcagcag cgtgcaagcc     240
gaggatctgg ctgactacca ctgcggccaa ggctacagct accctacac cttcggcggc     300 ggcaccaagc tcgagatcaa gagaactgtg gccgcgccgt cagtgtttat cttccctcca     360
tcggatgaac agcttaagtc cggcacggcg tctgtggtct gcctgctcaa taacttttac     420
cctagggaag ctaaagtcca atggaaagtg gataacgccc tgcagtcagg aaacagccag     480
gaatcggtta ccgaacagga cagcaaggac agcacttact ccttgtcgtc gactcttact     540
ctgagcaagg ccgattacga gaagcacaag gtctacgcct gcgaggtcac ccatcaggga     600
ctctcgtccc cggtgaccaa atccttcaat agaggcgaat gc                       642
```

<210> SEQ ID NO 27
<211> LENGTH: 7
<212> TYPE: PRT
<213> ORGANISM: Artificial Sequence
<220> FEATURE:

-continued

<223> OTHER INFORMATION: ONA-0-v1 VH CDR1 Chothia

<400> SEQUENCE: 27

Gly Tyr Thr Phe Thr Asp Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: ONA-0-v1 VH CDR2 Chothia

<400> SEQUENCE: 28

Tyr Pro Gly Ser Gly Asn
1               5

<210> SEQ ID NO 29
<211> LENGTH: 10
<212> TYPE: PRT
<213> ORGANISM: Artificial Sequence
<220> FEATURE:
<223> OTHER INFORMATION: ONA-0-v1 VH CDR3 Chothia; ONA-0-v1 VH CDR3
      Kabat; CDR-H3 ONA-0-v1, ONA-0-v1 Humanized v1-v16

<400> SEQUENCE: 29

Gly Ile Gly Gly Gly Phe Gly Met Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: ONA-0-v1 VL CDR1 Chothia; ONA-0-v1 VL CDR1
      Kabat; CDR-L1 ONA-0-v1, ONA-0-v1 Humanized
      v3/v4/v7/v8/v11/v12/v15/v16

<400> SEQUENCE: 30

Lys Ala Ser Gln Ser Val Ser Asp Asp Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: ONA-0-v1 VL CDR2 Chothia; ONA-0-v1 VL CDR2
      Kabat; CDR-L2 ONA-0-v1, ONA-0-v1 Humanized
      v1/v3/v5/v7/v9/v11/v13/v15

<400> SEQUENCE: 31

Tyr Ala Ser Asn Arg Tyr Thr
1               5

<210> SEQ ID NO 32
<211> LENGTH: 9
<212> TYPE: PRT
<213> ORGANISM: Artificial Sequence
<220> FEATURE:
<223> OTHER INFORMATION: ONA-0-v1 VL CDR3 Chothia; ONA-0-v1 VL CDR3
      Kabat; ONA-0-v1 VL CDR3 IMGT; CDR-L3 ONA-0-v1, ONA-0-v1 Humanized
      v1-v16

<400> SEQUENCE: 32

Gln Gln Asp Tyr Ser Ser Pro Leu Thr
1               5

-continued

```
<210> SEQ ID NO 33
<211> LENGTH: 11
<212> TYPE: PRT
<213> ORGANISM: Artificial Sequence
<220> FEATURE:
<223> OTHER INFORMATION: ONA-0-v2 VL CDR1 Chothia

<400> SEQUENCE: 33

Lys Ala Ser Glu Asn Val Val Thr Tyr Val Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: ONA-0-v2 VL CDR2 Chothia

<400> SEQUENCE: 34

Gly Ala Ser Asn Arg Tyr Thr
1               5

<210> SEQ ID NO 35
<211> LENGTH: 9
<212> TYPE: PRT
<213> ORGANISM: Artificial Sequence
<220> FEATURE:
<223> OTHER INFORMATION: ONA-0-v2 VL CDR3 Chothia

<400> SEQUENCE: 35

Gly Gln Gly Tyr Ser Tyr Pro Tyr Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic sequence

<400> SEQUENCE: 36

Met Tyr Pro Pro Pro Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: ONA-0-v1 VH CDR1 Kabat; CDR-H1 ONA-0-v1,
      ONA-0-v1 Humanized v1/v2/v3/v4/v9/v10/v11/v12

<400> SEQUENCE: 37

Asp Tyr Tyr Ile Asn
1               5

<210> SEQ ID NO 38
<211> LENGTH: 17
<212> TYPE: PRT
<213> ORGANISM: Artificial Sequence
<220> FEATURE:
<223> OTHER INFORMATION: ONA-0-v1 VH CDR2 Kabat; CDR-H2 ONA-0-v1,
      ONA-0-v1 Humanized v1/v2/v3/v4/v9/v10/v11/v12

<400> SEQUENCE: 38

Arg Ile Tyr Pro Gly Ser Gly Asn Thr Tyr Tyr Asn Glu Lys Phe Lys
1               5                   10                  15
```

-continued

```
Gly

<210> SEQ ID NO 39
<211> LENGTH: 8
<212> TYPE: PRT
<213> ORGANISM: Artificial Sequence
<220> FEATURE:
<223> OTHER INFORMATION: ONA-0-v1 VH CDR1 IMGT

<400> SEQUENCE: 39

Gly Tyr Thr Phe Thr Asp Tyr Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: ONA-0-v1 VH CDR2 IMGT

<400> SEQUENCE: 40

Ile Tyr Pro Gly Ser Gly Asn Thr
1               5

<210> SEQ ID NO 41
<211> LENGTH: 12
<212> TYPE: PRT
<213> ORGANISM: Artificial Sequence
<220> FEATURE:
<223> OTHER INFORMATION: ONA-0-v1 VH CDR3 IMGT

<400> SEQUENCE: 41

Ala Arg Gly Ile Gly Gly Gly Phe Gly Met Asp Tyr
1               5                   10

<210> SEQ ID NO 42
<211> LENGTH: 6
<212> TYPE: PRT
<213> ORGANISM: Artificial Sequence
<220> FEATURE:
<223> OTHER INFORMATION: ONA-0-v1 VL CDR1 IMGT

<400> SEQUENCE: 42

Gln Ser Val Ser Asp Asp
1               5

<210> SEQ ID NO 43
<211> LENGTH: 3
<212> TYPE: PRT
<213> ORGANISM: Artificial Sequence
<220> FEATURE:
<223> OTHER INFORMATION: ONA-0-v1 VL CDR2 IMGT

<400> SEQUENCE: 43

Tyr Ala Ser
1

<210> SEQ ID NO 44
<211> LENGTH: 5
<212> TYPE: PRT
<213> ORGANISM: Artificial Sequence
<220> FEATURE:
<223> OTHER INFORMATION: VH CDR1 Humanized variant Kabat; CDR-H1
      ONA-0-v1 Humanized v5/v6/v7/v8

<400> SEQUENCE: 44
```

```
Asp Tyr Tyr Met His
1               5

<210> SEQ ID NO 45
<211> LENGTH: 5
<212> TYPE: PRT
<213> ORGANISM: Artificial Sequence
<220> FEATURE:
<223> OTHER INFORMATION: VH CDR1 Humanized variant Kabat; CDR-H1
      ONA-0-v1 Humanized v13/v14/v15/v16

<400> SEQUENCE: 45

Asp Tyr Tyr Met Asn
1               5

<210> SEQ ID NO 46
<211> LENGTH: 17
<212> TYPE: PRT
<213> ORGANISM: Artificial Sequence
<220> FEATURE:
<223> OTHER INFORMATION: VH CDR2 Humanized variant Kabat; CDR-H2
      ONA-0-v1 Humanized v5/v6/v7/v8

<400> SEQUENCE: 46

Arg Ile Tyr Pro Gly Ser Gly Asn Thr Tyr Tyr Asn Glu Lys Phe Gln
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: VH CDR2 Humanized variant Kabat; CDR-H2
      ONA-0-v1 Humanized v13/v14/v15/v16

<400> SEQUENCE: 47

Arg Ile Tyr Pro Gly Ser Gly Asn Thr Tyr Tyr Asn Glu Lys Phe Thr
1               5                   10                  15

Gly

<210> SEQ ID NO 48
<211> LENGTH: 11
<212> TYPE: PRT
<213> ORGANISM: Artificial Sequence
<220> FEATURE:
<223> OTHER INFORMATION: VL CDR1 Humanized variant Kabat; CDR-L1
      ONA-0-v1 Humanized v1/v2/v5/v6/v9/v10/v13/v14

<400> SEQUENCE: 48

Gln Ala Ser Gln Ser Val Ser Asp Asp Val Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: VL CDR2 Humanized variant Kabat; CDR-L2
      ONA-0-v1 Humanized v2/v6/v10/v14

<400> SEQUENCE: 49

Tyr Ala Ser Asn Leu Tyr Thr
1               5

<210> SEQ ID NO 50
```

```
<211> LENGTH: 7
<212> TYPE: PRT
<213> ORGANISM: Artificial Sequence
<220> FEATURE:
<223> OTHER INFORMATION: VL CDR2 Humanized variant Kabat; CDR-L2
      ONA-0-v1 Humanized v4/v8/v12/v16

<400> SEQUENCE: 50

Tyr Ala Ser Asn Arg Tyr Ser
1               5

<210> SEQ ID NO 51
<211> LENGTH: 119
<212> TYPE: PRT
<213> ORGANISM: Artificial Sequence
<220> FEATURE:
<223> OTHER INFORMATION: Humanized ONA-0-v1 VH variant 1

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Arg Val Thr Leu Thr Ala Glu Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ile Gly Gly Gly Phe Gly Met Asp Tyr Trp Gly Gln Gly
            100                 105                 110

Thr Thr Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Humanized ONA-0-v1 VH variant 2

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Ala Arg Ile Tyr Pro Gly Ser Gly Asn Thr Tyr Tyr Asn Glu Lys Phe
    50                  55                  60

Gln Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Gly Gly Gly Phe Gly Met Asp Tyr Trp Gly Gln Gly
            100                 105                 110

Thr Thr Val Thr Val Ser Ser
        115
```

-continued

<210> SEQ ID NO 53
<211> LENGTH: 119
<212> TYPE: PRT
<213> ORGANISM: Artificial Sequence
<220> FEATURE:
<223> OTHER INFORMATION: Humanized ONA-0-v1 VH variant 3

<400> SEQUENCE: 53

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
        35                  40                  45

Ala Arg Ile Tyr Pro Gly Ser Gly Asn Thr Tyr Tyr Asn Glu Gly Phe
    50                  55                  60

Lys Gly Arg Phe Val Leu Ser Ala Glu Lys Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Ile Gly Gly Gly Phe Gly Met Asp Tyr Trp Gly Gln Gly
            100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Humanized ONA-0-v1 VH variant 4

<400> SEQUENCE: 54

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Ala Arg Ile Tyr Pro Gly Ser Gly Asn Thr Tyr Tyr Asn Glu Gly Phe
    50                  55                  60

Thr Gly Arg Phe Val Phe Ser Ala Asp Lys Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Ile Gly Gly Gly Phe Gly Met Asp Tyr Trp Gly Gln Gly
            100                 105                 110

Thr Thr Val Thr Val Ser Ser
        115

<210> SEQ ID NO 55
<211> LENGTH: 107
<212> TYPE: PRT
<213> ORGANISM: Artificial Sequence
<220> FEATURE:
<223> OTHER INFORMATION: Humanized ONA-0-v1 VL variant 1

<400> SEQUENCE: 55

-continued

```
Ser Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asp Asp
            20                  25                  30

Val Ala Trp Tyr Gln Gln Lys Pro Gly Lys Ala Pro Lys Leu Leu Ile
            35                  40                  45

Tyr Tyr Ala Ser Asn Arg Tyr Thr Gly Val Pro Ser Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Ser Ser Pro Leu
                85                  90                  95

Thr Phe Gly Gly Gly Thr Lys Leu Glu Ile Lys
            100                 105
```

```
<210> SEQ ID NO 56
<211> LENGTH: 107
<212> TYPE: PRT
<213> ORGANISM: Artificial Sequence
<220> FEATURE:
<223> OTHER INFORMATION: Humanized ONA-0-v1 VL variant 2

<400> SEQUENCE: 56
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asp Asp
            20                  25                  30

Val Ala Trp Tyr Gln Gln Lys Pro Gly Lys Ala Pro Lys Leu Leu Ile
            35                  40                  45

Tyr Tyr Ala Ser Asn Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Ser Ser Pro Leu
                85                  90                  95

Thr Phe Gly Gly Gly Thr Lys Leu Glu Ile Lys
            100                 105
```

```
<210> SEQ ID NO 57
<211> LENGTH: 107
<212> TYPE: PRT
<213> ORGANISM: Artificial Sequence
<220> FEATURE:
<223> OTHER INFORMATION: Humanized ONA-0-v1 VL variant 3

<400> SEQUENCE: 57
```

```
Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asp Asp
            20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Leu
                85                  90                  95
```

-continued

```
Thr Phe Gly Gly Gly Thr Lys Leu Glu Ile Lys
            100                     105

<210> SEQ ID NO 58
<211> LENGTH: 107
<212> TYPE: PRT
<213> ORGANISM: Artificial Sequence
<220> FEATURE:
<223> OTHER INFORMATION: Humanized ONA-0-v1 VL variant 4

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asp Asp
            20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Leu
                85                  90                  95

Thr Phe Gly Gly Gly Thr Lys Leu Glu Ile Lys
            100                     105

<210> SEQ ID NO 59
<211> LENGTH: 449
<212> TYPE: PRT
<213> ORGANISM: Artificial Sequence
<220> FEATURE:
<223> OTHER INFORMATION: 1G06 heavy chain

<400> SEQUENCE: 59

Gln Val Gln Leu Lys Gln Ser Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Gly Gly Gly Phe Gly Met Asp Tyr Trp Gly Gln Gly
            100                     105                 110

Thr Ser Val Thr Val Ser Ser Ala Ser Thr Lys Gly Pro Ser Val Phe
            115                     120                 125

Pro Leu Ala Pro Ser Ser Lys Ser Thr Ser Gly Gly Thr Ala Ala Leu
        130                     135                 140

Gly Cys Leu Val Lys Asp Tyr Phe Pro Glu Pro Val Thr Val Ser Trp
145                     150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

-continued

```
                 180              185                 190
Ser Ser Leu Gly Thr Gln Thr Tyr Ile Cys Asn Val Asn His Lys Pro
        195              200                 205

Ser Asn Thr Lys Val Asp Lys Lys Val Glu Pro Lys Ser Cys Asp Lys
        210              215                 220

Thr His Thr Cys Pro Pro Cys Pro Ala Pro Glu Ser Thr Arg Gly Pro
225              230                 235                 240

Ser Val Phe Leu Phe Pro Pro Lys Pro Lys Asp Thr Leu Met Ile Ser
                245              250                 255

Arg Thr Pro Glu Val Thr Cys Val Val Val Asp Val Ser His Glu Asp
            260              265              270

Pro Glu Val Lys Phe Asn Trp Tyr Val Asp Gly Val Glu Val His Asn
            275              280              285

Ala Lys Thr Lys Pro Arg Glu Glu Gln Tyr Asn Ser Thr Tyr Arg Val
        290              295                 300

Val Ser Val Leu Thr Val Leu His Gln Asp Trp Leu Asn Gly Lys Glu
305              310              315                 320

Tyr Lys Cys Lys Val Ser Asn Lys Ala Leu Pro Ala Pro Ile Glu Lys
            325              330                 335

Thr Ile Ser Lys Ala Lys Gly Gln Pro Arg Glu Pro Gln Val Tyr Thr
            340              345                 350

Leu Pro Pro Ser Arg Asp Glu Leu Thr Lys Asn Gln Val Ser Leu Thr
            355              360                 365

Cys Leu Val Lys Gly Phe Tyr Pro Ser Asp Ile Ala Val Glu Trp Glu
        370              375              380

Ser Asn Gly Gln Pro Glu Asn Asn Tyr Lys Thr Thr Pro Pro Val Leu
385              390                 395                 400

Asp Ser Asp Gly Ser Phe Phe Leu Tyr Ser Lys Leu Thr Val Asp Lys
                405              410                 415

Ser Arg Trp Gln Gln Gly Asn Val Phe Ser Cys Ser Val Met His Glu
            420              425                 430

Ala Leu His Asn His Tyr Thr Gln Lys Ser Leu Ser Leu Ser Pro Gly
        435              440                 445

Lys
```